(12) United States Patent
Wong et al.

(10) Patent No.: US 10,150,818 B2
(45) Date of Patent: *Dec. 11, 2018

(54) COMPOSITIONS AND METHODS FOR TREATMENT AND DETECTION OF CANCERS

(71) Applicant: Academia Sinica, Taipei (TW)

(72) Inventors: Chi-Huey Wong, Rancho Santa Fe, CA (US); Tsui-Ling Hsu, New Taipei (TW); Yi-Wei Lou, Taipei (TW); Chih-Wei Lin, Keelung (TW); Shih-Chi Yeh, Taipei (TW); Chung-Yi Wu, New Taipei (TW); Han-Chung Wu, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/798,312

(22) Filed: Jul. 13, 2015

(65) Prior Publication Data

US 2016/0102151 A1 Apr. 14, 2016

Related U.S. Application Data

(63) Continuation-in-part of application No. PCT/US2015/011748, filed on Jan. 16, 2015, and a continuation-in-part of application No. 14/599,174, filed on Jan. 16, 2015, now Pat. No. 9,982,041, and a continuation-in-part of application No. PCT/US2015/032745, filed on May 27, 2015, and a continuation-in-part of application No. 14/723,297, filed on May 27, 2015, now Pat. No. 1,002,892.

(60) Provisional application No. 61/928,132, filed on Jan. 16, 2014, provisional application No. 62/003,136, filed on May 27, 2014, provisional application No. 62/003,104, filed on May 27, 2014, provisional application No. 62/003,908, filed on May 28, 2014, provisional application No. 62/020,199, filed on Jul. 2, 2014, provisional application No. 62/110,338, filed on Jan. 30, 2015.

(51) Int. Cl.
| | |
|---|---|
| C07K 16/44 | (2006.01) |
| G01N 33/574 | (2006.01) |
| C07K 16/30 | (2006.01) |
| C07K 16/18 | (2006.01) |
| A61K 39/00 | (2006.01) |

(52) U.S. Cl.
CPC .............. *C07K 16/44* (2013.01); *C07K 16/18* (2013.01); *C07K 16/30* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3069* (2013.01); *G01N 33/57407* (2013.01); *G01N 33/57484* (2013.01); *G01N 33/57492* (2013.01); *A61K 2039/505* (2013.01); *C07K 2317/21* (2013.01); *C07K 2317/24* (2013.01); *C07K 2317/52* (2013.01); *C07K 2317/565* (2013.01); *C07K 2317/567* (2013.01); *C07K 2317/622* (2013.01); *C07K 2317/734* (2013.01); *C07K 2317/92* (2013.01); *G01N 2400/00* (2013.01); *G01N 2405/10* (2013.01); *G01N 2800/52* (2013.01)

(58) Field of Classification Search
CPC .......... C07K 2317/622; C07K 2317/24; C07K 2317/565; C07K 2317/567
USPC .............. 424/133.1, 135.1, 178.1; 530/387.3
See application file for complete search history.

(56) References Cited

U.S. PATENT DOCUMENTS

| | | | |
|---|---|---|---|
| 3,773,919 A | 11/1973 | Boswell et al. | |
| 3,896,111 A | 7/1975 | Kupchan et al. | |
| 4,137,230 A | 1/1979 | Hashimoto et al. | |
| 4,151,042 A | 4/1979 | Higashide et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,270,537 A | 6/1981 | Romaine | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,821 A | 3/1982 | Miyashita et al. | |

(Continued)

FOREIGN PATENT DOCUMENTS

| | | | |
|---|---|---|---|
| EP | 404097 A2 | 12/1990 | |
| EP | 0341735 B1 | 9/1992 | |

(Continued)

OTHER PUBLICATIONS

U.S. Appl. No. 15/011,543, filed Jan. 30, 2016, Chih-Huey Wong, et al.

(Continued)

*Primary Examiner* — Lynn A Bristol
(74) *Attorney, Agent, or Firm* — Duane Morris, LLP

(57) ABSTRACT

Pharmaceutical composition comprising antibodies or antigen binding fragments thereof that bind to globo H, SSEA3, and SSEA-4 are disclosed herein, as well as methods of use thereof. Methods of use include, without limitation, cancer therapies and diagnostics. The antibodies of the disclosure can bind to certain cancer cell surfaces. Exemplary targets of the antibodies disclosed herein can include carcinomas, such as those in brain, skin, bone, lungs, breast, esophagus, stomach, liver, bile duct, pancreas, colon, kidney, cervical, ovarian, and/or prostate cancer.

9 Claims, 38 Drawing Sheets

Specification includes a Sequence Listing.

(56) References Cited

U.S. PATENT DOCUMENTS

| | | |
|---|---|---|
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |

(56) References Cited

U.S. PATENT DOCUMENTS

| | | |
|---|---|---|
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,716,465 B2 | 5/2014 | Rossi et al. |
| 8,802,438 B2 | 8/2014 | Rossi et al. |
| 8,815,941 B2 | 8/2014 | Withers |
| 8,883,506 B2 | 11/2014 | Rossi et al. |
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 | 9/2016 | Wang |
| 9,759,726 B2 | 9/2017 | Wong et al. |
| 9,803,177 B2 | 10/2017 | Rossi et al. |
| 9,914,956 B2 | 3/2018 | Wong et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0221397 A1 | 10/2005 | Saito |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Power |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0322864 A1 | 12/2012 | Rossi et al. |
| 2012/0322865 A1 | 12/2012 | Rossi et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0302028 A1 | 10/2014 | Zha |
| 2014/0308746 A1 | 10/2014 | Rossi et al. |
| 2015/0087814 A1 | 3/2015 | Wang |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1 | 12/2015 | Wong et al. |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0102151 A1 | 4/2016 | Wong et al. |
| 2016/0215061 A1 | 7/2016 | Shaeen |
| 2016/0274121 A1 | 9/2016 | Wong et al. |
| 2016/0280794 A1 | 9/2016 | Wong et al. |
| 2016/0289340 A1 | 10/2016 | Wong et al. |
| 2017/0275389 A1 | 9/2017 | Wong et al. |
| 2017/0283878 A1 | 10/2017 | Wong et al. |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |

(56) References Cited

FOREIGN PATENT DOCUMENTS

| | | |
|---|---|---|
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2012/082635 A1 | 6/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |
| WO | WO 2007/146847 A2 | 12/2007 |
| WO | WO 2008/020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/0133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/094540 A2 | 7/2012 |
| WO | WO 2013/011347 A1 | 1/2013 |
| WO | WO 2013/024895 A1 | 2/2013 |
| WO | WO 2013/088395 A1 | 6/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/031762 A1 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |

OTHER PUBLICATIONS

U.S. Appl. No. 15/173,496, filed Jun. 3, 2016, Chi-Huey Wong, et al.
U.S. Appl. No. 15/005,930, filed Jan. 25, 2016, Chi-Huey Wong, et al.
U.S. Appl. No. 15/011,544, filed Jan. 30, 2016, Chi-Huey Wong, et al.
Abrahmsén et al, "Analysis of signals for secretion in the staphylococcal protein A gene," *EMBO J.*, Dec. 30, 1985, 4(13B):3901-3906.
Altschul SF et al., "Basic local alignment search tool", *J Mol Biol.* Oct. 5, 1990;215(3):403-10.
Altschul Sf, et al., "Gapped BLAST and PSI-BLAST: a new generation of protein database search programs", *Nucleic Acids Res.* Sep. 1, 1997;25(17):3389-402.
Anderson et al., "Stimulation of Natural Killer T Cells by Glycolipids", *Molecules*, May 2013, 18(12), 15662-15688.
Arié et al., "Chaperone function of FkpA, a heat shock prolyl isomerase, in the periplasm of *Escherichia coli*," *Mol. Microbiol.*, Jan. 2001, 39(1):199-210.
Bachmann, *Cellular and Molecular Biology*, vol. 2, Chapter 72: *Derivations and Genotypes of Some Mutant Derivatives of Escherichia coli K-12*, Neidhardt et al., eds., 1987, pp. 1190-1219, American Society for Microbiology, Washington, D.C.
Baldwin et al., "Monoclonal antibodies in cancer treatment," *Lancet*, Mar. 15, 1986, 327(8481):603-605.
Barbas et al., "Assembly of combinatorial antibody libraries on phage surfaces: the gene III site," *Proc. Natl. Acad. Sci. U.S.A.*, Sep. 15, 1991, 88(18):7978-7982.
Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.
Barbas et al., "Semisynthetic combinatorial antibody libraries: a chemical solution to the diversity problem," *Proc. Natl. Acad. Sci. U.S.A.*, May 15, 1992, 89(10):4457-4461.
Barnes et al., "Methods for growth of cultured cells in serum-five medium," *Anal. Biochem.*, Mar. 1, 1980, 102(2):255-270.
Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.
Bass et al., "Hormone phage: an enrichment method for variant proteins with altered binding properties," *Proteins*, 1990, 8(4):309-314.
Beck A., "Biosimilar, biobetter and next generation therapeutic antibodies" *MAbs.* Mar.-Apr. 2011;3(2):107-10. Epub Mar. 1, 2011.
Berra et al., "Correlation between ganglioside distribution and histological grading of human astrocytomas," *Int. J. Cancer*, Sep. 15, 1985, 36(3):363-366.
Birklé et al., "Role of tumor-associated gangliosides in cancer progression," *Biochimie*, Mar.-Apr. 2003, 85(3-4):455-463.
Bobo et al., "Convection-enhanced delivery of macromolecules in the brain," *Proc. Natl. Acad. Sci. U.S.A.*, Mar. 15, 1994, 91(6) 2076-2080.
Boerner et al., "Production of antigen-specific human monoclonal antibodies from in vitro-primed human splenocytes," *J. Immunol.*, Jul. 1, 1991, 147(1):86-95.
Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.
Brennan et al., "Preparation of bispecific antibodies by chemical recombination of monoclonal immunoglobulin G1 fragments," *Science*, Jul. 5, 1985, 229(4708):81-83.

(56) References Cited

OTHER PUBLICATIONS

Brimble et al., "The cell surface glycosphingolipids SSEA-3 and SSEA-4 are not essential for human ESC pluripotency," *Stem Cells*, Jan. 2007, 25(1):54-62.
Brodeur et al., *Monoclonal Antibody Production Techniques and Applications, Chapter 4: Mouse-Human Myeloma Partners for the Production of Heterohybridomas*, Schook, ed., 1987, pp. 51-63, Marcel Dekker, Inc., New York.
Brüggemann et al., "Designer mice: the production of human antibody repertoires in transgenic animals," *Year in Immunol.*, 1993, 7:33-40.
Capel PJ et al., "Heterogeneity of human IgG Fc receptors" *Immunomethods*. Feb. 1994;4(1):25-34.
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol*. May 2006;6(5):343-357.
Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.
Chen et al., "Chaperone activity of DsbC," *J. Bio. Chem.*, Jul. 9. 1999, 274(28):19601-19605.
Chen et al., "Selection and analysis of an optimized anti-VEGF antibody: crystal structure of an affinity-matured Fab in complex with antigen," *J. Mol. Biol.*, Nov. 5, 1999, 293(4):865-881.
Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.
Chothia et al., "Canonical structures for the hypervariable regions of immunoglobulins," *J. Mol. Biol.*, Aug. 20, 1987, 196(4):901-917.
Clackson et al., "Making antibody fragments using phage display libraries," *Nature*, Aug. 15, 1991, 352(6336):624-628.
Clark Ea et al., "Structure, function, and genetics of human B cell-associated surface molecules" *Adv Cancer Res*. 1989;52:81-149.
Clynes R, et al., "Fc receptors are required in passive and active immunity to melanoma" *Proc Natl Acad Sci USA*. Jan. 20, 1998;95(2):652-6.
Cunningham et al., "High-resolution epitope mapping of hGH-receptor interactions by alanine-scanning mutagenesis," *Science*, Jun. 2, 1989, 244(4908):1081-1085.
Daëron, "Fc receptor biology," *Annu. Rev. Immunol.*, 1997, 15:203-234.
De Almeida et al., "Thiacycloalkynes for copper-free click chemistry," *Angew. Chem. Int. Ed. Engl.*, Mar. 5, 2012, 51(10):2443-2447.
De Haas et al., "Fcγ receptors of phagocytes," *J. Lab. Clin. Med.*, Oct. 1995, 126(4):330-341.
Durrant et al., "Immunology in the clinic review series; focus on cancer: glycolipids as targets for tumour immunotherapy," *Clin. Exp. Immunol.*, Feb. 2012, 167(2):206-215.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)]," *Angew. Chem. Int. Ed. Engl.*, Jun. 1989, 28(6):716-734.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fishwild et al., "High-avidity human IgGκ monoclonal antibodies from a novel strain of minilocus transgenic mice," *Nature Biotechnol.*, Jul. 1996, 14(7):845-851.

Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujita M et al., "A novel disaccharide substrate having 1,2-oxazoline moiety for detection of transglycosylating activity of endoglycosidases" *Biochim Biophys Acta*. Sep. 3, 2001;1528(1):9-14.
Galfrè et al., "Preparation of monoclonal antibodies: strategies and procedures," *Methods Enzymol.*, 1981, 73(Pt B):3-46.
Gazzano-Santoro et al., "A non-radioactive complement-dependent cytotoxicity assay for anti-CD20 nonclonal antibody," *J. Immunol. Methods*, Mar. 28, 1997, 202(2):163-171.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
Gerson et al., "ESR. Spectra and Structures of Radical Anions in the Dibenzo[a, e]cyclooxtene Series," *Helvetica Chinica Acta*, Jan. 1, 1976, 59(6): 2038-2048.
Gill et al., "Direct brain infusion of glial cell line-derived neurotrophic factor in Parkinson disease," *Nature Med.*, May 2003, 9(5):589-595 and Addendum from Apr. 2006, 12(4):479.
Goding, *Monoclonal Antibodies: Principles and Practice 2$^{nd}$ ed., Chapter 3: Production of Monoclonal Antibodies*, 1986, pp. 59-103, Academic Press, London.
Golkowski et al., "Strategy for catch and release of azide-tagged biomolecules utilizing a photolabile strained alkyne construct," *Organic and Biomolecular Chemistry*, Jan. 1, 2012, 10(23):4496.
Goochee CF et al., "The oligosaccharides of glycoproteins: bioprocess factors affecting oligosaccharide structure and their effect on glycoprotein properties", Biotechnology (N Y). Dec. 1991;9(12):1347-55.
Gordon et al., "Reactivity of biarylazacyclooctynones in copper-free click chemistry," *J. Am. Chem. Soc.*, Jun. 6, 2012, 134(22): 9199-9208.
Gottschling et al., "Stage-specific embryonic antigen-4 is expressed in basaloid lung cancer and associated with poor prognosis," *Eur. Respir. J.*, Mar. 2013, 41(3):656-663.
Graham et al., "Characteristics of a human cell line transformed by DNA from human adenovirus type 5," *J. Gen. Virol.*, Jul. 1977, 36(1):59-72.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Green, "Targeting targeted therapy," *N. Engl. J. Med.*, May 20, 2004, 350(21):2191-2193.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.
Guss et al., "Structure of the IgG-binding regions of streptococcal protein G," *EMBO J.*, Jul. 1986, 5(7):1567-1575.
Guyer et al., "Immunoglobulin binding by mouse intestinal epithelial cell receptors," *J. Immunol.*, Aug. 1976, 117(2):587-593.

(56) References Cited

OTHER PUBLICATIONS

Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.
Hawkins et al., "Selection of phage antibodies by binding affinity. Mimicking affinity maturation," *J. Mol. Biol.*, 1992, 226(3):889-896.
Heyman, "Complement and Fc-receptors in regulation of the antibody response," *Immunol. Lett.*, Dec. 1996, 54(2-3):195-199.
Hinman et al., "Preparation and characterization of monoclonal antibody conjugates of the calicheamicins: a novel and potent family of antitumor antibiotics," *Cancer Res.*, Jul. 15, 1993, 53(14):3336-3342.
Hogrefe et al., "A bacteriophage lambda vector for the cloning and expression of immunoglobulin Fab fragments on the surface of filamentous phage," *Gene*, Jun. 15, 1993, 128(1):119-126.
Holliger et al., "'Diabodies': small bivalent and bispecific antibody fragments," *Proc. Natl. Acad. Sci. U.S.A.*, Jul. 15, 1993, 90(14):6444-6448.
Honegger et al., "Yet another numbering scheme for immunoglobulin variable domains: an automatic modeling and analysis tool," *J. Mol. Biol.*, Jun. 8, 2001, 309:657-670.
Hoogenboom et al., "By-passing immunisation: Human antibodies from synthetic repertoires of germline $V_H$ gene segments rearranged in vitro," *J. Mol. Biol.*, Sep. 20, 1992, 227(2):381-388.
Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.
Huang et al., "Carbohydrate-based vaccines with a glycolipid adjuvant for breast cancer," *Proc. Natl. Acad. Sci. U.S.A.*, Feb. 12, 2013, 110(7):2517-2522.
Hung et al., "Investigation of SSEA-4 binding protein in breast cancer cells," *J. Am. Chem. Soc.*, Apr. 24, 2013, 135(16):5934-5937.
Hurle et al., "Protein engineering techniques for antibody humanization," *Curr. Opin. Biotechnol.*, Aug. 1994, 5(4):428-433.
Inouye et al., "Single-step purification of $F(ab')_{2\mu}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.
Jackson et al., "In vitro antibody maturation: Improvement of a high affinity, neutralizing antibody against IL-1β," *J. Immunol.*, Apr. 1, 1995, 154(7):3310-3319.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Jenkins N, Curling EM., "Glycosylation of recombinant proteins: problems and prospects", *Enzyme Microb Technol.* May 1994;16(5):354-64.
Jewett et al., "Synthesis of a fluorogenic cyclooctyne activate by Cu-free click chemistry," *Org. Lett.*, Nov. 18, 2011, 13(22):5937-5939.
Jones et al., "Rapid PCR-cloning of full-length mouse immunoglobulin variable regions," *Nature Biotechnol.*, Jan. 1991, 9(1):88-89.

Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells, "*EMBO J.*, 1983, 2(12):2355-2361.
Karlin S. et al., "Methods for assessing the statistical significance of molecular sequence features by using general scoring schemes", *Proc Natl Acad Sci U S A*. Mar. 1990;87(6):2264-8.
Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kim et al., "Localization of the site of the murine IgG1 molecule that is involved in binding to the murine intestinal Fc receptor," *Eur. J. Immunol.*, 1994, 24:2429-2434.
Köhler et al., "Continuous cultures of fused cells secreting antibody of predefined specificity," *Nature*, Aug. 7, 1975, 256(5517):495-497.
Kontermann, "Intrabodies as therapeutic agents," *Methods*, Oct. 2004, 34(2):163-170.
Kostelny et al., "Formation of a bispecific antibody by the use of leucine zippers," *J. Immunol.*, Mar. 1, 1992, 148(5):1547-1553.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell*. Apr. 8, 1988;53(1):45-53.
Kudo et al., "Up-regulation of a set of glycosyltransferase genes in human colorectal cancer," *Lab. Invest.*, Jul. 1998, 78(7):797-811.
Lau et al., "N-Glycans in cancer progression," *Glycobiology*, Oct. 2008, 18(10):750-760.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lefranc et al., "IMGT, the international ImMunoGeneTics database," *Nucleic Acids Res.*, Jan. 1, 1999, 27(1):209-212.
Lehninger, *Biochemistry: The Molecular Basis of Cell Structure and Function*, $2^{nd}$ ed., 1975, pp. 73-75, Worth Publishers, New York.
Leung et al., "A method for random mutagenesis of a defined DNA segment using a modified polymerase chain reaction," *Technique—A Journal of Methods in Cell and Molecular Biology*, Aug. 1989, 1(1):11-15.
Lindmark et al., "Binding of immunoglobulins to protein A and immunoglobulin levels in mammalian sera," *J. Immunol. Meth.*, Aug. 12, 1983, 62(1):1-13.
Liu C, et al., "Expansion of spleen myeloid suppressor cells represses NK cell cytotoxicity in tumor-bearing host" *Blood*. May 15, 2007;109(10):4336-42. Epub Jan. 23, 2007.
Liu et al., "Eradication of large colon tumor xenografts by targeted delivery of maytansinoids," *Proc. Natl., Acad. Sci. U.S.A.*, Aug. 6, 1996, 93(16):8618-8623.
LoBuglio et al., "Mouse/human chimeric monoclonal antibody in man: kinetics and immune response," *Proc. Natl. Acad. Sci. U.S.A.*, Jun. 1989, 86(11):4220-4224.
Lode et al., "Targeted therapy with a novel enediyene antibiotic calicheamicin $\Theta^I_1$ effectively suppresses growth and dissemination

(56) References Cited

OTHER PUBLICATIONS of liver metastases in a syngeneic model of murine neuroblastoma," *Cancer Res.*, Jul. 15, 1998, 58(14):2925-2928.

Lonberg et al., "Antigen-specific human antibodies from mice comprising four distinct genetic modifications," *Nature*, Apr. 28, 1994, 368(6474):856-859.

Lonberg et al., "Human antibodies from transgenic mice," *Int. Rev. Immunol.*, 1995, 13(1):65-93.

Louis et al., "The 2007 WHO classification of tumours of the central nervous system," *Acta. Neuropathol.*, Aug. 2007, 114(2):97-109.

Lu et al., "Single chain anti-c-Met antibody conjugated nanoparticles for in vivo tumor-targeted imaging and drug delivery," *Biomaterials*, Apr. 2011, 32(12):3265-3274.

MacFarlane GT, et al., "Formation of glycoprotein degrading enzymes by Bacteroides fragilis" *FEMS Microbiol Lett.* Jan. 15, 1991;61(2-3):289-93.

Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.

Mandler et al., "Modifications in synthesis strategy improve the yield and efficacy of geldanamycin-herceptin immunoconjugates," *Bioconjugate Chem.*, Jul.-Aug. 2002, 13(4):786-791.

Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.

Månsson et al., "Characterization of new gangliosides of the lactotetraose series in murine xenografts of a human glioma cell line," *FEBS Lett.*, May 26, 1986, 201(1):109-113.

Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.

Marasco, "Intrabodies: turning the humoral immune system outside in for intracellular immunization," *Gene Therapy*, Jan. 1997, 4(1):11-15.

Marks et al., "By-passing immunization Human antibodies from V-gene libraries displayed on phage," *J. Mol. Biol.*, Dec. 5, 1991, 222(3):581-597.

Marks et al., "By-passing immunization. Building high affinity human antibodies by chain shuffling," *Nature Biotechnology*, Jul. 1992, 10(7):779-783.

Mather et al., "Culture of testicular cells in hormone-supplemented serum-five medium," *Annals N.Y. Acad. Sci.*, 1982, 383:44-68.

Mather, "Establishment and characterization of two distinct mouse testicular epithelial cell lines," *Biol. Reprod.*, Aug. 1980, 23(1):243-252.

Matsuda et al., "Structure and physical map of 64 variable segments in the 3' 0.8-megabase region of the human immunoglobulin heavy-chain locus," *Nature Genet.*, Jan. 1993, 3(1):88-94.

McCafferty et al., "Phage antibodies: Filamentous phage displaying antibody variable domains," *Nature*, Dec. 6, 1990, 348:552-554.

Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.

Meyer, "Malignant gliomas in adults," *N. Engl. J. Med.*, Oct. 23, 2008, 359(17):1850.

Mimura et al., "Role of oligosaccharide residues of IgG1-Fc in FcγRIIb binding," *J. Biol. Chem.*, Dec. 7, 2001, 276(49):45539-45547.

Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.

Morelle, W. et al., "The Mass Spectrometric Analysis of Glycoproteins and their Glycan Sturctures", *Review in Current Analytical Chemistry*, vol. 1, No. 1 (2005), pp. 29-57.

Mori K, et al., "Non-fucosylated therapeutic antibodies: the next generation of therapeutic antibodies" *Cytotechnology*. Dec. 2007;55(2-3):109-14. Epub Oct. 31, 2007.

Morimoto et al., "Single-step purification of F(ab')2 fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.

Morrison et al., "Chimeric human antibody molecules: mouse antigen-binding domains with human constant region domains," *Proc. Natl. Acad. Sci. U.S.A.*, Nov. 1984, 81(21):6851-6855.

Morrison, "Immunology. Success in specification," *Nature*, Apr. 28, 1994, 368(6474):812-813.

Munson et al., "Ligand: a versatile computerized approach for characterization of ligand-binding systems," *Anal. Biochem.*, Sep. 1, 1980, 107(1):220-239.

Neuberger et al., "Recombinant antibodies possessing novel effector functions," *Nature*, Dec. 13-19, 1984, 312(5995):604-608.

Neuberger, "Generating high-avidity human Mabs in mice," *Nature Biotechnol.*, Jul. 1996, 14(7):826.

Nicolaou et al., "Calicheamicin $\Theta^I_1$: A rationally designed molecule with extremely potent and selective DNA cleaving properties and apoptosis inducing activity,"*Angew. Chem. Intl. Ed. Engl.*, Feb. 1, 1994, 33(2):183-186.

Niculescu-Duvaz et al., "Antibody-directed enzyme prodrug therapy (ADEPT): A review," *Adv. Drg. Del. Rev.*, Jul. 7, 1997, 26(2-3):151-172.

Noto et al., "CD44 and SSEA-4 positive cells in an oral cancer cell line HSC-4 possess cancer stem-like cell characteristics," *Oral Oncol.*, Aug. 2013, 49(8):787-795.

Orlandi et al., "Cloning immunoglobulin variable domains for expression by the polymerase chain reaction," *Proc. Natl. Acad. Sci. U.S.A.*, May 1989, 86(10):3833-3837.

Ørum et al., "Efficient method for constructing comprehensive murine Fab antibody libraries displayed on phage." *Nucleic Acids Res.*, Sep. 25, 1993, 21(19):4491-4498.

Papanastassiou et al., "The potential for efficacy of the modified (ICP 34.5⁻) herpes simplex virus HSV1716 following intratumoural injection into human malignant glioma: a proof of principle study," *Gene Therapy*, Mar. 2002, 9(6):398-406.

Pearlman et al., *Peptide and Protein Drug Delivery, Chapter 6: Analysis of Protein Drugs*, Lee, ed., 1991, pp. 247-301, Marcel Dekker Publishing, New York.

Peipp et al., "Antibody fucosylation differentially impacts cytotoxicity mediated by NK and PMN effector cells," *Blood*, 2008, 112(6):2390-2399.

Plückthun, "Mono- and bivalent antibody fragments produced in *Escherichia coli*: Engineering, folding and antigen binding," *Immunol. Rev.*, Dec. 1992, 130:151-188.

Plückthun, *Handbook of Experimental Pharmacology, vol. 113: The Pharacology of Monoclonal Antibodies, Chapter 11: Antibodies from Escherichia coli*, Rosenberg et al., eds., 1994, pp. 269-315, Springer-Verlag, Berlin.

Poloukhtine et al., "Selective labeling of living cells by a photo-triggered click reaction, "*J. Am. Chem. Soc.*, Nov. 4, 2009, 131(43):15769-15776.

Presta et al., "Humanization of an antibody directed against IgE," *J. Immunol.*, Sep. 1, 1993, 151(5):2623-2632.

Presta et al., "Humanization of an anti-vascular endothelial growth factor monoclonal antibody for the therapy of solid tumors and other disorders," *Cancer Res.*, Oct. 15, 1997, 57(20):4593-4599.

Presta, "Antibody engineering," *Curr. Opin. Biotechnol.*, Aug. 1992, 3(4):394-398.

Presta, "Antibody engineering," *Curr. Opin. Struct. Biol.*, Aug. 1992, 2(4):593-596.

Proba et al., "Functional antibody single-chain fragments from the cytoplasm of *Escherichia coli*: influence of thioredoxin reductase (TrxB)," *Gene*, Jul. 4, 1995, 159(2):203-207.

Puigbò P, Guzmán E, Romeu A, Garcia-Vallvé S. Optimizer: a web server for optimizing the codon usage of DNA sequences. *Nucleic Acids Res.* Jul. 2007;35(Web Server issue):W126-31. Epub Apr. 16, 2007.

(56) References Cited

OTHER PUBLICATIONS

Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Roguska et al., "Humanization of murine monoclonal antibodies through variable domain resurfacing," *Proc. Natl. Acad. Sci. U.S.A.*, Feb. 1, 1994, 91(3):969-973.
Roos et al., "Specific inhibition of the classical complement pathway by C1q-binding peptides," *J. Immunol.*, Dec. 15, 2001, 167(12):7052-7059.
Rowland et al, "Drug localisation and growth inhibition studies of vindesine-monoclonal anti-CEA conjugates in a human tumour xenograft," *Cancer Immunol. Immunother.*, 1986, 21(3):183-187.
Ruiz et al., "IMGT, the international ImMunoGeneTics database," *Nucl. Acids Res.*, Jan. 1, 2000, 28(1):219-221.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Schenkel-Brunner, *Human Blood Groups, Chapter 8: P System*, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Sell, "Cancer-associated carbohydrates identified by monoclonal antibodies," *Hum. Pathol.*, Oct. 1990, 21(10):1003-1019.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 1980, 20(2):269-281.
Simmons et al., "Expression of full-length immunoglobulins in *Escherichia coli*: Rapid and efficient production of aglycosylated antibodies," *J. Immunol. Methods*, May 1, 2002, 263(1-2):133-147.
Sims et al., "A humanized CD18 antibody can block function without cell destruction," *J. Immunol.*, Aug. 15, 1993, 151(4):2296-2308.
Skerra, "Bacterial expression of immunoglobulin fragments," *Curr. Opinion in Immunol.*, Apr. 1993, 5(2):256-262.

Slamon DJ, et al., "Human breast cancer: correlation of relapse and survival with amplification of the HER-2/neu oncogene" *Science*. Jan. 9, 1987; 235(4785):177-82.
Sletten et al., "Bioorthogonal Chemistry: Fishing for Selectivity in a Sea of Functionality," *Angew. Che. Int. Ed. Engl.*, Aug. 27, 2009, 48(38):6974-6998.
Smith RA et al., "The active form of tumor necrosis factor is a trimer" *J Biol Chem.* May 25, 1987;262(15):6951-4.
Smyth MJ, et al., "CD4+CD25+ T regulatory cells suppress NK cell-mediated immunotherapy of cancer" *J Immunol.* Feb. 1, 2006;176(3):1582-7.
Suresh et al., "Bispecific monoclonal antibodies from hybrid hybridomas," *Methods in Enzymology*, 1986, 121:210-228.
Suzuki E, et al., "A nonfucosylated anti-HER2 antibody augments antibody-dependent cellular cytotoxicity in breast cancer patients" *Clin Cancer Res.* Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2): 109-117.
Syrigos et al., "Antibody directed enzyme prodrug therapy (ADEPT): a review of the experimental and clinical considerations," *Anticancer Research*, Jan.-Feb. 1999, 19(1A):605-614.
Takeda et al., "Construction of chimaeric processed immunoglobulin genes containing mouse variable and human constant region sequences," *Nature*, Apr. 4-10, 1985, 314(6010):452-454.
Taylor-Papadimitriou et al., "Exploiting altered glycosylation patterns in cancer: Progress and challenges in diagnosis and therapy," *Trends Biotechnol.*, Jun. 1994, 12(6):227-233.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Tsai TI, et al., "Effective sugar nucleotide regeneration for the large-scale enzymatic synthesis of Globo H and SSEA4" *J Am Chem Soc.* Oct. 2, 2013;135(39):14831-9, Epub Sep. 17, 2013.
Tutt et al., "Trispecific F(ab')3 derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology.* Jan. 1996;6(1):83-93.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Valentine Ma, et al., "Phosphorylation of the CD20 phosphoprotein in resting B lymphocytes. Regulation by protein kinase C" *J Biol Chem.* Jul. 5, 1989;264(19):11282-7.
Van Beek et al., "Increased sialic acid density in surface glycoprotein of transformed and malignant cells—a general phenomenon?" *Cancer Res.*, Nov. 1973, 33(11):2913-2922.
Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Vaswani et al., "Humanized antibodies as potential therapeutic drugs," *Ann. Allergy, Asthma Immunol.*, Aug. 1998, 81(2):105-116, 119.
Verhoeyen et al., "Reshaping human antibodies: grafting an antilysozyme activity," *Science*, Mar. 25, 1988, 239(4847):1534-1536.
Vermeer AW et al., "The thermal stability of immunoglobulin: unfolding and aggregation of a multi-domain protein" *Biophys J.* Jan. 2000;78(1):394-404.

(56) References Cited

OTHER PUBLICATIONS

Wang et al., "Glycan microarray of Globo H and related structures for quantitative analysis of breast cancer," Proc. Natl. Acad. Sci. U.S.A., Aug. 19, 2008, 105(33):11661-11666.
Ward et al., "Binding activities of a repertoire of single immunoglobulin variable domains secreted from Escherichia coli," Nature, Oct. 12, 1989, 341(6242):544-546.
Waterhouse et al., "Combinatorial infection and in vivo recombination: a strategy for making large phage antibody repertoires," Nuc. Acids Res., May 11, 1993, 21(9):2265-2266.
Wikstrand et al., "Monoclonal antibody therapy of human gliomas: Current status and future approaches," Cancer Metastasis Rev., 1999, 18(4):451-464.
Williams et al., "Cloning and sequencing of human immunoglobulin V lambda gene segments." Eur. J. Immunol., Jul. 1993, 23(7):1456-1461.
Winter et al., "Making antibodies by phage display technology," Annu. Rev. Immunol., 1994, 12:433-455.
Woof et al., "Human antibody-Fc receptor interactions illuminated by crystal structures," Nat. Rev. Immunol., Feb. 2004, 4(2):89-99.
Yansura et al., "Nucleotide sequence selection for increased expression of heterologous genes in Escherichia coli," Methods: A Companion to Methods in Enzymol., Aug. 1992, 4(2):151-158.
Ye et al., "Stage-specific embryonic antigen 4 expression in epithelial ovarian carcinoma," Int. J. Gynecol. Cancer, Aug. 2010, 20(6):958-964.
Yelton et al., "Affinity maturation of the BR96 anti-carcinoma antibody by codon-based mutagenesis." J. Immunol., Aug. 15, 1995, 155(4):1994-2004.
Yu et al., "Anti-GD2 antibody with GM-CSF, interleukin-2, and isotretinoin for neuroblastoma," N. Engl. J. Med., Sep. 30, 2010, 363(14):1324-1334.
Zapata et al., "Engineering linear F(ab')$_2$ fragments for efficient production in Escherichia coli and enhanced antiproliferative activity," Protein Eng., Oct. 1995, 8(10):1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," Glycobiology, Jan. 2010, 20(1):118-126.
International Search Report and Written Opinion issued for International application No. PCT/US2015/032738, dated Oct. 20, 2015, 15 pages.
International Search Report and Written Opinion issued for International application No. PCT/US2015/032744, dated Oct. 2, 2015, 12 pages.
International Search Report and Written Opinion issued for International application No. PCT/US2015/032740, dated Oct. 26, 2015, 13 pages.
International Search Report and Written Opinion issued for International application No. PCT/US2015/032737, dated Oct. 1, 2015, 13 pages.
International Search Report and Written Opinion issued for International application No. PCT/US2015/032745, dated Oct. 8, 2015, 13 pages.
International Search Report issued for International application No. PCT/US2015/049014, Dec. 14, 2015, 3 pages.
European Search Report issued in connection with corresponding European Patent Application No. 15181446.4, dated Dec. 7, 2015, 10 pages.
Extended European Search Report dated Jan. 5, 2016 in European Patent Application No. 13830785.5, in 10 pages.
Abbas et al., "Functional diversity of helper T lymphocytes," Nature, Oct. 31, 1996, 383(6603):787-793.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," Nat. Biotechnol., Aug. 2002, 20(8):805-809.

Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Amin, M. N. et al. Synthetic glycopeptides reveal the glycan specificity of HIV-neutralizing antibodies. Nat. Chem. Biol. 9, 521-526, (2013).
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," Chem. Rev., Feb. 2002, 102(2):439-469.
Anthony, Robert et al., Recapitulation of IVIG Anti-Inflammatory Activity with a Recombinant IgG Fc, Science Apr. 18, 2008. 320:373-376.
Arase et al., "NK1.1$^+$ CD4$^+$ CD8$^-$ thymocytes with specific lymphokine secretion," Eur. J. Immunol., Jan. 1993, 23(1):307-310.
Aspeslagh et al., "Galactose-modified iNKT cell agonists stabilized by an induced fit of CD1d prevent tumour metastasis," EMBO J., Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Banchereau et al., "Dendritic cells and the control of immunity," Nature, Mar. 19, 1998, 392(6673):245-252.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baskin, J.M.; Amacher, S. L.; Bertozzi, C.R."In vivo imaging of membraneassociated glycans in developing zebrafish." Science 2008, 320, 664-667.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beckman et al., Antibody constructs in cancer therapy: protein engineering strategies to improve exposure in solid tumors, cancer, 109(2): 170-179 (2007).

(56) References Cited

OTHER PUBLICATIONS

Bendayan, Moise, Possibilities of False Immunocytochemical Results Generated By the Use of Momoclonal Antibodies: The Example of the Anti-Proinsulin Antibody, J. Histochem. Cytochem, 43: 881-886, (1995).

Bennett, Clay et al., Chemoenzymatic Approaches to Glycoprotein Synthesis, Chem. Soc. Rev. 2007, 36:1227-1238.

Berg, Jan-Olof et al., Purification of Glycoside Hydrolases From Bacteroides Fragilis, Applied and Environmental Microbiology, vol. 40, No. 1, Jul. 1980, p. 40-47.

Berge, Steven et al. J. Pharmaceutical Sciences (1977) 66: 1-19.

Best, M. D. "Click chemistry and bioorthogonal reactions: unprecedented selectivity in the labeling of biological molecules." Biochemistry 2009, 48, 6571-6584.

Bertozzi, CR et al., Glycans in Cancer and Inflammation—Potential for Therapeutics and Diagnostics, Nat Rev Drug Discovery, 2005, 4, 477-488.

Bigi et al., "Human sialidase NEU4 long and short are extrinsic proteins bound to outer mitochondrial membrane and the endoplasmic reticulum, respectively," *Glycobiology*, Feb. 2010, 20(2):148-157.

Blixt, O. et al. Printed covalent glycan array for ligand profiling of diverse glycan binding proteins. Proc. Natl. Acad. Sci. U.S. A. 101, 17033-17038, (2004.

Boens, N. et al., "Fluorescent indicators based on BODIPY." Chem. Soc. Rev. 2012, 41, 1130-1172.

Borg et al., "CD1d-lipid-antigen recognition by the semi-invariant NKT T-cell receptor," Nature, Jul. 5, 2007, 448(7149):44-49.

Bosmann et al., "Enzyme activity in invasive tumors of human breast and colon," *Proc. Natl. Acad. Sci. USA*, May 1974, 71(5):1833-1837.

Bost, Kenneth et al., Antibodies Against a Peptide Sequence Within the HIV Envelope Protein Crossreacts With Human Interleukin-2, Immunol. Invest., 17: 577-586 (1988).

Boyer, David et al., Photothermal Imaging of Nanometer-Sized Metal Particles Among Scatterers, Science, 2002, 297, 1160-116 3.

Braun-Howland et al., Development of a Rapid Method for Detecting Bacterial Cell In Situ Using 16S rRNA-Targeted Probes, Biotechniques, 13, 928-931 (1992).

Bricard et al., "Enrichment of human CD4+ Vα24/Vβ11 invariant NKT cells in intrahepatic malignant tumors," *J. Immunol.*, Apr. 15, 2009, 182(2):5140-5151.

Bruchez, Marcel et al. Semiconductor Nanocrystals as Fluorescent Biological Labels, Science 281:2013-2016, 1998.

Buchini et al., "Towards a new generation of specific *Trypanosoma cruzi* trans-sialidase inhibitors," *Angew. Chem. Int. Ed. Engl.*, 2008, 47(14):2700-2703.

Burton, D.R., Mascola, J. R. Antibody responses to envelope glycoproteins in HIV-I infection. Nature Immunol. 16, 571-6, (2015).

Calarese, D. A. et al. Antibody domain exchange is an immunological solution to carbohydrate cluster recognition. Science 300, 2065-2071, (2003).

Cao, Y. C. et al., Nanoparticles with Raman Spectroscopic Fingerprints for DNA and RNA Detection, Science, 2002, 289, 1757-60.

Carlsson, Jan et al., Protein Thiolation and Reversible Protein-Protein Conjugation, Biochem J 173: 723-737 (1978).

Carter, A rationale for using steroids in the treatment of severe cases of H5N1 avian influenza. J Med Microbiol. Jul. 2007;56(Pt 7):875-83.

Centers for Disease Control and Prevention (CDC), "Influenza activity — United States and worldwide, 2007-08 season" *MMWR*, Jun. 27, 2008, 57(25):692-697.

Cespedes et al., Mouse models in oncogenesis and cancer therapy, Clin Transl Oncl., 8(5): 318-329 (2006).

Chan, Warren et al., Quantum Dot Bioconjugates for Ultrasensitive Nonisotopic Detection, Science 281:2016-2018 (1998).

Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-giuco-nononic acid. J Chem Soc Perkin Trans 1. 1995; 1173-1180.

Chang, S. H. et al. Glycan array on aluminum oxide-coated glass slides through phosphonate chemistry. J. Am. Chem. Soc. 132, 13371-13380, (2010).

Chang et al., "Potent immune-modulating and anticancer effects of NKT cell stimulatory glycolipids," *Proc. Natl. Acad. Sci. USA*, Jun. 19, 2007, 104(25):10299-10304.

Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.

Chari, Ravi et al., Immunoconjuates Containing Novel Maytansinoids: Promising Anticancer Drugs Cancer Research 52: 127-131 (1992).

Chauhan, D. P.; Saha, T.; Lahiri, M.; Talukdar, P. "BODIPY based 'click on' fluorogenic dyes: application in live cell imaging." Tetrahedron Lett. 2014, 55, 244-247.

Cheng, Peter et al., Oseltamivir-and Amandtadine-resistant Influenza Viruses A (H1N1), Emerg. Infect. Dis., Jun. 2009, 15(6): 966-968.

Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.

Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.

Chiari, M. et al., Advanced Polymers for Molecular Recognition and Sensing at the Interface. J Chromatography B, Apr. 15, 2008, 866(1-2):89-103.

Childs et al., Receptor-Binding Specificity of Pandemic Influenza A (H1N1) 2009 Virus Determined by Carbohydrate Microarray. Nat. Biotechnol. 2009, 27(9): 797-799.

Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.

Chong et al., Influenza Virus Sialidase: Effect of Calcium on Steady-State Kinetic Parameters, Biochim. Biophys. Acta, Mar. 8, 1991, 1077(1): 65-71.

Chothia et al., "Domain association in immunoglobulin molecules. The packing of variable domains," *J. Mol. Biol.*, Dec. 5, 1985, 186(3):651-663.

Chu, Kuo-CHINGet al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.

Codelli, J. A. et al., Second-Generation Difluorinated Cyloctynes for Copper-Free Click Chemistry, J. Am. Chem. Soc. 2008, 130, 11486-11493.

Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.

Coligan et al., Current Protocols in Immunology, sections 2.5.1-2.6.7, 1991.

Collins et al., Crystal Structures of Oseltamivir-Resistant Influenza Virus Neuraminidase Mutants, Nature, Jun. 26, 2008, 453(7199):1258-1261.

Connor, Robert et al., Receptor Specifcity in Human, Avian, and Equine H2 and H3 Influenza Virus Isolates, Virology, 205: 17, 1994.

Cox et al., New Options for the Prevention of Influenza, N. Engl. J. Med. Oct. 28, 1999, 341(18): 1387-1388.

Cragg, M.S. et al., Complement-Mediated Lysis by Anti-CD20 mAb Correlates with Segregation into Lipid Rafts, Blood 101 (2003) 1045-1052.

Cragg, M.S. et al., Antibody Specificity Controls in Vivo Effector Mechanism of Anti-CD20 Reagents, Blood, 103 (2004) 2738-2743.

Craigo, J. K., Montelaro, R. C. Lessons in AIDS vaccine development learned from studies of equine infectious, anemia virus infection and immunity. Viruses 5, 2963-76, (2013.

(56) References Cited

OTHER PUBLICATIONS

Crispin et al., "Carbohydrate and domain architecture of an immature antibody glycoform exhibiting enhanced effector functions," J. Mol. Biol., Apr. 17, 2009, 387(5):1061-1066.
Cyranoski, Threat of Pandemic Brings Flu Drug Back to Life, Nat. Med. Sep. 2005, 11(9): 909.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine $\alpha\beta$ T cells expressing invariant TCR alpha-chains," J. Immunol., Jun. 15, 1997, 158(12):5603-5611.
Debets, M. F. et al., Bioconjugation with Strained Alkenes and Alkynes, Acc. Chem. Res. 2011, 44, 805-815.
Dejong et al., Fatal outcome of human influenza A (H5N1) is associated with high viral load and hypercytokinemia. Nat Med Oct. 2006;12(10):1203-7. Epub Sep. 10, 2006.
Delente, Jacqubs, Glycosylation Revisited, Trends in Biotechnology 3, letters to editor, No. 9 (1985).
Dellabona et al., "An invariant V$\alpha$24-J$\alpha$Q/V$\beta$11 T cell receptor is expressed in all individuals by clonally expanded CD4$^-$8$^-$ T cells," J. Exp. Med., Sep. 1, 1994, 180(3):1171-1176.
Demchenko, A.V., Ed., Hanbook of Chemical Glycosylation: Advances in Stereoselectivity and Therapeutic Relevance (2008) Wiley-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "$\alpha$-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," J. Exp. Med., Jun. 16, 2003, 197(12):1667-1676.
Dicker, Martina et al., Using Glyco-Engineering to Produce Therapeutic Proteins, Expert Opinion on Biological Therapy, vol. 15, Jan. 1, 2015, pp. 1501-1516.
Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U. S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).
Dougan, Michael et al Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.

Eberl et al., "Selective bystander proliferation of memory CD4$^+$ and CD8$^+$ T cells upon NK T or T cell activation," J. Immunol., Oct. 15, 2000, 165(8):4305-4311.
Eberl et al., "Selective induction of NK cell proliferation and cytotoxicity by activated NKT cells," Eur. J. Immunol., Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Evans, Michael et al., "Mechanism-based profiling of enzyme families," Chem. Rev., Aug. 2006, 106(8):3279-3301.
Evans, "The rise of azide-alkyne 1,3-dipolar 'click' cycloaddition and its application to polymer science and surface modification," Australian J. Chem., Jun. 2007, 60(6):384-395.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Falkowska, E. et al. Broadly neutralizing HIV antibodies define a glycan-dependent epitope on the prefusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-$\beta$-N-acetylglucosaminidase from Streptococcus pneumoniae, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Fedson, Confronting the next influenza pandemic with anti-inflammatory and immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fraker, Pj et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Frank, Natasha et al., the Therapeutic Promise of the Cancer Stem Cell Concept, Journal of Clinical Investigation, 120(1) 41-50, Jan. 2010.
Friscourt, F. et al., A Fluorogenic Probe for the Catalyst-Free Detection of Azide-Tagged Molecules, J. Am. Chem. Soc. 2012, 134, 18809-18815.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).

(56) References Cited

OTHER PUBLICATIONS

Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fukui, S et al., Oligosaccharide microarrays for high-throughput detection and specificity assignments of carbohydrate- protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Giaccone, Giuseppe et al., "A phase I study of the natural killer T-cell ligand α-galactosylceramide (KRN7000) in patients with solid tumors," Clin. Cancer Res., Dec. 2002, 8(12):3702-3709.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun 2005, 73, 4803.
Goldenthal et al., "Safety Evaluation of Vaccine Adjuvants: National Cooperative Vaccine Development Working Group," AIDS Res. Hum. Retroviruses, 1993, 9(Supp.1):S47-S51.
Govorkova et al, Combination chemotherapy for influenza. Viruses. Aug. 2010;2(8):1510-29.
Graham, Duncan et al., Surface-Enhanced Resonance Raman Scattering as a Novel Method of DNA Discrimination, Angew. Chem., 2000, 112(6), 1103-1105.
Grandjean, C. et al., On the Preparation of Carbohydrate-Protein Conjugates Using the Traceless Staudinger Ligation, J Org Chem 2005, 70, 7123-7132.
Greenbaum et al., "Chemical approaches for functionally probing the proteome," Mol. Cell. Proteomics, 2002, 1:60-68.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, Ya et al., X-Ray Structure of the Hemagglutinin of a Potential H3 Avian Progenitor of the 1968 Hong Kong Pandemic Influenza Virus, Virology, 309:209-218, 2003.

Hajishengallis, "Mucosal immunization with a bacterial protein antigen genetically coupled to cholera toxin A2/B subunits," J. Immuol., May 1, 1995, 154(9):4322-4332.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hasegawa, Akira, et al., Synthesis of Sialyl Lewis X Ganglioside Analogues Containing Modified L-Fucose Residues, Carbohydr. Res. 1995, 274, 165-181.
Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Hirabayashi, J. et al., Oligosaccharide Microarrays for Glycomics, Trends in Biotechnology 21 (4): 141-143, 2003.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," Immunol. Today, Jun. 1992, 13(6):198-200.
Hsu et al., "Alkynyl sugar analogs for the labeling and visualization of glycoconjugates in cells," Proc. Natl. Acad. Sci. USA, Feb. 20, 2007, 104(8), 2614-2619.
Hsu, Nien-Yeen et al., Desorption Ionization of Biomolecules on Metals, Anal. Chem., 80, 5203-5210, 2008.
Huang, Wei et al., Chemoenzymatic Glycoengineering of Intact IgG Antibodies for Gain of Functions, Journal American Chemical Socirty, vol. 134, No. 9, Jul. 25, 2012, pp. 12308-12318.
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.
Immunogenicity, Wikipedia p. 1-3. Downloaded on Aug. 16, 2016 from https://en.wikipedia.org/wiki/Immunogenicity. (2016).
International Search Report and Written Opinion issued for International application No. PCT/US2015/011748, dated Aug. 21, 2015, 17 pages.

(56) References Cited

OTHER PUBLICATIONS

International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
International Search Report and Written Opinion in International Application No. PCT/US2017/048074, dated Dec. 26, 2017, 17 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihiro et al., a Novel Ganglioside Isolated From Renal Cell Carcinoma, Biol Chem 2001, 276, 16695.
Jacobs et al., "Metabolic labeling of glycoproteins with chemical tags through unnatural sialic acid biosynthesis," *Methods Enzymol.*, 2000, 327:260-275.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun , 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).
Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," *Chem. Commun.*, Jan. 28, 2010, 46(4):589-591.
Kamkaew, A. et al., "BODIPY dyes in photodynamic therapy." Chem. Soc. Rev. 2013, 42, 77-88.
Katagiri, Yohko et al., Laminin Binding Protein, 34/67 Laminin Receptor, Carries Stage-Specific Embryonic Antigen-4 Epitope Defined by Monoclonal Antibody Raft.2, Biochemical and Biophysical Research Communcations, 332, 1004-1011, 2005.
Kawakami et al., "Critical role of $V\alpha14^+$ natural killer T cells in the innate phase of host protection against Streptococcus pneumoniae infection," *Eur. J. Immunol.*, Dec. 2003, 33(12):3322-3330.
Kawano et al., "CD1d-restricted and TCR-mediated activation of $v_\alpha14$ NKT cells by glycosylceramides," *Science*, Nov. 28, 1997, 278(5343):1626-1629.
Kanie, Osmau et al., Orthogonal glycosylation strategy in synthesis of extended blood group B determinant. Tetrahedron Lett. 37, 4551-4554 (1996).
Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.
Karmakar, M. et al., Current Trends in Research and Application of Microbial Cellulases, Research Journal of Microbiology, (2001) 6(1): 41-53.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.
Kiick, K.L. et al., Identification of an Expanded Set of Translationally Active Methionine Analogues in *Escherichia coli*, tetrahedron 56:9487, 2001.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra Of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "α-galactosylceramide induces early B-cell activation through IL-4 production by NKT cells," *Cell. Immunol.*, Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Kolb et al., "Click chemistry: diverse chemical function from a few good reactions," *Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24):1128-1137.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GalN Intermediates, Carbohydr. Res. 2009, 344, 1453.

(56) References Cited

OTHER PUBLICATIONS

Kong, L. et al. Expression-system-dependent modulation of HIV-I envelope glycoprotein antigenicity and immunogenicity. J. Mol. Biol. 403, 131-147, (2010).
Kos, "Regulation of adaptive immunity by natural killer cells," *Immunol. Res.*, 1998, 17(3):303-312.
Koshihara et al., 1984, Biochmica et biophysica acta, 792(1), pp. 92-97.
Kotteas et al., Immunotherapy for pancreatic cancer, J cancer Res Clin Oncol, 142(8): 1795-1805, 2016.
Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor $\alpha$ chain is used by a unique subset of major histocompatibility complex class I-specific $CD4^+$ and $CD4^-8^-$ T cells in mice and humans," *J. Exp. Med.*, Sep. 1, 1994, 180(3):1097-1106.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected α,ω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004).
Lee et al Immunogenicity Study of Globo H Analogues with Modification at the Reducing or Nonreducing end of the tumor antigen, J Am Chem Soc, 136: 16844-16853 (2014).
Lei, Jianqing et al., Potential antitumor applications of a monoclonal antibody specifically targeting human papilloma virus 16 E749-57 peptide, Microbiology and Immunology, 2012, vol. 56, pp. 456-462.
Lemieux, R. U. et al., Halide ion catalyzed glycosidation reactions. Syntheses of a-linked disaccharides. J Am. Chem. Soc. 97(14), 4056-62, (1975).
Lew et al., Discovery and Development of GS 4104 (oseltamivir): an Orally Active Influenza Neuraminidase Inhibitor, Curr Med Chem, Jun. 2000, 7(6):663-672.
Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.

Li et al., β-endorphin omission analogs: Dissociation of Immunoreactivity from other biological activities, Proc Natl Avad Sci USA, 77:3211-3214 (1980).
Li, Y. L. et al., Crystallization and Melting Behaviors of PPC-BS/PVA Blends, 19, 1557-1566, 2003.
Li, Henghui et al., MALDI-MS Analysis of Sialylated N-Glycan Linkage Isomers Using Solid-Phase Two Step Derivatization Method, Analytica Chimica Acta 924 (2016) 77-85.
Li et al., "Design of a potent CD1d-binding NKT cell ligand as a vaccine adjuvant," *Proc. Natl. Acad. Sci. USA*, Jul. 20, 2010, 107:13010-13015.
Li, J.; Hu, M.; Yao, S. Q. "Rapid synthesis, screening, and identification of xanthone and xanthene-based fluorophores using click chemistry." Org. Lett. 2009, 11, 3008-3011.
Li, Lingling, et al., "Syntheses and spectral properties of functionalized, water-soluble BODIPY derivatives." J. Org. Chem. 2008, 73, 1963-1970.
Li, L. et al. Efficient chemoenzymatic synthesis of an N-glycan isomer library. Chem. Sci. 6, 5652-5661 (2015).
Liang et al., "Quantitative microarray analysis of intact glycolipid-CD1d interaction and correlation with cell-based cytokine production," *J. Am. Chem. Soc.*, Sep. 17, 2008, 130(37):12348-12354.
Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Liang, P.H. et al., Quantitative Analysis of Carbohydrate-Protein Interactions Using Glycan Microarrays: Determination of Surface and Solution Dissociation Constants, J. Amer. Chem. Sci. 2007, 129, 11177-11184.
Liao, Shih-Fen et al Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin et al., A common glycan structure on immunoglobulin G for enhancement of effector functions, PNAS, Aug. 25, 2015, vol. 112, No. 34, p. 10611-10616.
Liu et al., "Activity-based protein profiling: the serine hydrolases," *Proc. Natl. Acad. Sci. USA*, Dec. 21, 1999, 96(26):14694-14699.
Liu et al., Enhanced anti-influenza agents conjugated with anti-inflammatory activity. J Med Chem. Oct. 11, 2012;55(19):8493-501.
Liu et al., Intramolecular ion-pair prodrugs of znamivir nad guanidino-oseltamivir. Bioorganic & Medicinal Chemistry. Jun. 2011; 19(16):4796-4802.
Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.
Lopes, J.F. et al., Simulataneous Chromatographic Separation of Enantiomers, Anomers and Structural Isomers of Some Biologically Relevant Monsaccharides. J. Chomatogr. A, (2008) 1188:34-42.
Lou, et al., Stage-specific embryonic antigent-4 as a potential therapeutic target in glioblastoma multiforms and other cancers. Proc Natl Acad Sci USA 2014, 111(7):2482-7.
Loudet, A.; Burgess, K. "BODIPY dyes and their derivatives: syntheses and spectroscopic properties." Chem. Rev. 2007, 107, 4891-4932.
Lu et al., "Design of a mechanism-based probe for neuraminidase to capture influenza viruses," *Angew. Chem. Int. Ed. Engl.*, Oct. 28, 2005, 44(42):6888-6892.
Lu, Guokai et al., Reactivity-Based One-Pot Synthesis of Immunosuppressive Glycolipids From the Caribbean Sponge Plakortis Simplex, J. Chem. 2009, 27, 2217-2222.
MacBeath, G. and Schreiber, S. L., Printing Proteins as Microarrays for High-Throughput Function Determination, Science, 289, 1760-1763, 2000.
Makino et al., Predominant expression of invariant Vα14+ TCR α chain in NK1.1+ T cell populations, *Int. Immunol.*, Jul. 1995, 7(7):1157-1161.
Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).

(56) References Cited

OTHER PUBLICATIONS

Marcato et al., "Chapter 17: The Rocky Road from Cancer Stem Cell Discovery to Diagnostic Applicability," Cancer Stem Cells Theories and Practice, pp. 335-360, Mar. 22, 2011.
Massart, R., IEEE Transactions on Magnetics, 17, 1247 (1981).
Masuko, T. et al., Thiolation of Chitosan. Attachment of Proteins Via Thioether Formation, Biomacromolecules 2005, 6, 880-884.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matz et al., "Fluorescent proteins from nonbioluminescent Anthozoa species," *Nat. Biotechnol.*, Oct. 1999, 17(10):969-973.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1- 17.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.
Medelson et al., NKp46 O-glycan Sequences that are involved in the interaction with Hemagglutinin Type 1 of Influenza Virus. J. Virol. Feb. 10, 2010, 84(8):3789-3797.
Merck, MAB4304, Anti-Stage-Specific Embryonic Antigen-4 Antibody, Clone MC-813-70, 4 Pages, 2017.
McLellan, J. S. et al. Structure of HIV-I gpl20 V1/V2 domain with broadly neutralizing antibody PG9. Nature 480, 336-343, 2011.
Milstein, C & Cuello, AC, Hybrid Hydridomas and their use in immunohistochemistry, Nature 305, 537-540, Oct. 1993.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochem.*, Sep. 2008, 144(3):279-285.
Miyagi et al., "Sialidase and malignancy: a minireview," *Glycoconj. J.*, 2004, 20(3):189-198.
Miyagi, "Aberrant expression of sialidase and cancer progression," *Proc. Jpn. Acad. Ser. B. Phys. Biol. Sci.*, 2008(10), 84:407-418.
Miyaji, E. N. et al., Induction of Neutralizing Antibodies Against Diphtheria Toxin by Priming with Recombinant *Mycobacterium bovis* BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," *Nature*, Oct. 4, 2001, 413(6855):531-534.
Moal, E. LE et al., Enhanced Fluorescence Cell Imaging with Metal-Coated Slides, Biophysical Journal, vol. 92, 2150-2161, Mar. 2007.
Monti et al., "Sialidases in vertebrates: a family of enzymes tailored for several cell functions," *Adv. Carbohydr. Chem. Biochem.*, 2010, 64:403-479.
Moody, M. D. et al., Array-based ELISAs for High-Throughput Analysis of Human Cytokines. Biotechniques (2001), 31, 186-194.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," *Immunol. Today*, Mar. 1996, 17(3):138-146.

Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Ni, Jing et al., Immunoassay Readout Method Using Extrinsic Raman Labels Adsorbed on Immunogold Colloids, Anal. Chem., 1999, 71(21), pp. 4903-4908.
Nieuwenhuis et al., "CD1d-dependent macrophage-mediated clearance of *Pseudomonas aeruginosa* from lung," *Nat. Med.*, Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$-$V_H$ and $V_L$-$V_L$ domain dimers," *Proc. Natl. Acad. Sci. USA*, Jul. 1985, 82(14):4592-4596.
Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
O'Garra, "Cytokines induce the development of functionally heterogeneous T helper cell subsets," *Immunity*, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.
Okamura et al., "Interleukin-18: a novel cytokine that augments both innate and acquired immunity," *Adv. Immunol.*, 1998, 70:281-312.
Olden, Kenneth et al., Carbohydrate Moieties of Glycoproteins: A Re-Evaluation of Their Function, Biochem et Biophys Acta 650:209-232 (1982).
Otsubo N, et al., An Efficient and Straightforward Synthesis of Sialyl Lex Glycolipid as a Potent Selectin Blocker[[1]], Carbohydr. Res. 1998, 306, 517-530.
Ottolini et al., Combination anti- inflammatory and antiviral therapy of influenza in a cotton rat model. Pediatr. Pulmonol. 2003:36;290-4.
Oyelaran, 0. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gpl40. Biol. Chem. 393, 719-730, (2012).
Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pan, Yanbin et al., Synthesis and Immunological Properties of N-Modified GM3 Antigens as Therapeutic Cancer Vaccines, J. Med. Chem., 48(3), 875-883, 2005.

(56) References Cited

OTHER PUBLICATIONS

Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).
Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," *Biochemistry*, Jan. 16, 2007, 46(2):350-358.
Paulson, J. C., Blixt, 0. & Collins, B. E. Sweet spots in functional glycomics. Nat. Chem. Biol. 2, 238-248, (2006).
Peelle et al., "Characterization and use of green fluorescent proteins from *Renilla mulleri* and *Ptilosarcus guernyi* for the human cell display of functional peptides," *J. Protein Chem.*, Aug. 2001, 20(6):507-519.
Peiris et al., Re-emergence of fatal human influenza A subtype H5N1disease. Lancet. Feb. 21, 2004 ;363(9409):617-9.
Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," *Immunity*, Jul. 17, 2009, 31(1):47-59.
Perlmutter, R.M. et al., Subclass Restriction of Murine Anti-Carbohydrate Antibodies, Journal of Immunology 1978, 121, 566-572.
Pettit, George et al., Antineoplastic Agents. Part 189. The Absolute Configuration and Synthesis of Natural (−)-Dolastatin 10, J Am Chem Soc. 111:5463-5465 (1989).
Pettit, George et al., Dolastatins 23: Stereospecific Synthesis of Dolaisoleuine, J Chem Soc Perkin Trans. 15:853-858 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965 (1998).
Pettit, George et al., The Dolastatins; 18: Stereospecific Synthesis of Dolaproine, Synthesis, 719-725 (1996).
Piizi, G. and Hardinger, S., Stereochemistry: an Introduction, UCLA Chemistry 30A Presentation, Fall 2002, in 40 pages.
Porcelli, S.A., "Preparation of α-galactosylceramide derivatives as modulators of immunity and autoimmunity," CAPLUS 147:440317 (2007).
Potier et al., "Fluorometric assay of neuraminidase with a sodium (4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Pritchard, L. K. et al. Structural Constraints Determine the Glycosylation of HIV-I Envelope Trimers. Cell Rep. 11, 1604-13, (2015).
Pritchard, Laura et al., Cell- and Protein- Directed Glycosylation of Native Cleaved HIV-I Envelope. J. Virol. 89, 8932-44, (2015).
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Qi, Jianjun et al., Developing visible fluorogenic 'clickon' dyes for cellular imaging, Bioconjugate Chem. 2011, 22, 1758-1762.

Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"- and 4"-deoxy and -fluoro analogs of the immunostimulatory glycolipid, KRN7000," *Bioorg. Med. Chem. Lett.*, 2009, 19:4122-4125.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gpl20 depend on the type of expressing cells and affect antibody recognition. J. Biol. Chem. 285, 20860-20869, (2010).
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human lgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Romagnani, "Induction of $T_H1$ and $T_H2$ responses: a key role for the 'natural' immune response?" *Immunol. Today*, Oct. 1992, 13(10):379-381.
Rosenstein, N.E. et al, Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rudnick et al., Affinity and Avidity in Antibody-Based Tumor Targeting, Can Biotherp & Radoipharm, 24, 155-162 (2009).
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, 23 May 2012, pp. 1022-1024.
Salisbury et al., "Activity-based probes for proteomic profiling of histone deacetylase complexes," Proc. Natl. Acad. Sci. USA, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4G1cNAcβ-O-naphthalenemethanol," *Proc. Natl. Acad. Sci. USA*, Apr. 11, 1995, 92(8):3323-3327.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.

(56) References Cited

OTHER PUBLICATIONS

Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," J. Biol. Chem., May 10, 1972, 247(9):2742-2746.
Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143- 17155, (2010).
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," Microbiology, Sep. 2007, 153(Pt 9):2817-2822.
Seyrantepe et al., "Neu4, a novel human lysosomal lumen sialidase, confers normal phenotype to sialidosis and galactosialidosis cells," J. Biol. Chem., Aug. 27, 2004, 279(35):37021-37029.
Sheu et al., "Surveillance for neuraminidase inhibitor resistance among human influenza A and B viruses circulating worldwide from 2004 to 2008," Antimicrob. Agents Chemother., Sep. 2008, 52(9):3284-3292.
Shevinsky, LH et al., Monoclonal Antibody to Murine Embryos Defines a Stage-Specific Embryonic Antigen Expressed on Mouse Embryos and Human Teratocarinoma Cells., CELL vol. 30, Issue 3, Oct. 1982, pp. 697-705.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-BODIPY Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sieber et al., "Proteomic profiling of metalloprotease activities with cocktails of active-site probes," Nat. Chem. Biol., May 2006, 2(5):274-281.

Sivakumar, Krishnamoorthy et al., "A fluorogenic 1,3-dipolar cycloaddition reaction of 3-azidocoumarins and acetylenes." Org. Lett. 2004,24, 4603-4606.
Skehel, John et al., Receptor Binding and Membrane Fusion in Virus Entry: The Influenza Hemagglutinin, Ann. Rev Biochem, 69:531, 2000.
Sok, Devin et al., SnapShot: Broadly Neutralizing Antibodies. Cell 155, 728-728, (2013).
Solomons, G. and Fryhle, C., Chapter 5 Titled, Stereochemistry: Chiral Molecules, p. 184-228, in "Organic Chemistry," 7th Edition, Wiley, Jun. 18, 2001.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2001, 75, 3594-3603.
Srinivasan, Quantitative et al., Biochemical Rationale for Differences in Transmissibility of 1918 Pandemic Influenza A Viruses, Proc. Natl. Acad. Sci., 105, 2800-2805, 2008.
Stein, K.E. et al., The Immune Response to an Isomaltohexosyl-Protein Conjugate, a Thymus-Dependent Analogue of Alpha(1 Replaced by 6) Dextran., J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEALS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.
Stevens, James et al., Structure and Receptor Specificity of the Hemagglutinin From an H5N1 Influenza Virus, Science, 312:404, 2006.
Stevens et al., Glycan Microarry Analysis of the Hemagglutinins From Modern and Pandemic Influenza Viruses Reveals Different Receptor Specificities. Journal of Molecular Biology 355.5 (2006): 1143-1155.
Stickings, P. et al., nfect. Immun 2008, 76, 1766.
Stockmann, H. et al., Development and Evaluation of New Cyclootynes for Cell Surface Glycan Imaging in Cancer Cells, J. Chem. Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.
Stubbs et al., "Synthesis and use of mechanism-based protein-profiling probes for retaining β-D-glucosaminidases facilitate identification of Pseudomonas aeruginosa NagZ," J. Am. Chem. Soc., Jan. 9, 2008, 130(1):327-335.
Su, G. Hahner, W. Zhou "Investigation of the pore formation in anodic aluminum oxide" J Mater. Chem. 2008, 18 5787-5795.
Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).
Supplementary European Search Report in European Application No. EP 13775664.9, dated Oct. 27, 2015, in 7 pages.
Sutton, VR et al., Bcl-2 Prevents Apoptosis Induced by Perforin and Granzyme B, But Not That Mediated by Whole Cytotoxic Lymphocytes, J of Immunology 1997, 158(12), 5783.
Tahir et al., "Loss of IFN-γ production by invariant NK T cells in advanced cancer," J. Immunol., Oct. 1, 2001, 167(7):4046-4050.
Takakura, Yoshimitsu et al., Molecular cloning, expression and properties of an alpha/beta-Galactoside alpha 2,3-sialyltransferase from Vibrio sp. JT- FAJ-16. J. Biochem. 142, 403-412, (2007).

(56) References Cited

OTHER PUBLICATIONS

Takano, Ryo et al., Sialylation and Malignant Potential in Tumour Cell Glycosylation Mutants, Glycobiology 4, 665-674 (1994).
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.
Tanaka, Katsunori et al., Synthesis of a Sialic Acid Containing Complex-Type N-Glycan on a Solid Support, Chemistry—an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Trinchieri, "Interleukin-12: a proinflammatory cytokine with immunoregulatory functions that bridge innate resistance and antigen-specific adaptive immunity," *Annu. Rev. Immunol.*, 1995, 13:251-276.
Tsai et al., "Design and synthesis of activity probes for glycosidases," *Org. Lett.*, Oct. 17, 2002, 4(21):3607-3610.
Tsai, Tsung-I et al., An Effective Bacterial Ducosidase for Glycoprotein Remodeling, ACS Chemical Biology, vol. 12, No. 1, Jan. 20, 2017, pp. 63-72.
Tsai, Charng-sheng et al., Development of Trifunctional Probes for Glycoproteomic Analysis, Chem. Commun. 2010, 46, 5575-5577.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., *Photobacterium* sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.

Ulrich, G.; Ziessel, R.; Harriman, A. "The chemistry of fluorescent bodipy dyes: Versatility unsurpassed." Angew. Chem. Int. Ed. 2008, 47, 1184-1201.
Van der Horst et al., "Photoaffinity labeling of a bacterial sialidase with an aryl azide derivative of sialic acid," *J. Biol. Chem.*, Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 20090, 9(24): 5398-5399.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," *Nature*, Apr. 26, 2007, 446(7139):1023-1029.
Vasella et al., "Synthesis of a phosphoric acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vavricka, Christopher et al., Influenza Neuraminidase Operates Via a Nucleophilic Mechanism and Can Be Targeted by Covalent Inhibitors, Nature Communcations, 4:1491 (2013).
Vinogradova et al., "Molecular mechanism of lysosomal sialidase deficiency in galactosialidosis involves its rapid degradation," *Biochem. J.*, Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," Oncogene, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mol. Biol.*, 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).

(56) References Cited

OTHER PUBLICATIONS

Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by the IgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wilen et al., "Strategies in optical resolutions," Tetrahedron, 1977, 33(21):2725-2736.
Wiltshire, S. et al. Proc. Natl. Acad. Sci. (2000) 97, 10113-10119.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relpased or Refractory Low-Grade, Follicular, or Transformed B-Cell Non-Hodkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42):17275-17280.

Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yates AJ et al., Brain Tumors in Childhood. Childs Brain 5(1), 31-39 (1979).
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "CD4$^{pos}$, NK1.1$^{pos}$ T cells promptly produce interleukin 4 in response to in vivo challenge with anti-CD3," *J. Exp. Med.*, Apr. 1, 1994, 179(4):1285-1295.
Yuen et al., Human infection by avian influenza A H5N1. Hong Kong Med J. Jun. 2005;1 1(3):189-99.
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Zhang et al., "Selection of tumor antigens as targets for immune attack using immunohistochemistry: I. Focus on gangliosides," *Int. J. Cancer*, Sep. 26, 1997, 73(1):42-49.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.
Cheung et al., Meeting Info: 23rd International Symposium on Glycoconjugates, GLYCO 23. Split, Croatia. Sep. 15, 2015-Sep. 20, 2015, vol. 32, No. 5, pp. 323.
Tsai, Charng-Sheng et al., Cell-Permeable Probe for Identification and Imaging of Sialidases, PNAS, vol. 110, No. 7, 2013, 2466-2471.
Greene, Theodora et al., Protective Groups in Organic Synthesis, pp. 42-51 and 96-100, 1991.
Schelhaas, Michael et al., Protecting Group Strategies in Organic Synthesis, Angew. Chem. Int. Ed. Engl. 1996, 35, 2056-2083.

(56) References Cited

OTHER PUBLICATIONS

Unverzagt, Carlo et al., A Double Regio- and Stereoselective Glycosylation Strategy for the Synthesis of N-Glycans, Chem. Eur. J., 2008, 14, 1304-1311.

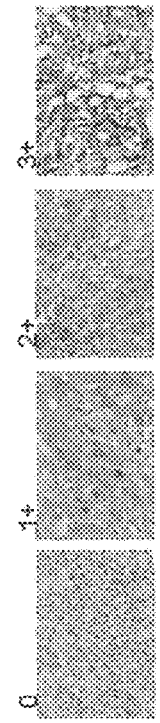
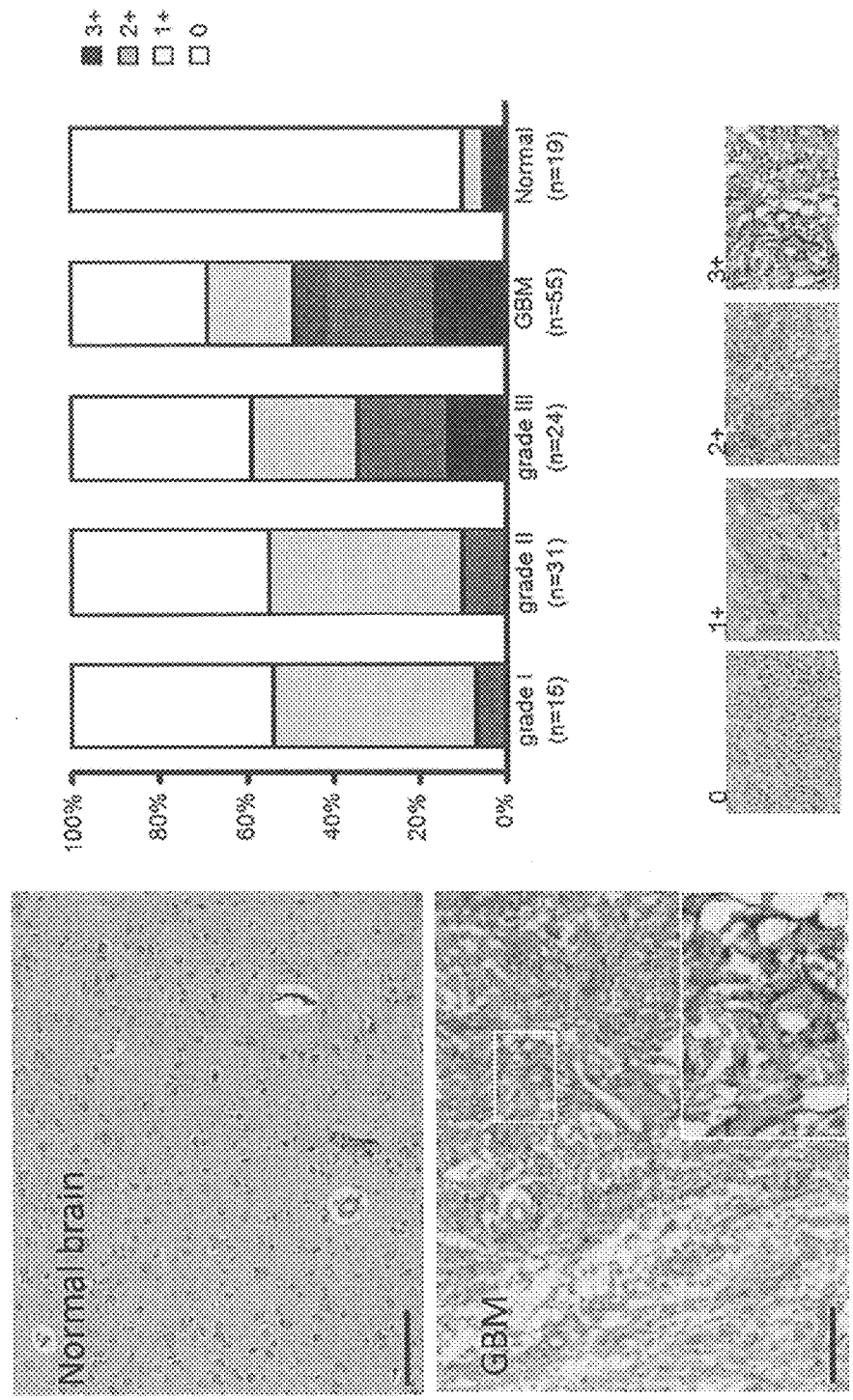
FIG. 4A
FIG. 4B
FIG. 4C

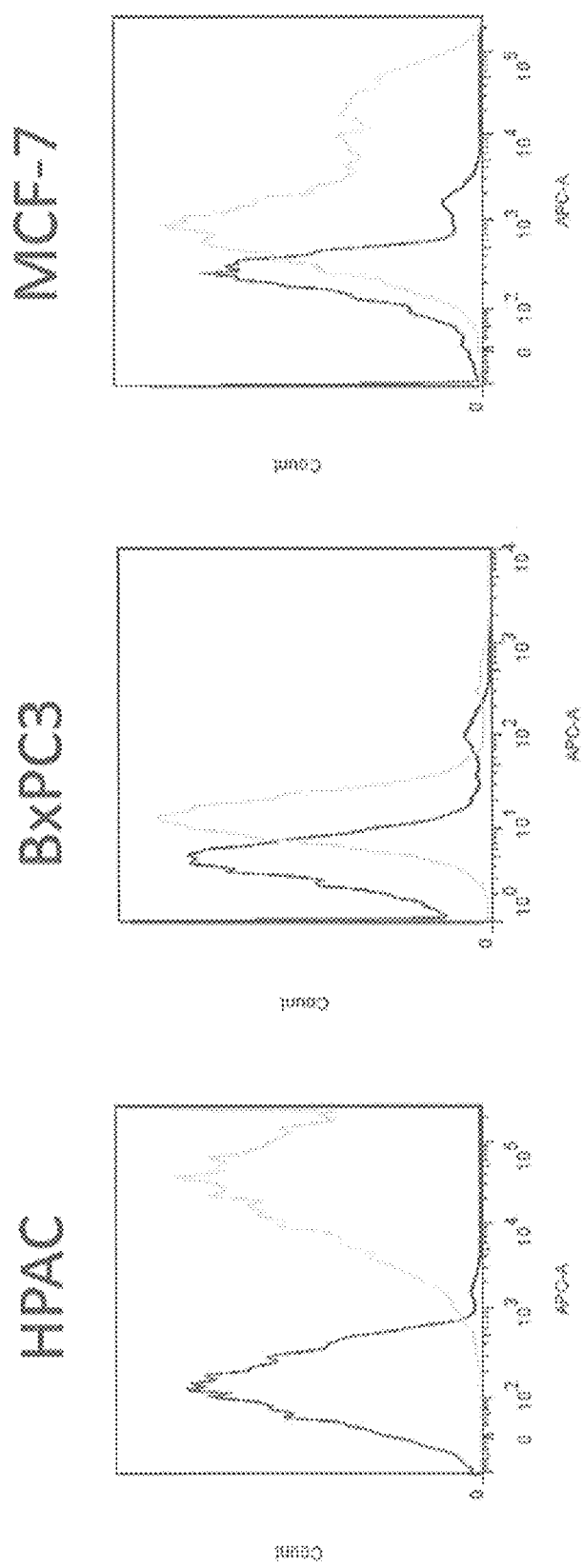

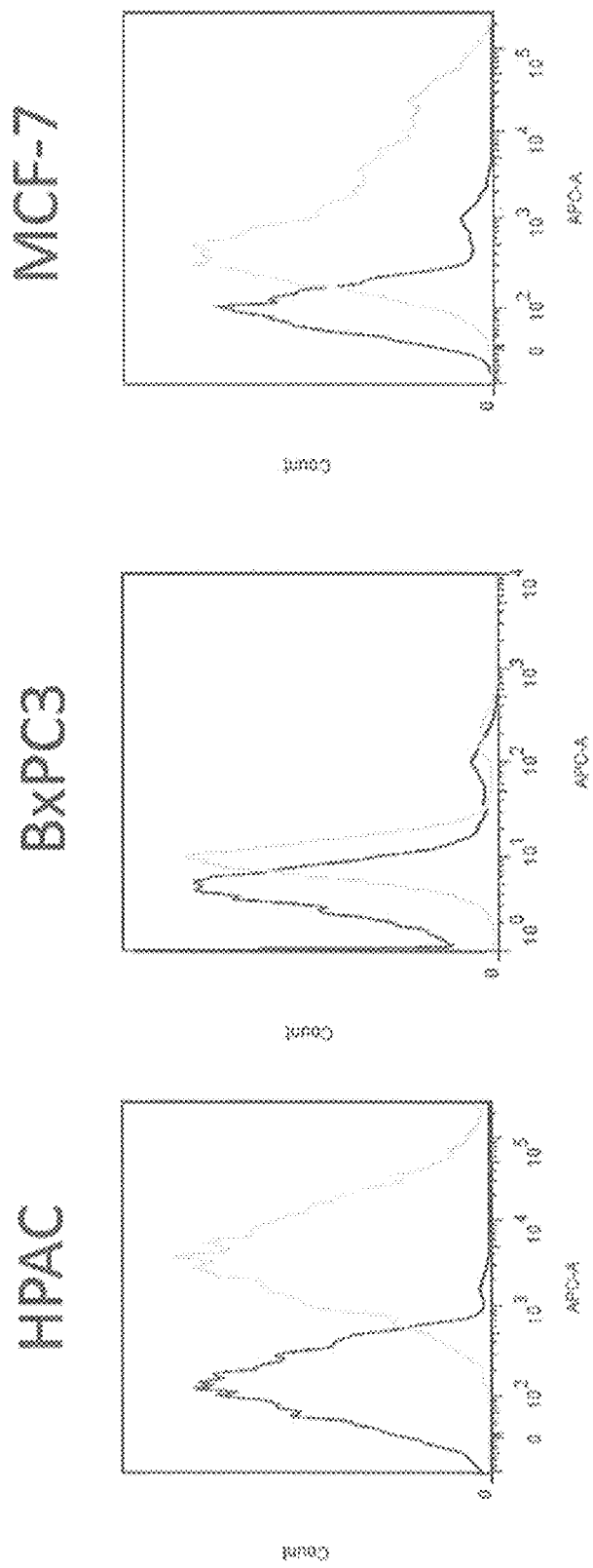

Table 17-1

| SEQ ID NO | DESCRIPTION | SEQUENCE |
|---|---|---|
| 135 | hMC48 VH nucleotide sequence | CAGGTCCAGCTGCAGGAAAGCGGACCCGGACTGGTGAAACCTAGC GAAACACTGAGCCTGACTTGTACCGTGAGCGGATTTTCCCTGACCTC TTATGGAGTGAGCTGGATCAGACAGCCCCCTGGCAAGGGACTGGAG TGGATCGGCGTGATTTGGGGAGAAGGCTCCACAAACTATCACAGTG TCCTGATCTCACGACTGACTATTTCTAAGGACAACTCTAAAAGTCAG GTCTTCCTGAAACTGAATAGTCTGCAGACTGACGATACCGCTACAT ACTATTGCGCAATGACAGGGACAGCATACTGGGGACAGGGAACCCT GGTGACAGTCAGCTCC |
| 136 | hMC48 VL nucleotide sequence | CAGATCGTGCTGACACAGTCCCCTGCAATTATGTCAGCCAGCCAG GGGAAAAGGTGACAATGACTTGTAGTGCTTCTAGTTCAGTCTCATA CATGCATTGGTATCAGCAGAAGCCAGGCCTGGCCCCCAGACTGCTG ATCTACGACACCTCCAAACTGAGCTCCGGCGTGCCCGGGAGATTTT CCGGCTCTGGGAGTGGAACTTCATATAGCCTGACCATTTCTAGGCTG GAGGCCGAAGATGCCGCTACATACTATTGCCACCAGTGGAGCAGTA GCCCCCATACATTCGGAGGCGGGACCAAAGTGGAAATCAAACGC |
| 137 | hMC48 VH amino acid sequence | QVQLQESGPGLVKPSETLSLTCTVSGFSLTSYGVSWIRQPPGKGLEWI GVIWGEGSTNYHSVLISRLTISKDNSKSQVFLKLNSLQTDDTATYYCA MTGTAYWGQGTLVTVSS |
| 138 | hMC48 VL amino acid sequence | QIVLTQSPAIMSASPGEKVTMTCSASSSVSYMHWYQQKPGLAPRLLIY DTSKLSSGVPGRFSGSGSGTSYSLTISRLEAEDAATYYCHQWSSSPHTF GGGTKVEIKR |
| 139 | hMC48 VL CDR1 | SSVSY |
| 140 | hMC48 VL CDR2 | DTS |
| 141 | hMC48 VL CDR3 | HQWSSSPHT |
| 142 | hMC48 VH CDR1 | GFSLTSYG |
| 143 | hMC48 VH CDR2 | IWGEGST |
| 144 | hMC48 VH CDR3 | AMTGTAY |

FIG. 17B

Table 17-2

| SEQ ID NO | DESCRIPTION | SEQUENCE |
|---|---|---|
| 145 | hMC48 VH nucleotide sequence | CAGGTCCAGCTGAAAGAGAGCGGCCCCGGACTGGTCGCCCCTTCAC AGAGCCTGAGCATTACTTGCACCGTGAGCGGATTTTCACTGACCAG CTACGGAGTGAGCTGGATTAGACAGCCTCCTGGCAAGGGACTGGAG TGGATCGGCGTGATTTGGGGAGAAGGCAGCACCAACTATCACAGTG TCCTGATCTCACGGCTGACAATTTCCAAGGACAACAGCAAATCCCA GGTCTTCCTGAAACTGAATTCTCTGCAGACTGACGATACCGCTACAT ACTATTGCGCAATGACAGGGACAGCATACTGGGGACAGGGAACCCT GGTGACAGTCAGTAGT |
| 146 | hMC48 VL nucleotide sequence | CAGATCGTGCTGACACAGTCCCCAGCAATTATGTCTGCCAGTCCCG GGGAGAAGGTGACAATGACTTGTAGTGCCAGCTCCTCTGTCTCATA CATGCATTGGTATCAGCAGAAGTCCGGCACATCTCCTAAACGGTGG ATCTACGACACTTCTAAACTGAGTTCAGGCGTGCCCGGGAGATTTTC AGGCAGCGGGTCCGGAACTTCTTATAGTCTGACCATTTCCCGACTG GAGGCCGAAGATGCCGCTACCTACTATTGCCATCAGTGGTCTTCAA GCCCTCATACTTTTGGGGGGGGAACTAAGGTGGAAATCAAGCGA |
| 147 | hMC48 VH amino acid sequence | QVQLKESGPGLVAPSQSLSITCTVSGFSLTSYGVSWIRQPPGKGLEWIG VIWGEGSTNYHSVLISRLTISKDNSKSQVFLKLNSLQTDDTATYYCAMT GTAYWGQGTLVTVSS |
| 148 | hMC48 VL amino acid sequence | QIVLTQSPAIMSASPGEKVTMTCSASSSVSYMHWYQQKSGTSPKRWIY DTSKLSSGVPGRFSGSGSGTSYSLTISRLEAEDAATYYCHQWSSSPHTF GGGTKVEIKR |
| 149 | hMC48 VL CDR1 | SSVSY |
| 150 | hMC48 VL CDR2 | DTS |
| 151 | hMC48 VL CDR3 | HQWSSSPHT |
| 152 | hMC48 VH CDR1 | GFSLTSYG |
| 153 | hMC48 VH CDR2 | IWGEGST |
| 154 | hMC48 VH CDR3 | AMTGTAY |
| 155 | hMC48 VL FR1 | QIVLTQSPAIMSASPGEKVTMTCSAS |
| 156 | hMC48 VL FR2 | MHWYQQKSGTSPKRWIY |
| 157 | hMC48 VL FR3 | KLSSGVPGRFSGSGSGTSYSLTISRLEAEDAATYYC |
| 158 | hMC48 VL FR4 | FGGGTKVEIKR |
| 159 | hMC48 VH FR1 | QVQLKESGPGLVAPSQSLSITCTVS |
| 160 | hMC48 VH FR2 | VSWIRQPPGKGLEWIG |
| 161 | hMC48 VH FR3 | NYHSVLISRLTISKDNSKSQVFLKLNSLQTDDTATYYC |
| 162 | hMC48 VH FR4 | WGQGTLVTVSS |

COMPOSITIONS AND METHODS FOR TREATMENT AND DETECTION OF CANCERS

RELATED APPLICATIONS

This application is a continuation-in-part and claims the benefit of priority to international PCT application no. PCT/US2015/011748, filed Jan. 16, 2015, which claims benefit of U.S. provisional application No. 61/928,132, filed Jan. 16, 2014; U.S. application Ser. No. 14/599,174, filed Jan. 16, 2015, which claims benefit of U.S. provisional application No. 61/928,132, filed Jan. 16, 2014; international PCT application no. PCT/US/2015/032745, filed May 27, 2015, which claims benefit of U.S. provisional application No. 62/110,338, filed Jan. 30, 2015, U.S. provisional application No. 62/020,199, filed Jul. 2, 2014, U.S. provisional application No. 62/003,908, filed May 28, 2014, U.S. provisional application No. 62/003,104, filed May 27, 2014 and U.S. provisional application No. 62/003,136, filed May 27, 2014; U.S. application Ser. No. 14/723,297, filed May 27, 2015, which claims benefit of U.S. provisional application No. 62/110,338, filed Jan. 30, 2015, U.S. provisional application No. 62/020,199, filed Jul. 2, 2014, U.S. provisional application No. 62/003,908, filed May 28, 2014, U.S. provisional application No. 62/003,104, filed May 27, 2014 and U.S. provisional application No. 62/003,136 filed May 27, 2014, the contents of which are hereby incorporated by reference as if set forth in their entirety.

FIELD

Antibodies that bind to Globo H, SSEA-3 and/or SSEA-4, are disclosed herein, as well as related compositions and methods of use. Methods of use include, without limitation, cancer therapies and diagnostics.

BACKGROUND OF THE INVENTION

Glioblastoma multiforme (GBM), accounting for 60 to 70% of malignant gliomas, is the most aggressive form of gliomas and the most common primary brain tumor in adults (Louis D N, et al. (2007) The 2007 WHO classification of tumours of the central nervous system. Acta Neuropathol 114(2):97-109). Despite many treatments, including surgery, and chemo- or radiotherapy available for GBM, the prognosis and survival rate for GBM patients are still poor, with the median survival rate of 14-15 months (Van Meir E G, et al. (2010) Exciting new advances in neuro-oncology: the avenue to a cure for malignant glioma. CA Cancer J Clin 60(Meyer M A (2008) Malignant gliomas in adults. N Engl J Med 359(17):1850; author reply 1850):166-193). GBM is notoriously resistant to most anti-cancer drugs and extremely infiltrative, which hampers complete surgical resection, and therefore most patients develop tumor recurrence or progression even after multiple therapies. Because of the high mortality, new therapeutic approaches, such as immunotherapy and gene therapy, have been proposed for the treatment of GBM (Meyer M A (2008) Malignant gliomas in adults. N Engl J Med 359(17):1850; author reply 1850).

Altered glycosylation is a feature of cancer cells, and several glycan structures are well-known tumor markers (Meezan E, Wu H C, Black P H, & Robbins P W (1969) Comparative studies on the carbohydrate-containing membrane components of normal and virus-transformed mouse fibroblasts. II. Separation of glycoproteins and glycopeptides by sephadex chromatography. Biochemistry 8(6): 2518-2524; Hakomori S (2002) Glycosylation defining cancer malignancy: new wine in an old bottle. Proc Natl Acad Sci USA 99(16):10231-10233). These aberrant changes include the overall increase in the branching of N-linked glycans (Lau K S & Dennis J W (2008) N-Glycans in cancer progression. Glycobiology 18(10):750-760) and sialic acid content (van Beek W P, Smets L A, & Emmelot P (1973) Increased sialic acid density in surface glycoprotein of transformed and malignant cells—a general phenomenon? Cancer Res 33(11):2913-2922), and the overexpression of certain glycan epitopes, such as sialyl Lewis x (sLex), sialyl Tn (sTn), Lewis y (Ley), Globo H, and polysialic acid (Sell S (1990) Cancer-associated carbohydrates identified by monoclonal antibodies. Hum Pathol 21(10):1003-1019; Hakomori S & Zhang Y (1997) Glycosphingolipid antigens and cancer therapy. Chem Biol 4(2):97-104; Taylor-Papadimitriou J & Epenetos A A (1994) Exploiting altered glycosylation patterns in cancer: progress and challenges in diagnosis and therapy. Trends Biotechnol 12(6):227-233). Many tumors also exhibit increased expression of certain glycolipids, especially the gangliosides, glycosphingolipids (GSLs) with sialic acid(s) attached to the glycan chain. Gangliosides are normally observed in neural systems, and are found to be elevated in tumors, particularly the complex gangliosides associated with malignancy (Birkle S, Zeng G, Gao L, Yu R K, & Aubry J (2003) Role of tumor-associated gangliosides in cancer progression. Biochimie 85(3-4):455-463).

It has been reported that human glioma show expression of gangliosides (Fredman P, et al. (1986) Potential ganglioside antigens associated with human gliomas. Neurol Res 8(2): 123-126; Yates A J, Becker L E, & Sachs L A (1979) Brain tumors in childhood. Childs Brain 5(1):31-39; Traylor T D & Hogan E L (1980) Gangliosides of human cerebral astrocytomas. J Neurochem 34(1):126-131; Berra B, Gaini S M, & Riboni L (1985) Correlation between ganglioside distribution and histological grading of human astrocytomas. Int J Cancer 36(3):363-366; Fredman P, von Holst H, Collins V P, Granholm L, & Svennerholm L (1988) Sialyl-lactotetraosylceramide, a ganglioside marker for human malignant gliomas. J Neurochem 50(3):912-919; Mansson J E, et al. (1986) Characterization of new gangliosides of the lactotetraose series in murine xenografts of a human glioma cell line. FEBS Lett 201(1): 109-113; Fredman P, von Holst H, Collins V P, Dellheden B, & Svennerholm L (1993) Expression of gangliosides GD3 and 3'-isoLM1 in autopsy brains from patients with malignant tumors. J Neurochem 60(1):99-105). Since some of glioma-associated gangliosides are rarely expressed or even absent in normal tissues (Svennerholm L, et al. (1989) Human brain gangliosides: developmental changes from early fetal stage to advanced age. Biochim Biophys Acta 1005(2): 109-117), they are suitable for targeted therapy (Kato Y, et al. (2010) GMab-1, a high-affinity anti-3'-isoLM1/3',6'-isoLD1 IgG monoclonal antibody, raised in lacto-series ganglioside-defective knockout mice. Biochem Biophys Res Commun 391(1):750-755). Hence, discovering novel glioma-associated GSLs would provide new targets for development of new therapies against gliomas.

The GSLs of globo-series feature a Galα1-4Gal linkage to lactosylceramides, and this linkage is catalyzed by lactosylceramide 4-alpha-galactosyltransferase (A4GALT). While globotriosylceramide (Gb3Cer) and globoside (Gb4Cer) constitute the basis of P-blood group system (Schenkel-Brunner H (1995) P System. Human Blood Groups, (Springer Vienna), pp 211-234), galactosyl globoside (Gb5Cer) and sialyl galactosyl globoside (sialyl Gb5Cer, SGG, MSGG), also known as stage-specific embryonic antigen-3 (SSEA-3) and SSEA-4 (Kannagi R, et al. (1983) Stage-specific embryonic antigens (SSEA-3 and -4) are epitopes of a unique globo-series ganglioside isolated from human teratocarcinoma cells. EMBO J 2(12):2355-2361), respectively, are widely used as cell-surface markers to define human embryonic stem cells. Globo-series GSLs have also been observed in tumors: Globo H (fucosyl Gb5Cer) is overexpressed in many epithelial cancers, such as ovarian, gastric, prostate, lung, breast, and pancreatic cancers (Zhang S, et al. (1997) Selection of tumor antigens as targets for immune attack using immunohistochemistry: I. Focus on gangliosides. Int J Cancer 73(1):42-49); SSEA-3, SSEA-4 and Globo H are expressed not only on breast cancer cells, but also on breast cancer stem cells (Chang W W, et al. (2008) Expression of Globo H and SSEA3 in breast cancer stem cells and the involvement of fucosyl transferases 1 and 2 in Globo H synthesis. Proc Natl Acad Sci USA 105(33):11667-11672; Huang Y L, et al. (2013) Carbohydrate-based vaccines with a glycolipid adjuvant for breast cancer. Proc Natl Acad Sci USA 110(7):2517-2522). Moreover, in renal cell carcinoma, high-level expressions of SSEA-4 and disialosyl galactosyl globoside (disialosyl Gb5Cer, DSGG) are observed (Saito S, et al. (1997) Expression of globo-series gangliosides in human renal cell carcinoma. Jpn J Cancer Res 88(7):652-659), but it is still not known whether globo-series GSLs are expressed on GBM.

It is of great interest to identify glycan markers associated with and/or predictive of cancers, and develop antibodies against the markers for use in diagnosing and treating a broad spectrum of cancers.

SUMMARY OF THE INVENTION

The present disclosure is also based on the discovery that Globo H, SSEA-3 and SSEA-4 are aberrantly expressed in a broad spectrum of cancers, but not on normal cells. Cancers cells expressing Globo H, SSEA-3 and SSEA-4 include, but are not limited to, brain cancer, lung cancer, breast cancer, oral cancer, esophageal cancer, stomach cancer, liver cancer, bile duct cancer, bone cancer (osteosarcoma), skin cancer, pancreatic cancer, colon cancer, kidney cancer, cervical cancer, ovarian cancer and prostate cancer.

In one aspect, the disclosure provides affinity-matured SSEA-3/SSEA-4/Globo H antibodies. These antibodies have increased affinity and specificity for SSEA-3/SSEA-4/Globo H. This increase in affinity and sensitivity permits the molecules of the invention to be used for applications and methods that are benefited by (a) the increased sensitivity of the molecules of the invention and/or (b) the tight binding of SSEA-3/SSEA-4/Globo H by the molecules of the invention.

In one embodiment, SSEA-3/SSEA-4/Globo H antibodies that are useful for treatment of SSEA-3/SSEA-4/Globo H-mediated disorders in which a partial or total blockade of one or more SSEA-3/SSEA-4/Globo H activities is desired. In one embodiment, the anti SSEA-3/SSEA-4/Globo H antibodies of the invention are used to treat cancer.

The anti-SSEA-3/SSEA-4/Globo H antibodies of the invention permit the sensitive and specific detection of the epitopes in immunoassays, for example, immunoprecipitations, sandwich immunoassays, ELISAs, or immunomicroscopy without the need for mass spectrometry or genetic manipulation. In turn, this provides a significant advantage in both observing and elucidating the normal functioning of these pathways and in detecting when the pathways are functioning aberrantly.

In one aspect, SSEA4/SSEA3/Globo H are three glycans that are specifically expressed for cancer cells and cancer stem cells. Knockdown of beta-3-GalT5, the key enzyme for the synthesis of these three glycolipids, causes apoptosis of cancer cells, but not normal cells. Thus, antibodies, especially glycoantibodies against SSEA4 preferentially or specifically and/or against SSEA3/SSEA4/Globo H simultaneously are effective cancer therapeutic agents. In another aspect, the three glycans, SSEA4/SSEA3/Globo H, especially SSEA3, are useful as cancer stem cell markers.

In one aspect, SSEA4 and/or SSEA4/SSEA3/Globo H in combination are useful as therapeutic targets for the treatment of different cancers, including for example, brain cancer, lung cancer, breast cancer, oral cancer, esophageal cancer, stomach cancer, liver cancer, bile duct cancer, skin cancer, bone cancer (osteosarcoma), pancreatic cancer, colon cancer, kidney cancer, cervical cancer, ovarian cancer and prostate cancer.

In one embodiment, human or humanized therapeutic antibodies against SSEA4 expressed on the cell surface of these exemplary cancer types are provided.

In another embodiment, human or humanized therapeutic antibodies against SSEA3/SSEA4/Globo H simultaneously expressed on the cell surface of these exemplary cancer types are provided.

In one aspect, the present disclosure features an isolated antibody specific to SSEA-4. The anti-SSEA-4 antibody binds to Neu5Acα2→3Galβ1→3GalNAcβ1→3Galα1→4Galβ1→4Glcβ1 (SSEA-4 hexasaccharide). In some examples, the antibody is capable of binding to Neu5Gcα2→3Galβ1→3GalNAcβ1→3Galα1→4Galβ1→4Glcβ1 (an analogue of SSEA-4 hexasaccharide).

Another aspect of the present disclosure features an isolated antibody specific to SSEA-4 and fragments thereof. The anti-SSEA-4 antibody binds to Neu5Acα2→3Galβ1→3GalNAcβ1→3Galα1→4Galβ1→4Glcβ1 (SSEA-4 hexasaccharide) and Neu5Acα2→3Galβ1→3GalNAcβ1→3Galα1 (fragment of SSEA-4 hexasaccharide). In some examples, the antibody is capable of binding to Neu5Acα2→3Galβ1→3GalNAcβ1→3Galβ1. In some examples, the antibody is capable of binding to Neu5Acα2→3Galβ1→3GalNAcβ1→3Galα1→4Galβ1→4Glcβ1 (an analogue of SSEA-4 hexasaccharide).

In one aspect, the present disclosure provides an isolated antibody, or antigen-binding fragment thereof, comprising H-CDR1, H-CDR2, and H-CDR3 selected from (i)-(iii) as set forth in Table 17-4 (FIG. 17):

(i) H-CDR1 selected from SEQ ID NO:152;
(ii) H-CDR2 selected from SEQ ID NO:153;
(iii) H-CDR3 selected from SEQ ID NO: 154, respectively;
and comprising L-CDR1, L-CDR2 and L-CDR3 selected from (iv)-(vi):
(iv) L-CDR1 selected from SEQ ID NO: 149;
(v) L-CDR2 selected from SEQ ID NO:150; and
(vi) L-CDR3 selected from SEQ ID NO: 151, respectively.

In one aspect, the present disclosure provides an isolated antibody, or antigen-binding fragment thereof, comprising VH having SEQ ID NO: 147 or SEQ ID No:137 and VL having SEQ ID No: 148 or SEQ ID No:138.

In one aspect, the present disclosure provides an isolated antibody or antigen-binding fragment wherein the antibody or the antigen binding fragment further comprises H-FR1, H-FR2, H-FR3, and HFR4 selected from (i)-(iv) as set forth in 17-4 (FIG. 17):
  (i) H-FR1 selected from SEQ ID NO:159;
  (ii) H-FR2 selected from SEQ ID NO: 160;
  (iii) H-FR3 selected from SEQ ID NO:161;
  (iv) H-FR4 selected from SEQ ID NO: 162; respectively;
  and comprising L-FR1, L-FR2, L-FR3 and L-FR4 selected from (v)-(viii):
  (v) L-FR1 selected from SEQ ID NO:155;
  (vi) L-FR2 selected from SEQ ID NO:156;
  (vii) L-FR3 selected from SEQ ID NO: 157;
  (viii) L-FR4 selected from SEQ ID NO: 158; respectively.

In one aspect, the present disclosure provides an isolated antibody, or antigen-binding fragment thereof, comprising H-CDR1, H-CDR2, and H-CDR3 selected from (i)-(iii) as set forth in FIG. 16A:
  (i) H-CDR1 selected from SEQ ID NO:52 or SEQ ID NO:56;
  (ii) H-CDR2 selected from of SEQ ID NO:54 or SEQ ID NO:58;
  (iii) H-CDR3 selected from SEQ ID NO:60 or SEQ ID NO:63, respectively;
  and comprising L-CDR1, L-CDR2 and L-CDR3 selected from (iv)-(vi):
  (iv) L-CDR1 selected from SEQ ID NO:66 or SEQ ID NO:70;
  (v) L-CDR2 selected from SEQ ID NO:68 or SEQ ID NO:72; and
  (vi) L-CDR3 selected from SEQ ID NO:74 or SEQ ID NO:77, respectively.

In certain embodiments, the isolated antibody or antigen-binding fragment further comprising H-FR1, H-FR2, H-FR3, and HFR4 selected from (i)-(iv) as set forth in FIG. 16A:
  (i) H-FR1 selected from SEQ ID NO:51 or SEQ ID NO:55;
  (ii) H-FR2 selected from SEQ ID NO:53 or SEQ ID NO:57;
  (iii) H-FR3 selected from SEQ ID NO:59 or SEQ ID NO:62,
  (iv) H-FR4 selected from SEQ ID NO:61 or SEQ ID NO:64, respectively;
  and comprising L-FR1, L-FR2, L-FR3 and L-FR4 selected from (v)-(viii):
  (v) L-FR1 selected from SEQ ID NO:65. or SEQ ID NO:69;
  (vi) L-FR2 selected from SEQ ID NO:67 or SEQ ID NO:71;
  (vii) L-FR3 selected from SEQ ID NO:73, or SEQ ID NO:76,
  (viii) L-FR4 selected from SEQ ID NO:75, or SEQ ID NO:78, respectively.

Exemplary antibodies described herein can have one or more characteristics of:
  a) is a recombinant antibody, a monoclonal antibody, a chimeric antibody, a humanized antibody, a human antibody, an antibody fragment, a bispecific antibody, a monospecific antibody, a monovalent antibody, an IgG1 antibody, an IgG2 antibody, or derivative of an antibody; b) is a human, murine, humanized, or chimeric antibody, antigen-binding fragment, or derivative of an antibody; c) is a single-chain antibody fragment, a multibody, a Fab fragment, and/or an immunoglobulin of the IgG, IgM, IgA, IgE, IgD isotypes and/or subclasses thereof; d) has one or more of the following characteristics: (i) mediates ADCC and/or CDC of cancer cells; (ii) induces and/or promotes apoptosis of cancer cells; (iii) inhibits proliferation of target cells of cancer cells; (iv) induces and/or promotes phagocytosis of cancer cells; and/or (v) induces and/or promotes the release of cytotoxic agents; e) does not bind an antigen expressed on non-cancer cells, non-tumor cells, and/or benign tumor cells.

In some examples, any of the antibodies described herein can be generated as Fab or single chain by phage display antibody library or single B cells using the B cells from patients or recovered patients or healthy persons.

In another aspect, the present disclosure provides therapeutic methods that include administering to a subject in need of such treatment a therapeutically effective amount of a composition that includes one or more antibodies described herein.

In some embodiments, the subject (e.g., a human patient) in need of the treatment is diagnosed with, suspected of having, or at risk for cancer. Examples of the cancer include, but are not limited to, brain cancer, lung cancer, breast cancer, oral cancer, esophagus cancer, stomach cancer, liver cancer, bile duct cancer, pancreatic cancer, colon cancer, kidney cancer, cervical cancer, ovarian cancer and prostate cancer. In some embodiments, the cancer is brain cancer, lung cancer, breast cancer, ovarian cancer, prostate cancer, colon cancer, or pancreatic cancer. In some preferred embodiments, the cancer is brain cancer or glioblastoma multiforme (GBM) cancer.

In some embodiments, the antibody is capable of targeting SSEA-4-expressing cancer cells.

The treatment results in reduction of tumor size, elimination of malignant cells, prevention of metastasis, prevention of relapse, reduction or killing of disseminated cancer, prolongation of survival and/or prolongation of time to tumor cancer progression.

In some embodiments, the treatment further comprises administering an additional therapy to said subject prior to, during or subsequent to said administering of the antibodies. In some embodiments, the additional therapy is treatment with a chemotherapeutic agent. In some embodiments, the additional therapy is radiation therapy.

Further, the present disclosure features a method for diagnosing cancer in a subject, comprising (a) applying a composition that can include one or more monoclonal antibodies that detect expression of a panel of markers consisting of GM3, GM2, GM1, GD1, GD1a, GD3, GD2, GT1b, A2B5, LeX, sLeX, LeY, SSEA-3, SSEA-4, Globo H, TF, Tn, sTn, CD44, CD24, CD45, CD90, CD133 to a cell or tissue sample obtained from the subject; (b) assaying the binding of the monoclonal antibody to the cell or the tissue sample; and (c) comparing the binding with a normal control to determine the presence of the cancer in the subject.

Examples of the cancer for detection and diagnosis include, but are not limited to, brain cancer, lung cancer, breast cancer, oral cancer, esophagus cancer, stomach cancer, liver cancer, bile duct cancer, pancreatic cancer, colon cancer, kidney cancer, cervical cancer, ovarian cancer and prostate cancer. In some embodiments, the cancer is brain cancer, lung cancer, breast cancer, ovarian cancer, prostate cancer, colon cancer, or pancreatic cancer.

In some embodiments, the cancer is brain cancer or glioblastoma multiforme (GBM) cancer, and the antibody is an anti-SSEA-4 monoclonal antibody.

In yet another aspect, the present disclosure features pharmaceutical compositions for use in treating cancer, such as brain cancer, lung cancer, breast cancer, oral cancer, esophagus cancer, stomach cancer, liver cancer, bile duct cancer, pancreatic cancer, colon cancer, kidney cancer, cervical cancer, ovarian cancer and prostate cancer, etc. The pharmaceutical composition comprises any of the antibodies or nucleic acid encoding such and a pharmaceutically acceptable carrier, and uses of such pharmaceutical compositions in manufacturing a medicament for treating cancer.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

As used herein, symbolic, graphic, and text nomenclature for describing glycans and related structures are well-established and understood in the art, including, for example, "Symbols Nomenclatures for Glycan Representation", Proteomics. 2009 December; 9(24): 5398-5399 by Ajit Varki et al.

(FIG. 1A) Schematic diagram of the biosynthesis of globoseries GSLs. SSEA-3, the precursor of SSEA-4 and Globo H, is synthesized from globoside. Glycosidic linkages and graphic notations are labelled (Glc, glucose; Gal, galactose; GalNAc, N-acetylgalactosamine; Fuc, fucose; NeuAc, N-acetylneuraminic acid). (FIG. 1B) GBM cells were stained with Alexa Fluor 488-conjugated MC813-70 and the staining intensity was analyzed with flow cytometry. All the cells examined were GBM cell lines except SVG p12, which is a normal human fetal glial cell line transformed with SV40 large T antigen. The histograms of the cells stained with MC813-70 and isotype control are shown in gray and white, respectively.

(FIG. 2A) binding profile of mAb 273 (FIG. 2B) binding profile of mAb 651 (FIG. 2C) binding profile of mAb VK9 (FIG. 2D) binding profile of mAb Mbr1 (FIG. 2E) binding profile of mAb 45 (FIG. 2F) binding profile of mAb 46 (FIG. 2G) binding profile of mAb 48 (FIG. 2H) binding profile of MC813-70.

(FIG. 3A) Gangliosides were separated on an HPTLC plate and detected with MC813-70 mAb. Gangliosides from 2012Ep (human embryonal carcinoma cell line) and YAC-1 (mouse lymphoma cell line) were applied to serve as the positive controls for SSEA-4 and GM1b, respectively. SSEA-4 with different chain lengths of fatty acids migrated as two close bands. (FIG. 3B) The extracted gangliosides from DBTRG GBM cells were permethylated and analyzed by MALDI-MS. The major gangliosides in DBTRG cells were GM3 (m/z=1371.9), GM2 (m/z=1617.0), Neu5Ac-(n)Lc4/Gg4Cer (m/z=1821.1), and Neu5Ac2-(n)Lc4/Gg4Cer (m/z=2182.3). Although in a relatively weak signal, SSEA-4 (Neu5Ac-Hex4-HexNAc-Cer, m/z=2025.2) was also observed. Gangliosides with the same glycan moiety but with different fatty acyl contents are bracketed.

FIGS. 4A-4C. Expression profile of SSEA-4 in GBM. Representative images of normal brain tissues (FIG. 4A) and GBM (FIG. 4B) after immunohistochemical staining with MC-813-70. The inset in panel B shows a magnified picture of the small rectangular area. Scale bar, 100 µm. (FIG. 4C) Statistical results of SSEA-4 IHC. The staining intensity of GBM specimens was graded as 0 (negative, i), 1+ (weak, ii), 2+ (moderate, iii), and 3+ (strong, iv). Scale bar, 100 µm. Grade I (n=15), grade II (n=31), grade III (n=24), grade IV (GBM, n=55) specimens and normal brain tissues (n=19) were counterstained with hematoxylin after IHC. The staining intensity of the tissues was graded as 0 (negative), 1+ (weak), 2+ (moderate), and 3+ (strong).

(FIG. 5A) MC813-70 on GBM. GBM cell lines were treated with 20 µg/mL and rabbit complement to observe MC813-70-induced cell lysis. The CDC activity of MC813-70 was measured by lactate dehydrogenase (LDH) release assay as described in "Materials and Methods." The data are shown as mean±SD. (FIG. 5B) mAb 273 on MCF-7 in vitro.

FIGS. 7A-7D. Binding of antibodies to cancer cells. (FIG. 7A) Breast cancer cells MCF-7 were stained with mAb 273. (FIG. 7B) Pancreatic cancer cells (HPAC and BxPC3) and breast cancer cells MCF-7 were stained with mAb 45. (FIG. 7C) Pancreatic cancer cells (HPAC and BxPC3) and breast cancer cells MCF-7 were stained with mAb 46. (FIG. 7D) Pancreatic cancer cells (HPAC and BxPC3) and breast cancer cells MCF-7 were stained with mAb 48. These cells were stained with Alexa Fluor 488-conjuagated antibodies and the staining intensity was analyzed with flow cytometry. The cells stained with mAbs and isotype controls are shown in blue and red, respectively.

The randomly selected phage clones were screened via ELISA to reveal different binding. (FIG. 11A) The colonies were selected from the PBS wash group. (FIGS. 11B-11D) The colonies were selected from the $PBST_{0.01}$ wash group. Eight phage clones were found to have superior binding activity to SSEA-4-BSA (A490≥0.2). Control phage was used as a negative control (Neg.) Commercial anti-SSEA-4 mAb (MC813-70) was used as a positive control (Pos.). A490: absorbance at 490 nm.

Figure 12:
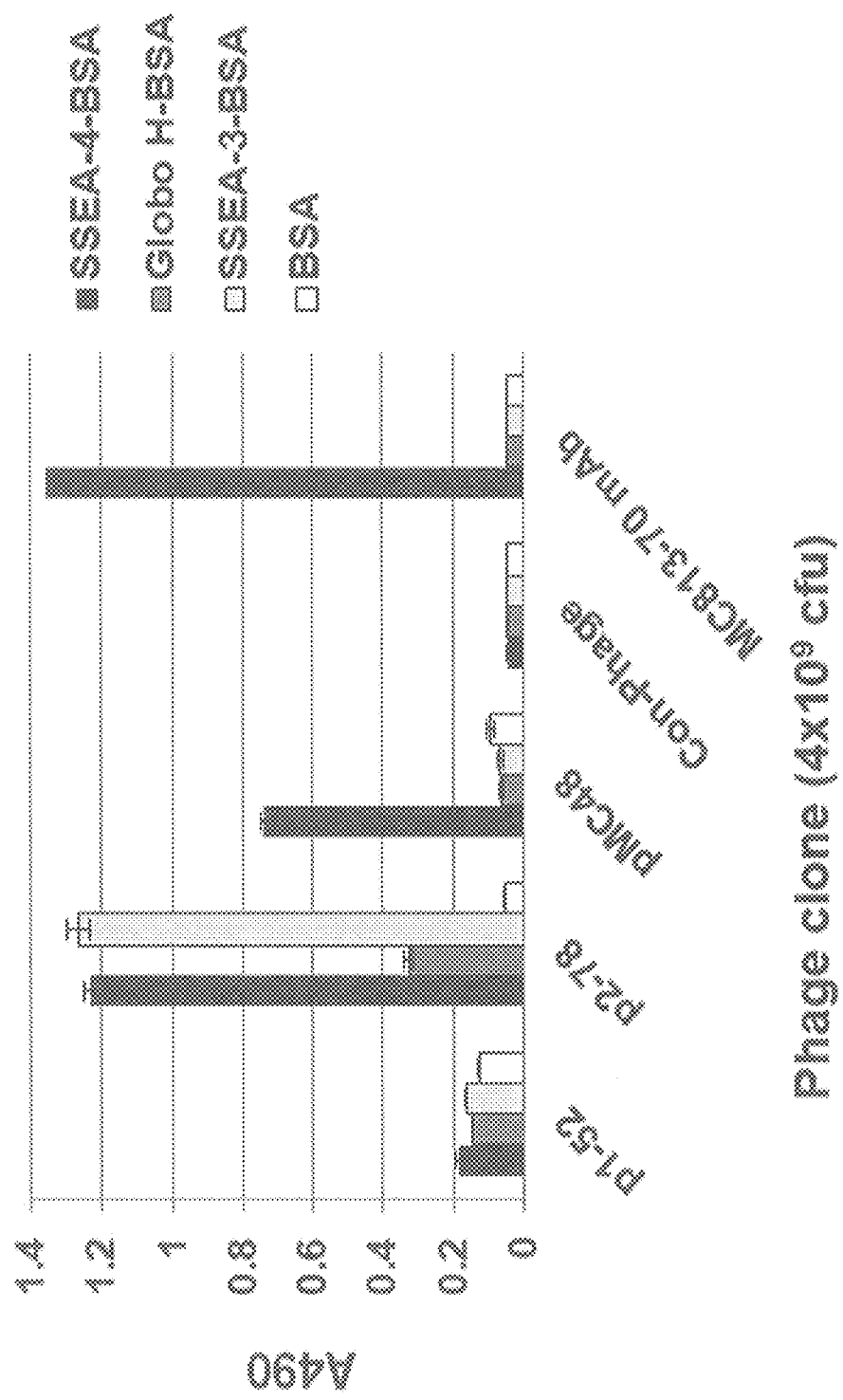

FIG. 12. Comparison of the binding activity of anti-SSEA-4 phage clones to Globo-series glycans. ELISA was performed to examine the binding of anti-SSEA-4 phage clones to SSEA-4-BSA, Globo H-BSA and SSEA-3-BSA. Commercial anti-SSEA-4 mouse monoclonal antibody (MC813-70) and control phage (Con-phage) were used as a positive and negative control, respectively. The pMC48 is the phage-displayed scFv format of anti-SSEA-4 mouse mAb created by Dr. Wong's Lab. A490: absorbance at 490 nm FIGS. 13A-13B. Analysis of the binding activity of p2-78 hAb by ELISA. (FIG. 13A) The purity of IgG was analyzed by SDS-PAGE with coomassie blue staining. (FIG. 13B) ELISA was performed to examine the binding of 1 µg/ml anti-SSEA-4 hAb to the glycans as figure indicated. Commercial anti-SSEA-4 mouse monoclonal antibody (MC813-70; 0.5 µg/ml) and normal human IgG (NHIgG) were used as a positive and negative control, respectively. H.C.: heavy chain. L.C.: light chain. A490: absorbance at 490 nm FIGS. 14A-14B. Analysis of the binding activity of p2-78 hAb by glycan array.

(FIG. 14A) The commercially available IgM antibody, MC631 (5 µg/ml), was used as a positive control. (FIG. 14B) The p2-78 hAb (7.5 µg/ml) recognized SSEA4, Sialyl-SSEA4, SSEA4Gc, and Gb5 (SSEA3), and GloboH.

Figure 15A:
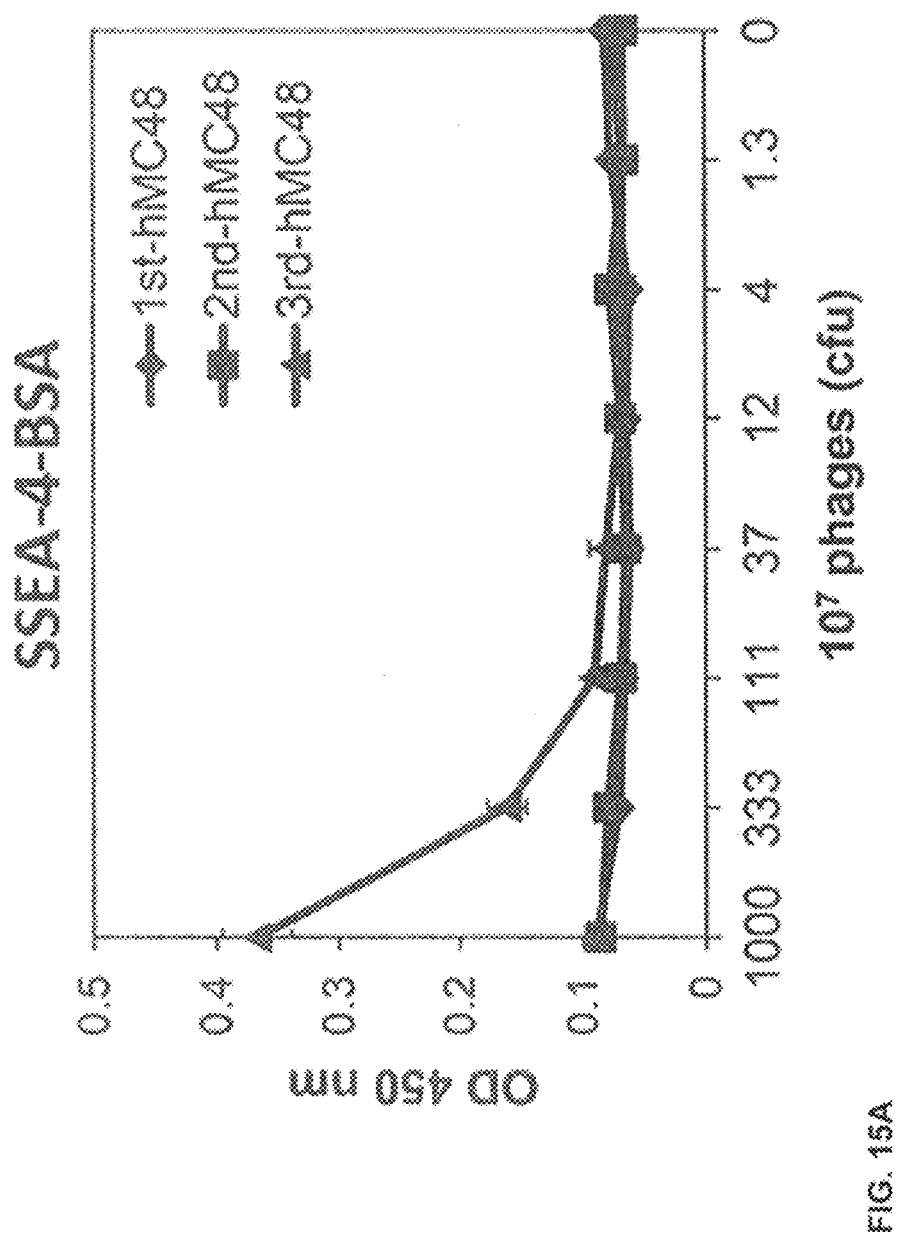
Figure 15B:
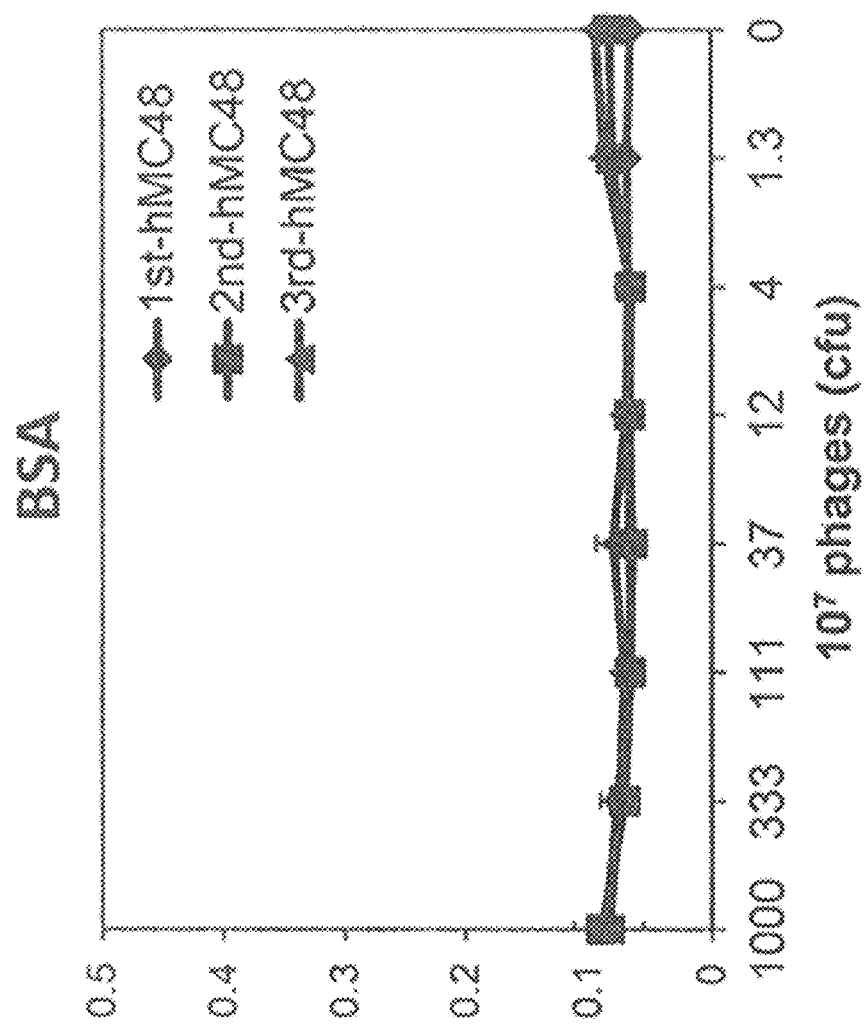

FIGS. 15A-15B. Binding assay of hMC48 scFv phage clones.

The binding activity of humanized MC48 clones was examined by ELISA. The $3^{rd}$ scFv phage clone of humanized MC48 variant could bind to SSEA-4 (FIG. 15A) in a dose-dependent manner but not to BSA control protein (FIG. 15B).

Figure 16A:
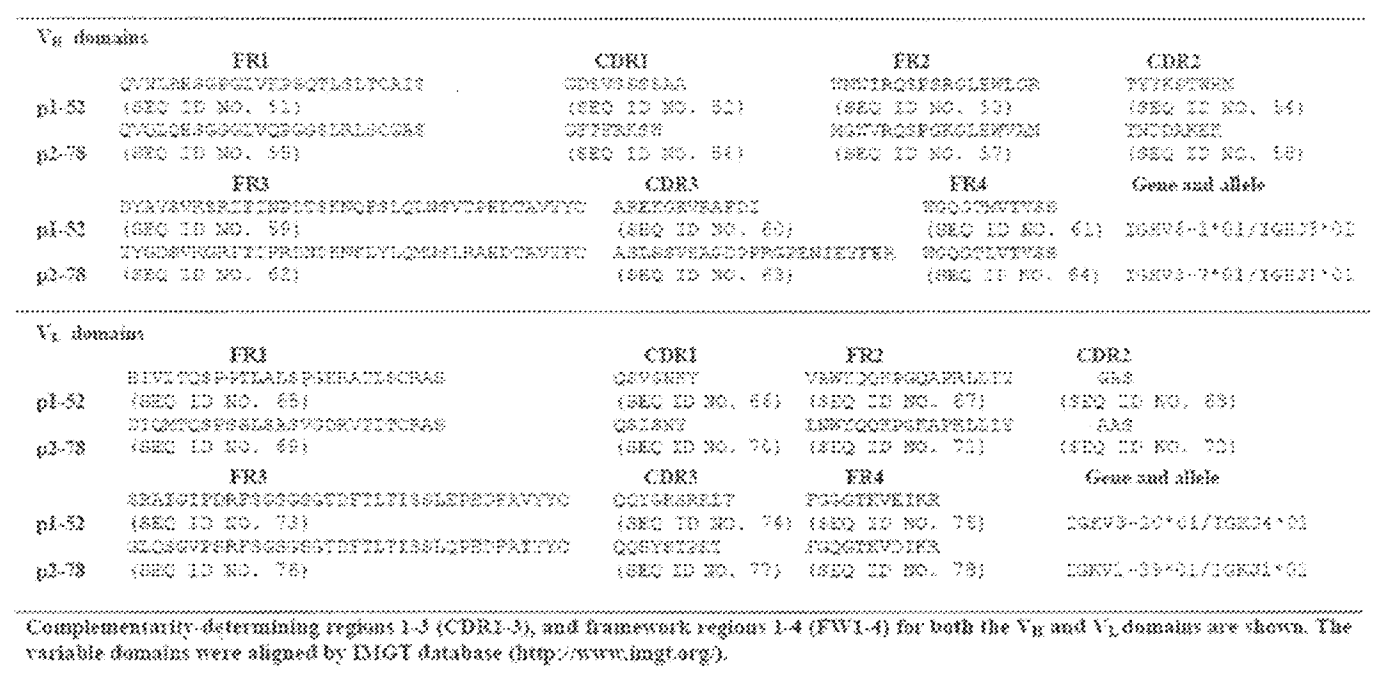
Figure 16B:
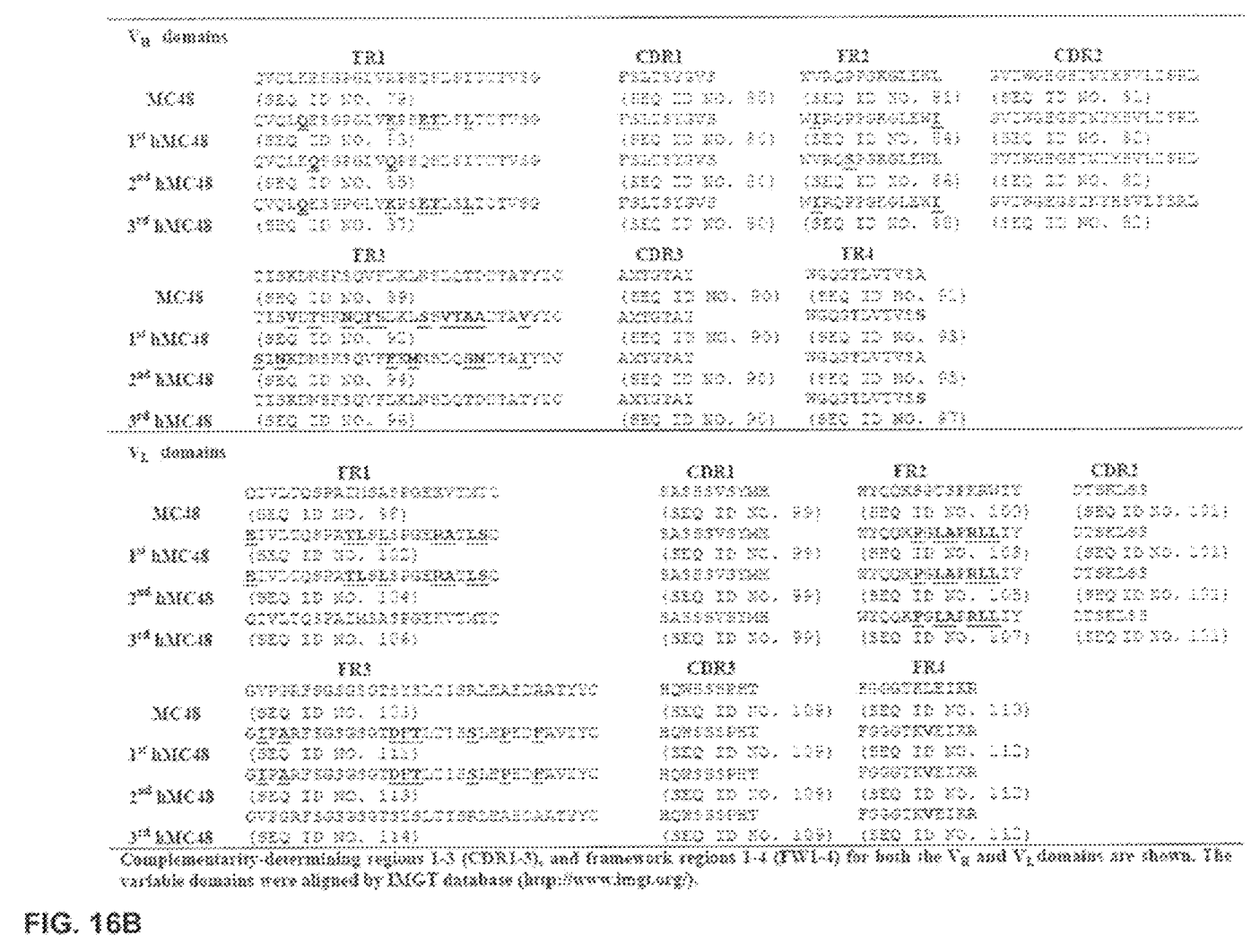

FIGS. 16A-16B. (FIG. 16A) Complementary-determining regions 1-3 (CDR1-3), and framework regions 1-4 (FW1-4) for both the $V_H$ and $V_L$ domains from exemplary antibody clones are shown. The variable domains were aligned by IMGT database. (FIG. 16B) Complementary-determining regions 1-3 (CDR1-3), and framework regions 1-4 (FW1-4) for both the VH and VL domains are shown. The variable domains were aligned by IMGT database.

FIG. 17A-17B. Illustrates exemplary amino acid and nucleotide sequences of exemplary glycoantibody variants based on mouse monoclonal antibody MC48 (MC48 is an exemplary anti-SSEA-4 mouse monoclonal antibody used for humanization). The exemplary humanized glycoantibody variants are generated as set forth in the examples sections. FIGS. 17A and 17B describe exemplary humanized glycoantibody sequences obtained from each corresponding round of humanization.

Figure 18:
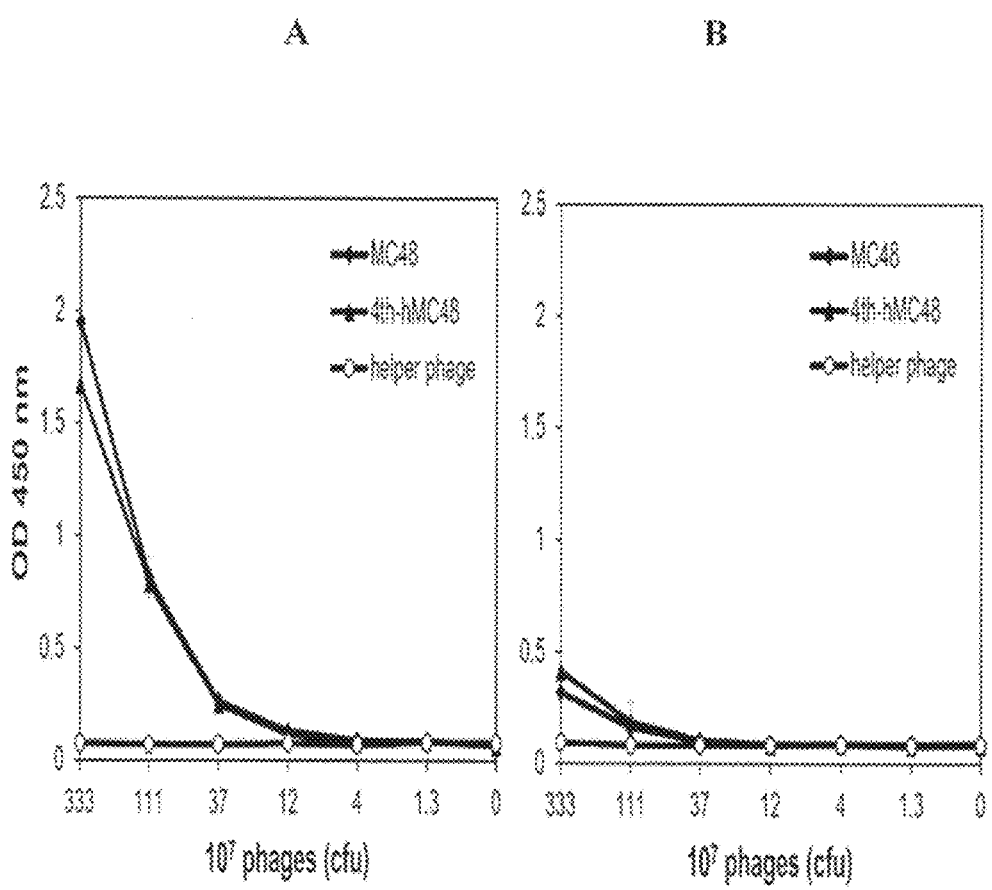

FIG. 18 Binding assay of hMC48 scFv phage clones. The binding activity of humanized MC48 clones was examined by ELISA. The $4^{th}$ scFv phage clone of humanized MC48 variant could bind to SSEA-4 (A) in a dose-dependent manner but not to BSA control protein (B).

DETAILED DESCRIPTION OF THE INVENTION

Accordingly, antibody methods and compositions directed to the markers for use in diagnosing and treating a broad spectrum of cancers are provided. Antibodies triple-targeting Globo H, SSEA-3 and SSEA-4, antibodies dual-targeting Globo H and SSEA-3, and anti-SSEA-4 antibodies were developed and disclosed herein. Methods of use include, without limitation, cancer therapies and diagnostics.

The antibodies described herein can bind to a broad spectrum of Globo H, SSEA3 and SSEA-4-expressing cancer cells, thereby facilitating cancer diagnosis and treatment. Cells that can be targeted by the antibodies include carcinomas, such as those in brain, lung, breast, mouse, esophagus, stomach, liver, bile duct, pancreas, colon, kidney, cervix, ovary, prostate cancer, etc.

Definitions

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except praline.

As used herein, the term "antigen" is defined as any substance capable of eliciting an immune response.

As used herein, the term "immunogenicity" refers to the ability of an immunogen, antigen, or vaccine to stimulate an immune response.

As used herein, the term "CD1d" refers to a member of the CD1 (cluster of differentiation 1) family of glycoproteins expressed on the surface of various human antigen-presenting cells. CD1d presented lipid antigens activate natural killer T cells. CD1d has a deep antigen-binding groove into which glycolipid antigens bind. CD1d molecules expressed on dendritic cells can bind and present glycolipids, including alpha-GalCer analogs such as C34.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "antigen specific" refers to a property of a cell population such that supply of a particular antigen, or a fragment of the antigen, results in specific cell proliferation.

As used herein, the term "specifically binding," refers to the interaction between binding pairs (e.g., an antibody and an antigen). In various instances, specifically binding can be embodied by an affinity constant of about 10-6 moles/liter, about 10-7 moles/liter, or about 10-8 moles/liter, or less.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In one embodiment, the antibody will be purified (1) to greater than 95% by weight of antibody as determined by, for example, the Lowry method, and in some embodiments more than 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 μM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. In each experiment, a spot was activated and ethanolamine blocked without immobilizing protein, to be used for reference subtraction. For kinetics measurements, two-fold serial dilutions of Fab (0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgrams. The equilibrium dissociation constant (Kd) is calculated as the ratio $k_{off}/k_{on}$. See, e.g., Chen, Y., et al., (1999) J. Mol Biol 293:865-881. If the on-rate exceeds 106 M–1s–1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

An "on-rate" or "rate of association" or "association rate" or "kon" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates (kon) and dissociation rates (koff) are calculated using a simple one-to-one Langmuir binding model (BIAcore Evaluation Software version 3.2) by simultaneously fitting the association and dissociation sensorgram. The equilibrium dissociation constant (Kd) was calculated as the ratio koff/kon. See, e.g., Chen, Y., et al., (1999) J. Mol Biol 293:865-881. However, if the on-rate exceeds 106 M–1s–1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (x) and lambda (k), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called $\alpha$, $\delta$, $\epsilon$, $\gamma$, and $\mu$, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, e.g., the individual antibodies comprising the population are identical except for possible naturally occurring mutations that may be present in minor amounts or comprising only homogeneous glycoform profile (having only a single glycan or single glycan profile on a glycoantibody in a population). Examples of homogeneous antibody composition to enhance the effector functions by using the 2,3- and 2,6-sialyl and defucosylated complex bi-antennary glycans at the Fc-297 position are described in U.S. Ser. No. 12/959,351. Thus, the modifier "monoclonal"

indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816,567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

Loop Kabat AbM Chothia Contact
L1 L24-L34 L24-L34 L26-L32 L30-L36
L2 L50-L56 L50-L56 L50-L52 L46-L55
L3 L89-L97 L89-L97 L91-L96 L89-L96
H1 H31-H35B H26-H35B H26-H32 H30-H35B
(Kabat Numbering)
H1 H31-H35 H26-H35 H26-H32 H30-H35
(Chothia Numbering)
H2 H50-H65 H50-H58 H53-H55 H47-H58
H3 H95-H102 H95-H102 H96-H101 H93-H101

Hypervariable regions may comprise "extended hypervariable regions" as follows: 24-36 or 24-34 (L1), 46-56 or 50-56 or 49-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO93/1161; and Hollinger et al., Proc. Natl. Acad. Sci. USA 90: 6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" or a "subject" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells. The term is intended to include radioactive isotopes (e.g., At211, 1131, 1125, Y90, Re186, Re188, Sm153, Bi212, P32, Pb212 and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolyticenzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Antibodies Triple-Targeting Globo H, SSEA3 and SSEA-4

One aspect of the present disclosure features the new antibody triple-targeting Globo H, SSEA3 and SSEA-4. The triple-targeting antibody specifically binds to Fucα1→2Galβ1→3GalNAcβ1→3Galα1→4Galβ1→4Glcβ1 (Globo H hexasaccharide) and Galβ1→3GalNAcβ1→3Galα1→4Galβ1→4Glcβ1 (SSEA-3 pentasaccharide) and Neu5Acα2→3Galβ1→3GalNAcβ1→3Galα1→4Galβ1→4Glcβ1 (SSEA-4 hexasaccharide). In one example, the triple-targeting antibody is mAb 651.

The mAb 651 is a mouse monoclonal antibody, produced by the hybridoma cell line. The triple-targeting antibody described herein can contain the same $V_H$ and $V_L$ chains as antibody MC651. Antibodies binding to the same epitope as MC651 are also within the scope of this disclosure.

TABLE 1

Amino Acid and Nucleotide Sequences of Antibody MC651

| SEQ ID NO | DESCRIPTION | SEQUENCE |
|---|---|---|
| 11 | MC651 VH nucleotide sequence | GAGGTCCAGCTGCAACAATCTGGGTCTGT GCTGGTGAGGCCTGGAGCTTCAGTGAAGC TGTCCTGCAAGGCTTCTGGCTACACCTTC ACCAACTCCTGGATGCACTGGGCGAAGCA GAGGCCTGGACAAGGCCTTGTGTGGATTG GAGAGATTGATCCTAATACTGGTAATACT AACTACAATGAGAACTTCAAGGGCAAGGC CACACTGACTGTAGACACATCCTCCACCA CAGCCTACGTGGATCTCAGCAGCCTGACA TCTGAAGACTCTGCGGTCTATTACTGTGC AAGAGGACTCGGGCTACTTGTTTACTGGG GCCAAGGGACTCTGGTCACTGTCTCTGCA |
| 12 | MC651 VL nucleotide sequence | CAAATTGTTCTCACCCAGTCTCCAGCAAT CCTGTCTGCATCTCCAGGGGAGAAGGTCA CAATGACTTGCAGGGCCAGCTCAAGTGTA AGTTACATGCACTGGTACCAGCAGAAGCC AGGATCCTCCCCCAAACCCTGGATTTATG TCACATCCAACCTGACTTCTGGAGTCCCT GTTCGCTTCAGTGGCAGTGGGTCTGGGAC CTCTTACTCTCTCACAATCAGCAGAGTGG AGGCTGAAGATGCTGCCACTTATTACTGC CAGCAGTGGAGTAATAACCCGTGGACGTT CGGTGGAGGCACCAAGCTGGAAATCAAA |
| 13 | MC651 VH amino acid sequence | EVQLQQSGSVLVRPGASVKLSCKASGYTF TNSWMHWAKQRPGQGLVWIGEIDPNTGNT NYNENFKGKATLTVDTSSTTAYVDLSSLT SEDSAVYYCARGLGLLVYWGQGTLVTVSA |
| 14 | MC651 VL amino acid sequence | QIVLTQSPAILSASPGEKVTMTCRASSSV SYMHWYQQKPGSSPKPWIYVTSNLTSGVP VRFSGSGSGTSYSLTISRVEAEDAATYYC QQWSNNPWTFGGGTKLEIK |
| 15 | MC651 VL CDR1 | SSVSY |
| 16 | MC651 VL CDR2 | VTS |
| 17 | MC651 VL CDR3 | QQWSNNPWT |
| 18 | MC651 VH CDR1 | GYTFTNSW |
| 19 | MC651 VH CDR2 | IDPNTGNT |
| 20 | MC651 VH CDR3 | ARGLGLLVY |

Antibodies Dual-Targeting Globo H and SSEA3

One aspect of the present disclosure features the new antibodies dual-targeting Globo H and SSEA3. The dual-targeting antibody specifically binds to Fucα1→2Galβ1→3GalNAcβ1→3Galα1→4Galβ1→4 Glcβ1 (Globo H hexasaccharide) and Galβ1→3GalNAcβ1→3Galα1→4Galβ1→4Glcβ1 (SSEA-3 pentasaccharide). In one example, the dual-targeting antibody is mAb 273.

The mAb 273 is a mouse monoclonal antibody, produced by the hybridoma cell line. The dual-targeting antibodies described herein can contain the same $V_H$ and $V_L$ chains as antibody MC273. Antibodies binding to the same epitope as MC273 are also within the scope of this disclosure.

TABLE 2

Amino Acid and Nucleotide Sequences of Antibody MC273

| SEQ ID NO | DESCRIPTION | SEQUENCE |
|---|---|---|
| 1 | MC273 VH nucleotide sequence | CAGGTGCAGCTGAAGCAGTCTGGACCTG AGCTAGTGAAGACTGGGGCTTCAGTGAA GATATCCTGCAAGGCTTCTGGTTACTCA TTCACTGGTTACTACATGCACTGGGTCA AGCAGAGCCATGGAAAGAGCCTTGAGTG GATTGGATATATTAGTTGTTACAATGGT GGTACTAGGTACAACCTGAAGTTCAAGG GCAAGGCCACATTTACTGTAGACACATC CTCCACCACAGCCTACATGCAGTTCAAC AACCTGACATCTGAAGACTCTGCGGTCT ATTACTGTGCAAGAGGGGGGTACGACGA GGGTGACTACTGGGGCCAAGGCACCACT CTCACAGTCTCCTCA |
| 2 | MC273 VL nucleotide sequence | GATATTGTAATGACACAGTCTCCCAAAT CCATATTCATGTCAGTTGGAGAGAGGGT CACCTTGAGCTGCAAGGCCAGTGAGAAT GTGGGTACTTATGTATCCTGGTATCAAC AGAAACCAGAGCAGTCTCCTAAACTGAT GATATACGGGGCATCCAACCGGAACACT GGGGTCCCCGATCGCTTCACAGGCAGTG GATCTGCAACAGATTTCACTCTGACCAT CAGCAGTGTGCAGGCTGAAGACCTTGCA GATTATCACTGTGGACAGAGTTACACCT ATCCGTACACGTTCGGAGGGGGGACCAA GCTGGAAATCAAA |
| 3 | MC273 VH amino acid sequence | QVQLKQSGPELVKTGASVKISCKASGYS FTGYYMHWVKQSHGKSLEWIGYISCYNG GTRYNLKFKGKATFTVDTSSTTAYMQFN NLTSEDSAVYYCARGGYDEGDYWGQGTT LTVSS |
| 4 | MC273 VL amino acid sequence | DIVMTQSPKSIFMSVGERVTLSCKASEN VGTYVSWYQQKPEQSPKLMIYGASNRNT GVPDRFTGSGSATDFTLTISSVQAEDLA DYHCGQSYTYPYTFGGGTKLEIK |
| 5 | MC273 VL CDR1 | ENVGTY |
| 6 | MC273 VL CDR2 | GAS |
| 7 | MC273 VL CDR3 | GQSYTYPYT |
| 8 | MC273 VH CDR1 | GYSFTGYY |
| 9 | MC273 VH CDR2 | ISCYNGGT |
| 10 | MC273 VH CDR3 | ARGGYDEGDY |

Antibodies Specific To SSEA4

One aspect of the present disclosure features the new antibodies specific to SSEA-4. The anti-SSEA-4 antibody binds to Neu5Acα2→3Galβ1→3GalNAcβ1→3Galα1→4Galβ1→4Glcβ1 (SSEA-4 hexasaccharide). In some examples, the antibody is capable of binding Neu5Gcα2→3Galβ1→3GalNAcβ1→3Galα1→4Galβ1→4Glcβ1 (an analogue of SSEA-4 hexasaccharide). Preferably, the antibody is not a mouse IgG3 (e.g., mAb MC-831-70), and the antibody is not amouse IgM (e.g., anti-RM1). Examples of the antibodies include, but are not limited to, mAbs 45 and 48.

Monoclonal antibody MC45 is an anti-SSEA-4 mouse monoclonal antibody, produced by the hybridoma cell line. The anti-SSEA-4 antibody described herein can contain the same $V_H$ and $V_L$ chains as antibody MC45. Antibodies binding to the same epitope as MC45 are also within the scope of this disclosure.

TABLE 3

Amino Acid and Nucleotide Sequences of Antibody MC45

| SEQ ID NO | DESCRIPTION | SEQUENCE |
|---|---|---|
| 21 | MC45 VH nucleotide sequence | CAGGTGCAGCTGAAGGAGTCAGGACCTGG CCTGGTGGCGCCCTCACAGAGCCTGTCCA TCACATGCACTGTCTCAGGGTTCTCATTA AGCAGATATGGTGTAAGCTGGGTTCGCCA GCCTCCAGGAAAGGGTCTGGAGTGGCTGG GAGTAATATGGGGTGACGGGAGCACAAAT TATCATTCAGCTCTCATATCCAGACTGAG CATCAGCAAGGATAACTCCAAGAGCCAAG TTTTCTTAAAACTGAACAGTCTGCAAACT GATGACACAGCCACGTACTACTGTGCCAT GACTGGGACAGCTTACTGGGGCCAAGGGA CTCTGGTCACTGTCTCTGCA |
| 22 | MC45 VL nucleotide sequence | CAAATTGTTCTCACCCAGTCTCCAGCAAT CATGTCTGCATCTCCAGGGGAGAAGGTCA CCATGACCTGCAGTGCCAGCTCAAGTGTA AATTACATGCACTGGTACCAGCAGAAGTC AGGCACCTCCCCCAAAAGATGGATTTATG ACACATCCAAACTGGCTTCTGGAGTCCCT GCTCGCTTCAGTGGCAGTGGGTCTGGGAC CTCTTACTCTCACAATCAGCGGCATGG AGGCTGAAGATGCTGCCACTTATTACTGC CACCAGTGGAATAGTAGCCCACACACGTT CGGAGGGGGGACCAAGCTGGAAATAAAA |
| 23 | MC45 VH amino acid sequence | QVQLKESGPGLVAPSQSLSITCTVSGFSL SRYGVSWVRQPPGKGLEWLGVIWGDGSTN YHSALISRLSISKDNSKSQVFLKLNSLQT DDTATYYCAMTGTAYWGQGTLVTVSA |
| 24 | MC45 VL amino acid sequence | QIVLTQSPAIMSASPGEKVTMTCSASSSV NYMHWYQQKSGTSPKRWIYDTSKLASGVP ARFSGSGSGTSYSLTISGMEAEDAATYYC HQWNSSPHTFGGGTKLEIK |
| 25 | MC45 VL CDR1 | SSVNY |
| 26 | MC45 VL CDR2 | DTS |
| 27 | MC45 VL CDR3 | HQWNSSPHT |
| 28 | MC45 VH CDR1 | GFSLSRYG |
| 29 | MC45 VH CDR2 | IWGDGST |
| 30 | MC45 VH CDR3 | AMTGTAY |

Monoclonal antibody MC48 is produced by the hybridoma cell line. The anti-SSEA-4 antibody described herein can contain the same V$_H$ and V$_L$ chains as antibody MC48 or variants thereof. Antibodies binding to the same epitope as MC48 are also within the scope of this disclosure.

TABLE 4

Amino Acid and Nucleotide Sequences of Antibody MC48

| SEQ ID NO | DESCRIPTION | SEQUENCE |
|---|---|---|
| 41 | MC48 VH nucleotide sequence | CAGGTGCAGCTGAAGGAGTCAGGACCTGG CCTGGTGGCGCCCTCACAGAGCCTGTCCA TCACATGCACTGTCTCAGGGTTCTCATTA ACCAGCTATGGTGTAAGCTGGGTTCGCCA GCCTCCAGGAAAGGGTCTGGAGTGGCTGG GAGTAATATGGGGTGAGGGGAGCACAAAT TATCATTCAGTTCTCATATCCAGACTGAC CATTAGTAAGGATAACTCCAAGAGCCAAG TTTTCTTAAAACTGAACAGTCTGCAAACT GATGACACAGCCACGTACTACTGTGCCAT GACTGGGACAGCTTACTGGGGCCAAGGGA CTCTGGTCACTGTCTCTGCA |
| 42 | MC48 VL nucleotide sequence | CAAATTGTTCTCACCCAGTCTCCAGCAAT CATGTCTGCATCTCCAGGGGAGAAGGTCA CCATGACCTGCAGTGCCAGCTCAAGTGTA AGTTACATGCACTGGTACCAGCAGAAGTC AGGCACCTCCCCCAAAAGATGGATTTATG ACACATCCAAACTGTCTTCTGGAGTCCCT GGTCGCTTCAGTGGCAGTGGGTCTGGGAC CTCTTACTCTCTCACAATCAGCAGGTTGG AGGCTGAAGATGCTGCCACTTATTACTGC CATCAGTGGAGTAGTAGTCCACACACGTT CGGAGGGGGGACCAAGTTGGAGATAAAA |
| 43 | MC48 VH amino acid sequence | QVQLKESGPGLVAPSQSLSITCTVSGFSL TSYGVSWVRQPPGKGLEWLGVIWGEGSTN YHSVLISRLTISKDNSKSQVFLKLNSLQT DDTATYYCAMTGTAYWGQGTLVTVSA |
| 44 | MC48 VL amino acid sequence | QIVLTQSPAIMSASPGEKVTMTCSASSSV SYMHWYQQKSGTSPKRWIYDTSKLSSGVP GRFSGSGSGTSYSLTISRLEAEDAATYYC HQWSSSPHTFGGGTKLEIK |
| 45 | MC48 VL CDR1 | SSVSY |
| 46 | MC48 VL CDR2 | DTS |
| 47 | MC48 VL CDR3 | HQWSSSPHT |
| 48 | MC48 VH CDR1 | GFSLTSYG |
| 49 | MC48 VH CDR2 | IWGEGST |
| 50 | MC48 VH CDR3 | AMTGTAY |

One aspect of the present disclosure provides humanized glycoantibodies based on the modification of the MC48. Exemplars and their amino acid and nucleic acid structures/sequences are provided below:

TABLE 17-0

Amino Acid and Nucleotide Sequences of Mouse Monoclonal Antibody MC48.

| SEQ ID NO | DESCRIPTION | SEQUENCE |
|---|---|---|
| 41 | MC48 VH nucleotide sequence | CAGGTGCAGCTGAAGGAGTCAGGACCTGG CCTGGTGGCGCCCTCACAGAGCCTGTCCA TCACATGCACTGTCTCAGGGTTCTCATTA ACCAGCTATGGTGTAAGCTGGGTTCGCCA GCCTCCAGGAAAGGGTCTGGAGTGGCTGG GAGTAATATGGGGTGAGGGGAGCACAAAT TATCATTCAGTTCTCATATCCAGACTGAC CATTAGTAAGGATAACTCCAAGAGCCAAG TTTTCTTAAAACTGAACAGTCTGCAAACT GATGACACAGCCACGTACTACTGTGCCAT GACTGGGACAGCTTACTGGGGCCAAGGGA CTCTGGTCACTGTCTCTGCA |
| 42 | MC48 VL nucleotide sequence | CAAATTGTTCTCACCCAGTCTCCAGCAAT CATGTCTGCATCTCCAGGGGAGAAGGTCA CCATGACCTGCAGTGCCAGCTCAAGTGTA AGTTACATGCACTGGTACCAGCAGAAGTC AGGCACCTCCCCCAAAAGATGGATTTATG ACACATCCAAACTGTCTTCTGGAGTCCCT GGTCGCTTCAGTGGCAGTGGGTCTGGGAC CTCTTACTCTCTCACAATCAGCAGGTTGG |

TABLE 17-0 -continued

Amino Acid and Nucleotide Sequences of Mouse Monoclonal Antibody MC48.

| SEQ ID NO | DESCRIPTION | SEQUENCE |
|---|---|---|
| | | AGGCTGAAGATGCTGCCACTTATTACTGC CATCAGTGGAGTAGTAGTCCACACACGTT CGGAGGGGGGACCAAGTTGGAGATAAAA |
| 43 | MC48 VH amino acid sequence | QVQLKESGPGLVAPSQSLSITCTVSGFSL TSYGVSWVRQPPGKGLEWLGVIWGEGSTN YHSVLISRLTISKDNSKSQVFLKLNSLQT DDTATYYCAMTGTAYWGQGTLVTVSA |
| 44 | MC48 VL amino acid sequence | QIVLTQSPAIMSASPGEKVTMTCSASSSV SYMHWYQQKSGTSPKRWIYDTSKLSSGVP GRFSGSGSGTSYSLTISRLEAEDAATYYC HQWSSSPHTFGGGTKLEIK |
| 45 | MC48 VL CDR1 | SSVSY |
| 46 | MC48 VL CDR2 | DTS |
| 47 | MC48 VL CDR3 | HQWSSSPHT |
| 48 | MC48 VH CDR1 | GFSLTSYG |
| 49 | MC48 VH CDR2 | IWGEGST |
| 50 | MC48 VH CDR3 | AMTGTAY |

TABLE 17-1

Amino Acid and Nucleotide Sequences of Humanized Monoclonal Antibody MC48 (1$^{st}$)

| SEQ ID NO | DESCRIPTION | SEQUENCE |
|---|---|---|
| 115 | hMC48 VH nucleotide sequence | CAGGTGCAGCTGCAAGAGTCAGGACCTG GCCTGGTGAAACCCTCAGAAACTCTGTC CCTTACATGCACTGTCTCCAGGGTTCTCA TTAACCAGCTATGGTGTAAGCTGGATTC GCCAGCCTCCAGGAAAGGGTCTGGAGTG GATTGGAGTAATATGGGGTGAGGGGAGC ACAAATTATCATTCAGTTCTCATATCCA GACTGACCATTAGTGTGGATACCTCCAA GAATCAATTTAGCTTAAAACTGAGCAGT GTTACCGCTGCTGACACAGCCGTTTACT ACTGTGCCATGACTGGGACAGCTTACTG GGGCCAAGGGACTCTGGTCACTGTCTCT AGC |
| 116 | hMC48 VL nucleotide sequence | GAGATTGTGCTGACCCAGAGCCCTGCCA CACTGTCACTGAGCCCAGGCGAGCGAGC CACACTGTCCTGTTCTGCTAGCTCCTCT GTCTCCTACATGCATTGGTATCAGCAGA AGCCAGGACTGGCACCACGACTGCTGAT CTATGACACTTCTAAACTGAGTTCAGGC ATTCCCGCCAGATTCAGTGGCTCAGGGA GCGGAACCGACTTTACTCTGACCATTAG CTCCCTGGAGCCTGAAGATTTCGCCGTG TACTATTGCCATCAGTGGTCATCAAGCC CTCATACCTTCGGGGGGGGACTAAGGT GGAAATCAAACGC |
| 117 | hMC48 VH amino acid sequence | QVQLQESGPGLVKPSETLSLTCTVSGFS LTSYGVSWIRQPPGKGLEWIGVIWGEGS TNYHSVLISRLTISVDTSKNQFSLKLSS VTAADTAVYYCAMTGTAYWGQGTLVTVS S |
| 118 | hMC48 VL amino acid sequence | EIVLTQSPATLSLSPGERATLSCSASSS VSYMHWYQQKPGLAPRLLIYDTSKLSSG IPARFSGSGSGTDFTLTISSLEPEDFAV YYCHQWSSSPHTFGGGTKVEIKR |

TABLE 17-1 -continued

Amino Acid and Nucleotide Sequences of Humanized Monoclonal Antibody MC48 (1$^{st}$)

| SEQ ID NO | DESCRIPTION | SEQUENCE |
|---|---|---|
| 119 | hMC48 VL CDR1 | SSVSY |
| 120 | hMC48 VL CDR2 | DTS |
| 121 | hMC48 VL CDR3 | HQWSSSPHT |
| 122 | hMC48 VH CDR1 | GFSLTSYG |
| 123 | hMC48 VH CDR2 | IWGEGST |
| 124 | hMC48 VH CDR3 | AMTGTAY |

TABLE 17-2

Amino Acid and Nucleotide Sequences of Humanized Monoclonal Antibody MC48 (2$^{nd}$)

| SEQ ID NO | DESCRIPTION | SEQUENCE |
|---|---|---|
| 125 | hMC48 VH nucleotide sequence | CAGGTGCAGCTGAAGCAGAGCGGACCTG GCCTGGTGCAGCCCTCACAGAGCCTGAG CATCACTTGTACCGTCAGTGGATTCTCC CTGACATCTTACGGCGTGTCTTGGGTCA GGCAGAGCCCTGGCAAGGGGCTGGAGTG GCTGGGCGTGATCTGGGGAGAAGGCTCA ACTAACTATCACAGCGTCCTGATCAGTC GCCTGTCAATTAACAAGGACAATTCTAA AAGTCAGGTGTTCTTTAAAATGAACAGC CTGCAGTCCAATGATACCGCCATCTACT ATTGCGCTATGACCGGCACAGCATACTG GGGCAGGGAACACTGGTGACTGTCTCC GCT |
| 126 | hMC48 VL nucleotide sequence | GAGATTGTGCTGACCCAGAGCCCTGCCA CACTGTCACTGAGCCCAGGCGAGCGAGC CACACTGTCCTGTTCTGCTAGCTCCTCT GTCTCCTACATGCATTGGTATCAGCAGA AGCCAGGACTGGCACCACGACTGCTGAT CTATGACACTTCTAAACTGAGTTCAGGC ATTCCCGCCAGATTCAGTGGCTCAGGGA GCGGAACCGACTTTACTCTGACCATTAG CTCCCTGGAGCCTGAAGATTTCGCCGTG TACTATTGCCATCAGTGGTCATCAAGCC CTCATACCTTCGGGGGGGGACTAAGCT GGAAATCAAACGC |
| 127 | hMC48 VH amino acid sequence | QVQLKQSGPGLVQPSQSLSITCTVSGFS LTSYGVSWVRQSPGKGLEWLGVIWGEGS TNYHSVLISRLSINKDNSKSQVFFKMNS LQSNDTAIYYCAMTGTAYWGQGTLVTVS A |
| 128 | hMC48 VL amino acid sequence | EIVLTQSPATLSLSPGERATLSCSASSS VSYMHWYQQKPGLAPRLLIYDTSKLSSG IPARFSGSGSGTDFTLTISSLEPEDFAV YYCHQWSSSPHTFGGGTKVLEIKR |
| 129 | hMC48 VL CDR1 | SSVSY |
| 130 | hMC48 VL CDR2 | DTS |
| 131 | hMC48 VL CDR3 | HQWSSSPHT |
| 132 | hMC48 VH CDR1 | GFSLTSYG |
| 133 | hMC48 VH CDR2 | IWGEGST |
| 134 | hMC48 VH CDR3 | AMTGTAY |

TABLE 17-3

Amino Acid and Nucleotide Sequences of Humanized Monoclonal Antibody MC48 (3rd)

| SEQ ID NO | DESCRIPTION | SEQUENCE |
|---|---|---|
| 135 | hMC48 VH nucleotide sequence | CAGGTGCAGCTGCAGGAAAGCGGACCCG GACTGGTGAAACCTAGCGAAACACTGAG CCTTGACTTGTACCGTGAGCGGATTTTCC CTGACCTCTTATGGAGTGAGCTGGATCA GACAGCCCCTGGCAAGGGACTGGAGTG GATCGGCGTGATTTGGGGAGAAGGCTCC ACAAACTATCACAGTGTCCTGATCTCAC GACTGACTATTTCTAAGGACAACTCTAA AAGTCAGGTCTTCCTGAAACTGAATAGT CTGCAGACTGACGATACCGCTACATACT ATTGCGCAATGACAGGACAGCATACTG GGGACAGGGAACCCTGGTGACAGTCAGC TCC |
| 136 | hMC48 VL nucleotide sequence | CAGATCGTGCTGACACAGTCCCCTGCAA TTATGTCAGCCAGCCCAGGGGAAAAGGT GACAATGACTTGTAGTGCTTCTAGTTCA GTCTCATACATGCATTGGTATCAGCAGA AGCCAGGCCTGGCCCCCAGACTGCTGAT CTACGACACCTCCAAACTGAGCTCCGGC GTGCCCGGGAGATTTTCCGGCTCTGGGA GTGGAACTTCATATAGCCTGACCATTTC TAGGCTGGAGGCCGAAGATGCCGCTACA TACTATTGCCACCAGTGGAGCAGTAGCC CCCATACATTCGGAGGCGGGACCAAAGT GGAAATCAAACGC |
| 137 | hMC48 VH amino acid sequence | QVQLQESGPGLVKPSETLSLTCTVSGFS LTSYGVSWIRQPPGKGLEWIGVIWGEGS TNYHSVLISRLTISKDNSKSQVFLKLNS LQTDDTATYYCAMTGTAYWGQGTLVTVS S |
| 138 | hMC48 VL amino acid sequence | QIVLTQSPAIMSASPGEKVTMTCSASSS VSYMHWYQQKPGLAPRLLIYDTSKLSSG VPGRFSGSGSGTSYSLTISRLEAEDAAT YYCHQWSSSPHTFGGGTKVEIKR |
| 139 | hMC48 VL CDR1 | SSVSY |
| 140 | hMC48 VL CDR2 | DTS |
| 141 | hMC48 VL CDR3 | HQWSSSPHT |
| 142 | hMC48 VH CDR1 | GFSLTSYG |
| 143 | hMC48 VH CDR2 | IWGEGST |
| 144 | hMC48 VH CDR3 | AMTGTAY |

TABLE 17-4

Amino Acid and Nucleotide Sequences of Humanized Monoclonal Antibody MC48 (4th)

| SEQ ID NO | DESCRIPTION | SEQUENCE |
|---|---|---|
| 145 | hMC48 VH nucleotide sequence | CAGGTCCAGCTGAAAGAGAGCGGCCCCG GACTGGTCGCCCCTTCACAGAGCCTGAG CATTACTTGCACCGTGAGCGGATTTTCA CTGACCAGCTACGGAGTGAGCTGGATTA GACAGCCTCCTGGCAAGGGACTGGAGTG GATCGGCGTGATTTGGGGAGAAGGCAGC ACCAACTATCACAGTGTCCTGATCTCAC GCCTGACAATTTCCAAGGACAACAGCAA ATCCCAGGTCTTCCTGAAACTGAATTCT CTGCAGACTGACGATACCGCTACATACT ATTGCGCAATGACAGGGACAGCATACTG GGGACAGGGAACCCTGGTGACAGTCAGT AGT |
| 146 | hMC48 VL nucleotide sequence | CAGATCGTGCTGACACAGTCCCCAGCAA TTATGTCTGCCAGTCCCGGGGAGAAGGT GACAATGACTTGTAGTGCCAGCTCCTCT GTCTCATACATGCATTGGTATCAGCAGA AGTCCGGCACATCTCCTAAACGGTGGAT CTACGACACTTCTAAACTGAGTTCAGGC GTGCCCGGGAGATTTTCAGGCAGCGGGT CCGGAACTTCTTATAGTCTGACCATTTC CCGACTGGAGGCCGAAGATGCCGCTACC TACTATTGCCATCAGTGGTCTTCAAGCC CTCATACTTTTGGGGGGGGAACTAAGGT GGAAATCAAGCGA |
| 147 | hMC48 VH amino acid sequence | QVQLKESGPGLVAPSQSLSITCTVSGFS LTSYGVSWIRQPPGKGLEWIGVIWGEGS TNYHSVLISRLTISKDNSKSQVFLKLNS LQTDDTATYYCAMTGTAYWGQGTLVTVS S |
| 148 | hMC48 VL amino acid sequence | QIVLTQSPAIMSASPGEKVTMTCSASSS VSYMHWYQQKSGTSPKRWIYDTSKLSSG VPGRFSGSGSGTSYSLTISRLEAEDAAT YYCHQWSSSPHTFGGGTKVEIKR |
| 149 | hMC48 VL CDR1 | SSVSY |
| 150 | hMC48 VL CDR2 | DTS |
| 151 | hMC48 VL CDR3 | HQWSSSPHT |
| 152 | hMC48 VH CDR1 | GFSLTSYG |
| 153 | hMC48 VH CDR2 | IWGEGST |
| 154 | hMC48 VH CDR3 | AMTGTAY |
| 155 | hMC48 VL FR1 | QIVLTQSPAIMSASPGEKVTMTCSAS |
| 156 | hMC48 VL FR2 | MHWYQQKSGTSPKRWIY |
| 157 | hMC48 VL FR3 | KLSSGVPGRFSGSGSGTSYSLTISRLEA EDAATYYC |
| 158 | hMC48 VL FR4 | FGGGTKVEIKR |
| 159 | hMC48 VH FR1 | QVQLKESGPGLVAPSQSLSITCTVS |
| 160 | hMC48 VH FR2 | VSWIRQPPGKGLEWIGV |
| 161 | hMC48 VH FR3 | NYHSVLISRLTISKDNSKSQVFLKLNSL QTDDTATYYC |
| 162 | hMC48 VH FR4 | WGQGTLVTVSS |

Antibodies Specific to SSEA4 and Fragment Thereof

One aspect of the present disclosure features the new antibodies that bind to SSEA-4 and fragments thereof. The anti-SSEA-4 antibody binds to Neu5Acα2→3 Galβ1→3GalNAcβ1→3Galα1→4Galβ1→4Glcβ1 (SSEA-4 hexasaccharide) and Neu5Acα2→3Galβ1→3GalNAcβ1→3Galα1 (fragment of SSEA-4 hexasaccharide). In some examples, the antibody is capable of Neu5Acα2→3Galβ1→3GalNAcβ1→3Galβ1. In some examples, the antibody is capable of Neu5Gcα2→3Galβ1→3GalNAcβ1→3Galα1→ 4Galβ1→4Glcβ1 (an analogue of SSEA-4 hexasaccharide). In one example, the antibody is mAb 46.

Monoclonal antibody MC46 is produced by the hybridoma cell line. The anti-SSEA-4 antibody described herein can contain the same $V_H$ and $V_L$ chains as antibody MC46. Antibodies binding to the same epitope as MC46 are also within the scope of this disclosure.

TABLE 5

Amino Acid and Nucleotide Sequences of Antibody MC46

| SEQ ID NO | DESCRIPTION | SEQUENCE |
|---|---|---|
| 31 | MC46 VH nucleotide sequence | CAGGTGCAGCTGAAGGAGTCAGGACCTGG CCTGGTGGCGCCCTCACAGAGCCTGTCCA TCACATGCACTGTCTCAGGATTCTCATTA ACCAGCTATGGTATAAGCTGGGTTCGCCA GCCTCCAGGAAAGGGTCTGGAGTGGCTGG GAGTAATATGGGGTGACGGGAGCACAAAT TATCATTCAGCTCTCGTATCCAGACTGAG CATCAGCAAGGATAACTCCAAGAGCCAAG TTTTCTTAAAACTGAACAGTCTGCAAACT GATGACACAGCCACGTACTACTGTGCCAA AACTGGGACATCTTACTGGGGCCAAGGGA CTCTGGTCACTGTCTCTGCA |
| 32 | MC46 VL nucleotide sequence | CAAATTGTTCTCACCCAGTCTCCAGCAAT CATGTCTGCATCTCCAGGGGAGAAGGTCA CCATGACCTGCAGTGCCAGCTCAAGTGTA AGTTACATGCACTGGTACCAGCAGAAGTC AGGCACCTCCCCCAAAAGATGGATTTATG ACACATCCAAACTGGCTTCTGGAGTCCCT GCTCGCTTCAGTGGCAGTGGGTCTGGGAC CTCTTACTCTCTCACAATCAGCAGCATGG AGGCTGAAGATGCTGCCACTTATTACTGC CAGCAGTGGAGTAGTGCCCCACACACGTT CGGAGGGGGGACCAAGCTGGAAATAAAA |
| 33 | MC46 VH amino acid sequence | QVQLKESGPGLVAPSQSLSITCTVSGFSL TSYGISWVRQPPGKGLEWLGVIWGDGSTN YHSALVSRLSISKDNSKSQVFLKLNSLQT DDTATYYCAKTGTSYWGQGTLVTVSA |
| 34 | MC46 VL amino acid sequence | QIVLTQSPAIMSASPGEKVTMTCSASSSV SYMHWYQQKSGTSPKRWIYDTSKLASGVP ARFSGSGSGTSYSLTISSMEAEDAATYYC QQWSSAPHTFGGGTKLEIK |
| 35 | MC46 VL CDR1 | SSVSY |
| 36 | MC46 VL CDR2 | DTS |
| 37 | MC46 VL CDR3 | QQWSSAPHT |
| 38 | MC46 VH CDR1 | GFSLTSYG |
| 39 | MC46 VH CDR2 | IWGDGST |
| 40 | MC46 VH CDR3 | AKTGTSY |

A "MC45 antibody" or "mAb 45" or "antibody from clone MC45" refers to an antibody expressed by clone 45 or to an antibody synthesized in other manners, but having the same CDRs and optionally, the same framework regions as the antibody expressed by clone MC45. Similarly, antibodies MC46 (mAb 46 or clone 46), MC48 (mAb 48 or clone 48), MC273 (mAb 273 or clone 273), MC651 (mAb 651 or clone 651) and the like refer to antibodies expressed by the corresponding clone(s) and/or to antibodies synthesized in other manners, but having the same CDRs and optionally, the same framework regions as the referenced antibodies.

TABLE 6

Comparison of Binding Epitope and Isotype of Antibodies

| Antibody | Isotype | Binding Epitope |
|---|---|---|
| Mbr1 | Mouse IgM | Fucα1→ 2Galβ1→ 3GalNAcβ1→ 3Galα1→ 4Galβ1→ 4Glcβ1 (Globo H) |
| | | Fucα1→ 2Galβ1→ 3GalNAcβ1→ 3Galα1 |
| VK9 | Mouse IgG3 | Fucα1→ 2Galβ→ 3GalNAcβ1→ 3Galα1→ 4Galβ1→ 4Glcβ1 (Globo H) |
| | | Fucα1→ 2Galβ1→ 3GalNAcβ1→ 3Galα1 |
| MC-813-70 | Mouse IgG3 | Neu5Acα2→ 3Galβ1→ 3GalNAcβ1→ 3Galα1→ 4Galβ1→ 4Glcβ1 (SSEA-4) |
| | | Neu5Gcα2→ 3Galβ1→ GalNAcβ1→ 3Galα1→ 4Galβ1→ 4Glcβ1 |
| MC-651 | Mouse IgG1 | Fucα1→ 2Galβ1→ 3GalNAcβ1→ 3Galα1→ 4Galβ1→ 4Glcβ1 (Globo H) |
| | | Galβ1→ 3GalNAcβ1→ 3Galα1→ 4Galβ1→ 4Glcβ1 (SSEA-3) |
| | | Neu5Acα2→ 3Galβ1→ 3GalNAcβ1→ 3Galα1→ 4Galβ1→ 4Glcβ1 (SSEA-4) |
| MC-273 | Mouse IgG1 | Fucα1→ 2Galβ1→ 3GalNAcβ1→ 3Galα1→ 4Galβ1→ 4Glcβ1 (Globo H) |
| | | Galβ1→ 3GalNAcβ1→ 3Galα1→ 4Galβ1→ 4Glcβ1 (SSEA-3) |
| MC-45 | Mouse IgG1 | Neu5Acα2→ 3Galβ1→ 3GalNAcβ1→ 3Galα1→ 4Galβ1→ 4Glcβ1 (SSEA-4) |
| | | Neu5Gcα2→ 3Galβ1→ 3GalNAcβ1→ 3Galα1→ 4Galβ1→ 4Glcβ1 |
| MC-46 | Mouse IgG1 | Neu5Acα2→ 3Galβ1→ 3GalNAcβ1→ 3Galα1→ 4Galβ1→ 4Glcβ1 (SSEA-4) |
| | | Neu5Gcα2→ 3Galβ1→ 3GalNAcβ1→ 3Galα1→ 4Galβ1→ 4Glcβ1 |
| | | Neu5Acα2→ 3Galβ1→ 3GalNAcβ1→ 3Galα1 |
| | | Neu5Acα2→ 3Galβ1→ 3GalNAcβ1→ 3Galβ1 |
| MC-48 | Mouse IgG1 | Neu5Acα2→ 3Galβ1→ 3GalNAcβ1→ 3Galα1→ 4Galβ1→ 4Glcβ1 (SSEA-4) |
| | | Neu5Gcα2→ 3Galβ1→ 3GalNAcβ1→ 3Galα1→ 4Galβ1→ 4Glcβ1 |

Any of the antibodies described herein can be a full length antibody or an antigen-binding fragment thereof. In some examples, the antigen binding fragment is a Fab fragment, a F(ab')2 fragment, or a single-chain Fv fragment. In some examples, the antigen binding fragment is a Fab fragment, a F(ab')2 fragment, or a single-chain Fv fragment. In some examples, the isolated antibody is a human antibody, a humanized antibody, a chimeric antibody, or a single-chain antibody.

Any of the antibodies described herein has one or more characteristics of:
a) is a recombinant antibody, a monoclonal antibody, a chimeric antibody, a humanized antibody, a human antibody, an antibody fragment, a bispecific antibody, a monospecific antibody, a monovalent antibody, an IgG1 antibody, an IgG2 antibody, or derivative of an antibody; b) is a human, murine, humanized, or chimeric antibody, antigen-binding fragment, or derivative of an antibody; c) is a single-chain antibody fragment, a multibody, a Fab fragment, and/or an immunoglobulin of the IgG, IgM, IgA, IgE, IgD isotypes and/or subclasses thereof; d) has one or more of the following characteristics: (i) mediates ADCC and/or CDC of cancer cells; (ii) induces and/or promotes apoptosis of cancer cells; (iii) inhibits proliferation of target cells of cancer cells; (iv) induces and/or promotes phagocytosis of cancer cells; and/or (v) induces and/or promotes the release of cytotoxic agents; e) specifically binds the tumor-associated carbohydrate antigen, which is a tumor-specific carbohydrate antigen; f) does not bind an antigen expressed on non-cancer cells, non-tumor cells, benign cancer cells and/or benign tumor cells; and/or g) specifically binds a tumor-associated carbohydrate antigen expressed on cancer stem cells and on normal cancer cells.

Preferably the binding of the antibodies to their respective antigens is specific. The term "specific" is generally used to refer to the situation in which one member of a binding pair will not show any significant binding to molecules other than its specific binding partner (s) and e.g. has less than about 30%, preferably 20%, 10%, or 1% cross-reactivity with any other molecule other than those specified herein.

The antibodies are suitable bind to its target epitopes with a high affinity (low KD value), and preferably KD is in the nanomolar range or lower. Affinity can be measured by methods known in the art, such as, for example; surface plasmon resonance.

Exemplary Antibody Preparation

Exemplary Antibodies capable of binding to the Globo H epitopes and SSEA-4 epitopes described herein can be made by any method known in the art. See, for example, Harlow and Lane, (1988) Antibodies: A Laboratory Manual, Cold Spring Harbor Laboratory, New York.

Immunization of Host Animals and Hybridoma Technology

Exemplary Polyclonal antibodies against the anti-Globo Hand anti-SSEA-4 antibodies may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum.

Polyclonal antibodies are generally raised in host animals (e.g., rabbit, mouse, horse, or goat) by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, etc.

Any mammalian animal may be immunized with the antigen for producing the desired antibodies. In general, animals of Rodentia, Lagomorpha, or Primates can be used. Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Animals are immunized against the antigen, immunogenic conjugates, or derivatives by combining 1 mg or 1 µg of the peptide or conjugate (for rabbits or mice, respectively) with 3 volumes of Freund's incomplete adjuvant.

Animals can be boosted until the titer plateaus by several administrations of antigen mixed with an appropriately amount of Freund's incomplete adjuvant every 4 to 21 days. Animals are boosted with ⅕ to 1/10 the original amount of peptide or conjugate in Freund's complete adjuvant by subcutaneous injection at multiple sites. Seven to 14 days later the animals are bled and the serum is assayed for antibody titer. An appropriate carrier may also be used for immunization. After immunization as above, serum is examined by a standard method for an increase in the amount of desired antibodies. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Over the past two to three decades, a number of methodologies have been developed to prepare chimeric, humanized or human antibodies for human in-vivo therapeutic applications. The most used and proven methodology is to prepare mouse mAbs using hybridoma methodology and then to humanize the mAbs by converting the framework regions of the $V_H$ and $V_L$ domains and constant domains of the mAbs into most homologous human framework regions of human $V_H$ and $V_L$ domains and constant regions of a desirable human γ immunoglobulin isotype and subclass. Many mAbs, such as Xolair, used clinically are humanized mAbs of human γ1, K isotype and subclass and prepared using this methodology.

In some embodiments, antibodies can be made by the conventional hybridoma technology. Kohler et al., Nature, 256:495 (1975). In the hybridoma method, a mouse or other appropriate host animal, such as a hamster or rabbit, is immunized as hereinabove described to elicit lymphocytes that produce or are capable of producing antibodies that will specifically bind to the protein used for immunization. Alternatively, lymphocytes may be immunized in vitro.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

The above immunocyte and myeloma cells can be fused according to known methods, for example, the method of Milstein et al. (Galfre et al., Methods Enzymol. 73:3-46, 1981). Lymphocytes are fused with myeloma cells using a suitable fusing agent, such as polyethylene glycol, to form a hybridoma cell (Goding, Monoclonal Antibodies: Principles and Practice, pp. 59-103 (Academic Press, 1986)). Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay. Measurement of absorbance in enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, protein of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the protein, such as a C-terminal or N-terminal fragment may be used in this method. BIAcore (Pharmacia) may be used to evaluate the activity of the antibody according to the present invention. The binding affinity of the monoclonal antibody can, for example, be determined by the Scatchard analysis of Munson et al., Anal. Biochem., 107:220 (1980).

Applying any of the conventional methods, including those described above, hybridoma cells producing antibodies that bind to epitopes described herein can be identified and selected for further characterization.

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In addition, the hybridoma cells may be grown in vivo as ascites tumors in an animal. For example, the obtained hybridomas can be subsequently transplanted into the abdominal cavity of a mouse and the ascites are harvested.

The obtained monoclonal antibodies can be purified by, for example, ammonium sulfate precipitation, a protein A or protein G column, DEAE ion exchange chromatography, or an affinity column to which the protein of the present invention is coupled. The antibody of the present invention can be used not only for purification and detection of the protein of the present invention, but also as a candidate for agonists and antagonists of the protein of the present invention. In addition, this antibody can be applied to the antibody treatment for diseases related to the protein of the present invention.

Recombinant Technology

The monoclonal antibodies thus obtained can be also recombinantly prepared using genetic engineering techniques (see, for example, Borrebaeck C. A. K. and Larrick J. W. Therapeutic Monoclonal Antibodies, published in the United Kingdom by MacMillan Publishers LTD, 1990). A DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

When the obtained antibody is to be administered to the human body (antibody treatment), a human antibody or a humanized antibody is preferable for reducing immunogenicity. For example, transgenic animals having a repertory of human antibody genes may be immunized with an antigen selected from a protein, protein expressing cells, or their lysates. Antibody producing cells are then collected from the animals and fused with myeloma cells to obtain hybridoma, from which human antibodies against the protein can be prepared. Alternatively, an immune cell, such as an immunized lymphocyte, producing antibodies may be immortalized by an oncogene and used for preparing monoclonal antibodies.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Rev., 130:151-188 (1992).

DNAs encoding the antibodies produced by the hybridoma cells described above can be genetically modified, via routine technology, to produce genetically engineered antibodies. Genetically engineered antibodies, such as humanized antibodies, chimeric antibodies, single-chain antibodies, and bi-specific antibodies, can be produced via, e.g., conventional recombinant technology. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad Sci. USA, 89:4285 (1992); Presta et al., J. Immnol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993). Human antibodies can also be derived from phage-display libraries (Hoogenboom et al., J. Mol. Biol., 227:381 (1991); Marks et al., J. Mol. Biol., 222:581-597 (1991)).

Any of the nucleic acid encoding the anti-Globo Hand anti-SSEA-4 antibodies described herein (including heavy chain, light chain, or both), vectors such as expression vectors comprising one or more of the nucleic acids, and host cells comprising one or more of the vectors are also within the scope of the present disclosure. In some examples, a vector comprising a nucleic acid comprising a nucleotide sequence encoding either the heavy chain variable region or the light chain variable region of an anti-Globo H antibody as described herein. In some examples, a vector comprising a nucleic acid comprising a nucleotide sequence encoding either the heavy chain variable region or the light chain variable region of an anti-SSEA-4 antibody as described herein. In other examples, the vector comprises nucleotide sequences encoding both the heavy chain variable region and the light chain variable region, the expression of which can be controlled by a single promoter or two separate promoters. Also provided here are methods for producing any of the anti-Globo Hand anti-SSEA-4 antibodies as described herein, e.g., via the recombinant technology described in this section.

Other Technology for Preparing Antibodies

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Alternatively, the anti-Globo Hand anti-SSEA-4 antibodies described herein can be isolated from antibody phage libraries (e.g., single-chain antibody phage libraries) generated using the techniques described in McCafferty et al., Nature, 348:552-554 (1990). Clackson et al., Nature, 352: 624-628 (1991) and Marks et al., J. Mol Biol., 222:581-597 (1991). Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

Antibodies obtained as described herein may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultra-filtration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but are not limited thereto. The concentration of the antibodies obtained as above may be determined by the measurement of absorbance, Enzyme-linked immunosorbent assay (ELISA), or so on. Exemplary chromatography, with the exception of affinity includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographic procedures can be carried out by liquid-phase chromatography, such as HPLC, FPLC.

The antibodies can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays.

In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various residues in the binding epitope for the candidate antibody have been replaced (swapped) with sequences from a closely related, but antigenically distinct protein (such as another member of the neurotrophin protein family). By assessing binding of the antibody to the mutant target protein, the importance of the particular antigen fragment to antibody binding can be assessed.

Alternatively, competition assays can be performed using other antibodies known to bind to the same antigen to determine whether an antibody binds to the same epitope (e.g., the MC45 antibody described herein) as the other antibodies. Competition assays are well known to those of skill in the art.

Additional Aspects of Exemplary Suitable General Antibody Production Methods

Methods of making monoclonal and polyclonal antibodies and fragments thereof in animals (e.g., mouse, rabbit, goat, sheep, or horse) are well known in the art. See, for example, Harlow and Lane, (1988) Antibodies: A Laboratory Manual, Cold Spring Harbor Laboratory, New York. The term "antibody" includes intact immunoglobulin molecules as well as fragments thereof, such as Fab, F(ab')2, Fv, scFv (single chain antibody), and dAb (domain antibody; Ward, et. al. (1989) Nature, 341, 544).

The compositions disclosed herein can be included in a pharmaceutical composition together with additional active agents, carriers, vehicles, excipients, or auxiliary agents identifiable by a person skilled in the art upon reading of the present disclosure.

The pharmaceutical compositions preferably comprise at least one pharmaceutically acceptable carrier. In such pharmaceutical compositions, the compositions disclosed herein form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Compositions comprising at least one anti-SSEA-3/SSEA-4/Globo H antibody or at least one polynucleotide comprising sequences encoding an anti-SSEA-3/SSEA-4/Globo H antibody are provided. In certain embodiments, a composition may be a pharmaceutical composition. As used herein, compositions comprise one or more antibodies that bind to one or more SSEA-3/SSEA-4/Globo H and/or one or more polynucleotides comprising sequences encoding one or more antibodies that bind to one or more SSEA-3/SSEA-4/Globo H. These compositions may further comprise suitable carriers, such as pharmaceutically acceptable excipients including buffers, which are well known in the art.

Isolated antibodies and polynucleotides are also provided. In certain embodiments, the isolated antibodies and polynucleotides are substantially pure.

In one embodiment, anti-SSEA-3/SSEA-4/Globo H antibodies are monoclonal. In another embodiment, fragments of the anti-SSEA-3/SSEA-4/Globo H antibodies (e.g., Fab, Fab'-SH and F(ab')2 fragments) are provided. These antibody fragments can be created by traditional means, such as enzymatic digestion, or may be generated by recombinant techniques. Such antibody fragments may be chimeric, humanized, or human. These fragments are useful for the diagnostic and therapeutic purposes set forth below.

A variety of methods are known in the art for generating phage display libraries from which an antibody of interest can be obtained. One method of generating antibodies of interest is through the use of a phage antibody library as described in Lee et al., J. Mol. Biol. (2004), 340(5): 1073-93.

The anti-SSEA-3/SSEA-4/Globo H antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-SSEA-3/SSEA-4/Globo H antibodies of the invention can be obtained by designing a suitable antigen screening procedure to select for the phage clone of interest followed by construction of a full length anti-SSEA-3/SSEA-4/Globo H antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., Nucl. Acids Res., 19: 4133-4137 (1991).

In general, nucleic acids encoding antibody gene fragments are obtained from immune cells harvested from humans or animals. If a library biased in favor of anti-SSEA-3/SSEA-4/Globo H clones is desired, the subject is immunized with SSEA-3/SSEA-4/Globo H to generate an antibody response, and spleen cells and/or circulating B cells or other peripheral blood lymphocytes (PBLs) are recovered for library construction. In one embodiment, a human antibody gene fragment library biased in favor of anti-human SSEA-3/SSEA-4/Globo H clones is obtained by generating an anti-human SSEA-3/SSEA-4/Globo H antibody response in transgenic mice carrying a functional human immunoglobulin gene array (and lacking a functional endogenous antibody production system) such that SSEA-3/SSEA-4/Globo H immunization gives rise to B cells producing human antibodies against SSEA-3/SSEA-4/Globo H. The generation of human antibody-producing transgenic mice is described below.

Additional enrichment for anti-SSEA-3/SSEA-4/Globo H reactive cell populations can be obtained by using a suitable screening procedure to isolate B cells expressing SSEA-3/SSEA-4/Globo H-specific antibody, e.g., by cell separation with SSEA-3/SSEA-4/Globo H affinity chromatography or adsorption of cells to fluorochrome-labeled SSEA-3/SSEA-4/Globo H followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which SSEA-3/SSEA-4/Globo H is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). However, for amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To maximize complementarity, degeneracy can be incorporated in the primers as described in Orlandi et al. (1989) or Sastry et al. (1989). In certain embodiments, the library diversity is maximized by using PCR primers targeted to each V-gene family in order to amplify all available VH and VL arrangements present in the immune cell nucleic acid sample, e.g. as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes can be derived in vitro from V gene segments. Most of the human VH-gene segments have been cloned and sequenced (reported in Tomlinson et al., J. Mol. Biol., 227: 776-798 (1992)), and mapped (reported in Matsuda et al., Nature Genet., 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., Proc. Natl. Acad. Sci. USA, 89: 4457-4461 (1992). Human VK and Vh segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., Gene, 128: 119-126 (1993), or in vivo by combinatorial infection, e.g., the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about 1012 clones). Both vectors contain in vivo recombination signals so that the VH and VL genes are recombined onto a single replicon and are co-packaged into phage virions. These huge libraries provide large numbers of diverse antibodies of good affinity (Kd-1 of about 10-8 M).

Alternatively, the repertoires may be cloned sequentially into the same vector, e.g. as described in Barbas et al., Proc. Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

Screening of the libraries can be accomplished by any art-known technique. For example, SSEA-3/SSEA-4/Globo H targets can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized SSEA-3/SSEA-4/Globo H under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci. USA, 88: 7978-7982 (1991), or by alkali, e.g. as described in Marks et al., J. Mol. Biol., 222: 581-597 (1991), or by SSEA-3/SSEA-4/Globo H antigen competition, e.g. in a procedure similar to the antigen competition method of Clackson et al., Nature, 352: 624-628 (1991). Phages can be enriched from about 20× to about 1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for SSEA-3/SSEA-4/Globo H. However, random mutation of a selected antibody (e.g. as performed in some of the affinity maturation techniques described above) is likely to give rise to many mutants, most binding to antigen, and a few with higher affinity. With limiting SSEA-3/SSEA-4/Globo H, rare high affinity phage could be competed out. To retain all the higher affinity mutants, phages can be incubated with excess biotinylated SSEA-3/SSEA-4/Globo H, but with the biotinylated SSEA-3/SSEA-4/Globo H at a concentration of lower molarity than the target molar affinity constant for SSEA-3/SSEA-4/Globo H. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-SSEA-3/SSEA-4/Globo H clones may be activity selected. In one embodiment, the invention provides anti-SSEA-3/SSEA-4/Globo H antibodies that block the binding between a SSEA-3/SSEA-4/Globo H ligand and SSEA-3/SSEA-4/Globo H, but do not block the binding between a SSEA-3/SSEA-4/Globo H ligand and a second protein. Fv clones corresponding to such anti-SSEA-3/SSEA-4/Globo H antibodies can be selected by (1) isolating anti-SSEA-3/SSEA-4/Globo H clones from a phage library as described in Section B(I)(2) above, and optionally amplifying the isolated population of phage clones by growing up the population in a suitable bacterial host; (2) selecting SSEA-3/SSEA-4/Globo H and a second protein against which blocking and non-blocking activity, respectively, is desired; (3) adsorbing the anti-SSEA-3/SSEA-4/Globo H phage clones to immobilized SSEA-3/SSEA-4/Globo H; (4) using an excess of the second protein to elute any undesired clones that recognize SSEA-3/SSEA-4/Globo H-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol. Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In one embodiment, a Fv clone derived from human variable DNA is fused to human constant region DNA to form coding sequence(s) for all human, full or partial length heavy and/or light chains.

The antibodies produced by naive libraries (either natural or synthetic) can be of moderate affinity (Kd-1 of about 106 to 107 M−1), but affinity maturation can also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities in the 10-9 M range.

Other Methods of Generating Anti-SSEA-3/SSEA-4/ Globo H Antibodies

Other methods of generating and assessing the affinity of antibodies are well known in the art and are described, e.g., in Kohler et al., Nature 256: 495 (1975); U.S. Pat. No. 4,816,567; Goding, Monoclonal Antibodies: Principles and Practice, pp. 59-103 (Academic Press, 1986; Kozbor, J. Immunol., 133:3001 (1984); Brodeur et al., Monoclonal Antibody Production Techniques and Applications, pp. 51-63 (Marcel Dekker, Inc., New York, 1987; Munson et al., Anal. Biochem., 107:220 (1980); Engels et al., Agnew. Chem. Int. Ed. Engl., 28: 716-734 (1989); Abrahmsen et al., EMBO J., 4: 3901 (1985); Methods in Enzymology, vol. 44 (1976); Morrison et al., Proc. Natl. Acad. Sci. USA, 81: 6851-6855 (1984).

General Methods

Accordingly, one aspect of the present disclosure features an isolated antibody triple-targeting Globo H, SSEA3 and SSEA-4. The triple-targeting antibody specifically binds to Fucα1→2Galβ1→3GalNAcβ1→3Galα1→4Galβ1→4Glcβ1 (Globo H hexasaccharide) and Galβ1→3GalNAcβ1→3Galα1→4Galβ1→4Glcβ1 (SSEA-3 pentasaccharide) and Neu5Acα2→3Galβ1→3GalNAcβ1→3Galα1→4Galβ1→4Glcβ1 (SSEA-4 hexasaccharide). In one example, the triple-targeting antibody is mAb 651.

Another aspect of the present disclosure features an isolated antibody dual-targeting Globo H and SSEA3. The dual-targeting antibody specifically binds to Fucα1→2Galβ1→3GalNAcβ1→3Galα1→4Galβ1→4Glcβ1 (Globo H hexasaccharide) and Galβ1→3GalNAcβ1→3Galα1→4Galβ1→4Glcβ1 (SSEA-3 pentasaccharide). In one example, the dual-targeting antibody is mAb 273.

In yet another aspect, the present disclosure features an isolated antibody specific to SSEA-4. The anti-SSEA-4 antibody binds to Neu5Acα2→3Galβ1→3GalNAcβ1→3Galα1→4Galβ1→4Glcβ1 (SSEA-4 hexasaccharide). In some examples, the antibody is capable of binding Neu5Acα2→3Galβ1→3GalNAcβ1→3Galα1→4Galβ1→4Glcβ1 (an analogue of SSEA-4 hexasaccharide). Preferably, the antibody is not a mouse IgG3 (e.g., mAb MC-831-70), and the antibody is not a mouse IgM (e.g., anti-RM1). Examples of the antibodies include, but are not limited to, mAbs 45 and 48.

Another aspect of the present disclosure features an isolated antibody specific to SSEA-4 and fragments thereof. The anti-SSEA-4 antibody binds to Neu5Acα2→3Galβ1→3GalNAcβ1→3Galα1→4Galβ1→4Glcβ1 (SSEA-4 hexasaccharide) and Neu5Acα2→3Galβ1→3GalNAcβ1→3Galα1 (fragment of SSEA-4 hexasaccharide). In some examples, the antibody is capable of Neu5Acα2→3Galβ1→3GalNAcβ1→3Galβ1. In some examples, the antibody is capable of Neu5Gcα2→3Galβ1→3GalNAcβ1→3Galα1→4Galβ1→4Glcβ1 (an analogue of SSEA-4 hexasaccharide). In one example, the antibody is mAb 46.

Antibodies triple-targeting Globo H, SSEA-3 and SSEA-4, antibodies dual-targeting Globo H and SSEA-3, and anti-SSEA-4 antibodies were developed and disclosed herein. The antibodies according to the disclosure can be used in therapeutics, diagnosis or as a research tool.

Accordingly, one aspect of the present disclosure relates to a composition of a homogeneous population of monoclonal antibodies comprising a single, uniform N-glycan on Fc, wherein the structure is an optimized N-glycan structure for enhancing the efficacy of effector cell function.

In preferred embodiments, the N-glycan is attached to the Asn-297 of the Fc region.

In preferred embodiments, wherein the N-glycan consists of the structure of $Sia_2(\alpha2\text{-}6)Gal_2GlcNAc_2Man_3GlcNAc_2$.

The glycoantibodies described herein may be produced in vitro. The glycoantibodies may be generated by Fc glycoengineering. In certain embodiments, the glycoantibodies are enzymatically or chemoenzymatically engineered from the monoclonal antibodies obtained by mammalian cell culturing.

In some embodiments, the Fc region of the glycoantibodies described herein exhibits an increased binding affinity for FcγRIIA or FcγRIIIA relative to a wild-type Fc region in the corresponding monoclonal antibodies.

In some embodiments, the glycoantibodies described herein exhibit an enhanced antibody-dependent cell mediated cytotoxicity (ADCC) activity relative to wild-type immunoglobulins.

In some embodiments, the glycoantibodies are selected from a group consisting of human IgG1, IgG2, IgG3, and IgG4. The monoclonal antibodies may be humanized, human or chimeric.

The glycoantibodies described herein may bind to an antigen associated with cancers, autoimmune disorders, inflammatory disorders or infectious diseases. Exemplary cancer associated antigens can include, for example, Globo-H, SSEA-3, SSEA-4.

In other aspects, the antibodies disclosed herein can detect glycan variants and derivatives. For example, the reducing end of the glycan is free or linked to a tail which is natural (e.g. SSEA4 glycolipid) or non-natural (e.g. a linker for making glycan array or for conjugation for diagnostic purposes). All these derivatives can be recognized by the antibody.

In certain diagnostic and array embodiments, the antibodies of this invention can therefore detect not only the glycan described herein, but also oxidized variants thereof. The antibodies of this invention can also detect conjugation products to said oxidized variants.

In certain aspects, the disclosure provides isolated humanized monoclonal glycoantibody that specifically binds to Neu5Acα2→3Galβ1→3GalNAcβ1→3Galα1→4Galβ1→4Glcβ1, and oxidized variants thereof, and conjugation products to said oxidized variants, and oxidized variants thereof, and conjugation products to said oxidized variants; wherein said oxidized variants are the conversion products of the glycan primary alcohols to carbonyls, and wherein the conjugation products are the conversion products of carbonyls to imines with a primary or secondary amine moiety.

For example, the glycans comprising primary alcohols can be converted to an oxidized variant by methods known to those skilled in the art. As a non-limiting example, a primary alcohol on a galactose can be converted to an aldehyde by contacting the glycan with an oxidant, e.g. sodium periodate (sodium m-periodate), or another salt of periodate (e.g., potassium, ammonium, manganese, lithium). One or a plurality of sugar moieties in the glycan can be oxidized. The concentration of oxidant can be 1 micromolar, 5 micromolar, 10 micromolar, 25 micromolar, 50 micromolar, 100 micromolar, 200 micromolar, 500 micromolar, 750 micromolar, 1 millimolar, 5 millimolar, 10 millimolar, 25 millimolar, 50 millimolar, 100 millimolar, or 500 millimolar in water or a suitable buffer. The temperature can be from 5 to 45 degrees Celsius, preferably 15 to 40 degrees Celsius, more preferably 35 to 40 degrees Celsius.

The reaction time can be from 10 seconds to 20 minutes, preferably from 30 seconds to 10 minutes. Suitable buffers can include or exclude saline, phosphate, CHES, MES, borate, acetate, carbonate, formate, citrate, oxalate. Preferably, mildly acidic buffers are used. Preferably, buffers without TRIS or glycine or free sugars are used as these will compete in the reaction. The conversion can be purified by dialysis or centrifugal dialysis by methods known those skilled in the art.

The conjugation products can be formed from the reaction of the oxidized products with an appropriate amine, hydrazine, hydrazide, or oxo-amine by methods known to those skilled in the art, and as described in G. Hermanson, *Bioconjugate Techniques*, $3^{rd}$ Ed., ISBN: 978-0-12-382239-0, Academic Press, 2013, herein incorporated by reference. As a non-limiting example, a primary amine can be reacted to a glycan with a single aldehyde functional group formed from the periodate-oxidized primary alcohol of a galactose within the glycan. The net product would be an imine. The imine can be optionally further reduced to an alcohol by methods known the those skilled in the art, e.g. cyanoborohydride reduction, to form a more stable conjugation product to hydrolysis. In some aspects, the amine, hydrazine, hydrazide, or oxo-amine can be further covalently linked to an array, a reporter molecule, or a biotin for further modification of the conjugation product. In some aspects, the reporter molecule can be a fluorescent molecule. In some aspects, the reporter molecule can be a radiolabelled molecule. In some aspects, the reporter molecule can be a molecule with a unique spectral characteristic (e.g., IR spectra, Raman spectra, or NMR spectra). In some aspects, the array can be a solid surface, a chemically modified surface, a polymer-coated surface, a bead, a gel, a particle, or a nanoparticle. In some aspects, the nanoparticle can be fluorescent or exhibit photoluminescence. In some aspects, the conjugation products can be the conversion products of carbonyls to imines with a primary or secondary amine moiety.

In general, the invention provides affinity-matured SSEA-3/SSEA-4/Globo H antibodies. These antibodies have increased affinity and specificity for SSEA-3/SSEA-4/Globo H. This increase in affinity and sensitivity permits the molecules of the invention to be used for applications and methods that are benefited by (a) the increased sensitivity of the molecules of the invention and/or (b) the tight binding of SSEA-3/SSEA-4/Globo H by the molecules of the invention.

In one aspect, SSEA4/SSEA3/GloboH are three glycans that are specifically expressed for cancer cells and cancer stem cells. Knockdown of beta-3-GalT5, the key enzyme for the synthesis of these three glycolipids, causes apoptosis of cancer cells, but not normal cells. Antibodies, especially glycoantibodies against SSEA4 preferentially or specifically and/or against SSEA3/SSEA4/GloboH simultaneously are effective cancer therapeutic agents. In another aspect, the three glycans, SSEA4/SSEA3/GloboH, especially SSEA3, are useful as cancer stem cell markers.

In one aspect, SSEA4 and/or SSEA4/SSEA3/GloboH in combination are useful as therapeutic targets for the treatment of different cancers, including for example, brain cancer, lung cancer, breast cancer, oral cancer, esophageal cancer, stomach cancer, liver cancer, bile duct cancer, pancreatic cancer, colon cancer, kidney cancer, bone cancer (osteosarcoma), skin cancer, cervical cancer, ovarian cancer, and prostate cancer.

In one embodiment, human or humanized therapeutic antibodies against SSEA4 expressed on the cell surface of these exemplary cancer types are provided.

In another embodiment, human or humanized therapeutic antibodies against SSEA3/SSEA4/Globo-H simultaneously expressed on the cell surface of these exemplary cancer types are provided.

Additionally, the present disclosure is also directed to immunogenic conjugate compositions targeting the SSEA-3/SSEA-4/Globo H associated epitopes (natural and modified) which can elicit antibodies and/or binding fragment production useful for modulating the globoseries glycosphingolipid synthesis. Moreover, the present disclosure is also directed to the method of using the compositions described herein for the treatment or detection of hyperproliferative diseases and/or conditions.

In one embodiment, SSEA-3/SSEA-4/Globo H antibodies that are useful for treatment of SSEA-3/SSEA-4/Globo H-mediated disorders in which a partial or total blockade of one or more SSEA-3/SSEA-4/Globo H activities is desired. In one embodiment, the anti SSEA-3/SSEA-4/Globo H antibodies of the invention are used to treat cancer.

The anti-SSEA-3/SSEA-4/Globo H antibodies of the invention permit the sensitive and specific detection of the epitopes in immunoassays such as sandwich assays, immunoprecipitations, ELISAs, or immunomicroscopy without the need for mass spectrometry or genetic manipulation. In turn, this provides a significant advantage in both observing and elucidating the normal functioning of these pathways and in detecting when the pathways are functioning aberrantly.

The SSEA-3/SSEA-4/Globo H antibodies of the invention can also be used to determine the role in the development and pathogenesis of disease. For example, as described above, the SSEA-3/SSEA-4/Globo H antibodies of the invention can be used to determine whether the TACAs are normally temporally expressed which can be correlated with one or more disease states.

The SSEA-3/SSEA-4/Globo H antibodies of the invention can further be used to treat diseases in which one or more SSEA-3/SSEA-4/Globo Hs are aberrantly regulated or aberrantly functioning without interfering with the normal activity of SSEA-3/SSEA-4/Globo Hs for which the anti-SSEA-3/SSEA-4/Globo H antibodies of the invention are not specific.

In another aspect, the anti-SSEA-3/SSEA-4/Globo H antibodies of the invention find utility as reagents for detection of cancer states in various cell types and tissues.

In yet another aspect, the present anti-SSEA-3/SSEA-4/Globo H antibodies are useful for the development of SSEA-3/SSEA-4/Globo H antagonists with blocking activity patterns similar to those of the subject antibodies of the invention. For example, anti-SSEA-3/SSEA-4/Globo H antibodies of the invention can be used to determine and identify other antibodies that have the same SSEA-3/SSEA-4/Globo H binding characteristics and/or capabilities of blocking SSEA-3/SSEA-4/Globo H-pathways.

As a further example, anti-SSEA-3/SSEA-4/Globo H antibodies of the invention can be used to identify other anti-SSEA-3/SSEA-4/Globo H antibodies that bind substantially the same antigenic determinant(s) of SSEA-3/SSEA-4/Globo H as the antibodies exemplified herein, including linear and conformational epitopes.

The anti-SSEA-3/SSEA-4/Globo H antibodies of the invention can be used in assays based on the physiological pathways in which SSEA-3/SSEA-4/Globo H is involved to screen for small molecule antagonists of SSEA-3/SSEA-4/

Globo H which will exhibit similar pharmacological effects in blocking the binding of one or more binding partners to SSEA-3/SSEA-4/Globo H as the antibody does.

Generation of antibodies can be achieved using routine skills in the art, including those described herein, such as the hybridoma technique and screening of phage displayed libraries of binder molecules. These methods are well-established in the art.

Briefly, the anti-SSEA-3/SSEA-4/Globo H antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-SSEA-3/SSEA-4/Globo H antibodies of the invention can be obtained by designing a suitable antigen screening procedure to select for the phage clone of interest followed by construction of a full length anti-SSEA-3/SSEA-4/Globo H antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

In one embodiment, anti-SSEA-3/SSEA-4/Globo H antibodies of the invention are monoclonal. Also encompassed within the scope of the invention are antibody fragments such as Fab, Fab', Fab'-SH and F(ab')2 fragments, and variations thereof, of the anti-SSEA-3/SSEA-4/Globo H antibodies provided herein. These antibody fragments can be created by traditional means, such as enzymatic digestion, or may be generated by recombinant techniques. Such antibody fragments may be chimeric, human or humanized. These fragments are useful for the experimental, diagnostic, and therapeutic purposes set forth herein.

Monoclonal antibodies can be obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-SSEA-3/SSEA-4/Globo H monoclonal antibodies of the invention can be made using a variety of methods known in the art, including the hybridoma method first described by Kohler et al., Nature, 256:495 (1975), or alternatively they may be made by recombinant DNA methods (e.g., U.S. Pat. No. 4,816,567).

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Host cells include, but are not limited to, cells of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells

Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli* λ1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, growth occurs at a temperature range including, but not limited to, about 20° C. to about 39° C., about 25° C. to about 37° C., and at about 30° C. The pH of the medium may be any pH ranging from about 5 to about 9, depending mainly on the host organism. For *E. coli*, the pH can be from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In one embodiment, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, for example about 1,000 to 100,000 liters of capacity. These fermentors use agitator impellers to distribute oxygen and nutrients, especially glucose (a common carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent non-specific adherence of contaminants.

As the first step of purification, the preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected generally is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II (e.g., primate metallothionein genes), adenosine deaminase, ornithine decarboxylase, etc.

For example, cells transformed with the DHFR selection gene may first be identified by culturing all of the transformants in a culture medium that contains methotrexate (Mtx), a competitive antagonist of DHFR. Appropriate host cells when wild-type DHFR is employed include, for example, the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to nucleic acid encoding a polypeptide of interest (e.g., an antibody). Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding an antibody polypeptide of the invention by higher eukaryotes can often be increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is generally located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are generally removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a generally acceptable purification technique. The suitability of affinity reagents such as protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification steps, as necessary, for example by low pH hydrophobic interaction chromatography using an elution buffer at a pH between about 2.5-4.5, generally performed at low salt concentrations (e.g., from about 0-0.25M salt).

It should be noted that, in general, techniques and methodologies for preparing antibodies for use in research, testing and clinical use are well-established in the art, consistent with the above and/or as deemed appropriate by one skilled in the art for the particular antibody of interest.

Activity Assays

Antibodies of the invention can be characterized for their physical/chemical properties and biological functions by various assays known in the art.

Purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

Where necessary, antibodies are analyzed for their biological activity. In some embodiments, antibodies of the invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, chemiluminescent immunoassays, nanoparticle immunoassays, aptamer immunoassays, and protein A immunoassays.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10: 163-167 (1992)). According to another approach, F(ab')2 fragments can be isolated directly from recombinant host cell culture. Fab and F(ab')2 fragment with increased in vivo half-life comprising salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-SSEA-3/SSEA-4/Globo H antibodies of the invention can be constructed by combining Fv clone variable domain sequence(s) selected from human-derived phage display libraries with known human constant domain sequences(s) as described above. Alternatively, human monoclonal anti-SSEA-3/SSEA-4/Globo H antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for SSEA-3/SSEA-4/Globo H including a specific lysine linkage and the other is for any other antigen. In certain embodiments, bispecific antibodies may bind to two different SSEA-3/SSEA-4/Globo Hs having two different lysine linkages. Bispecific antibodies can be prepared as full length antibodies or antibody fragments (e.g. F(ab')2 bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., EMBO J., 10: 3655 (1991).

According to a different embodiment, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules can be engineered to maximize the percentage of heterodimers which are recovered from recombinant cell culture. The interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The dimerization domain comprises (or consists of), for example, an Fc region or a hinge region. In this scenario, the antibody will comprise an Fc region and three or more antigen binding sites amino-terminal to the Fc region. In one embodiment, a multivalent antibody comprises (or consists of), for example, three to about eight, or four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. Antibody Variants In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as Arg, Asp, His, Lys, and Glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table A under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

| Original | Exemplary | Preferred Residue Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Leu Phe; Norleucine | |
| Leu (L) | Norleucine; Ile; Val; Ile Met; Ala; Phe | |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |

TABLE A-continued

Original Exemplary Preferred Residue Substitutions

Thr (T) Val; Ser Ser
Trp (W) Tyr; Phe Tyr
Tyr (Y) Trp; Phe; Thr; Ser Phe
Val (V) Ile; Leu; Met; Phe; Leu
Ala; Norleucine Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
 (1) non-polar: Ala (A), Val (V), Leu (L), Ile (I), Pro (P), Phe (F), Trp (W), Met (M)
 (2) uncharged polar: Gly (G), Ser (S), Thr (T), Cys (C), Tyr (Y), Asn (N), Gln (Q)
 (3) acidic: Asp (D), Glu (E)
 (4) basic: Lys (K), Arg (R), His (H)

Alternatively, naturally occurring residues may be divided into groups based on common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity) as herein disclosed. In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

Immunoconjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Antibody Derivatives

Antibodies of the invention can be further modified to contain additional nonproteinaceous moieties that are known in the art and readily available. In one embodiment, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, the polymers can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Pharmaceutical Formulations

Therapeutic formulations comprising an antibody of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, including, but not limited to those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the invention may be used in, for example, in vitro, ex vivo and in vivo therapeutic methods. Antibodies of the invention can be used as an antagonist to partially or fully block the specific antigen activity in vitro, ex vivo and/or in vivo. Moreover, at least some of the antibodies of the invention can neutralize antigen activity from other species. Accordingly, antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, an antibody of the invention can be used for inhibiting antigen activities by contacting the antibody with the antigen such that antigen activity is inhibited. In one embodiment, the antigen is a human protein molecule.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. In one embodiment, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Antibodies of the invention can be used to treat, inhibit, delay progression of, prevent/delay recurrence of, ameliorate, or prevent diseases, disorders or conditions associated with abnormal expression and/or activity of SSEA-3/SSEA-4/Globo Hs and SSEA-3/SSEA-4/Globo Hated proteins, including but not limited to cancer, muscular disorders, ubiquitin-pathway-related genetic disorders, immune/inflammatory disorders, neurological disorders, and other ubiquitin pathway-related disorders.

In one aspect, a blocking antibody of the invention is specific for a SSEA-3/SSEA-4/Globo H.

In certain embodiments, an immunoconjugate comprising an antibody of the invention conjugated with a cytotoxic agent is administered to the patient. In some embodiments, the immunoconjugate and/or antigen to which it is bound is/are internalized by cells expressing one or more proteins on their cell surface which are associated with SSEA-3/SSEA-4/Globo H, resulting in increased therapeutic efficacy of the immunoconjugate in killing the target cell with which it is associated. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, and/or adjuvant/therapeutic agents (e.g., steroids). For instance, an antibody of the invention may be combined with an anti-inflammatory and/or antiseptic in a treatment scheme, e.g. in treating any of the diseases described herein, including cancer, muscular disorders, ubiquitin-pathway-related genetic disorders, immune/inflammatory disorders, neurological disorders, and other ubiquitin pathway-related disorders. Such combined therapies noted above include combined administration (where the two or more agents are included in the same or separate formulations), and separate administration, in which case, administration of the antibody of the invention can occur prior to, and/or following, administration of the adjunct therapy or therapies.

An antibody of the invention (and adjunct therapeutic agent) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described in Marasco, Gene Therapy 4: 11-15 (1997); Kontermann, Methods 34: 163-170 (2004); U.S. Pat. Nos. 6,004,940 and 6,329,173; U.S. Patent Application Publication No. 2003/0104402, and PCT Publication No. WO2003/077945. Intracellular expression of an intrabody is effected by introducing a nucleic acid encoding the desired antibody or antigen-binding portion thereof (lacking the wild-type leader sequence and secretory signals normally associated with the gene encoding that antibody or antigen-binding fragment) into a target cell. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest. One or more nucleic acids encoding all or a portion of an anti-SSEA-3/SSEA-4/Globo H antibody of the invention can be delivered to a target cell, such that one or more intrabodies are expressed which are capable of intracellular binding to a SSEA-3/SSEA-4/Globo H and modulation of one or more SSEA-3/SSEA-4/Globo H-mediated cellular pathways.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the binding domain of the target protein is generally advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993).

Entry of modulator polypeptides into target cells can be enhanced by methods known in the art. For example, certain sequences, such as those derived from HIV Tat or the Antennapedia homeodomain protein are able to direct efficient uptake of heterologous proteins across cell membranes. See, e.g., Chen et al., Proc. Natl. Acad. Sci. USA (1999), 96:4325-4329.

When the binding target is located in the brain, certain embodiments of the invention provide for the antibody or antigen-binding fragment thereof to traverse the blood-brain barrier. Certain neurodegenerative diseases are associated with an increase in permeability of the blood-brain barrier, such that the antibody or antigen-binding fragment can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or antigen-binding fragment across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)), interstitial infusion/convection-enhanced delivery (see, e.g., Bobo et al., Proc. Natl. Acad. Sci. USA 91: 2076-2080 (1994)), and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or antigen-binding fragment across the blood-brain barrier include, but are not limited to, encapsulating the antibody or antigen-binding fragment in liposomes that are coupled to antibody binding fragments that bind to receptors on the vascular endothelium of the blood-brain barrier (see, e.g., U.S. Patent Application Publication No. 20020025313), and coating the antibody or antigen-binding fragment in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or antigen-binding fragment across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

The antibody composition of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

Pharmaceutical Compositions and Formulations

After preparation of the antibodies as described herein, "pre-lyophilized formulation" can be produced. The antibody for preparing the formulation is preferably essentially pure and desirably essentially homogeneous (i.e. free from contaminating proteins etc). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition. In certain embodiments, the protein is an antibody.

The amount of antibody in the pre-lyophilized formulation is determined taking into account the desired dose volumes, mode(s) of administration etc. Where the protein of choice is an intact antibody (a full-length antibody), from about 2 mg/mL to about 50 mg/mL, preferably from about 5 mg/mL to about 40 mg/mL and most preferably from about 20-30 mg/mL is an exemplary starting protein concentration. The protein is generally present in solution. For example, the protein may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine in that, as demonstrated below, this can have lyoprotective properties. Succinate was shown to be another useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. Where the lyoprotectant is a sugar (such as sucrose or trehalose) and the protein is an antibody, exemplary lyoprotectant concentrations in the pre-lyophilized formulation are from about 10 mM to about 400 mM, and preferably from about 30 mM to about 300 mM, and most preferably from about 50 mM to about 100 mM.

The ratio of protein to lyoprotectant is selected for each protein and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

In preferred embodiments of the invention, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

In certain embodiments of the invention, a mixture of the lyoprotectant (such as sucrose or trehalose) and a bulking agent (e.g. mannitol or glycine) is used in the preparation of the pre-lyophilization formulation. The bulking agent may allow for the production of a uniform lyophilized cake without excessive pockets therein etc.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable. A "stable" formulation/composition is one in which the antibody therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, lyoprotectant and other optional components are mixed together, the formulation is lyophilized. Many different freeze-dryers are available for this purpose such as Hull50® (Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). A secondary drying stage may be carried out at about 0-40° C., depending primarily on the type and size of container and the type of protein employed. However, it was found herein that a secondary drying step may not be necessary. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the protein to the patient, the lyophilized formulation may be reconstituted with a diluent such that the protein concentration in the reconstituted formulation is at least 50 mg/mL, for example from about 50 mg/mL to about 400 mg/mL, more preferably from about 80 mg/mL to about 300 mg/mL, and most preferably from about 90 mg/mL to about 150 mg/mL. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/mL, or from about 10-40 mg/mL protein in the reconstituted formulation). In certain embodiments, the protein concentration in the reconstituted formulation is significantly higher than that in the pre-lyophilized formulation. For example, the protein concentration in the reconstituted formulation may be about 2-40 times, preferably 3-10 times and most preferably 3-6 times (e.g. at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%. Preferably, the reconstituted formulation has less than 6000 particles per vial which are >10 µm size.

Therapeutic Applications

Described herein are therapeutic methods that include administering to a subject in need of such treatment a therapeutically effective amount of a composition that includes one or more antibodies described herein.

In some embodiments, the subject (e.g., a human patient) in need of the treatment is diagnosed with, suspected of having, or at risk for cancer. Examples of the cancer include, but are not limited to, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. In some embodiments, the cancer is brain cancer, lung cancer, breast cancer, ovarian cancer, prostate cancer, colon cancer, or pancreas cancer. In some preferred embodiments, the cancer is brain cancer or glioblastoma multiforme (GBM) cancer.

In preferred embodiments, the antibody is capable of targeting Globo H, SSEA-3 and SSEA-4-expressing cancer cells. In some embodiments, the antibody is capable of targeting Globo H and SSEA on cancer cells. In some embodiments, the antibody is capable of targeting SSEA in cancers.

Accordingly, the antibody is a triple-targeting antibody against Globo H, SSEA-3 and SSEA-4. In some embodiments, the antibodies are a mixture of a dual-targeting antibody against Globo H and SSEA-3, and an anti-SSEA-4 antibody. In some embodiments, the antibodies are a mixture of a triple-targeting antibody against Globo H, SSEA-3 and SSEA-4, and an anti-SSEA-4 antibody. In some embodiments, the antibody is a mixture of an anti-Globo H, an anti-SSEA-3 and an anti-SSEA-4 antibody. In some embodiments, the antibody is a mixture of an anti-Globo H and an anti-SSEA-4 antibody. In some embodiments, the antibody is an anti-SSEA-4 antibody.

The treatment results in reduction of tumor size, elimination of malignant cells, prevention of metastasis, prevention of relapse, reduction or killing of disseminated cancer, prolongation of survival and/or prolongation of time to tumor cancer progression.

In some embodiments, the treatment further comprises administering an additional therapy to said subject prior to, during or subsequent to said administering of the antibodies. In some embodiments, the additional therapy is treatment with a chemotherapeutic agent. In some embodiments, the additional therapy is radiation therapy.

The methods of the invention are particularly advantageous in treating and preventing early stage tumors, thereby preventing progression to the more advanced stages resulting in a reduction in the morbidity and mortality associated with advanced cancer. The methods of the invention are also advantageous in preventing the recurrence of a tumor or the regrowth of a tumor, for example, a dormant tumor that persists after removal of the primary tumor, or in reducing or preventing the occurrence of a tumor.

In some embodiments, the methods as disclosed herein are useful for the treatment or prevention of a cancer, for example where a cancer is characterized by increased Globo H, SSEA-3 and/or SSEA-4 expression. In some embodiments the cancer comprises a cancer stem cell. In some embodiments, the cancer is a pre-cancer, and/or a malignant cancer and/or a therapy resistant cancer. In some embodiments, the cancer is a brain cancer.

For the methods of the invention, the cancer may be a solid tumor, e.g., such as, breast cancer, colorectal cancer, rectal cancer, lung cancer, renal cell cancer, a glioma (e.g., anaplastic astrocytoma, anaplastic oligoastrocytoma, anaplastic oligodendroglioma, glioblastoma multiforme (GBM)), kidney cancer, prostate cancer, liver cancer, pancreatic cancer, soft-tissue sarcoma, carcinoid carcinoma, head and neck cancer, melanoma, and ovarian cancer. In one embodiment, the cancer is a brain cancer or GBM. To practice the method disclosed herein, an effective amount of the pharmaceutical composition/formulation described above, containing at least one antibody described herein, can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having cancer, which include, but not limited to, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. A subject having cancer can be identified by routine medical examination.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of cancer. Alternatively, sustained continuous release formulations of the antibodies described herein may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antibody. To assess efficacy of the antibody, an indicator of the disease (e.g., cancer) can be followed according to routine practice.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate cancer, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

For the purpose of the present disclosure, the appropriate dosage of an antibody described herein will depend on the specific antibody (or compositions thereof) employed, the type and severity of the cancer, whether the antibody is administered for preventive or therapeutic purposes, previous therapy, the patient's clinical history and response to the antibody, and the discretion of the attending physician. The administration of the antibodies described herein may be essentially continuous over a preselected period of time or may be in a series of spaced dose, e.g., either before, during, or after developing cancer.

As used herein, the term "treating" refers to the application or administration of a composition including one or more active agents to a subject, who has cancer, a symptom of cancer, or a predisposition toward cancer, with the purpose to cure, heal, alleviate, relieve, alter, remedy, ameliorate, improve, or affect cancer, the symptom of cancer, or the predisposition toward cancer.

Alleviating cancer includes delaying the development or progression of cancer, or reducing cancer severity. Alleviating cancer does not necessarily require curative results. As used therein, "delaying" the development of cancer means to defer, hinder, slow, retard, stabilize, and/or postpone progression of cancer. This delay can be of varying lengths of time, depending on the history of cancer and/or individuals being treated. A method that "delays" or alleviates the development of cancer, or delays the onset of cancer, is a method that reduces probability (the risk) of developing one or more symptoms of cancer in a given time frame and/or reduces extent of the symptoms in a given time frame, when compared to not using the method. Such comparisons are typically based on clinical studies, using a number of subjects sufficient to give a statistically significant result.

"Development" or "progression" of cancer means initial manifestations and/or ensuing progression of cancer. Development of cancer can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of cancer includes initial onset and/or recurrence.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

Diagnostic Applications

Described herein is a method for diagnosing cancer in a subject, comprising (a) applying a composition that includes one or more monoclonal antibodies that detect expression of a panel of markers consisting of GM3, GM2, GM1, GD1, GD1a, GD3, GD2, GT1b, A2B5, LeX, sLeX, LeY, SSEA-3, SSEA-4, Globo H, TF, Tn, sTn, CD44, CD24, CD45, CD90, CD133 to a cell or tissue sample obtained from the subject; (b) assaying the binding of the monoclonal antibody to the cell or the tissue sample; and (c) comparing the binding with a normal control to determine the presence of the cancer in the subject.

Examples of the cancer for detection and diagnosis include, but are not limited to, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. In some embodiments, the cancer is brain cancer, lung cancer, breast cancer, ovarian cancer, prostate cancer, colon cancer, or pancreas cancer.

In some embodiments, the markers consist of GM2, GM1, GD1a, GT1b, A2B5, Tf, Tn, Globo H, SSEA3, SSEA4, CD24, CD44 and CD90. In some embodiments, thecomposition includes a plurality of monoclonal antibodies capable of detecting GM2, GM1, GD1a, GT1b, A2B5, Tf, Tn, Globo H, SSEA3, SSEA4, CD24, CD44 and CD90.

In some embodiments, the antibody is capable of detecting Globo H, SSEA-3 and SSEA-4-expressing cancer cells. In some embodiments, the antibody is capable of detecting Globo H and SSEA on cancer cells. In some embodiments, the antibody is capable of detecting SSEA in cancers. In some embodiments, the cancer is brain cancer or glioblastoma multiforme (GBM) cancer, and the antibody is an anti-SSEA-4 monoclonal antibody.

Globo H, SSEA-3 and/or SSEA-4-specific monoclonal antibodies can be used alone or in combination for in vitro and in vivo diagnostic assays to detect Globo H, SSEA-3 and SSEA-4-expressing cancer cells (e.g., GBM, certain solid tumor cells, and hematopoietic cancer cells as indicated herein). For example, a sample (e.g., blood sample or tissue biopsy) can be obtained from a patient and contacted with a triple-targeting antibody against Globo H, SSEA-3 and SSEA-4, or a Globo H/SSEA-3dual-targeting antibody in combination with an anti-SSEA-4, and the presence of Globo H, SSEA-3 and SSEA-4 expressing cancer cells in the patient sample can be determined by detecting antibody binding. Antibody binding can be detected directly (e.g., where the antibody itself is labeled) or by using a second detection agent, such as a secondary antibody. The detectable label can be associated with an antibody of the invention, either directly, or indirectly, e.g., via a chelator or linker.

In some embodiments, Globo H, SSEA-3 and/or SSEA-4 specific monoclonal antibodies are contacted with a biological sample from an individual having or suspected of having cancer, and antibody binding to a cell in the sample is determined when higher or lower than normal antibody binding indicates that the individual has cancer. In some embodiments, the biological sample is a blood sample or blood fraction (e.g., serum, plasma, platelets, red blood cells, white blood cells). In some embodiments, the biological sample is a tissue sample (biopsy), e.g., from a suspected tumor site, or from a tissue that is known to be affected, e.g., to determine the boundaries of a known tumor. In some embodiments, the biological sample is obtained from a site of inflammation.

Biopsies are typically performed to obtain samples from tissues, i.e., non-fluid cell types. The biopsy technique applied will depend on the tissue type to be evaluated (e.g., breast, skin, colon, prostate, kidney, lung, bladder, lymph node, liver, bone marrow, airway or lung). In the case of a cancer the technique will also depend on the size and type of the tumor (e.g., solid, suspended, or blood), among other factors. Biopsy techniques are discussed, for example, in Harrison's Principles of Internal Medicine, Kasper, et al., eds., 16th ed., 2005, Chapter 70, and throughout Part V.

Any method of detecting antibody binding to a cell in a sample can be used for the present diagnostic assays. Methods of detecting antibody binding are well known in the art, e.g., flow cytometry, fluorescent microscopy, ELISAs, etc. In some embodiments, the method comprises preparing the biological sample for detection prior to the determining step. For example, a subpopulation of cells (e.g., white blood cells) can be separated from the rest of the sample from the individual (e.g., other blood components) or cells in a tissue can be suspended for easier detection.

In some embodiments, the percentage of Globo H/SSEA-3/SSEA-4 expressing cells in the sample is determined and compared to a control, e.g., a sample from an individual or group of individuals that are known to have cancer (positive control) or from an individual or group of individuals that are known not to have cancer (normal, non-disease, or negative control). In some embodiments, the control is a standard range of Globo H/SSEA-3/SSEA-4 expression established for a given tissue. A higher or lower than normal percentage of Globo H/SSEA-3/SSEA-4 expressing cells, or higher or lower expression level, indicates that the individual has cancer.

In one embodiment, a kit is provided for detecting Globo H, SSEA-3 and SSEA-4 in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of Globo H, SSEA-3 and SSEA-4. Kits for detecting a polypeptide will typically comprise one or more antibodies that specifically bind Globo H, SSEA-3 and SSEA-4, such as any of the antibodies disclosed herein. In a further embodiment, the antibodies are labeled (for example, with a fluorescent, radioactive, or an enzymatic label).

In one embodiment, a kit includes instructional materials disclosing means of use of one or more antibodies that specifically bind Globo H, SSEA-3 and SSEA-4. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbent assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind to Globo H, SSEA-3 and SSEA-4, as disclosed herein, can be used in these assays. Thus, the antibodies can be used in a conventional immunoassay, including, without limitation, an ELISA, an RIA, FACS, tissue immunohistochemistry, Western blot or immunoprecipitation.

Methods for Staging and/or Determining Prognosis of Tumors

Another aspect of the present disclosure features a method for staging and/or determining prognosis of tumors in a human patient, the method comprising: (a) applying a composition that includes one or more antibodies that detect the expression of markers consisting of SSEA-3, SSEA-4 and Globo H to a cell or tissue sample obtained from the patient; (b) assaying the binding of the monoclonal antibodies to the cell or the tissue sample; (c) comparing the expression level of the markers in the test sample with the level in a reference sample, and (d) determining the stage and/or prognosis of tumors in the patient based upon the outcome identified in step (c).

In some embodiments, the cancer is brain cancer, lung cancer, breast cancer, ovarian cancer, prostate cancer, colon cancer, or pancreas cancer. In some preferred embodiments, the cancer is brain cancer or GBM.

In some embodiments, the antibody is capable of detecting Globo H, SSEA-3 and SSEA-4 expressing cancer cells. In some embodiments, the antibody is capable of detecting Globo H and SSEA on cancer cells. In some embodiments, the antibody is capable of detecting SSEA in cancers. In some embodiments, the cancer is brain cancer or glioblastoma multiforme (GBM) cancer, and the antibody is an anti-SSEA-4 monoclonal antibody. In some embodiments, the antibody is an anti-SSEA-4 when the cancer is brain cancer or GBM.

Isolation and Enrichment of Stem Cells

Another aspect of the present invention features the isolation of GBM stem cells, and more particularly to GBM stem cells positive for markers $GD2^+SSEA4^+CD133^+$. Disclosed herein include methods for the isolation, enrichment, and self-renewal of stem cells from GBM tumor cells, using cell surface markers GD2, SSEA4 and CD133 and flow cytometry to separate stem cells from other cells. A composition comprising an isolated population of $GD2^+SSEA4^+CD133^+$ GBM stem cells is disclosed herein.

Accumulating evidence shows that bulk tumors can harbor a small subpopulation of cells called cancer-initiating cells or cancer stem-like cells (CSCs). They have the features of poor differentiation, self-renewal competence and initiating tumors in immunodeficient mice. Prospective identification and isolation of CSCs from bulk tumors is thus critical for development of therapeutic paradigms. Although many reports on CSC enrichment have been achieved by sorting CD133, A2B5, SSEA-1 or integrin-positive cancer cells, the identity of these cells is still ambiguous and the roles of these makers in CSC remain unclear.

Many specific glycans are reported for their distribution on tumor cell surface and the ability to regulate tumor proliferation, metastasis and angiogenesis. This implies that glycans on tumors can act as a functional biomarker, which can be therapeutic targets for cancers. To look for glycan-related markers in CSC of GBM, we first cultured a variety of glioma cell lines in EGF and FGF-supplemented neurobasal medium to enrich stem-like cells. In order to unravel this problem, we observed the expression of glycan-related molecules on the surface of neurosphere-like cells with a panel of available antibodies staining in flow cytometry. Interestingly, GD2, a b series disialoganglioside, prominently expresses on the surface of neurosphere cultured from different GBM cell lines. GD2 has been found to express markedly in neuroblastomas, melanomas and some other tumors. Notably, GD2 distribution is restricted in neurons, skin melanocytes, and sensory nerve fibers. Therefore, the restricted expression of GD2 in normal tissues makes it appropriate to be the therapeutic targets. Moreover, several reports indicated that GD2 also presents on the surface of the mouse and human neural stem cells. Most importantly, GD2 can identify the breast cancer stem cells. On the basis of these findings, we hypothesize that GD2 can function as the marker to identify the glioblastoma stem cells (GSCs), or in combination with current markers to recognize the definite GSCs exactly.

In order to understand whether the combination of GD2 plus SSEA4 and CD133 could more specifically determine the population of GBM stem cells, we compare the self-renewal ability and tumorigenicity of GD2$^+$SSEA4$^+$CD133$^+$ population to the other populations.

Cells from GBM tumor were dissociated into single cell suspensions and labeled with anti-GD2 antibody (BD), anti-SSEA4 (Biolegend), anti-CD133 (Miltenyi Biotec). These labeled cells were then physically sorted using the FACS Aria II flow cytometer (BD). For detection of self-renewal ability, GBM tumor cells were dissociated, stained and plated in 96-well plates. The numbers of neurospheres whose diameter is over 100 um were calculated. For tumorigenicity, various numbers of cells, including 10,000-10 cells, were subcutaneously or intracranially inject into the immunodeficient mice. It is observed the onset of tumors is significantly faster in the GD2$^+$SSEA4$^+$CD133$^+$ population compared to the other populations.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Flow Cytometric Analysis of Glycan Epitopes on GBM Cell Lines

Figure 1A:
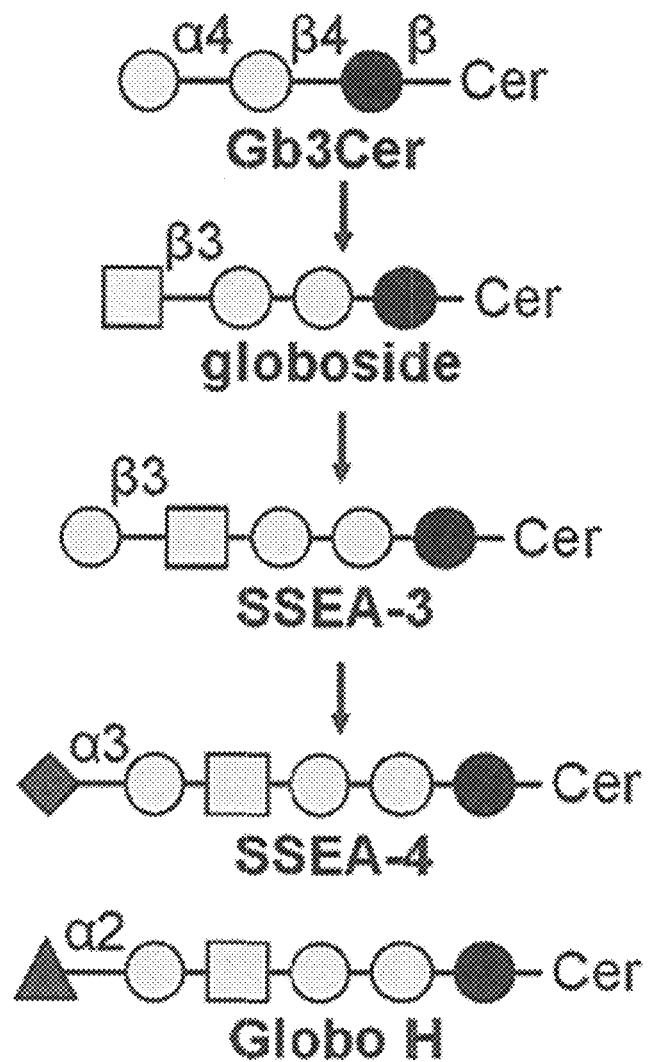
FIGS. 1A-1B. The binding characteristics of anti-SSEA-4 mAb to GBM cell lines.
Figure 1B:
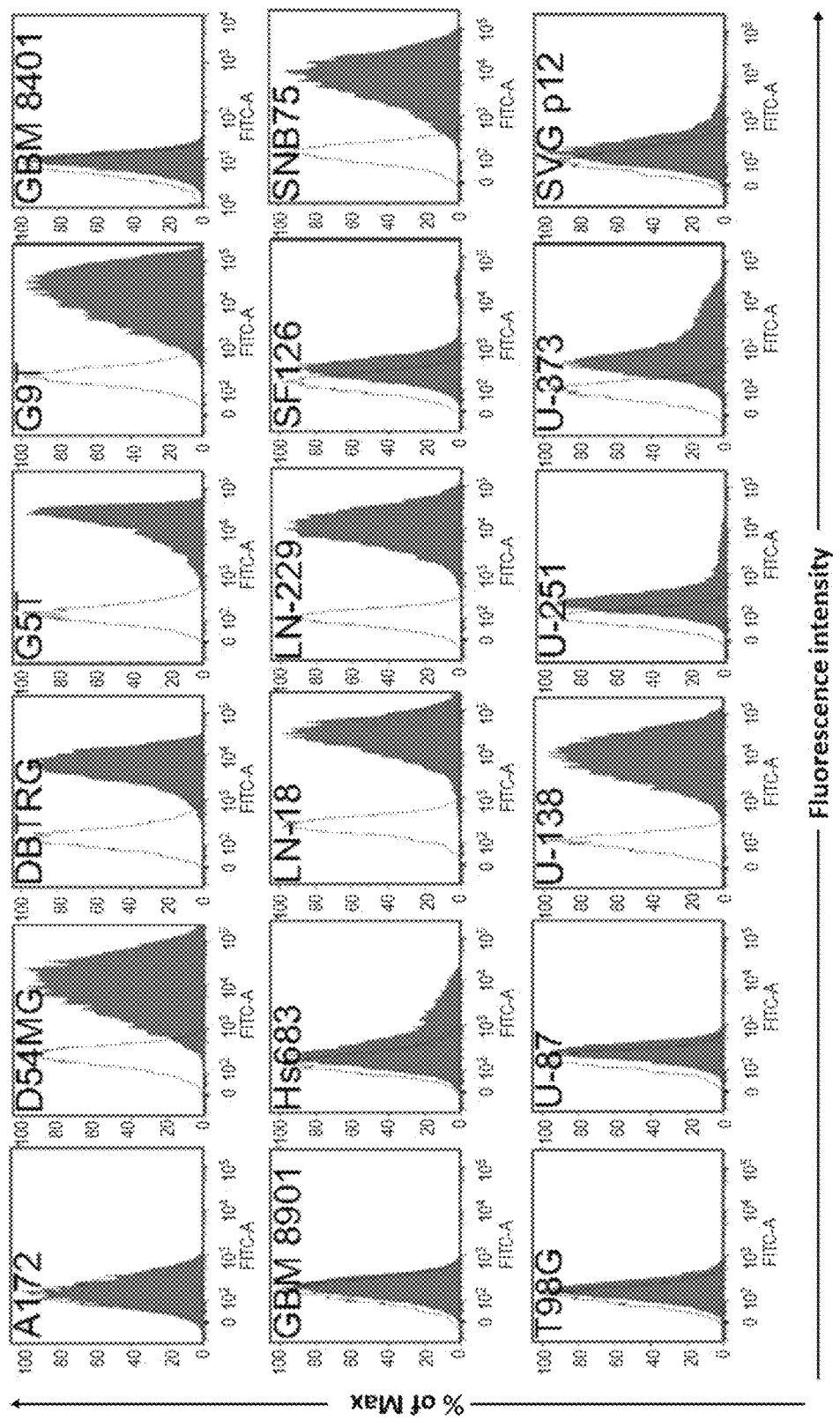

We analyzed the expression levels of various glycan epitopes by flow cytometry in four human GBM cell lines: G5T, LN-18, U-138 and U-251. The glycan epitopes examined include O-linked glycans (Tn, sTn, TF), Lewis antigens (Le$^x$, Le$^y$ and sLe$^x$), complex gangliosides [GM2, GM1, GD1a, GD3, GD2, GT1b and A2B5 (c-series gangliosides)], and globo-series GSLs (SSEA-3, SSEA-4 and Globo H; FIG. 1A). Our results showed that most of these four GBM cell lines expressed high levels of Tn, TF, Le$^x$, and Le$^y$, a low level of sLe$^x$, and no sTn (Table 7). In addition, these four GBM cell lines were positive for all the gangliosides we examined. Regarding the expression levels of globo-series GSLs, U-251 showed a weak staining for an anti-SSEA-4 antibody, MC813-70, and G5T, U-138 and LN-18 displayed a high staining intensity for MC813-70 (FIG. 1B). Positive staining for an anti-SSEA-3 antibody, MC631, was only observed on G5T among these four cell lines, and none showed positive staining for an anti-Globo H antibody, VK9 (Table 7). We further looked into the expression patterns of globo-series GSLs in more GBM cell lines, and found that of the 17 GBM cell lines, nine showed strong MC813-70 staining signal (SSEA-4$^{hi}$); three were weakly stained (SSEA-4$^{lo}$), and five not stained by MC813-70 (FIG. 1A). Nine out of 17 cell lines were positive for MC631 staining and six were positive for VK9 staining. SVG p12, an immortalized human fetal glia cell, showed a very weak MC813-70 staining signal, but no MC631 or VK-9 staining signal (FIG. 1). These results indicated that most of the GBM cell lines examined were positively stained by anti-SSEA-4 antibody using MC813-70 as an example.

Example 2: Verification of SSEA-4 Expression in GBM Cancer Cells

To exclude the possibility that anti-SSEA-4 antibody may bind to the extended core 1 O-glycan on glycoproteins in GBM cells, we treated DBTRG cells with methanol to remove lipids before staining with an anti-SSEA-4 antibody, MC813-70. Upon methanol treatment, the immunoreactivity of MC813-70 disappeared, as analyzed by flow cytometry and immunofluorescence microscopy, suggesting that the immunoreactivity of MC813-70 was toward glycolipids, not glycoproteins. To confirm the existence of SSEA-4 epitope on GBM cell surface, we further performed the MC631 staining on α2,3-sialidase-treated DBTRG cells, and the result showed that when treating with α2,3-sialidase, the cells became MC813-70 negative and MC631 positive, supporting that the GBM cells did express SSEA-4.

Figures 3A, 3B:
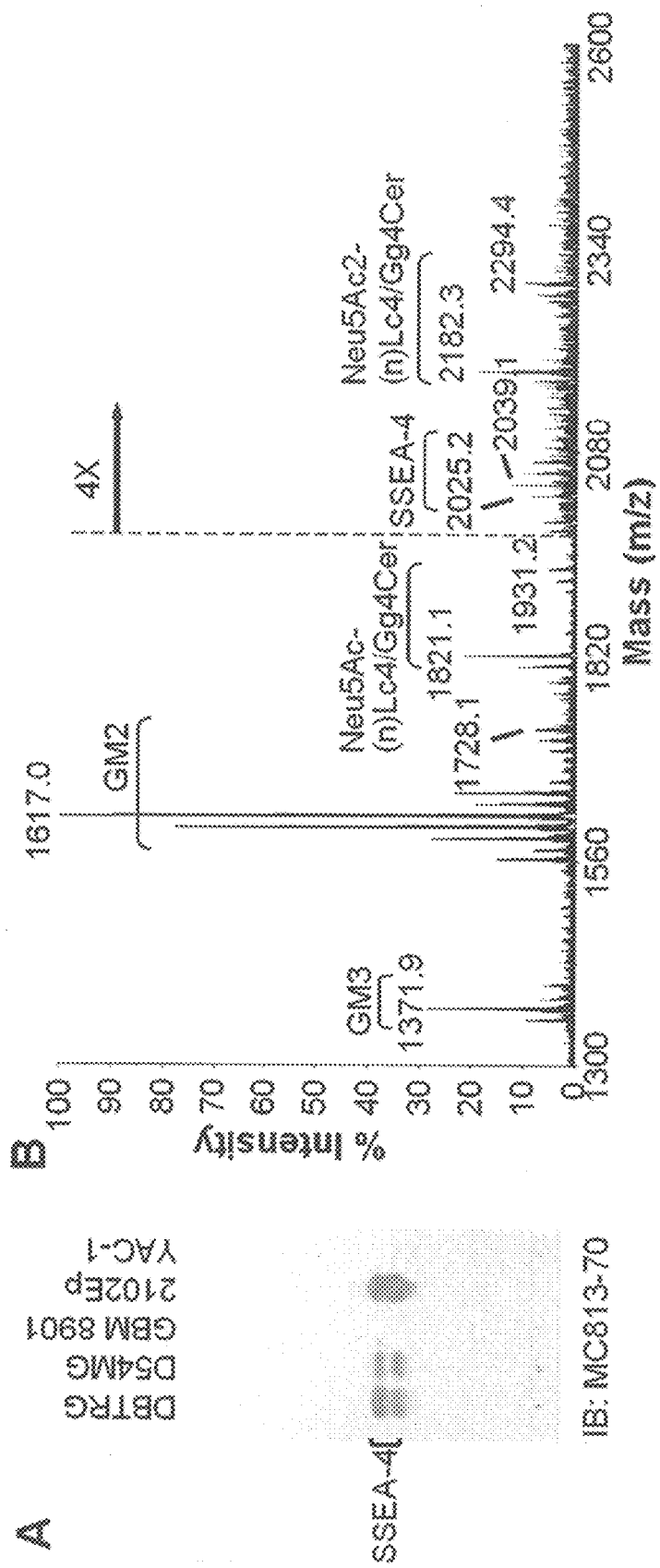
FIGS. 3A-3B. HPTLC immunostaining and MALDI-MS profiles of gangliosides from GBM cell lines.

To further verify the expression of SSEA-4, we next purified the gangliosides (the glycolipids with sialic acids) using anion-exchange chromatography, developed the purified gangliosides on HPTLC plates, and visualized by orcinol-H$_2$SO$_4$ stain or immunoblotting. The purified gangliosides from three different GBM cell lines exhibited similar patterns, with abundant GM3, GM2, Neu5Ac-(n)Lc4/Gg4Cer and Neu5Ac2-(n)Lc4/Gg4Cer. Consistent with the results of flow cytometric analysis, MC813-70 recognized two gangliosides (due to a different chain length of fatty acids) on TLC from DBTRG and D54MG, but not GBM 8901 cells (FIG. 3A). The positions of the immuno-reactive double bands in GBM gangliosides were the same as in the gangliosides purified from 2102Ep cells (FIG. 3A, lane 4), embryonal carcinoma cells known to express a high level of SSEA-4 glycolipid (Kannagi R, et al. (1983) Stage-specific embryonic antigens (SSEA-3 and -4) are epitopes of a unique globo-series ganglioside isolated from human teratocarcinoma cells. EMBO J 2(12):2355-2361). A double-band developed at a shorter distance than MC813-70 positive glycolipid was detected by MC813-70 in YAC-1 cells (FIG. 3A, lane 5), in which GM1b is a major ganglioside (Zarei M, Muthing J, Peter-Katalinic J, & Bindila L (2010) Separation and identification of GM1b pathway Neu5Ac- and Neu5Gc gangliosides by on-line nanoHPLC-QToF MS and tandem MS: toward glycolipidomics screening of animal cell lines. Glycobiology 20(1): 118-126), supporting that MC813-70 harbors a weak cross-reactivity toward GM1b. Immunoblotting with MC631 revealed that it could also recognize MC813-70 positive glycolipid with a lower affinity than MC813-70 did. To examine the number of sialic acids on MC813-70 positive glycolipids, we eluted gangliosides in different salt conditions and performed immunoblotting with MC813-70. The result supported that MC813-70 reactive gangliosides were monosialylated as the two bands appeared at the fraction eluted in low salt condition. We next used sialidases to elucidate the linkage of the sialic acid on this MC813-70-reactive monosialoganglioside. The gangliosides developed on TLC plate were treated with α2,3-sialidase or the sialidase that cleaves all linkages of sialic acids, and blotted with MC813-70 and MC631. The results showed that the immunoreactivity of MC813-70 disappeared after sialidase treatment, while MC631 could detect strong signals at the positions resembled MC813-70 reactive doublets, indicating the presence of an α2,3-linked sialic acid.

We also analyzed the gangliosides from DBTRG cells by MALDI-MS profiling (FIG. 3B). The spectra were dominated by several major peaks that occurred in signal clusters due to the expected heterogeneity of the ceramide (Cer) portions. Based on the m/z values of major molecular ions, as fitted to permethylation ofhexose (Hex), N-acetylhexosamine (HexNAc), or NeuAc residues, in combination with sphingosine and fatty acyl chains, the respective gangliosides profiles were assigned. Consistent with the HPTLC results, the MS profiling revealed that the major species of gangliosides in DBTRG cells were GM3, GM2, Neu5Ac-(n)Lc4/Gg4Cer, and Neu5Ac2-(n)Lc4/Gg4Cer. The signal with Neu5Ac-Hex4-HexNAc-Cer (m/z=2025.2) that represented SSEA-4, although with low intensity, was also detected, reflecting the existence of SSEA-4 in DBTRG cells. These data support that the MC813-70 reactive ganglioside was SSEA-4, and despite of being a minor constituent of total gangliosides, SSEA-4 was expressed in GBM cells.

Example 3: Expression of SSEA-4 in GBM Tissues

SSEA-4 is a widely used marker for stem cells, but the information about the expression of SSEA-4 in GBM tissues as well as normal brain tissues is not known. To understand if SSEA-4 is overexpressed in clinical GBM specimens, in addition to GBM cell lines, we analyzed the expression of SSEA-4 among astrocytomas from grade I to IV and normal brain tissues by immunohistochemistry on human tissue microarrays (FIG. 4). We found that 38 out of 55 GBM tissue specimens (69%) were positive for MC813-70 staining, and around half of GBM specimens were intensely stained (≥2+). As shown in the positive specimens, SSEA-4 was situated on the plasma membrane of GBM cells. Furthermore, around 55% of low-grade astrocytoma specimens were weakly stained (scored as 1+) by MC813-70, and the scores of SSEA-4 intensity was positively correlated with the grades of astrocytomas. On the contrary, most normal brain tissues were SSEA-4 negative. The result showed SSEA-4 is highly expressed in tumors, in particular, in GBM tumors.

Example 4: Anti-SSEA-4 Mediates CDC Against GBM Cell Lines

Figure 5A:
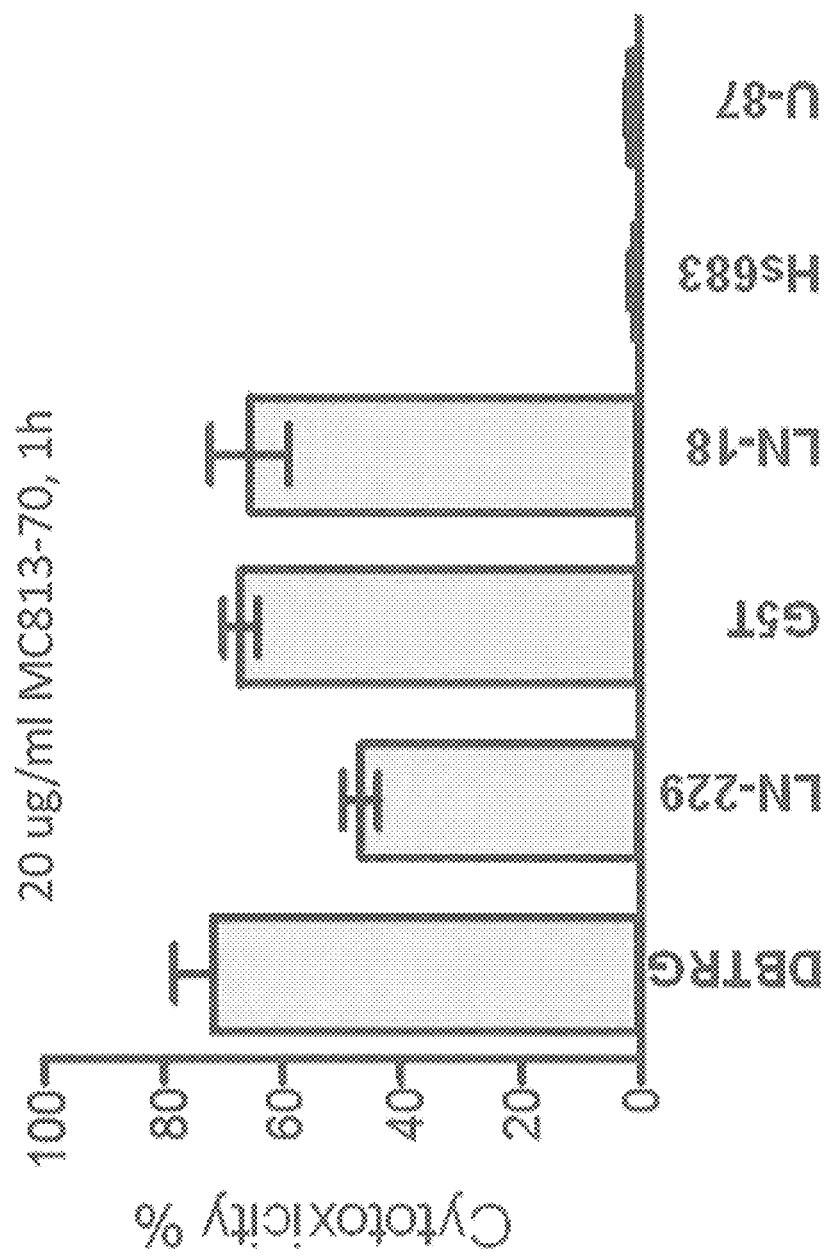
FIGS. 5A-5B. Complement dependent cytotoxicity (CDC) effects of anti-SSEA-4.

To test if targeting SSEA-4 would trigger complement-dependent cytotoxicity (CDC) in GBM cells, GBM cell lines were treated with MC813-70 and rabbit complement, and the degree of CDC was evaluated by detecting the level of released lactate dehydrogenase caused by cell death. FIG. 5 showed that in the presence of complement, mAb MC813-70 remarkably reduced the number of viable GBM cells. We observed a significant CDC in SSEA-4hi GBM cell lines: 71.7% cytotoxicity of DBTRG, 46.6% of LN-229, 67% of G5T, and 65.4% of LN-18 cells. MC813-70-mediated CDC did not kill two GBM cell lines, Hs683 and U87, which expressed low or no SSEA-4. Therefore, the level of MC813-70 mediated CDC positively correlated with the expression level of SSEA-4 in each GBM cell line.

Example 5: Anti-SSEA-4 Suppresses Brain Tumor Growth In Vivo

Figure 6:
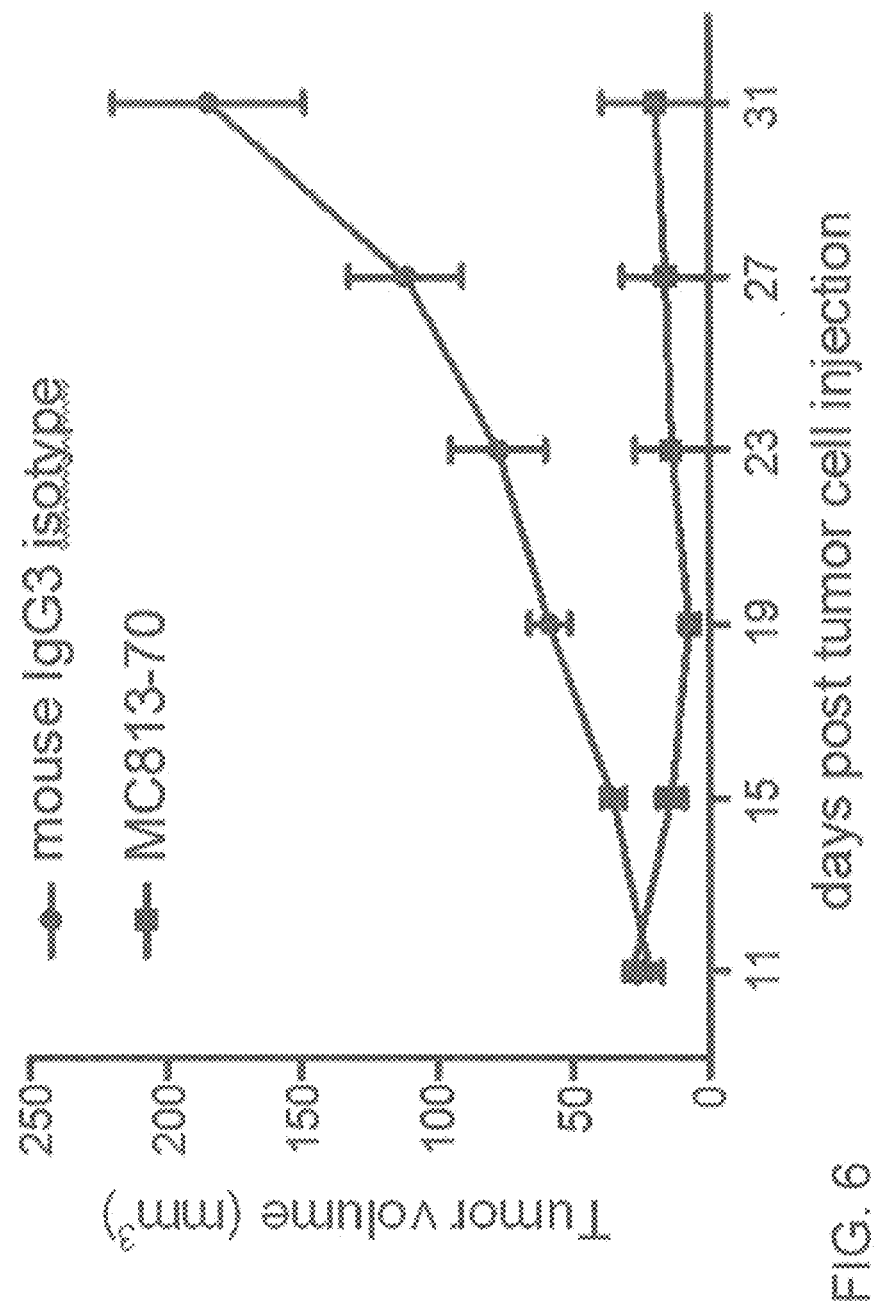
FIG. 6. Inhibition of DBTRG tumor growth by anti-SSEA-4. Male nude mice were inoculated with DBTRG cells on the right flank at day 0, intraperitoneally administered with MC813-70 or mouse IgG3 isotype control (200 µg per dose) at day 11, 15, and 19, and sacrificed at day 31. The tumor volume in each group (n=3) was measured at different time points and shown as mean±SD. P=0.001 was obtained by two-way ANOVA.

To check if MC813-70 was able to suppress GBM tumor growth in vivo, MC813-70 was administered to the nude mice injected with DBTRG cells subcutaneously, when the tumors grew to palpable bumps (15-30 mm3 at day 11 post-injection). MC813-70 (200 μg) was given intraperitoneally to each mouse every four days for a total of three times, with an irrelevant mouse IgG3 (isotype control) injected in parallel for comparison. The experiment revealed that the administration of MC813-70 could inhibit DBTRG tumor growth (FIG. 6). The growth of DBTRG tumors were completely suppressed in two of three mice treated with MC813-70, and the third mice developed tumor after the cease of antibody treatment. Comparing to the mice receiving MC813-70 treatment, DBTRG tumor grew aggressively (with the tumor volume of 184 mm3 in average at day 31) in the control group injected with mouse IgG3. These data demonstrated that MC813-70 was able to inhibit the growth of SSEA-4-expressing GBM tumors, possibly through CDC and antibody-dependent cell-mediated cytotoxicity (ADCC) in vivo.

Example 6: Expression of Globo H, SSEA3 and SSEA-4 on Various Cancer Cell Lines

SSEA-4 has been reported to be expressed on renal carcinoma (Saito S, et al. (1997) Expression of globo-series gangliosides in human renal cell carcinoma. Jpn J Cancer Res 88(7):652-659), basaloid lung cancer (Gottschling S, et al. (2013) Stage-specific embryonic antigen-4 is expressed in basaloid lung cancer and associated with poor prognosis. Eur Respir J 41(3):656-663), epithelial ovarian carcinoma (Ye F, Li Y, Hu Y, Zhou C, & Chen H (2010) Stage-specific embryonic antigen 4 expression in epithelial ovarian carcinoma. Int J Gynecol Cancer 20(6):958-964), breast cancer (Huang Y L, et al. (2013) Carbohydrate-based vaccines with a glycolipid adjuvant for breast cancer. Proc Natl Acad Sci USA 110(7):2517-2522), and oral cancer (Noto Z, et al. (2013) CD44 and SSEA-4 positive cells in an oral cancer cell line HSC-4 possess cancer stem-like cell characteristics. Oral Oncol). Here, we analyzed the expression levels of SSEA-3, Globo H and SSEA-4 on various cancer cell lines by flow cytometry. As shown in Table 7, we have examined a total of 134 cancer cell lines (17 brain cancer cell lines, 20 lung cancer cell lines, 23 breast cancer cell lines, 13 oral cancer cell lines, 2 esophageal cancer cell lines, 6 gastric cancer cell lines, 10 liver cancer cell lines, 5 bile duct cancer cell lines, 8 pancreatic cancer cell lines, 7 colon cancer cell lines, 6 renal cancer cell lines, 4 cervical cancer cell lines, 9 ovarian cancer cell lines and 4 prostate cancer cell lines).

TABLE 7

Expression of Globo H, SSEA-3 and SSEA-4 on various cancer cell lines.

|  | SSEA-3 | SSEA-4 | Globo H |
|---|---|---|---|
| Brain Cancer Cell Line |  |  |  |
| A172 | − | − | − |
| D54MG | + | + | + |
| DBTRG | − | + | − |
| G5T | + | + | − |
| G9T | + | + | + |
| GBM 8401 | − | − | − |
| GBM 8901 | − | − | − |
| Hs683 | − | + | − |
| LN-18 | + | + | + |
| LN-229 | + | + | + |
| SF126 | − | + | + |
| SNB75 | + | + | − |
| T95G | − | − | − |

TABLE 7-continued

Expression of Globo H, SSEA-3 and SSEA-4 on various cancer cell lines.

| | SSEA-3 | SSEA-4 | Globo H |
|---|---|---|---|
| U-138 MG | + | + | − |
| U-251 MG | + | + | − |
| U-373 MG | + | + | + |
| U-87 MG | − | − | − |
| Lung cancer cell line | | | |
| A549 | − | + | + |
| Calu-3 | − | + | − |
| CL1 | − | + | − |
| CL1-0 | − | + | + |
| CL1-5 | − | + | + |
| CL2 | − | − | + |
| CL3 | − | − | − |
| H1299 | − | − | − |
| H1355 | − | + | + |
| H157 | + | + | + |
| H441 | − | + | + |
| H460 | − | − | − |
| H480 | + | + | + |
| H520 | − | − | + |
| H661 | + | + | + |
| H928 | + | + | + |
| NuLi-1 | + | + | + |
| PC-13 | − | − | + |
| PC-14 | − | − | − |
| PC-9 | − | + | − |
| Breast cancer cell line | | | |
| Au565 | − | − | − |
| BT-20 | − | − | − |
| BT-474 | − | − | − |
| BT-483 | − | + | − |
| BT-549 | − | + | − |
| DU4475 | − | + | + |
| HBL-100 | − | + | + |
| HBL-435 | − | − | − |
| HCC1395 | + | + | + |
| HCC1599 | − | + | + |
| HCC1806 | + | + | + |
| HCC1937 | − | + | − |
| HCC38 | − | + | + |
| Hs578T | + | + | + |
| MCF-7 | + | + | + |
| MDA-MB-157 | + | + | + |
| MDA-MB-231 | + | + | + |
| MDA-MB-361 | − | + | + |
| MDA-MB-453 | − | + | + |
| MDA-MB-468 | − | + | − |
| SK-BR-3 | − | − | + |
| T47D | + | + | + |
| ZR75 | − | + | + |
| Oral cancer cell line | | | |
| Ca922 | − | + | + |
| Cal27 | − | + | + |
| HSC3 | − | + | + |
| OC3 | − | − | + |
| OECM1 | − | − | + |
| SAS | − | − | + |
| SCC25 | − | − | + |
| SCC4 | + | + | + |
| Tu-183 | − | − | + |
| Tw1.5 | − | + | + |
| Tw2.6 | − | + | + |
| UMSCC-1 | + | + | + |
| YD-15 | + | + | + |
| Esophageal cancer cell line | | | |
| CE81T | − | − | + |
| KYSE70 | − | + | + |
| Gastric cancer cell line | | | |
| AGS | − | − | + |
| AZ521 | + | + | + |
| KATO III | + | + | + |

TABLE 7-continued

Expression of Globo H, SSEA-3 and SSEA-4 on various cancer cell lines.

| | SSEA-3 | SSEA-4 | Globo H |
|---|---|---|---|
| NCI-N87 | − | − | + |
| SCM-1 | + | + | + |
| SNU-1 | − | + | + |
| Liver cancer cell line | | | |
| 59T | + | + | + |
| Changliver | − | − | + |
| HA22T | − | − | + |
| Hep3b | + | + | + |
| HepG2 | − | + | + |
| Huh-7 | − | + | + |
| J5 | − | − | + |
| Mahlavu | − | − | + |
| NTU-BL | + | + | + |
| SK-HEP-1 | + | + | + |
| Bile duct cancer cell line | | | |
| HuccT1 | + | + | + |
| SNU-1079 | − | − | − |
| SNU-1196 | − | − | + |
| SNU-245 | − | + | + |
| SNU-308 | − | − | − |
| Pancreatic cancer cell line | | | |
| AsPC1 | − | + | − |
| BxPC3 | − | + | + |
| HPAC | − | + | + |
| KP-4 | + | + | + |
| MIA PaCa-2 | + | + | + |
| Panc0203 | − | + | + |
| PANC1 | − | + | − |
| PL45 | + | + | + |
| Colon cancer cell line | | | |
| CX-1 | − | + | + |
| DLD-1 | − | − | + |
| H3347 | − | + | + |
| HCT1116 | − | + | − |
| HT-29 | − | − | + |
| SW480 | − | + | + |
| SW620 | − | + | + |
| Renal cancer cell line | | | |
| 769-P | + | + | + |
| A498 | − | + | − |
| A704 | − | − | + |
| ACHN | + | + | + |
| Caki-1 | + | + | + |
| Caki-2 | + | + | + |
| Cervical cancer cell line | | | |
| Hela | + | + | − |
| Hela 229 | + | + | − |
| Hela S3 | − | − | − |
| ME-180 | − | + | + |
| Ovarian cancer cell line | | | |
| C33A | − | + | − |
| CAOV3 | − | + | − |
| ES-2 | − | + | + |
| NUGCC | + | + | + |
| OVCAR-3 | − | + | + |
| SiHa | − | − | − |
| SKOV3 | − | + | − |
| TOV-112D | − | + | + |
| TOV-21G | + | + | + |
| Prostate cancer cell lines | | | |
| 22Rr1 | − | + | + |
| Du145 | − | + | − |
| hTERT-HPNE | + | + | − |
| PC-3 | − | + | − |

TABLE 8

Summary of expression of globo-series GSLs on cancer cell lines.

| Tumor origin | SSEA-4+ | SSEA-3+ | Globo H+ | SSEA4+ or SSEA3+ or Globo H+ | SSEA-4+ SSEA-3+ | SSEA-4+ Globo H+ | SSEA-4+ SSEA-3+ Globo H+ |
|---|---|---|---|---|---|---|---|
| Brain | 12/17 | 9/17 | 6/17 | 12/17 | 9/17 | 6/17 | 5/17 |
| Lung | 13/20 | 5/20 | 13/20 | 16/20 | 5/20 | 10/20 | 5/20 |
| Breast | 17/23 | 6/23 | 14/23 | 18/23 | 6/23 | 13/23 | 6/23 |
| Mouth | 8/13 | 2/13 | 11/13 | 12/13 | 2/13 | 7/13 | 2/13 |
| Esophagus | 1/2 | 0/2 | 2/2 | 2/2 | 0/2 | 1/2 | 0/2 |
| Stomach | 4/6 | 3/6 | 6/6 | 6/6 | 3/6 | 4/6 | 3/6 |
| Liver | 6/10 | 4/10 | 9/10 | 9/10 | 4/10 | 6/10 | 4/10 |
| Bile duct | 2/5 | 1/5 | 3/5 | 3/5 | 1/5 | 2/5 | 1/5 |
| Pancreas | 8/8 | 3/8 | 6/8 | 8/8 | 3/8 | 6/8 | 3/8 |
| Colon | 5/7 | 0/7 | 6/7 | 7/7 | 0/7 | 4/7 | 0/7 |
| Kidney | 5/6 | 0/6 | 5/6 | 6/6 | 0/6 | 4/6 | 0/6 |
| Cervix | 3/4 | 2/4 | 1/4 | 3/4 | 2/4 | 1/4 | 0/4 |
| Ovary | 8/9 | 2/9 | 5/9 | 8/9 | 2/9 | 5/9 | 2/9 |
| Prostate | 4/4 | 1/4 | 1/4 | 4/4 | 1/4 | 1/4 | 0/4 |

Expression of globo-series GSLs was determined by flow cytometry. Those cell lines in which over 15% of total cells are positive in flow cytometry are labelled positive.

We found that SSEA-4 was expressed in every type of cancer cell line (96 of 134 cancer cell lines). Globo H was also expressed in many of cancer cell lines (88 of 134), preferentially in lung, breast, pancreas, colon, stomach, mouth, liver, kidney cancer cell lines. We also observed that many of cancer cell lines (70 of 134) expressed SSEA-4 and Globo H simultaneously. On the other hand, the expression of SSEA-3 always followed a high expression of SSEA-4, indicating that SSEA-4 and Globo H were the major globo-series GSLs on the cancer cells.

To validate the identity of SSEA-4, we purified the gangliosides from nine MC813-70-positive cell lines as well as TF1a, a MC813-70-negative leukemia cell line, and performed immunostaining on HPTLC plates. As expected, SSEA-4 was detected in these nine cancer cell lines but not TF1a, and the intensity was well correlated with the geometric mean fluorescence intensity as examined by flow cytometry. These results revealed that SSEA-4 could be expressed in a variety of cancer cell lines and may serve as a potential target for multiple types of cancers.

Example 7: Expression of Glycan-Related Molecules on Cancer Cells and Cancer Stem-Like Cells For cancer stem-like cells, 8 glioblastoma cell lines were collected from ATCC and were maintained in the ultra-low attachment dish (Corning) with NSM consisting of neurobasal media (Invitrogen), B27 supplement (invitrogen), and human recombinant bFGF and EGF (20 ng/ml each; Upstate). The media were refreshed every 3 days and all cells were cultured in 5% CO2 and humidified atmosphere at 37° C.

The expression profiles of various markers on LN18, U138, U251, DBTRG and G5T cell lines and their spheres were examined. A total of 22 markers were examined including 17 glycans (GM3, GM2, GM1, GD1a, GD3, GD2, GT1b, A2B5, LeX, sLeX, LeY, SSEA-3, SSEA-4, Globo H, TF, Tn and sTn), and 5 glycoproteins (CD44, CD24, CD45, CD90, CD133). Anti-Globo H monoclonal antibody was generated in house. Other antibodies specific to the markers were purchased from vendors listed below. CD133/1 and CD133/2 were antibodies against different epitopes of CD133 glycoprotein.

| Antibody | Vendor |
|---|---|
| GM3 | seikagaku |
| GM2 | Merck Calbiochem |
| GM1 | Merck Calbiochem |
| GD1a | Millipore |
| GD1a | Millipore |
| GD3 | BD |
| GD2 | BD |
| GT1b | Millipore |
| A2B5 | Millipore |
| LeX | BD |
| sLeX | BD |
| LeY | Abcam |
| SSEA-3 | eBioscience |
| SSEA-4 | eBioscience |
| Globo H | Purified in Wong's Lab |
| TF | Thermo Scientific |
| Tn | DakoCytomation |
| sTn | Abnova |
| CD44 | eBioscience |
| CD24 | eBioscience |
| CD90 | BD |
| CD133/1 | Miltenyi Biotec |
| CD133/2 | Miltenyi Biotec |

Cells ($1 \times 10^5$) were resuspended in 50 μL FACS buffer (1% BSA/PBS solution) containing various concentration antibodies and incubated on ice for 30 min. After being washed twice with FACS buffer, if necessary, cells were incubated with Alexa488-labeled goat anti-mouse or FITC-anti-rabbit antibody (1:100; Jackson ImmunoResearch) for 30 min on ice before analysis on a FACSCalibur system (BD Biosciences).

Among the gangliosides expression patterns, we found that GD2 highly predominated and consistently expressed in 5 GBM neurosphere cells. However, in the neolactoseries pathway, LeX, a well-known marker for pluripotent stem cells, did not show any significant difference between these groups. Besides, GM2, GM1, GD1a, GT1b, A2B5, Tf, Tn, SSEA3, SSEA4, CD24, CD44 and CD90 were highly expressed in 5 GBM cells. Interestingly, in the globoseries pathway, SSEA4 abundantly expressed in parental cells instead of the neurosphere cells, indicating that SSEA4 may serve as the therapeutic targets of GBM cells.

TABLE 9

Expression of Glycans and Glycoproteins on Cancer Cells and Cancer Stem-Like Cells

| Antibody | LN18 parental | LN18 sphere | U138 parental | U138 sphere | U251 parental | U251 sphere | DBTRG parental | DBTRG sphere | G5T parental | G5T sphere |
|---|---|---|---|---|---|---|---|---|---|---|
| GM3 | ++ | + | ++ | + | − | − | N.D. | N.D. | − | − |
| GM2 | +++ | +++ | ++++ | ++++ | ++++ | +++ | N.D. | N.D. | ++ | ++ |
| GM1 | +++ | +++ | ++++ | ++++ | ++++ | +++ | N.D. | N.D. | ++ | ++ |
| GD1a | ++++ | ++++ | ++++ | ++++ | ++++ | ++++ | N.D. | N.D. | + | +++ |
| GD3 | − | + | N.D. | N.D. | N.D. | N.D. | − | ++ | − | + |
| GD2 | + | +++ | + | ++ | − | +++ | − | +++ | + | +++ |
| GT1b | ++++ | ++++ | ++++ | ++++ | ++ | ++ | N.D. | N.D. | + | + |
| A2B5 | ++ | ++ | ++ | ++ | + | + | N.D. | N.D. | + | + |
| LeX | − | − | − | + | +++ | ++ | N.D. | N.D. | +++ | +++ |
| sLeX | − | − | − | − | ++ | − | N.D. | N.D. | − | − |
| LeY | ++ | + | − | + | ++ | +++ | N.D. | N.D. | − | ++ |
| SSEA3 | ++ | + | ++ | − | − | − | − | − | ++++ | +++ |
| SSEA4 | ++++ | + | ++++ | + | +++ | − | ++++ | ++ | ++++ | ++++ |
| Globo H | + | − | − | − | − | − | N.D. | N.D. | − | − |
| TF | +++ | + | ++ | ++ | + | +++ | N.D. | N.D. | − | + |
| Tn | +++ | ++ | + | ++ | ++ | + | N.D. | N.D. | + | + |
| sTn | − | − | + | ++ | − | − | N.D. | N.D. | − | − |
| CD44 | ++++ | ++++ | ++++ | ++++ | ++++ | ++++ | N.D. | N.D. | ++++ | ++++ |
| CD24 | ++ | + | + | − | + | − | +++ | + | ++++ | + |
| CD90 | ++++ | ++++ | ++++ | ++++ | ++++ | ++++ | N.D. | N.D. | ++++ | ++++ |
| CD133/1 | − | − | − | − | − | − | − | − | − | − |
| CD133/2 | − | − | − | − | N.D. | N.D. | N.D. | N.D. | − | − |

Example 8: Enrichment of GBM Stem Cells by GD2 Plus SSEA-4 and CD133

In order to understand whether the combination of GD2 plus SSEA4 and CD133 could more specifically determine the population of GBM stem cells, we compare the self-renewal ability and tumorigenicity of GD2$^+$SSEA4$^+$CD133$^+$ population to the other populations.

Cells from GBM tumor were dissociated into single cell suspensions and labeled with anti-GD2 antibody (BD), anti-SSEA4 (Biolegend), anti-CD133 (Miltenyi Biotec). These labeled cells were then physically sorted using the FACS Aria II flow cytometer (BD). For detection of self-renewal ability, GBM tumor cells were dissociated, stained and plated in 96-well plates. The numbers of neurospheres whose diameter is over 100 um were calculated. For tumorigenicity, various number of cells, including 10,000-10 cells, were subcutaneously or intracranially inject into the immunodeficient mice. It is observed that the onset of tumors will be significantly faster in the GD2$^+$SSEA4$^+$CD133$^+$ population compared to the other populations.

Example 9: Generation of Anti-Globo H Monoclonal Antibodies

Hybridoma methodology was employed for the development of mAbs specific to Globo H. Female BALB/c mice, aged 6-8 weeks old, were immunized three times subcutaneously with the Globo H vaccine. Three immunizations were given at 2-wk intervals. Each vaccination contained 2 µg of Globo H. All of the sera were obtained by centrifugation at 4,000×g for 10 min. The serologic responses were analyzed by glycan microarray. A final boost was given intraperitoneally with 2 µg of Globo H, and 3 days later, the spleen cells from immunized mice were used for generating hybridomas.

Hybridoma cells secreting antibodies with the desired antigen-binding activities were screened as follows. Microtiter plates were coated by incubating with 4 µg/mL of neutravidin in carbonate buffer, 0.1M, pH 9.6, overnight at 4 C. The wells were blocked with 1% BSA in PBS, pH=7.3 for 1 hour and incubated with 4 µg/mL GloboH-biotin for 1 hour. The antisera were at various dilutions for 1 hour at 37° C. After washing, the ligand-bound antibodies were detected by HRP-conjugated goat anti-mouse IgG, Fcγ fragment specific (Jackson ImmunoResearch) at 1: 10,000 and incubated for 1 hour at 37° C., followed by incubation with TMB substrate. The OD was determined at 450 nm. Positive clones were selected for further characterization. Two exemplary clones, mAb 273 and 651, were identified in this study as specifically binding to Globo H. For mouse monoclonal isotyping, the IsoQuick Strips and Kits was used (sigma, 19535). Add hybridoma medium to the reaction vial. Insert the strip into the sample making sure the strips are upright. The sample will travel up the strip. Allow the strip to develop for 5 minutes before making final interpretations.

The $V_H$ and $V_L$ gene segments of the mAbs 273 and 651 were amplified by PCR from the hybridoma clone secreting the antibody. The gene segments thus obtained were sequenced to determine the $V_H$ and $V_L$ sequences of mAb 273 and 651, which are shown in Tables 1 and 2.

Example 10: Generation of Anti-SSEA-4 Monoclonal Antibodies

Hybridoma methodology was employed for the development of mAbs specific to SSEA-4. Female BALB/c mice, aged 6-8 weeks old, were immunized three times subcutaneously with the SSEA-4 vaccine. Three immunizations were given at 2-wk intervals. Each vaccination contained 2 µg of SSEA-4. All of the sera were obtained by centrifugation at 4,000×g for 10 min. The serologic responses were analyzed by glycan microarray. A final boost was given intraperitoneally with 2 µg of SSEA-4, and 3 days later, the spleen cells from immunized mice were used for generating hybridomas.

Hybridoma cells secreting antibodies with the desired antigen-binding activities were screened as follows. Microtiter plates were coated by incubating with 4 µg/mL of neutravidin in carbonate buffer, 0.1M, pH 9.6, overnight at 4° C. The wells were blocked with 1% BSA in PBS, pH=7.3 for 1 hour and incubated with 4 µg/mL SSEA-4-biotin for 1 hour. The antisera were at various dilutions for 1 hour at 37° C. After washing, the ligand-bound antibodies were detected by HRP-conjugated goat anti-mouse IgG or IgM antibody (Jackson ImmunoResearch) at 1: 10,000 and incubated for 1 hour at 37° C., followed by incubation with TMB substrate. The OD was determined at 450 nm. Positive clones were selected for further characterization. Three exemplary clones 45, 46 and 48, were identified in this study as specifically binding to SSEA-4. For mouse monoclonal isotyping, the IsoQuick Strips and Kits was used (sigma, 19535). Add hybridoma medium to the reaction vial. Insert the strip into the sample making sure the strips are upright. The sample will travel up the strip. Allow the strip to develop for 5 minutes before making final interpretations.

The $V_H$ and $V_L$ gene segments of the mAbs 45, 46 and 48 were amplified by PCR from the hybridoma clone secreting the antibody. The gene segments thus obtained were sequenced to determine the $V_H$ and $V_L$ sequences of mAbs 45, 46 and 48, which are shown in Tables 3-5.

Example 11: Generations of Chimeric Antibodies

Figure 9:
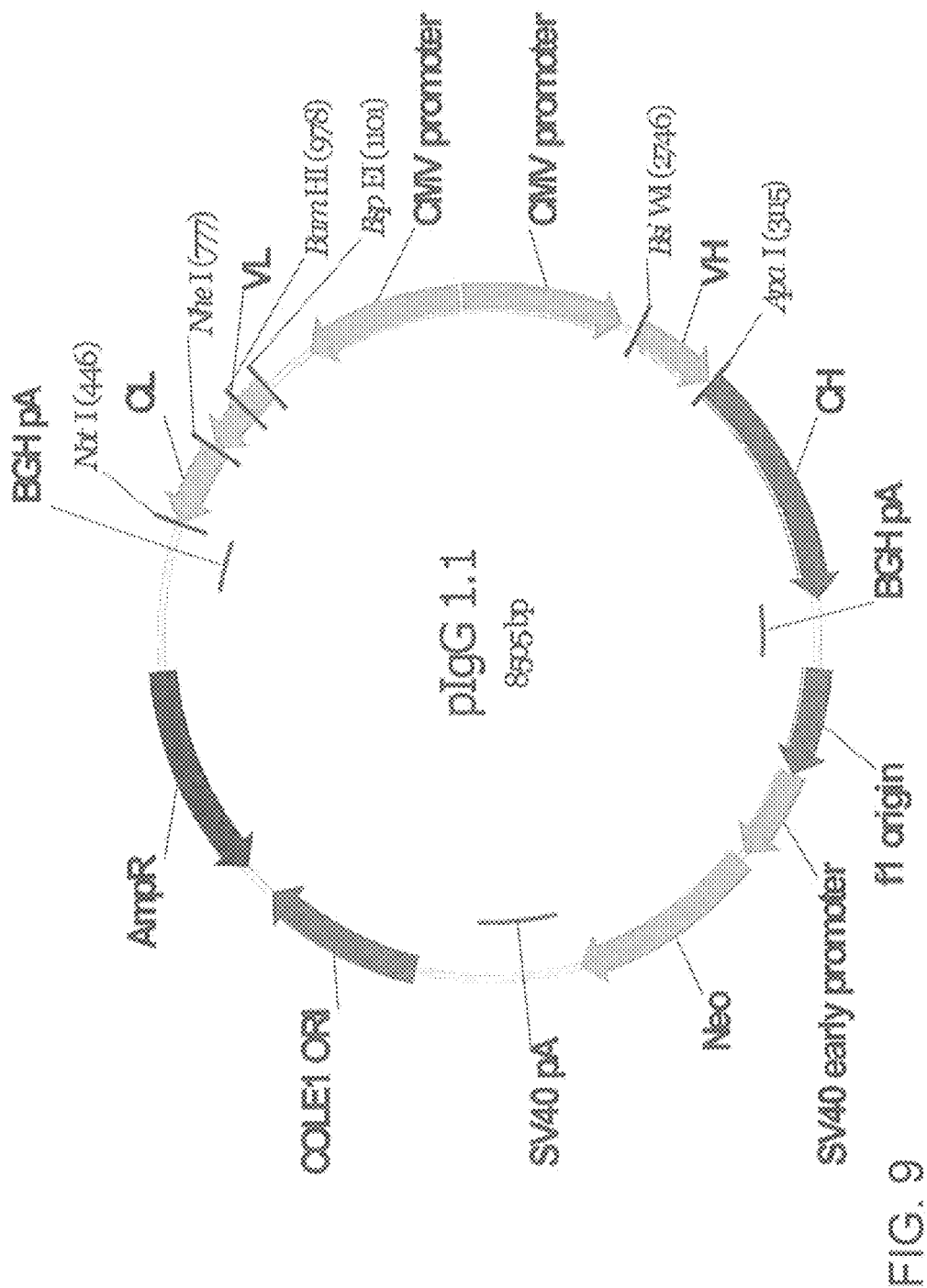
FIG. 9. Human IgG antibody expression vector.

The $V_H$ and $V_L$ gene segments of the mAb 273 and 651 were amplified by PCR from the hybridoma clone secreting the antibody. The gene segments thus obtained were sequenced to determine the $V_H$ and $V_L$ sequences of mAb 273 and 651, which are shown in Tables 1 and 2. The heavy chain and light chain variable region were cloned to human IgG1 antibody expression vector show as FIG. 9. VH was using enzyme site BsiWI and ApaI, and VL was using enzyme site BsPEI and NheI. Vectors were transiently transfected into either 293F or CHO-S cells. Recombinant chimeric Ab was purified and further study for binding assay and complement-dependent tumor cell lysis assay.

The $V_H$ and $V_L$ gene segments of the mAb 46 and 48 were amplified by PCR from the hybridoma clone secreting the antibody. The gene segments thus obtained were sequenced to determine the $V_H$ and $V_L$ sequences of mAb 46 and 48, which are shown in Tables 5 and 4. The heavy chain and light chain variable region were cloned to human IgG1 antibody expression vector show as FIG. 9. VH was using enzyme site BsiWI and ApaI, and VL was using enzyme site BsPEI and NheI. Vectors were transiently transfected into either 293F or CHO-S cells. Recombinant chimeric Ab was purified and further study for binding assay and complement-dependent tumor cell lysis assay.

Example 12: Binding Analysis of Antibodies By Glycan Array

The mAbs 273 and 651, and anti-SSEA-4 (mAbs 45, 46 and 48) were subjected to glycan binding studies as described below. 152 chemically synthesized glycans were synthesized and spotted on the glycan microarray. Glycan array were incubated with antibodies at various dilutions for 1 hour at 37° C. Then the slides were washed three times each with 0.05% Tween 20/PBS buffer (PBST). Next, Cy5-conjugated goat anti-mouse IgM or IgG antibody was added to the slide. Finally, the slides were washed three times with PBST. The microarray slides were dried before being scanned at 635 nm with a microarray fluorescence chip reader (4000B; Genepix). Data were analyzed by the software GenePix Pro-6.0 (Axon Instruments). The results obtained from this study are shown in FIG. 2.

The mAb 273 is capable of binding the Globo H hexasaccharide epitope of Fucα1-2Galβ1→3GalNAcβ1→3Galα1→4Galβ1→4Glcβ1 (#53 on glycan array), and a segment of Galβ1→3GalNAcβ1→3Galα1→4Galβ1→4Glcβ1 (#57 on glycan array). The mAb 651 recognizes the glycan epitopes of Fucα1→2Galβ1→3GalNAcβ1→3Galα1→4Galβ1→4Glcβ1 (#53 on glycan array), Galβ1→3GalNAcβ1→3Galα1→4Galβ1→4Glcβ1 (#57 on glycan array) and Neu5Acα2→3Galβ1→3GalNAcβ1→3Galα1→4Galβ1→4Glcβ1 (#12 on glycan array).

The mAb 45 is capable of binding the SSEA-4 hexasaccharide epitope of Neu5Acα2→3Galβ1→3GalNAcβ1→3Galα1→4Galβ1→4Glcβ1 (#12 on glycan array), and an analogue Neu5Acα2→3Galβ1→3GalNAcβ1→3Galα1→4Galβ1→4Glcβ1 (#49 on glycan array). The mAb 46 binds to Neu5Acα2→3Galβ1→3GalNAcβ1→3Galα1→4Galβ1→4Glcβ1 (#12 on glycan array), Neu5Gcα2→3Galβ1→3GalNAcβ1→3Galα1→4Galβ1→4Glcβ1 (#49 on glycan array), Neu5Acα2→3Galβ1→3GalNAcβ1→3Galα1 (#11 on glycan array) and Neu5Acα2→3Galβ1→3GalNAcβ1→3Galβ1 (#10 on glycan array). The mAb 48 is capable of binding Neu5Acα2→3Galβ1→3GalNAcβ1→3Galα1→4Galβ1→4Glcβ1 (#12 on glycan array), and Neu5Gcα2→3Galβ1→3GalNAcβ1→3Galα1→4Galβ1→4Glcβ1 (#49 on glycan array).

Figure 2A:
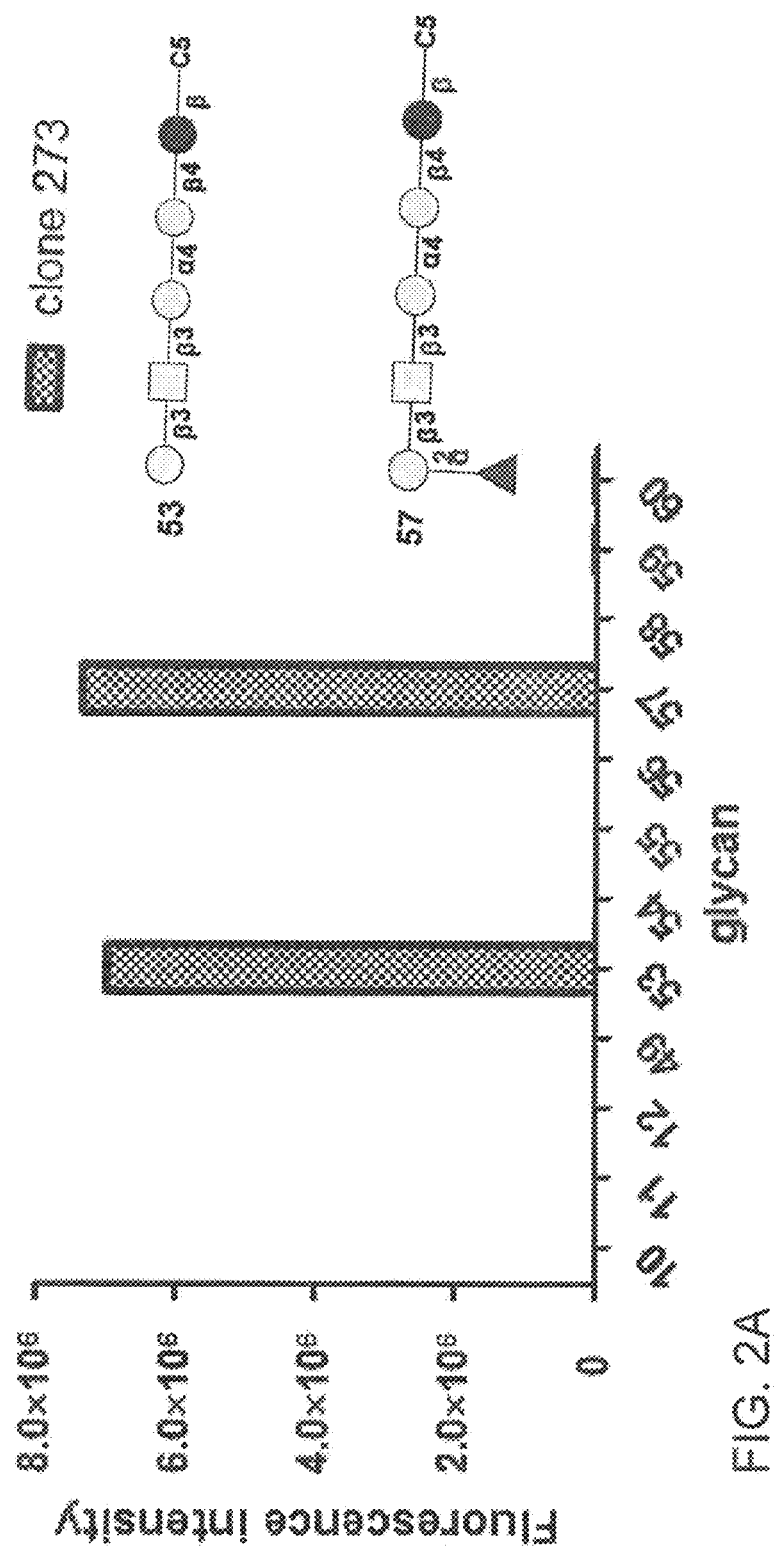
FIGS. 2A-2H. Glycan binding profiles of antibodies. The glycan microarrays on glass slides were interacted with Alexa Flour 647-conjugated antibody (10 µg/mL) and read in an array scanner at 635 nm. Data are presented as mean±SD.
Figure 2B:
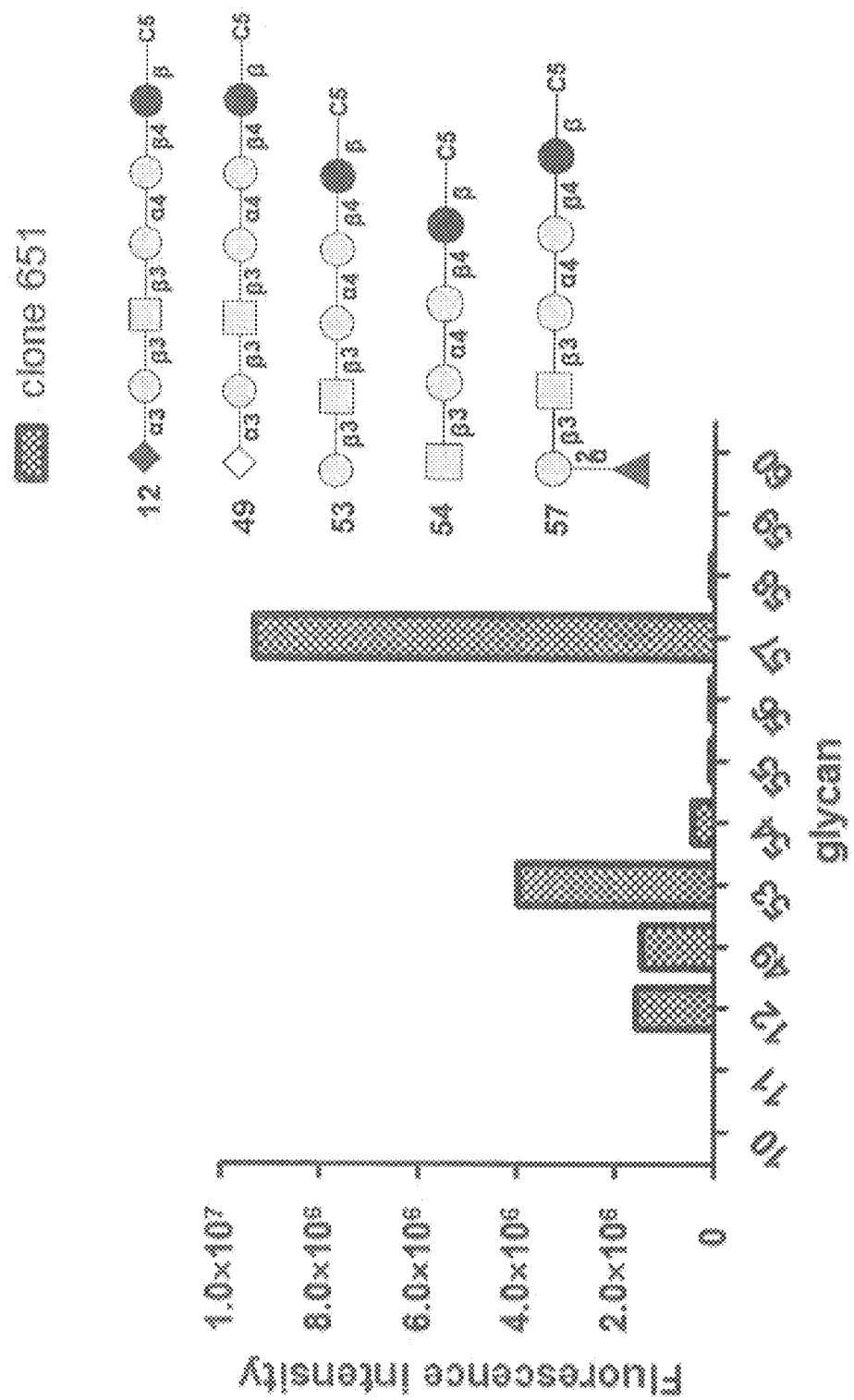
Figure 2C:
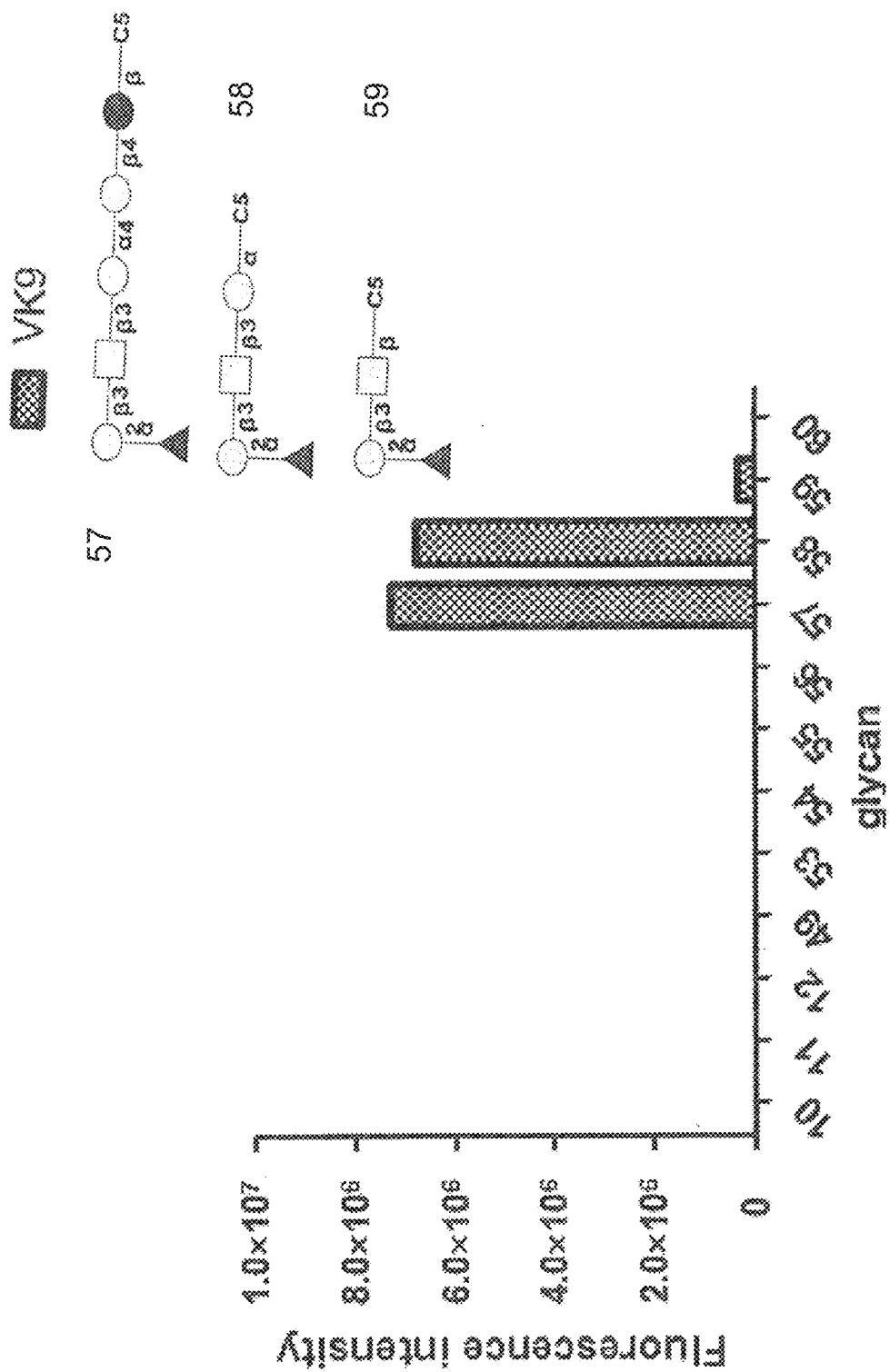
Figure 2D:
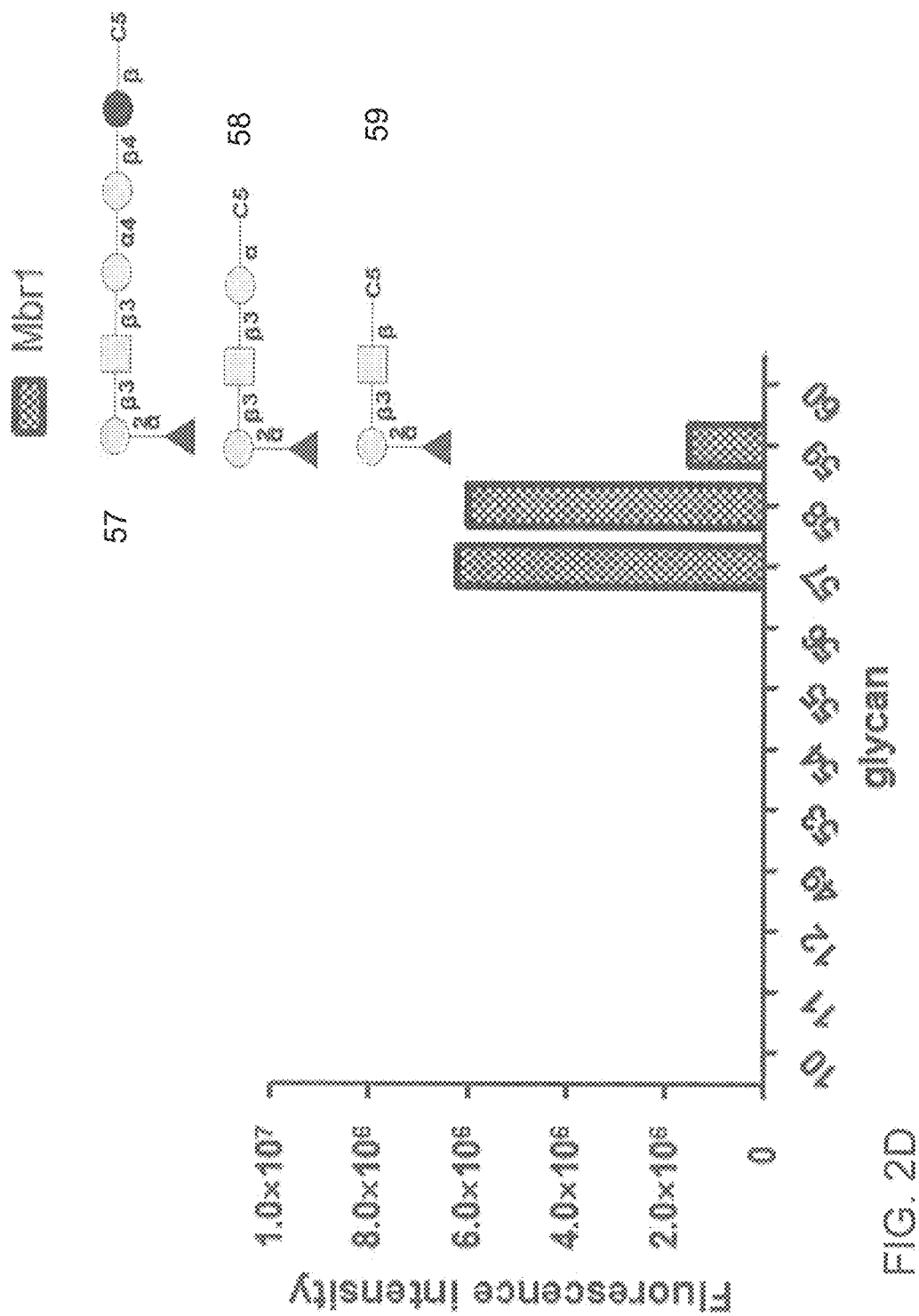
Figure 2E:
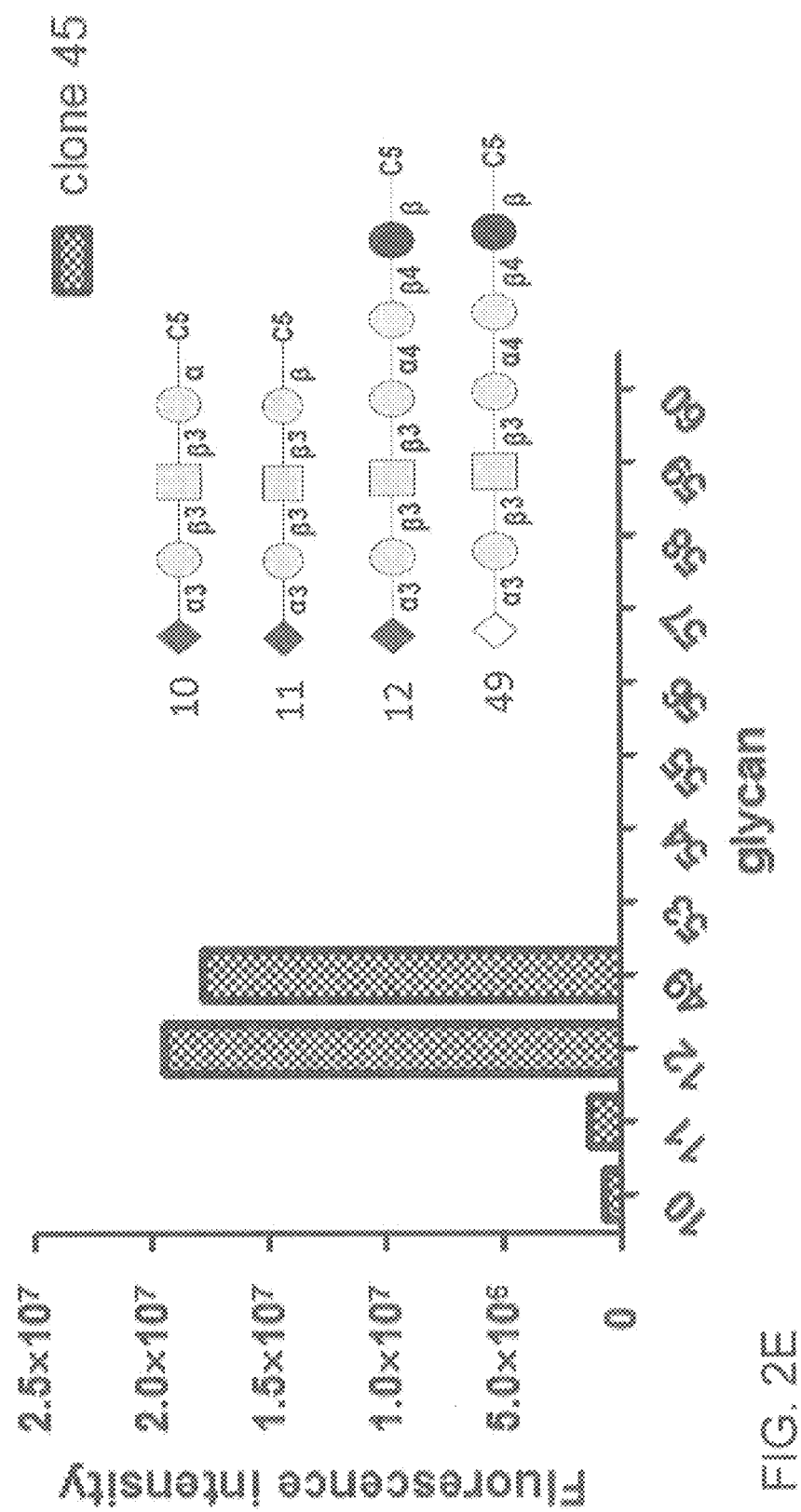
Figure 2F:
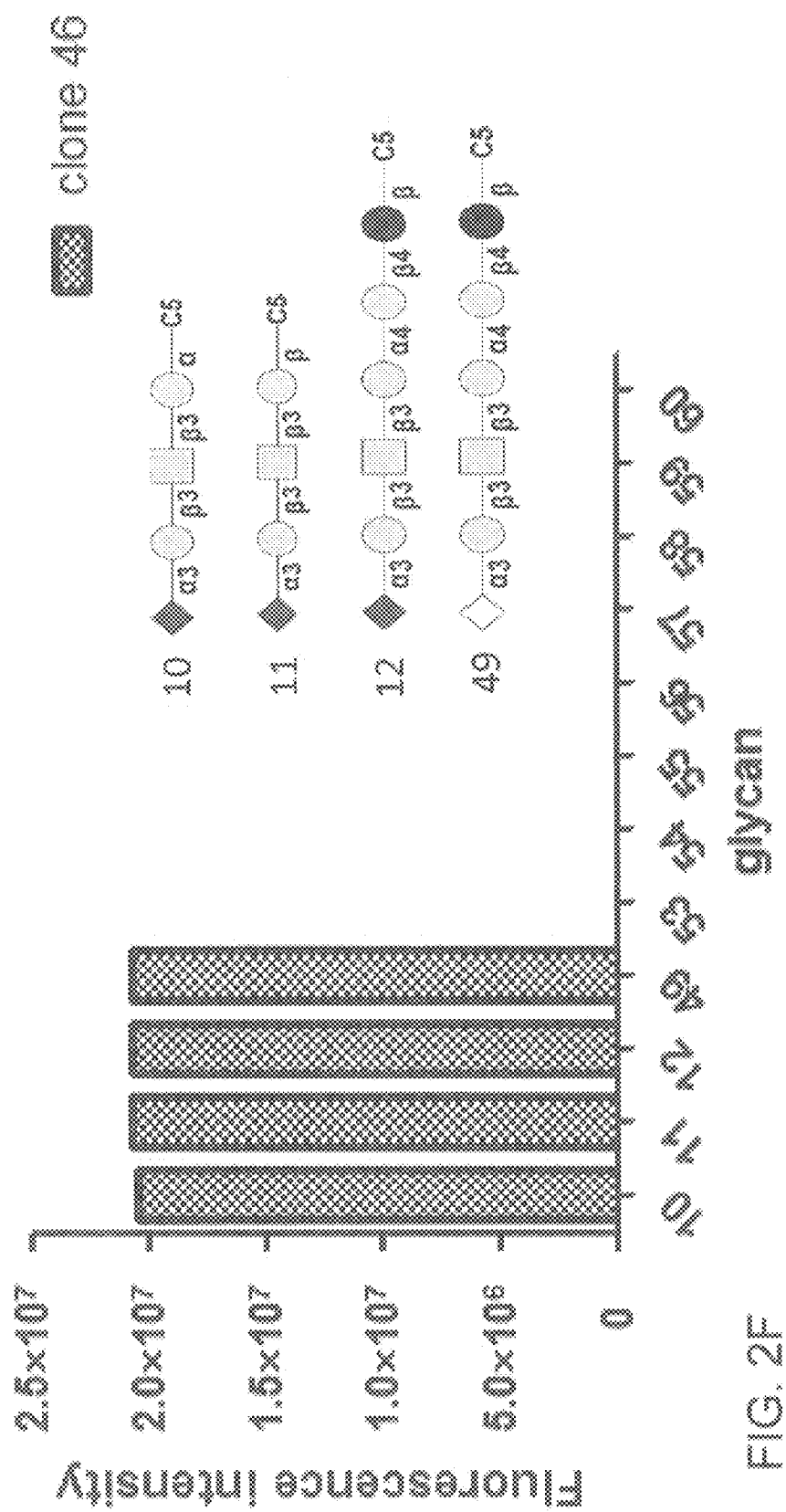
Figure 2G:
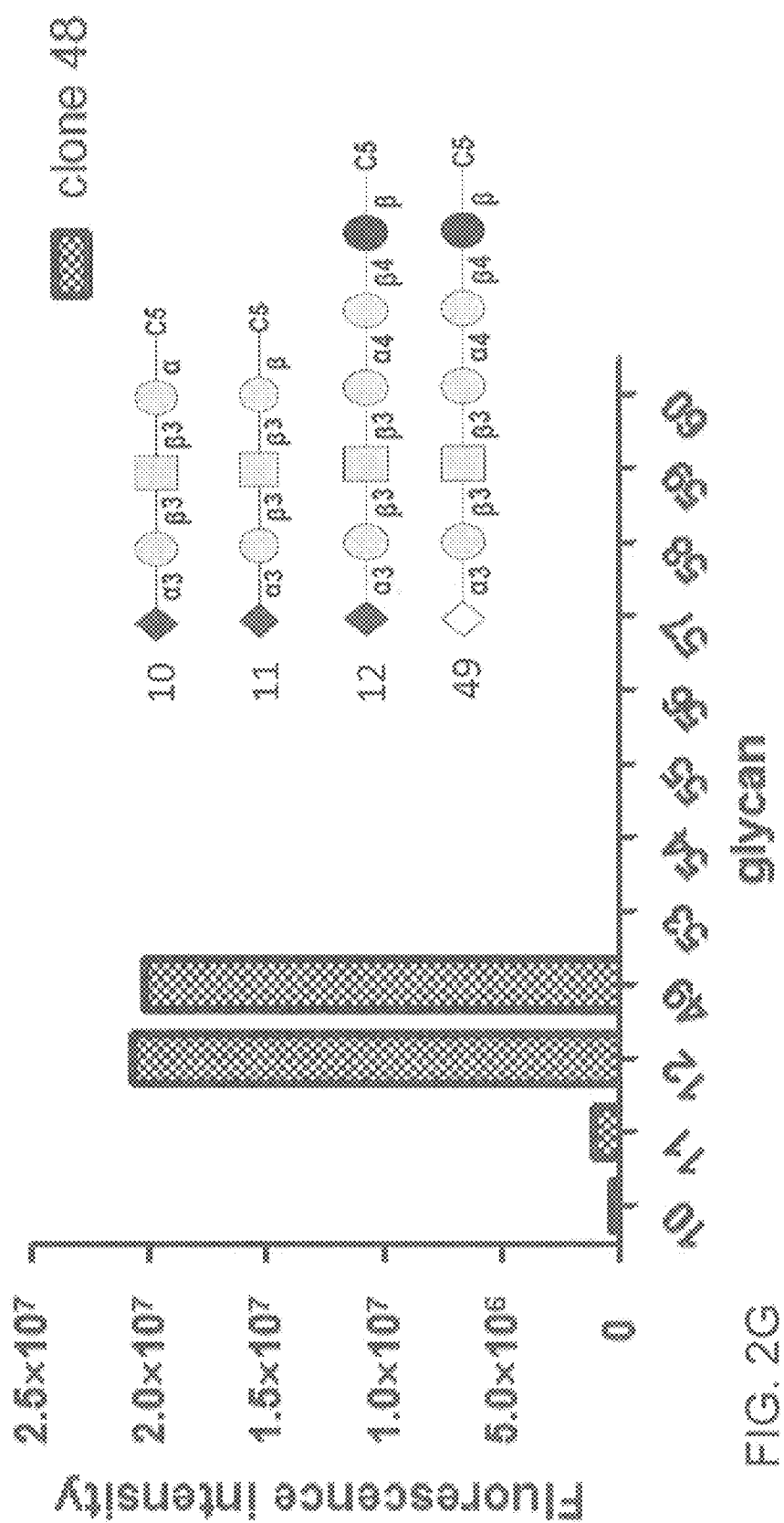
Figure 2H:
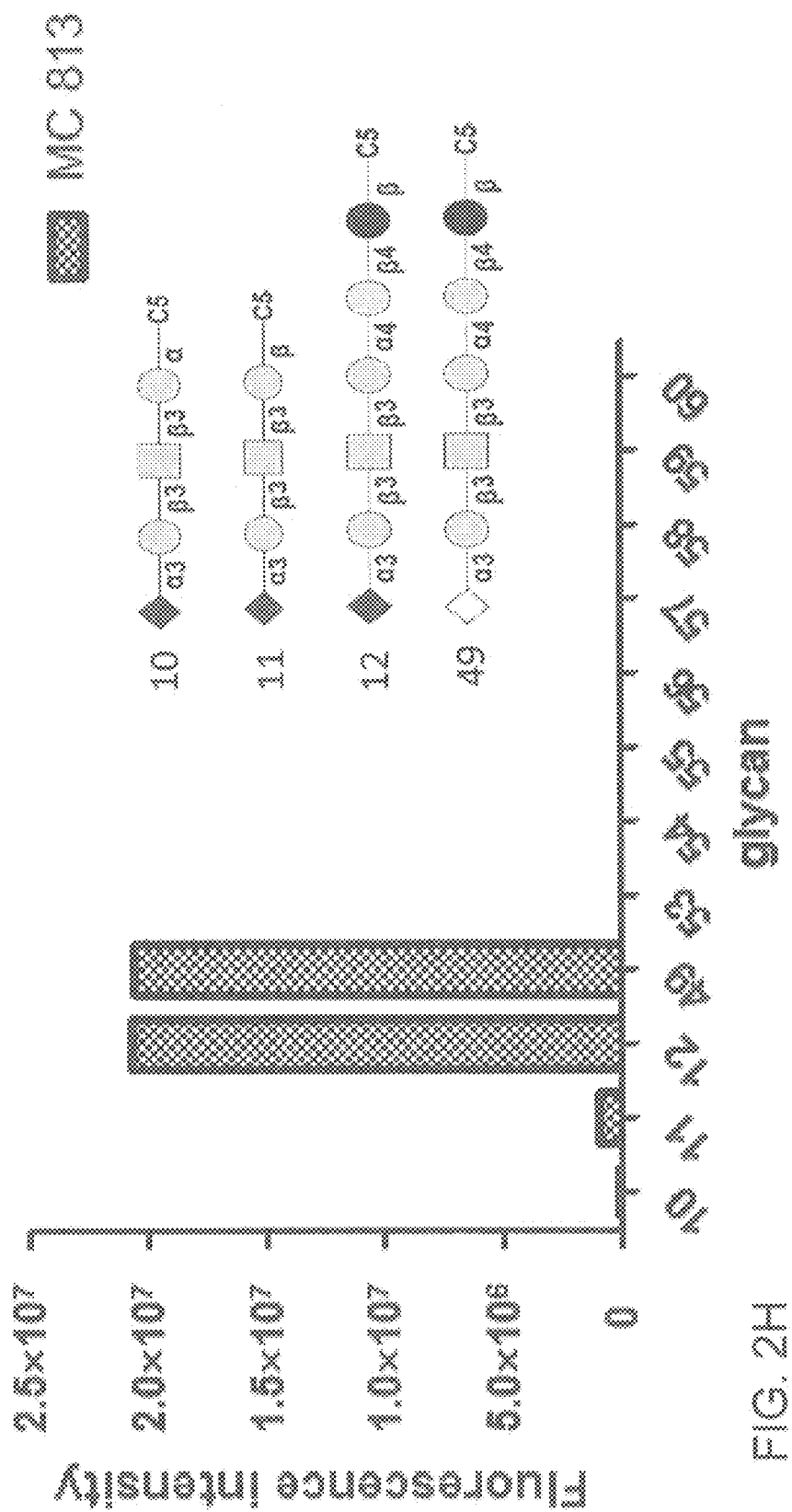

The glycan microarray was also used to investigate the binding specificity of MC813-70. As shown in FIG. 2(H), we found that among the 152 chemically synthesized glycans on the glycan microarray, MC813-70 recognizes Neu5Acα2→3Galβ1→3GalNAcβ1→3Galα1→4Galβ1→4Glcβ1 (#12 on glycan array) and Neu5Acα2→3Galβ1→3GalNAcβ1→3Galα1→4Galβ1→4Glcβ1 (#49 on glycan array). MC813-70 does not bind GM1b (#104 on glycan array) or GD1a (#106 on glycan array).

We also used the glycan array to determine the dissociation constants of MC45, MC48 and MC813-70 with SSEA-4 hexasaccharide on surface, and the Kd values for MC45, 48 and 813 are shown below. These results showed that these mAbs are highly specific for SSEA4.

|  | Kd (nM) ± SD(nM) |
| --- | --- |
| MC45 | 0.37 ± 0.08 |
| MC48 | 0.46 ± 0.1 |
| MC813-70 | 4.21 ± 0.26 |

Example 13: Binding Analysis of Antibodies to Cancer Cells by Flow Cytometry

Figure 7A:
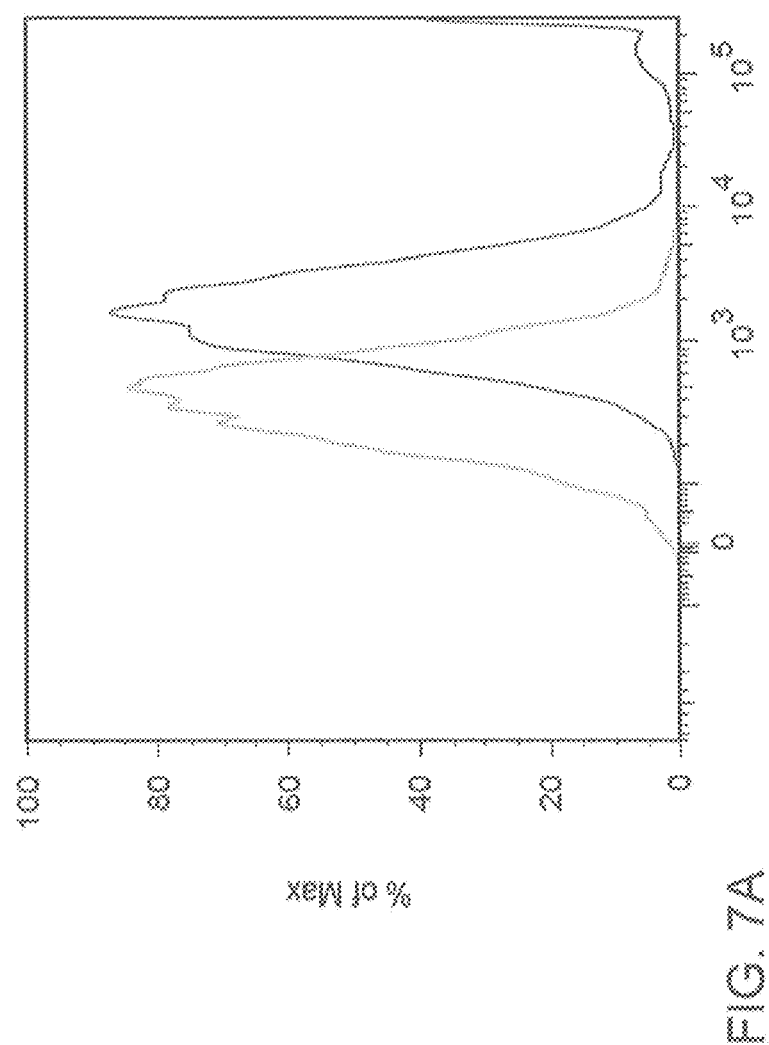
Figure 7B:
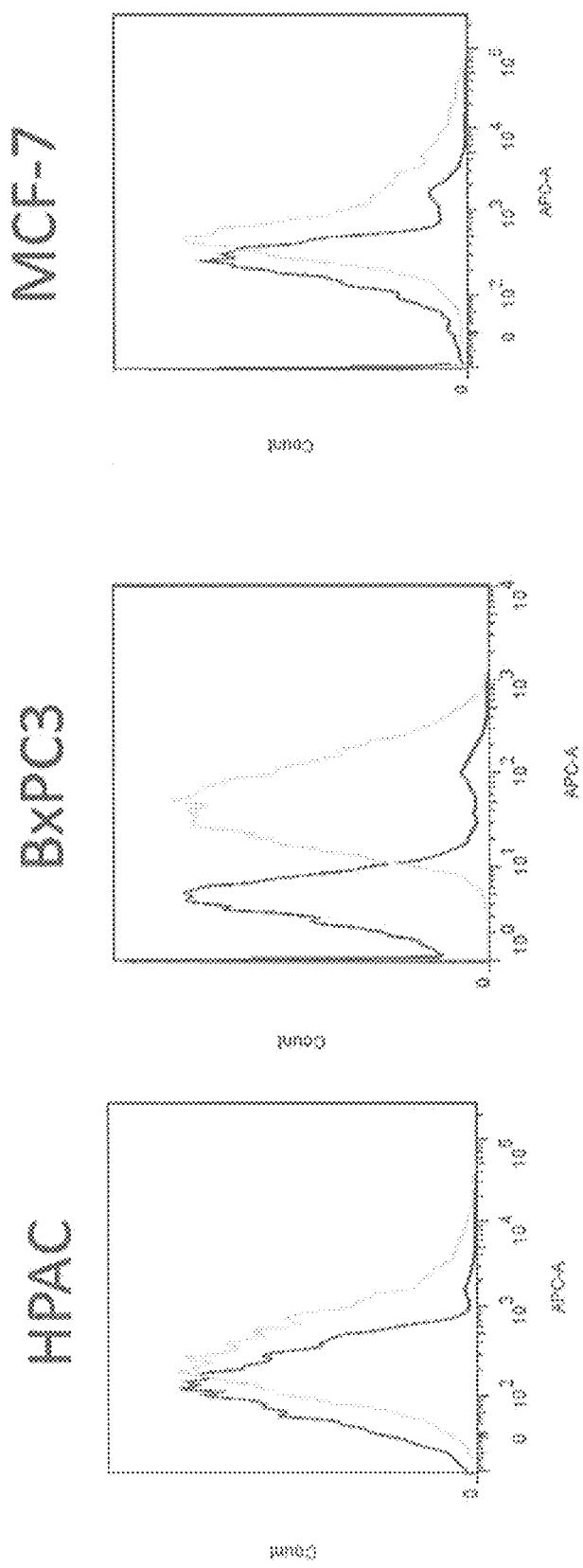
Figure 8:
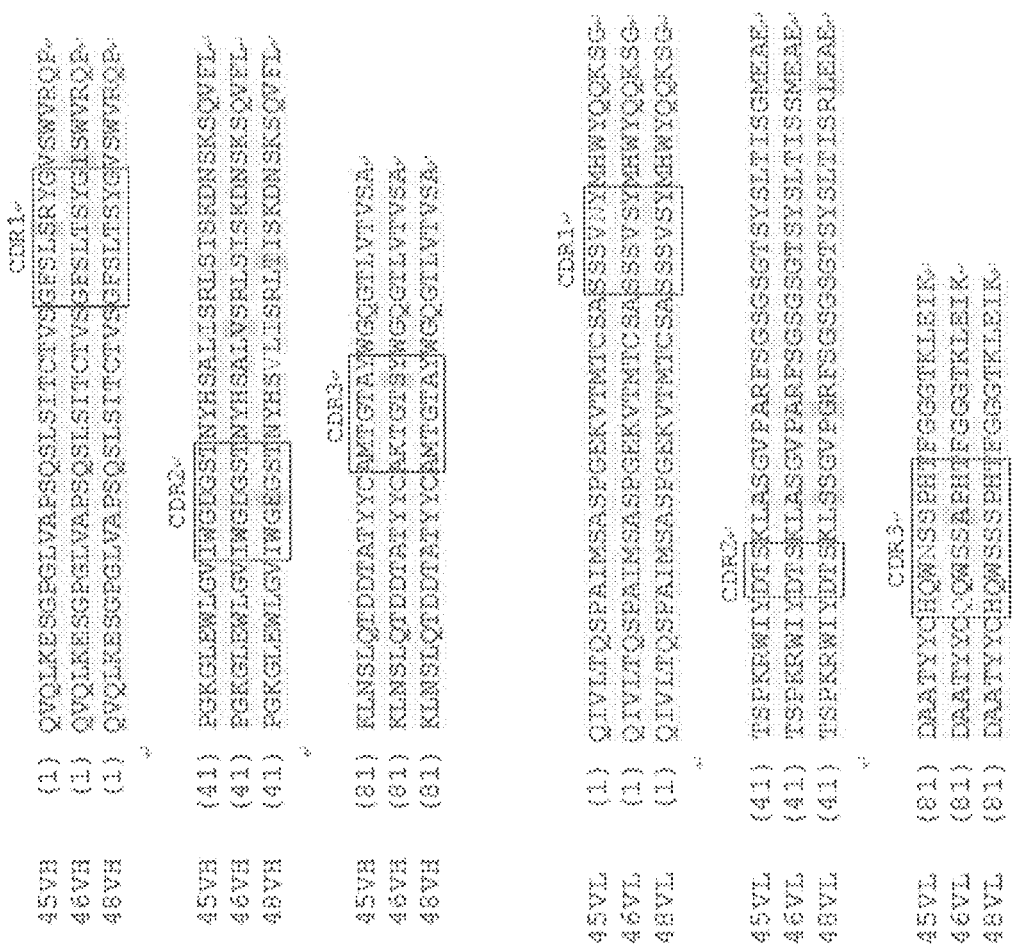
FIG. 8. Comparison of amino acid sequences mAb 45 (SEQ ID NOS 23 and 24, respectively, in order of appearance), mAb 46 (SEQ ID NOS 33 and 34, respectively, in order of appearance) and mAb 48 (SEQ ID NOS 43 and 44, respectively, in order of appearance). For multi-sequence alignments, ClustalW uses progressive alignment methods.

Binding of mAb 273 and anti-SSEA-4 (mAbs 45, 46 and 48) to cancer cell lines were examined. Cells ($1 \times 10^5$) were resuspended in 100 µL FACS buffer (1% BSA/PBS solution) containing various concentration antibody and incubated on ice for 30 min. After being washed twice with FACS buffer, cells were incubated with 649-labeled goat anti-mouse antibody (1:100; Jackson ImmunoResearch) for 30 min on ice before analysis on a FACSCalibur system (BD Biosciences). The results are shown in FIGS. 7A-D. Breast cancer cells MCF-7 were stained with mAb 273 (FIG. 7A). Pancreatic cancer cells (HPAC and BxPC3) and breast cancer cells MCF-7 were stained with mAb 45 (FIG. 7B). Pancreatic cancer cells (HPAC and BxPC3) and breast cancer cells MCF-7 were stained with mAb 46 (FIG. 7C). Pancreatic cancer cells (HPAC and BxPC3) and breast cancer cells MCF-7 were stained with mAb 48 (FIG. 7D).

Example 14-1: Antibodies Mediate Complement-Dependent Cytotoxicity (CDC)

Figure 5C:
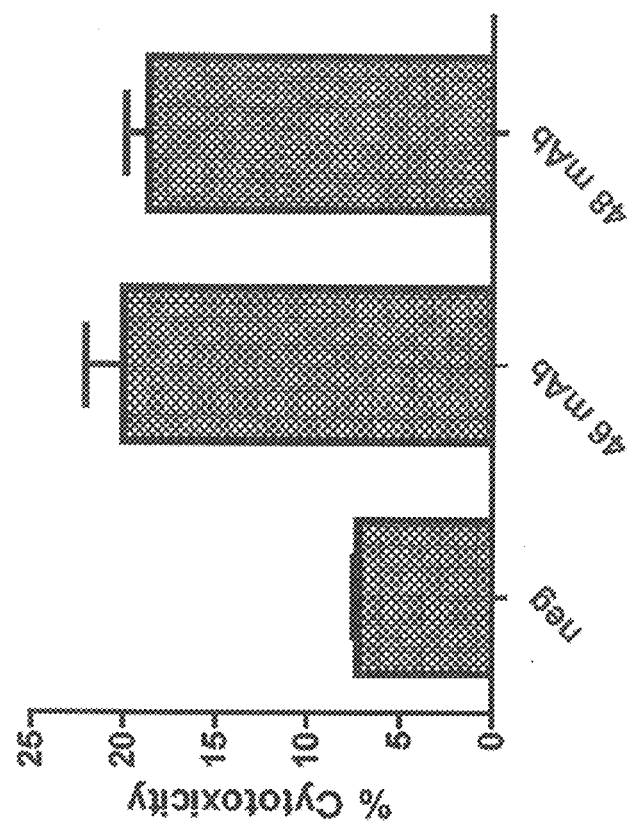
(FIG. 5C) mAbs 46 and 48 on human pancreatic cancer cells BxPC3 in vitro. Aliquots of tumor cells ($10^4$ cells) were incubated with 80 µL of antibody at various concentrations in the presence of 20 µL of human-serum or rabbit serum as complement source for 2 hour at 37° C. Cytotoxicity was determined within the tumor cell population after addition of 7-amino-actinomycin D (7-AAD).
Figure 5B:
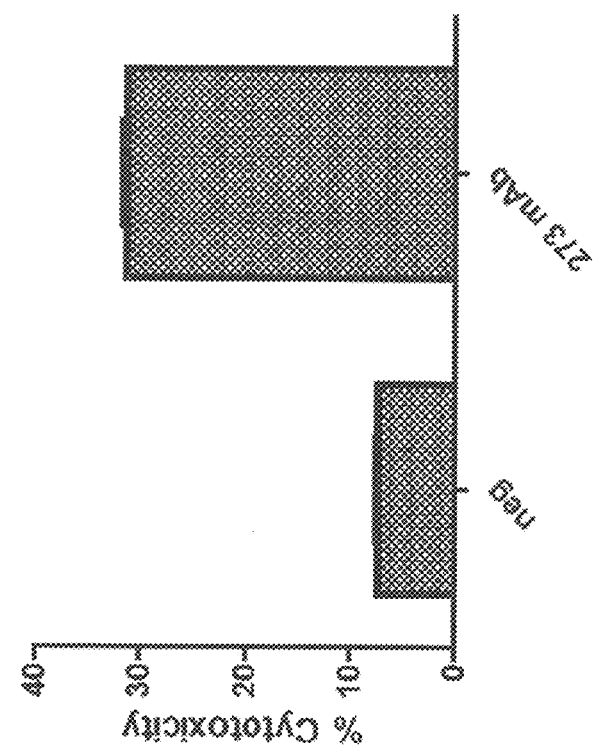

The ability of mAb 273 to mediate CDC of Globo H expressing cells was examined. MCF-7 cells in the presence of human serum as a source of complement. Cell death was assessed by the addition of the viability probe 7-AAD. Based on the results of the 7-AAD measurement, percentage-specific lysis was calculated using a FACScan flow cytometer. The antibodies showed about 30% killing activity at 40 µg/mL. As shown in FIG. 5(B), mAb273 can mediate successfully Complement-Dependent Cytotoxicity of Globo H expressing cell.

Example 14-2

The ability of exemplary mAbs 46 and 48 to mediate CDC of SSEA-4 expressing cells was examined. *Homo sapiens* pancreas adenocarcinoma cell (BxPC3) in the presence of rabbit serum as a source of complement. Cell death was assessed by the addition of the viability probe 7-AAD. Based on the results of the 7-AAD measurement, percentage-specific lysis was calculated using a FACScan flow cytometer. The antibodies showed about 20% killing activity at 40 µg/mL. As shown in FIG. 5(C), mAbs 46 and 48 successfully mediated CDC of SSEA-4 expressing cells.

Materials and Methods

Reagents. Anti-Le$^x$, anti-sLe$^x$, and anti-GD2 antibodies were purchased from BD Biosciences (Franklin Lakes, N.J.). Anti-GD1a, anti-GT1b and Alexa Fluor® 488 anti-A2B5 antibodies were purchased from Millipore (Billerica, Mass.). Anti-GM1 and anti-GM2 antibodies were purchased from Calbiochem (Merck, Darmstadt, Germany). Anti-Le$^y$ and anti-sTn antibodies were purchased from Abcam (Cambridge, UK). Anti-TF antibody was purchased from Thermo Scientific (Waltham, Mass.). Anti-Tn antibody was purchased from DakoCytomation (Glostrup, Denmark). Fluorescence-labelled or purified MC813-70 and MC631 were purchased from Biolegend (San Diego, Calif.). MC813-70 ascites were purchased from Developmental Studies Hybridoma Bank at the University of Iowa. The usages of these antibodies in individual experiments were descried in the following paragraphs.

Cell Culture. U-251, U-138, LN-18, T98, LN-229, U87, U-373, Hs683, D54MG, GBM 8401, GBM 8901, G5T, G9T, SNB75, A172 and SF126 cells were routinely maintained in high glucose DMEM (Life Technologies, Carlsbad, Calif.) supplemented with 10% FBS (Biological Industries, Israel). DBTRG cells were maintained in RPMI 1640 (Life Technologies) with 10% FBS.

Flow Cytometry. Cells ($1 \times 10^5$) were stained with 0.5 µg Alexa Flour 488-conjugated anti-SSEA-3 mAb (MC-631), anti-SSEA-4 mAb (MC813-70) or allophycocyanin (APC)-conjugated anti-Globo H mAb (VK9, a gift from Philip O. Livingston, Memorial Sloan-Kettering Cancer Center, New York, N.Y.) in 50 µL FACS buffer (PBS solution with 1% FBS) on ice for 30 min. For lectin staining, cells were incubated in lectin binding buffer % BSA, 0.5×Carbo-Free Blocking buffer (Vector Laboratories, Burlingame, Calif.), 2 mM MgCl$_2$, 2 mM CaCl$_2$] containing biotinylated lectin for 30 min on ice. After being washed twice with lectin binding buffer, cells were incubated with streptavidin-APC (1:500 diluted in FACS buffer; Biolegend) on ice for 30 min. After washing twice with 200 µL FACS buffer, cells were resuspended in 200 µL FACS buffer containing 1 µg/ml propidium iodide (PI) and subjected to analysis. Data acquisition was performed on a FACSCanto (BD Biosciences) with FACSDiva software (BD Biosciences), and data analyses were performed using FlowJo software (TreeStar, Ashland, Oreg.). Live cells (PI-negative) were gated for analysis. For methanol washing, cells were washed and fixed with 4% paraformaldehyde in PBS for 15 min at room temperature, followed by incubation in methanol for 10 min before staining with specific antibodies.

Immunofluorescent Staining. Cells were plated on tissue culture plastic chamber slides (Nunc, Roskilde, Denmark) overnight to allow sufficient attachment, fixed with 4% paraformaldehyde for 15 min at room temperature, washed three times with PBS, and then blocked with 3% BSA in PBS. Cells were then incubated overnight with 10 µg/mL of mAb MC813-70 (Biolegend), washed three times with PBS and incubated for 2 h at room temperature with 5 µg/ml FITC-conjugated anti-mouse IgG (eBioscience, San Diego, Calif.). Nuclei were counterstained with Hoechst 33342 (2 µg/mL, Life Technologies). All images were acquired by an Olympus IX71 microscope.

Immunohistochemistry. For MC813-70 staining on normal brain and GBM specimens, three different tissue microarray slides (Biomax, Rockville, Md.), comprising a total of 19 normal brain sections and 55 GBM sections were tested. The slides were dried at 56° C. for 1 h, deparaffinized in xylene and rehydrated in graded alcohols, followed by treating with blocking buffer [2% Blocking Reagent (Roche, Basel, Switzerland) in PBS with 0.1% Triton X-100] for 30 min at room temperature. The slides were then incubated at 4° C. for overnight with mAb MC813-70 (10 µg/mL in blocking buffer). After gently washing with PBST, the immunoreactivity on sepecimens was detected with Super-Sensitive™ Polymer-HRP IHC Detection System (BioGenex, Fremont, Calif.), and the slides were counterstained with hematoxylin and prepped for mounting.

Glycan Array Fabrication. Microarrays were printed (BioDot; Cartesian Technologies, Irvine, Calif.) by robotic pin (SMP3; TeleChem International Inc., Sunnyvale, Calif.) with the deposition of ~0.6 nL per spot. Amine-containing glycans in printing buffer (300 mM sodium phosphate, pH 8.5, 0.01% Triton X-100) were spotted onto N-Hydroxysuccinimide (NHS)-activated glass slides. Each glycan was printed at 100 M in a replicate of four or 50 µM in a replicate of six for Kd determination. Printed slides were allowed to incubate in 80% humidity for 30 min, followed by desiccation for overnight. Remaining NHS groups were blocked by immersing the slides for 1 h in SuperBlock (PBS) Blocking Buffer (Pierce, Appleton, Wis.).

Ab Binding Assay. MAb MC813-70 Alexa Fluor 647 (Biolegend) was prepared in 100 µL of PBS-B-T (pH 7.4, with 3% BSA and 0.05% Tween-20) and applied to cover the grid. After incubation in a moist chamber for 30 minutes, the slides were rinsed with PBST and deionized water and blow-dried. The slides were scanned at 635 nm in genepix 4300A (Molecular device, Sunnyvale, Calif.). Data were analyzed by GenePix Pro-6.0 (Molecular Devices).

Sialidase Treatment. Cells were washed and resuspended in PBS buffer at $1 \times 10^7$ cells/mL. Cells were incubated with or without 500 mU α2,3 sialidase (NEB, Ipswich, Mass.)/ $10^6$ cells/100 µL for 1 h at 37° C., and washed twice with FACS buffer followed by surface staining and flow cytometry. The efficiency of sialidase treatment was measured by biotinylated *Maackia amurensis* lectin II (MAL II; Vector Laboratories), which recognizes α2,3-linked sialic acids.

Extraction of Glycosphingolipids. Cells ($4 \times 10^7$) were harvested, washed with PBS and homogenized in water. Per 3 vol. homogenate was added with 8 vol. methanol and 4 vol. chloroform and the sample was incubated in a bath sonicator for 30 min. After centrifugation at 3000×g for 15 min, the pellet was repeatedly extracted with 4:8:3 chloroform/methanol/water, and the combined supernatant was dried under a stream of nitrogen. The total lipid extract was then dissolved in chloroform/methanol/water (30/60/8, v/v/v), and gangliosides were purified by DEAE-Sephadex A-25 (GE Healthcare, Buckinghamshire, UK) based anion-exchange chromatogrpahy. Unbound flow-through containing neutral glycolipids was collected and dried. After washing with chloroform/methanol/water (30/60/8, v/v/v), gangliosides were eluted with chloroform/methanol/aqueous NaCl (0.02, 0.2 and 0.8 M stepwisely) (30/60/8, v/v/v), followed by desalting with Sep-Pak C18 Cartridges (Waters, Milford, Mass.). The extracts were dried under nitrogen and the ganglioside residues as well as neutral glycolipid residues were redissolved in 100 μL chloroform/methanol (2/1, v/v).

High-Performance Thin-Layer Chromatograhy. GSLs were separated on glass-packed silica gel 60 precoated high-performance thin-layer chromatography (HPTLC) plates (Merck). Gangliosides were chromatographed in chloroform/methanol/water(120/85/20, v/v/v) and neutral GSLs in chloroform/methanol/water (120/70/17, v/v/v), respectively, each supplemented with 2 mM $CaCl_2$. For analytic purposes, GSLs were stained with 0.3% orcinol in 3 M $H_2SO_4$ and then transferred to a preheated heating plate (110° C.) until bluepurple spots appeared. For preparative purposes, gangliosides were stained with 0.02% primulin (Sigma, St. Louis, Mo.) in acetone/water (4/1, v/v). Spots of gangliosides were marked with a pencil under UV light and scraped from the plate with an adsorbent scraper (Sigma) and the gangliosides were extracted with chloroform/methanol/water (30/60/8, v/v/v) under sonication for 10 min. The silica was removed by centrifugation, re-extracted again, and the combined supernatant were dried and redissolved in methanol.

TLC Immunostaining. GSLs were separated on HPTLC plates as described above. After chromatography, the TLC plate was air-dried, immersed in 2.1% poly(isobutyl-methacrylate) (Sigma) in hexane/chloroform (42:8, v/v) three times and soaked in PBS at 37° C. for overnight. The plate was dried, blocked with in PBS for 30 min at room temperature and reacted with MC813-70 or MC-631 (5 μg/mL) for 2 h at room temperature. Gently washed with PBST (0.05% Tween-20) for three times, the plate was incubated with biotinylated secondary antibody (1 μg/mL) for 1 h, followed by incubation with streptavidin-alkaline phosphatase (1:1000; Millipore). After washing with PBST, the TLC plate was developed with NBT/BCIP (Thermo Scientific). The reaction was stopped by washing with distilled water and the plates were air-dried.

MALDI-MS Profiling and MS/MS Analysis. MALDI-MS analysis of permethylated glycans were conducted in an ABI 4700 Proteomics Analyzer (Applied Biosystems, Foster City, Calif.) using 2,5-dihydroxybenzoic acid (DHB) as the matrix (10 mg/mL). MALDI-MS/MS sequencing with low- and high-energy collision-induced dissociation was operated in a Q/TOF Ultima MALDI (Waters Micromass) and a 4700 Proteomics Analyzer using the DHB matrix as described above.

Complement-Dependent Cytotoxicity (CDC) Assay. The CDC activity of exemplary anti-SSEA4 mAb, such as (MC813-70) mAb, was measured by lactate dehydrogenase (LDH)-release assay using the CytoTox 96 Non-Radioactive Cytotoxicity Assay kit (Promega, Fitchburg, Wis.). Cells ($1 \times 10^4$) were plated in each well of 96-well plates and washed with PBS twice after growth for overnight. The cells were then incubated with 1 g of MC813-70 or mouse IgG3 isotype control in 50 μL phenol red-free DMEM or RPMI with rabbit complement (dilution of 1:5; Life Technologies). After incubation in a 5% CO2 incubator at 37° C. for 1 h, the degree of cell lysis was determined by measuring the amount of LDH released into the culture supernatant. Maximum LDH release was determined by lysing the cells with Lysis Solution provided by the kit. Percentage of specific lysis was calculated according to the equation: % lysis= [experimental release−spontaneous release]/[maximum release−spontaneous release]×100.

In vivo Tumor Growth. BALB/cAnN.Cg-Foxn1nu/Crl-Narl mice were purchased from National Laboratory Animal Center (Taiwan) and maintained under specific pathogen-free conditions. The health status of animal was monitored daily. Procedures involving animals and their care were conducted according to Academia Sinica Institutional Animal Care and Utilization Committee in compliance with national and international laws and policies. DBTRG cells ($1 \times 10^7$/250 μL PBS) were subcutaneously injected to the flank regions of mice (8- to 10-weeks old) to generate the xenograft model. On day 11, 15 and 19, each mouse was peritoneally injected with 200 μg of MC813-70 (purified from the ascites) or mouse IgG3 isotype control Ab. The tumor size was determined by vernier caliper by measuring the length (L) and width (W), and the tumor volume was calculated (in $mm^3$) as $½ \times LW^2$.

Example 15: Exemplary Phage Display Biopanning Procedures

The phage-displayed human naïve scFv library contained $2.5 \times 10^{10}$ clones (Lu et al., 2011) was subtracted with non-specific binding in PEG-conjugated carboxyl Dynabeads (Invitrogen) at room temperature (RT) for 1 hour, and subsequently incubated with SSEA-4-PEG immobilized Dynabeads at 4° C. for 1 hour. After washing with PBS or PBS containing 0.01% Tween 20 (PBST0.01), the phages that bound to SSEA-4-PEG-Dynabeads were recovered by infection with *E-coli* TG1 cells at 37° C. for 0.5 hour. Some of the infected cells were serially diluted to determine titer, and the others were rescued by M13KO7 phage and amplified. After determination of rescued phages titer, the next round of biopanning was performed. In the fourth and fifth round of biopanning, the phage clones were randomly selected to culture for ELISA screening.

ELISA Screening of Selected Phage Clones

For detection of antigen recognition, microwell plates (Nunc) were coated with 0.2 μg/ml of SSEA-4-BSA, Globo H-BSA, SSEA-3-BSA and BSA, respectively. The selected phage clones were diluted 1:2 in PBS containing 3% BSA and added to each well. The plates were incubated at RT for 1 hour, washed with PBST0.1, and incubated with horseradish peroxidase (HRP)-conjugated mouse anti-M13 phage antibody (GE Healthcare). The plates were washed again, and OPD and H2O2 were added. After termination of reaction by 3 N HCl, the absorbance was measured using a 490 nm using microplate reader (Model 680, BioRad). We extracted phagemids from ELISA-positive phage clones to identity scFv coding regions by auto-sequencing.

Construction and Expression of Anti-SSEA-4 Human IgG

The VH region of selected scFv was cloned with AgeI and NheI site into modified expression vector pcDNA5-FRT-Gamma1 containing a signal peptide and the constant region of human immunoglobulin gamma 1 heavy chain. The VL region of selected scFv was cloned with AgeI and EcoRV site into modified expression vector p-Kappa-HuGs containing a signal peptide and constant region of human immunoglobulin kappa light chain. Both plasmids were transfected into FreeStyle293 cells (Invitrogen) and continuously incubated in serum-free medium at 37° C. for 1 week to produce human antibody.

Purification of Anti-SSEA-4 Human IgG

The culture medium was collected, centrifuged and filtrated with 0.45 μm pore-size membrane. The supernatant then was subjected to protein G column chromatography (GE healthcare) for purification of anti-SSEA-4 human IgG. After dialysis of eluents with PBS, the antibody was examined by SDS-PAGE analysis with coomassie blue staining as usual. The concentration of antibody was assessed by Bradford reagent (Thermo Scientific) and spectrophotometer.

Humanization of MC48

Two human genes, GenBank accession Q9UL73 and AY577298, were the most similar to MC48 VH and VL, respectively. We humanized three sequences of MC48, including the 1st humanized MC48 (hMC48) VH consisted of modified framework (FR) 1 to FR4 of Q9UL73 gene and the 1st hMC48 VL consisted of four FRs from the accession AY577298, the 2nd hMC48 FRs of VH followed 1YY8 from PDB, while the 2nd hMC48 VL same as 1st sequence, and the 3rd hMC48 VH sequence modified FR1, 2 and 4 of Q9UL73 gene and the 3rd hMC48 VL changed FR2 and FR4 to human AY577298 gene. All of these humanized sequences were conserved CDR1 to CDR3 of VH and VL of MC48.

Construction of Single Chain Fragments Variable (scFv) of Humanized MC48 Variants The scFv form of humanized MC48 sequences (VH-GGGGSGGGGSGGGGS-VL (SEQ ID NO: 115)) were gene synthesized (Genomics) and cut by Sfi I and Not I (Fermentas). After gel extraction, the digested products were cloned to pCANTAB-5E phagemid (GE Healthcare).

Generation of Humanized MC48 (hMC48) scFv Phage Clones.

hMC48 variant phagemids were transformed to TG1 E-coli and recovered in 2×YT medium (BD Pharmingen) containing 100 μg/ml ampicillin and 2% glucose and rescued by M13KO7 helper phage (NEB) for 1 hour at 37° C. After centrifugation by 1,500×g for 10 min, these pellets were resuspended in 2×YT medium containing 100 μg/ml ampicillin and 50 μg/ml kanamycin overnight to generate scFv-phages.

Binding Assay of hMC48 scFv Phage Clones by ELISA

SSEA-4-BSA was coated on an ELISA plate at the concentration of 0.2 μg/ml. After washing and blocking, the serial diluted phages were incubated at RT for 1.5 hour. After washing, 1:1000 diluted HRP-conjugated anti-M13 antibody (GE Healthcare) was added at RT for 1 hour. Then, liquid substrate 3,3',5,5'-tetramethylbenzidine (TMB) developed and was terminated with 3N HCl. Optical density was measured at 450 nm.

Results

Identification of Phage-Displayed scFv that Binds to SSEA-4

Figure 10A:
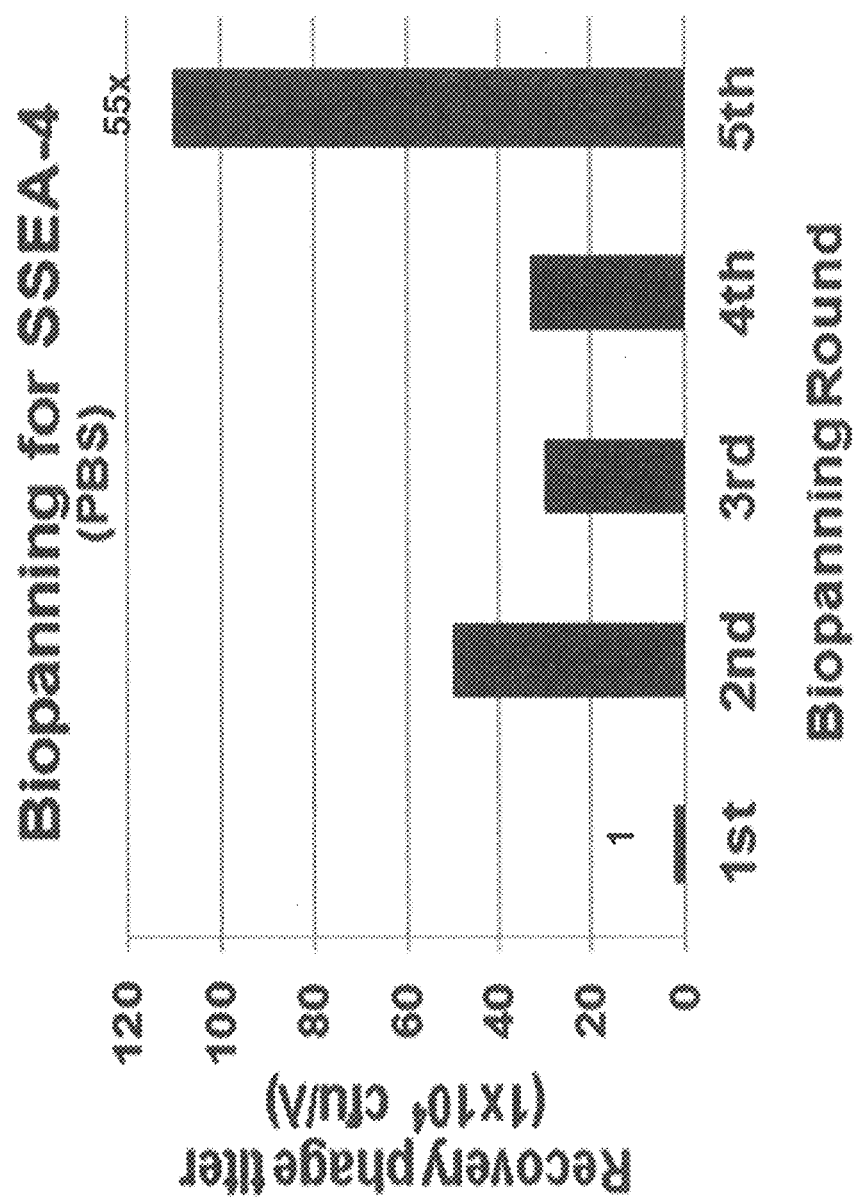
FIGS. 10A-10B. Biopanning for SSEA-4 by phage-displayed human naïve scFv library. Selection of phage-displayed scFv that bound to SSEA-4. A phage-displayed human naïve scFv library was used to select phages that bound to SSEA-4-PEG-conjugated Dynabeads. The recovery rate of the phages was increased after the fifth round of biopanning compared to first round. PBS (FIG. 10A) and PBS containing 0.01% Tween20 (FIG. 10B) was used as wash buffer system during biopanning process.
Figure 10B:
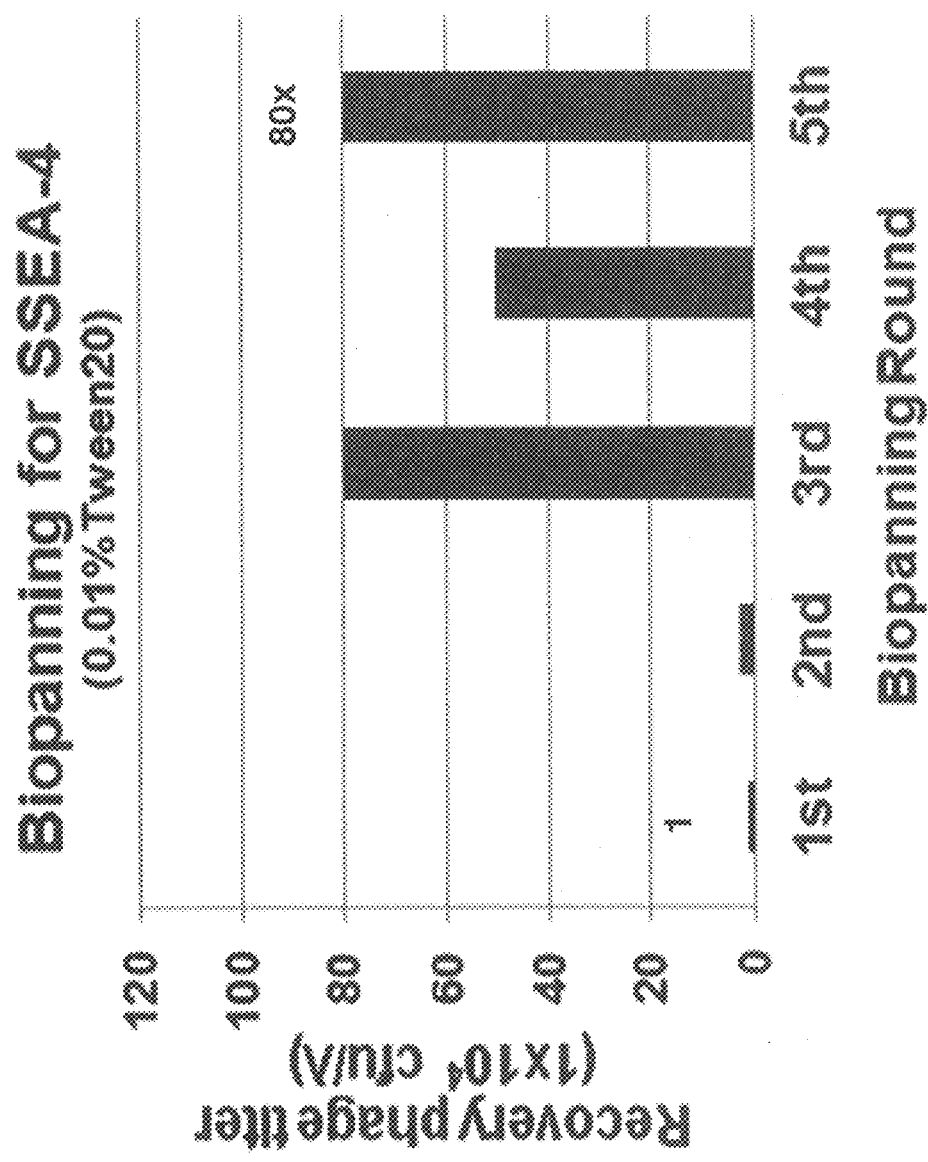
Figure 11A:
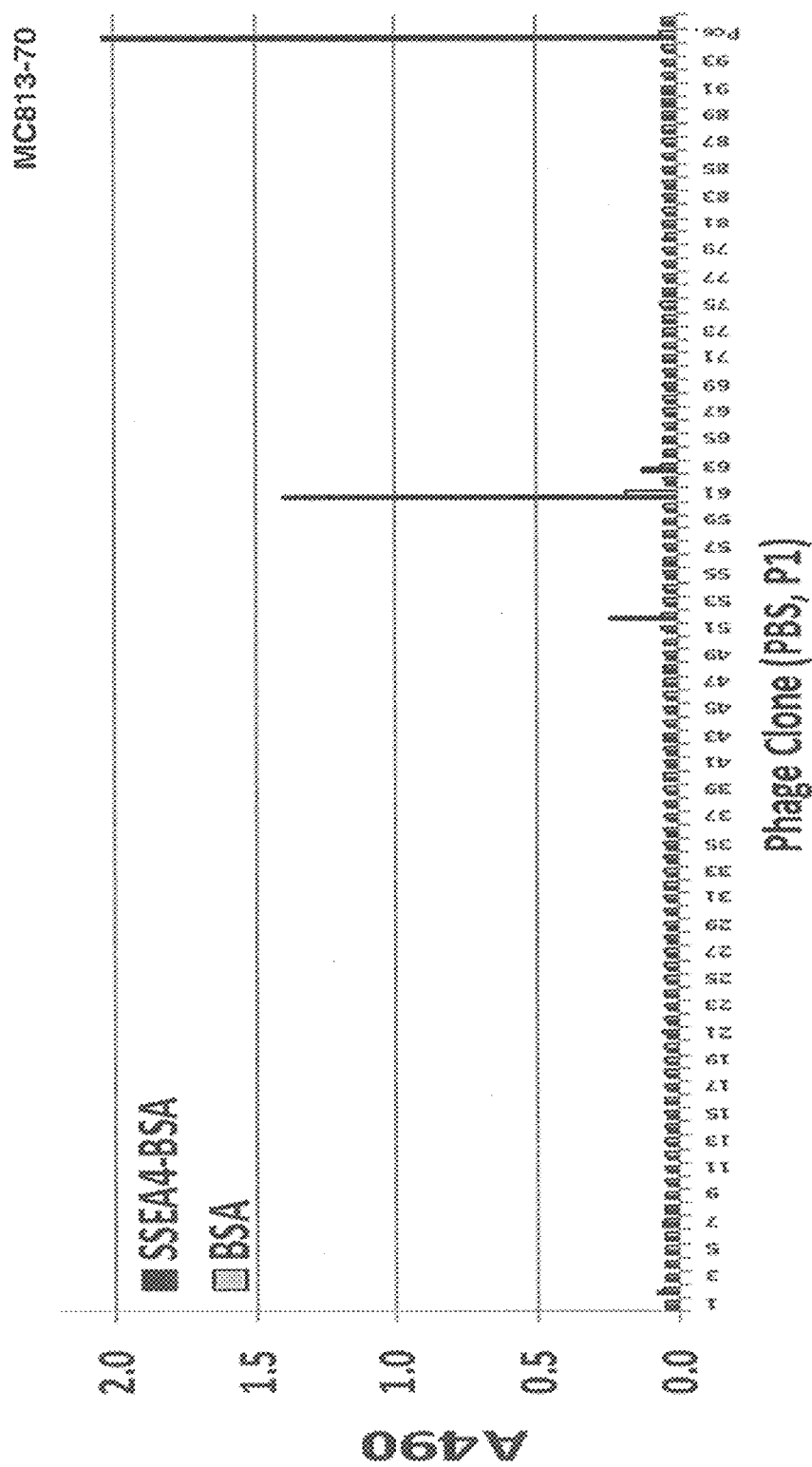
FIGS. 11A-11D. Screening of phage-displayed scFv that bound to SSEA-4 by ELISA.
Figure 11B:
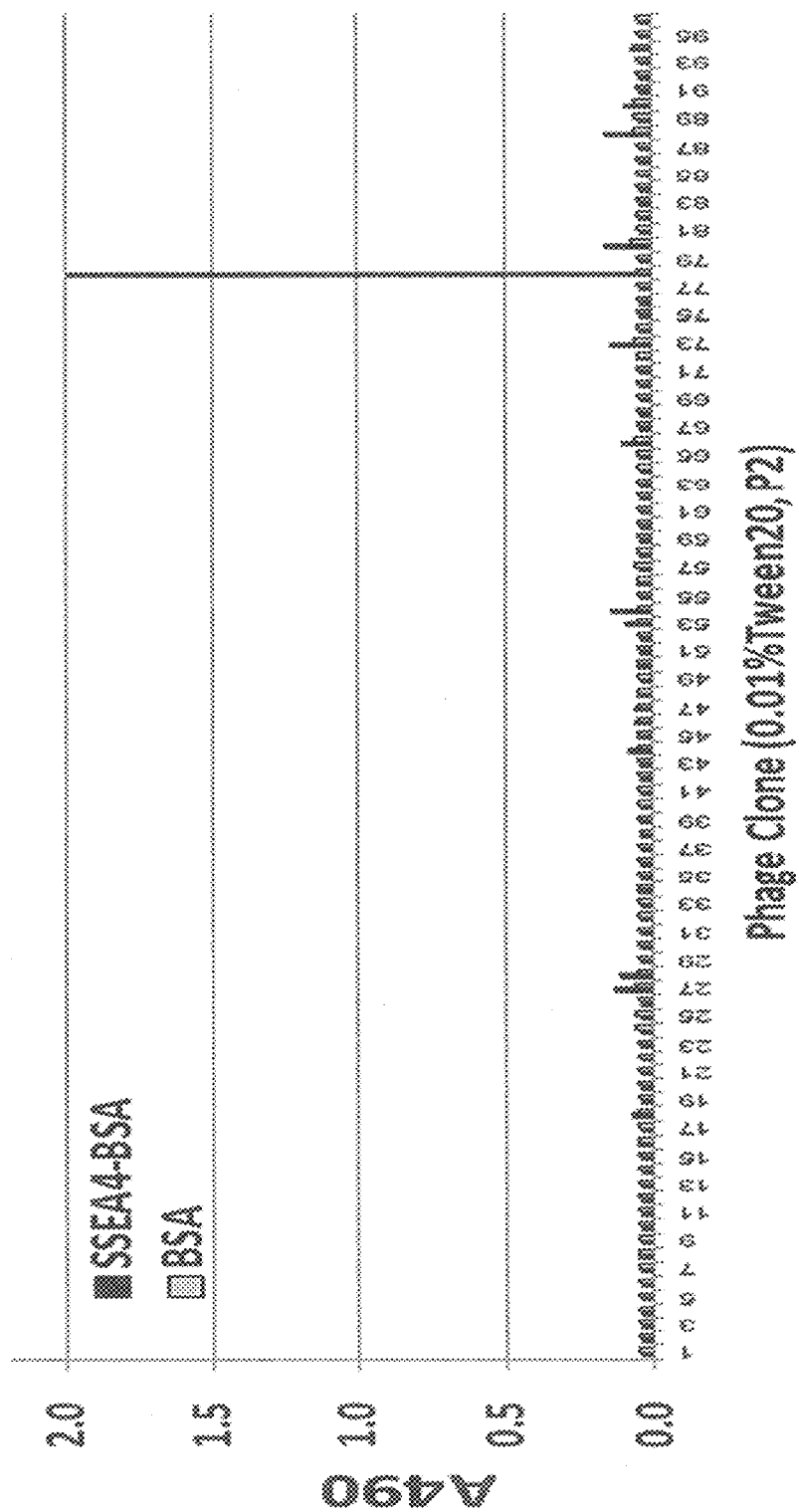
Figure 11C:
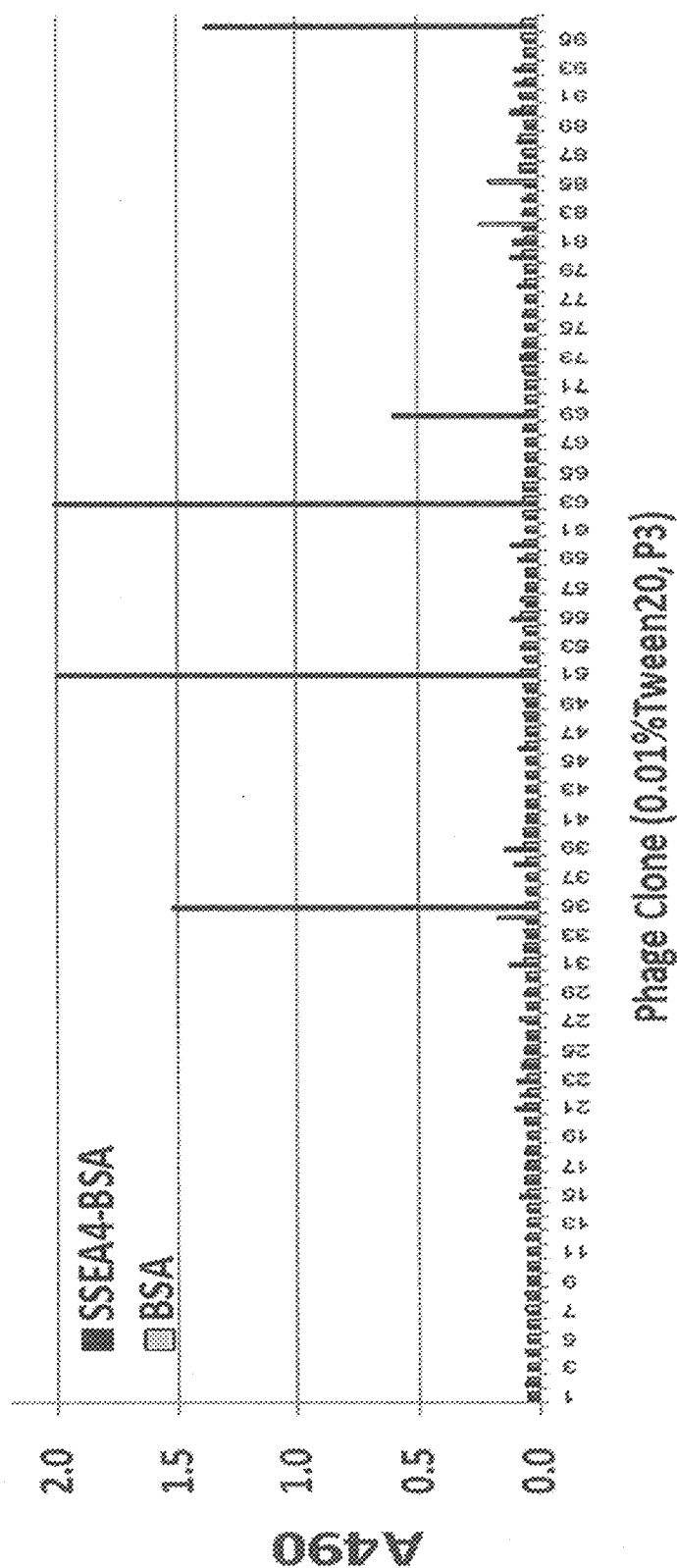
Figure 11D:
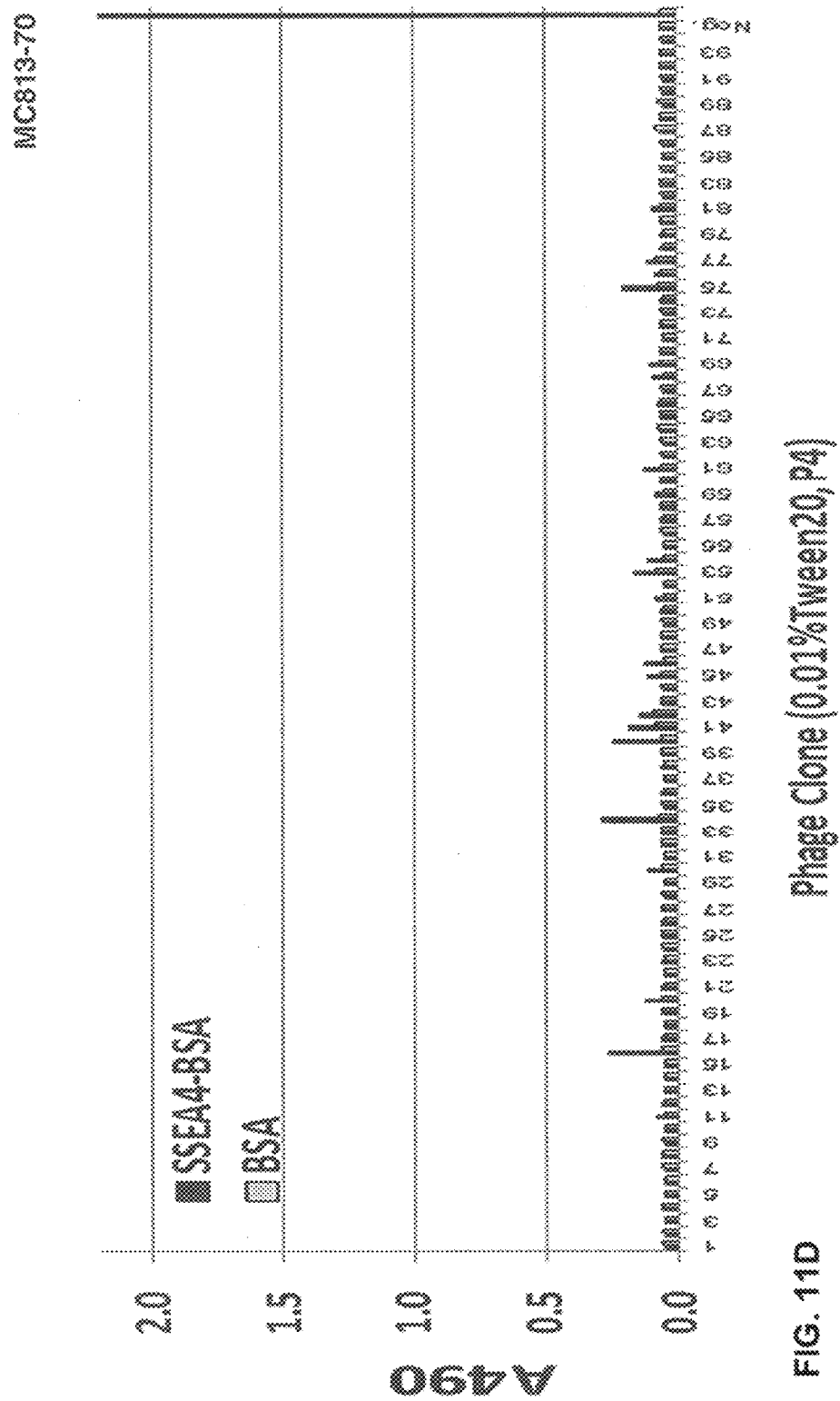

To identify the antibodies that bind to SSEA-4, we used phage-displayed human naïve scFv library containing 2.5× $10^{10}$ members which was established as our previous report described (Lu et al., 2011). This library was first removed Dynabeads-binding phages and then selected for SSEA-4-binding phages by SSEA-4-PEG-conjugated Dynabeads. We used two buffer systems, PBS and PBS containing 0.01% Tween20 (PBST0.01), during biopanning. After five rounds of affinity selection, the phage recovery of the fifth round had increased about 55-fold and 80-fold than that of the first round in PBS and PBST0.01 system, respectively (FIG. 10). The phage clones were randomly selected and tested for SSEA-4 binding by ELISA (FIG. 11). We found seven clones that specifically bound to SSEA-4-BSA, but not to BSA control protein. By sequencing all 8 individual clones, we identified two unique anti-SSEA-4 phage clones (p1-52 and p2-78) which contain distinct human VH and VL coding regions (FIG. 16A).

To examine the specificity and binding affinity of the two phage clones, we performed a comparative ELISA using the same phage titer to Globo-series glycans including SSEA-4-BSA, Globo H-BSA and SSEA-3-BSA (FIG. 12). The p2-78 phage clone showed the strong binding to SSEA-4-BSA and SSEA-3-BSA, and slightly weaker binding to Globo H-BSA. However, we found that the binding activity of p1-52 phage clone to SSEA-4-BSA is very weak. Thus we focused on p2-78 clone for further study.

Figure 13A:
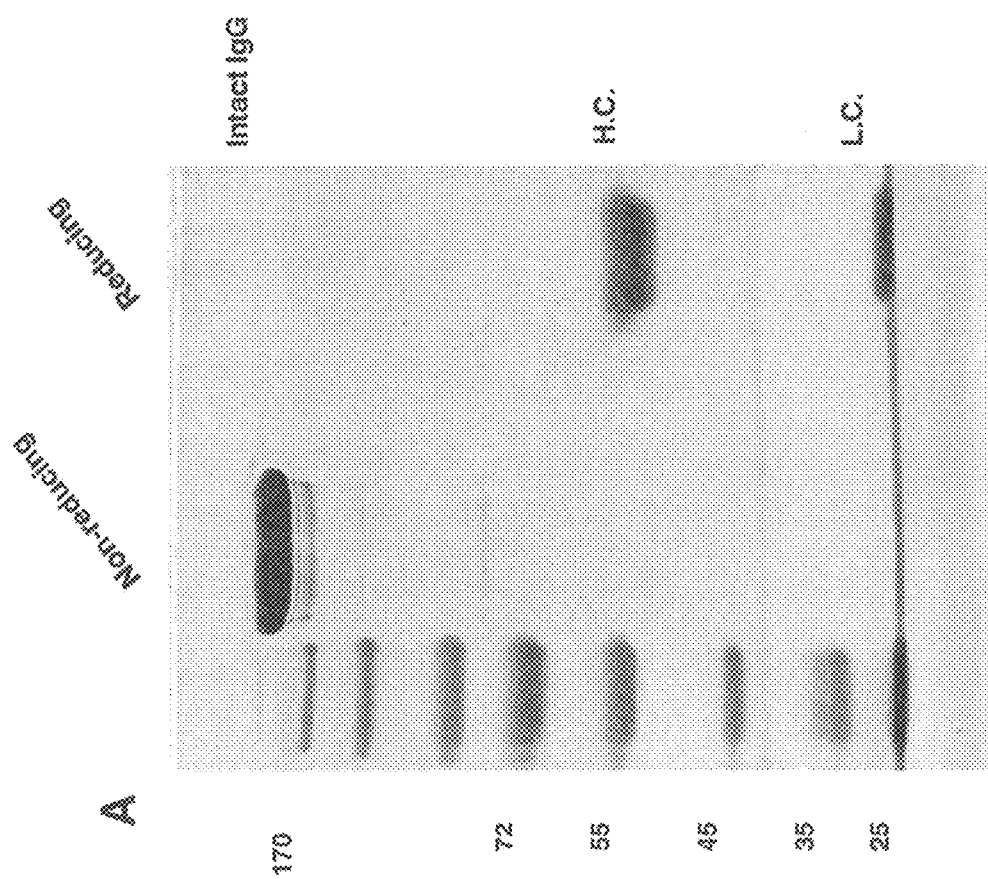
Figure 13B:
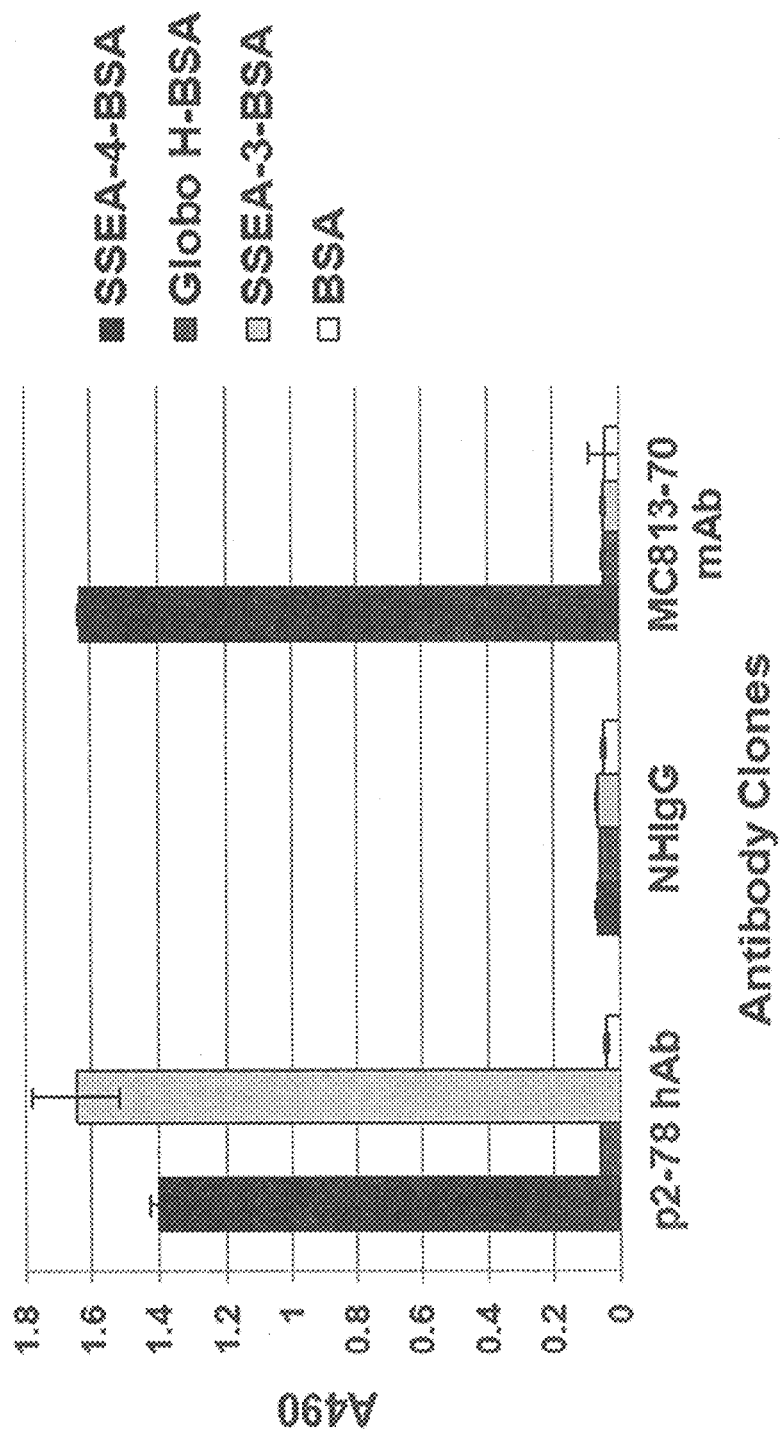

To establish the fully human antibody (hAb) against SSEA-4, we molecularly engineered the VH and VL coding sequences of p2-78 scFv into human IgG1 backbone, respectively. The anti-SSEA-4 p2-78 hAb was produced using FreeStyle 293 expression system and then purified through the protein G sepharose column. We examined the purity of antibody by SDS-PAGE analysis with coomassie blue staining (FIG. 13A). The result shows the purity level of antibody exceed 95%. Subsequently, we performed ELISA to investigate the binding activity of p2-78 hAb for Globo-series glycans (FIG. 13B). We found that p2-78 hAb bound to SSEA-4 and SSEA-3, but not to Globo H, which demonstrates the human IgG version of p2-78 retains the activity of its parental scFv version to recognize the binding epitope of SSEA-4.

Figure 14A:
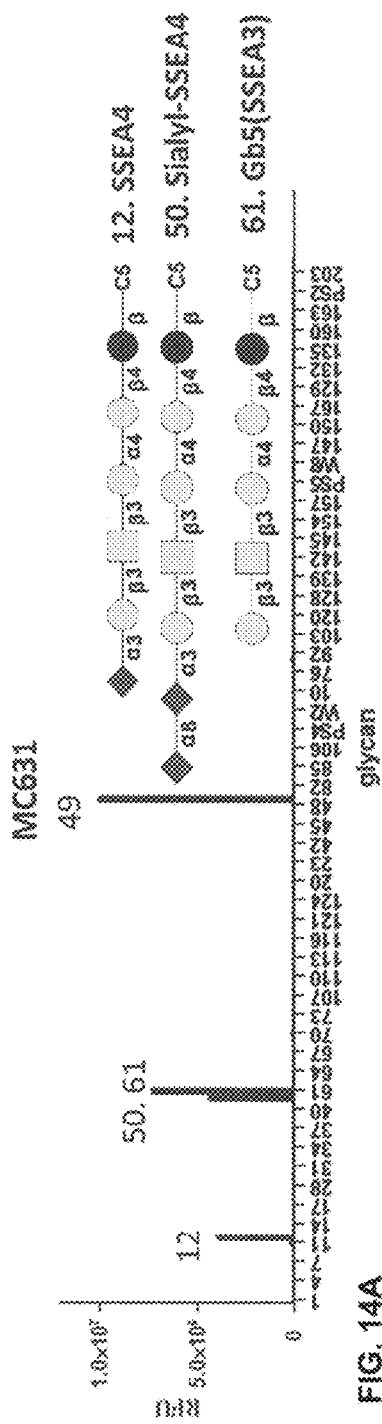
Figure 14B:
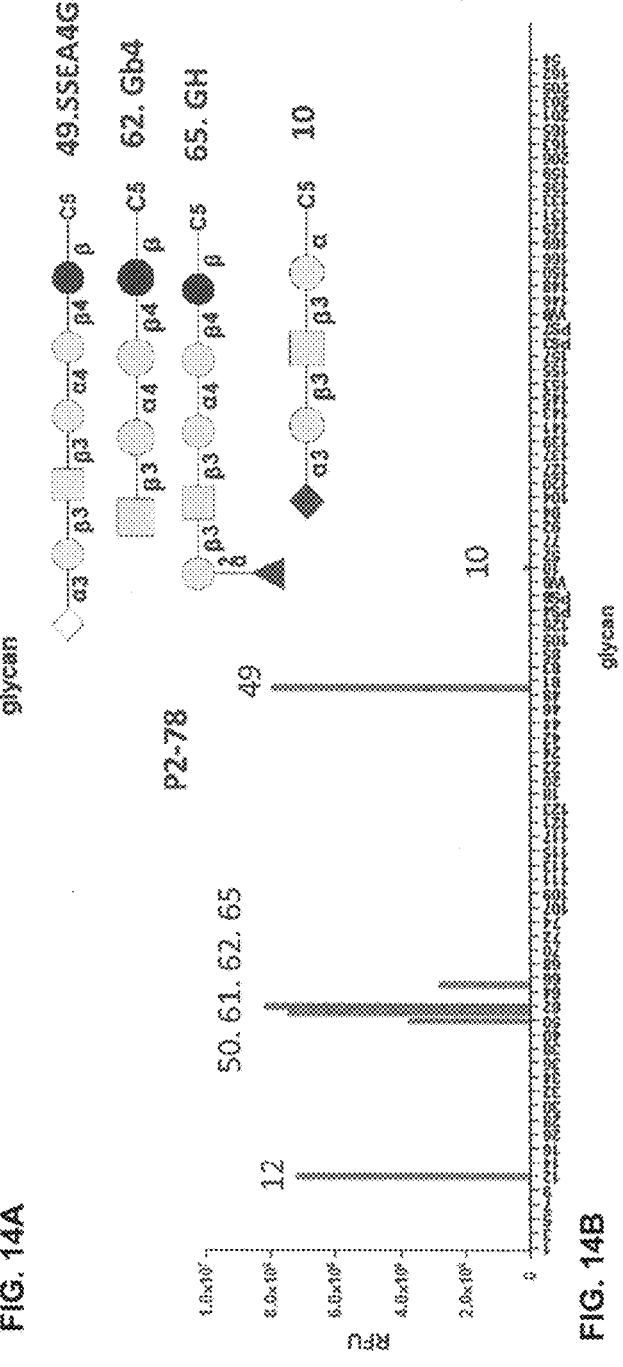

We used glycan array containing 203 different glycans to further confirm the specificity of p2-78 hAb. The results showed that p2-78 hAb recognized SSEA4, Sialyl-SSEA4, SSEA4Gc, and Gb5 (SSEA3) (FIG. 14B). Interestingly, p2-78 hAb also recognized GloboH, similar to the results from ELISA assay (FIG. 12). The commercially available IgM antibody, MC631, was used as a positive control (FIG. 14A).

Development of Humanized MC48 mAbs

Non-humanized Murine mAbs may have certain limitations in clinical settings, including their short serum half-life, inability to trigger human effector functions and the production of human anti-murine antibodies (HAMA) response (LoBuglio et al., 1989). Therefore, mAbs can be humanized by grafting their CDRs onto the VH and VL FRs of human Ig molecules (Roguska et al., 1994).

To develop humanized MC48, we sequenced $V_H$ and $V_L$ variable region of MC48 from a hybridoma cell (Table 4). After alignment of $V_H$ and $V_L$ variable region of MC48 with the NCBI IgBLAST database, we modified FRs of MC48 and generated $1^{st}$, $2^{nd}$, $3^{rd}$ and $4^{th}$ humanized MC48 sequences (Table 17, FIG. 17). We next constructed and generated the phage-displayed scFv formats according to these humanized MC48 sequences. To determine the binding activity of the humanized MC48 phage clones, we carried out solid-based ELISA coating SSEA-4-BSA (FIGS. 15 and 18). We found that the humanized MC48 scFv phage could recognize SSEA-4 in a dose-dependent manner. The data indicated that the 4th humanized MC48 scFv phage maintained its binding affinity compared with the murine mAb MC48.

Example 16: Complement-Dependent Cytotoxicity (CDC) Assay

The ability of exemplary humanized MC 48 to mediate CDC of SSEA-4 expressing cells is examined. *Homo sapiens* breast or pancreatic carcinoma cells were plated in each well of 96-well plates for growth of overnight prior to the assay. The cells were then incubated with serially diluted concentrations of humanized MC 48 or human IgG1 isotype control in RPMI in the presence of rabbit serum as a source of complement (dilution of 1:5; Life Technologies). Cell death is assessed by the addition of the viability probe 7-AAD. Based on the results of the 7-AAD measurement, percentage-specific lysis is calculated using a FACScan flow cytometer. The antibodies show significant killing activity at 10 μg/mL compared to isotype control. As shown, humanized MC48-4 successfully mediates CDC of SSEA-4 expressing cells.

---

What is claimed is:

1. An isolated humanized monoclonal antibody that specifically binds to Neu5Acα2→3Galβ1→3GalNAcβ1→3Galα1→4Galβ1→4Glcβ1, wherein the antibody comprises an H-CDR1, an H-CDR2, an H-CDR3, an L-CDR1, an L-CDR2, and an L-CDR3 wherein
   (i) the H-CDR1 comprises the sequence of SEQ ID NO:152 (GFSLTSYG);
   (ii) the H-CDR2 comprises the sequence of SEQ ID NO: 153 (IWGEGST);
   (iii) the H-CDR3 comprises the sequence of SEQ ID NO:154 (AMTGTAY);
   (iv) the L-CDR1 comprises the sequence of SEQ ID NO: 149 (SSVSY);
   (v) the L-CDR2 comprises the sequence of SEQ ID NO:150 (DTS); and
   (vi) the L-CDR3 comprises the sequence of SEQ ID NO: 151(HQWSSSPHT).

2. The isolated humanized monoclonal antibody of claim 1, wherein the antibody is an IgG.

3. The isolated humanized monoclonal antibody of claim 2, wherein the antibody is an IgG1.

4. The isolated humanized monoclonal antibody of claim 1, wherein the antibody is a glycoantibody and wherein the glycoantibody comprises an N-glycan attached to the Asn-297 of the Fc region of said antibody wherein the N-glycan consists of the structure of $Sia_2(\alpha2-6)Gal_2GlcNAc_2Man_3GlcNAc_2$ and wherein the glycoantibody specifically binds to an SSEA-4 antigen.

5. The isolated humanized monoclonal antibody of claim 1, wherein the antibody comprises a VH having SEQ ID NO: 147 and a VL having SEQ ID No: 148 or a VH having SEQ ID No:137 and a VL having SEQ ID No:138.

6. A pharmaceutical composition comprising the antibody according to claim 1.

7. An antigen binding fragment of the isolated humanized monoclonal antibody of claim 1.

8. The antigen binding fragment of claim 7, wherein the antigen-binding fragment is an Fab fragment, an F(ab')2 fragment, or a single-chain Fv fragment.

9. The isolated humanized monoclonal antibody of claim 1 wherein the antibody comprises an H-FR1, an H-FR2, an H-FR3, an H-FR4, an L-FR1, an L-FR2, an L-FR3, and an L-FR4 wherein,
   (i) the H-FR1 comprises the sequence of SEQ ID NO:159 (QVQLKESGPGLVAPSQSLSITCTVS);
   (ii) the H-FR2 comprises the sequence of SEQ ID NO:160 (VSWIRQPPGKGLEWIGV);
   (iii) the H-FR3 comprises the sequence of SEQ ID NO:161 (NYHSVLISRLTISKDNSKSQVFLKLNSLQTDDTATYYC);
   (iv) the H-FR4 comprises the sequence of SEQ ID NO:162 (WGQGTLVTVSS);
   (v) the L-FR1 comprises the sequence of SEQ ID NO: 155 (QIVLTQSPAIMSASPGEKVTMTCSAS);
   (vi) the L-FR2 comprises the sequence of SEQ ID NO:156 (MHWYQQKSGTSPKRWIY);
   (vii) the L-FR3 comprises the sequence of SEQ ID NO: 157 (KLSSGVPGRFSGSGSGTSYSLTISRLEAEDAATYYC); and
   (viii) the L-FR4 comprises the sequence of SEQ ID NO: 158 (FGGGTKVEIKR).

* * * * *

UNITED STATES PATENT AND TRADEMARK OFFICE
CERTIFICATE OF CORRECTION

Page 1 of 1

PATENT NO. : 10,150,818 B2
APPLICATION NO. : 14/798312
DATED : December 11, 2018
INVENTOR(S) : Chi-Huey Wong et al.

It is certified that error appears in the above-identified patent and that said Letters Patent is hereby corrected as shown below:

On the Title Page

Under item (63) in Line 8, Pat No. "1,002,892" should read as --10,023,892--

On page 4 under section OTHER PUBLICATIONS in the second column, after Line 10, please add --Almagro & Fransson. "Humanization of antibodies." Frontiers in Bioscience, 2008, 13.1: 1619-1633.--

On page 5 under section OTHER PUBLICATIONS in the first column, after Line 56, please add --De Genst, E., et al. "Antibody repertoire development in camelids." Dev. Comp. Immunol., 2006, 30(1-2): 187-198.--

In the Specification

Column 1, Line 11, after Jan. 16, 2014; add --this application is also a continuation-in-part and claims the benefit of priority to--

Column 1, Line 12, after Jan. 16, 2015, add --now patented as U.S. Patent No. 9,982,041 issued May 29, 2018,--

Column 1, Line 13, after Jan. 16, 2014; add --this application is also a continuation-in-part and claims the benefit of priority to--

Column 1, Line 14, "PCT/US/2015/032745" should read --PCT/US2015/032745--

Column 1, Line 21, after 27, 2014; add --additionally, this application is also a continuation-in-part and claims the benefit of priority to--

Column 1, Line 22, after 27, 2015; add --now patented as U.S. Patent No. 10,023,892 issued July 17, 2018,--

Signed and Sealed this
Fourth Day of June, 2019

Andrei Iancu
*Director of the United States Patent and Trademark Office*

SEQUENCE LISTING

```
<160> NUMBER OF SEQ ID NOS: 163

<210> SEQ ID NO 1
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tgaagcagtc tggacctgag ctagtgaaga ctggggcttc agtgaagata        60
tcctgcaagg cttctggtta ctcattcact ggttactaca tgcactgggt caagcagagc       120
catggaaaga gccttgagtg gattggatat attagttgtt acaatggtgg tactaggtac       180
aacctgaagt tcaagggcaa ggccacattt actgtagaca tcctccac cacagcctac         240 atgcagttca caacctgac atctgaagac tctgcggtct attactgtgc aagagggggg        300
tacgacgagg gtgactactg gggccaaggc accactctca cagtctcctc a                351

<210> SEQ ID NO 2
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gatattgtaa tgacacagtc tcccaaatcc atattcatgt cagttggaga gagggtcacc        60
ttgagctgca aggccagtga gaatgtgggt acttatgtat cctggtatca acagaaacca       120
gagcagtctc ctaaactgat gatatacggg gcatccaacc ggaacactgg ggtccccgat       180
cgcttcacag gcagtggatc tgcaacagat ttcactctga ccatcagcag tgtgcaggct       240
gaagaccttg cagattatca ctgtggacag agttacacct atccgtacac gttcggaggg       300
gggaccaagc tggaaatcaa a                                                   321

<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Lys Gln Ser Gly Pro Glu Leu Val Lys Thr Gly Ala
1               5                   10                  15

Ser Val Lys Ile Ser Cys Lys Ala Ser Gly Tyr Ser Phe Thr Gly Tyr
            20                  25                  30
```

```
Tyr Met His Trp Val Lys Gln Ser His Gly Lys Ser Leu Glu Trp Ile
        35                  40                  45

Gly Tyr Ile Ser Cys Tyr Asn Gly Gly Thr Arg Tyr Asn Leu Lys Phe
    50                  55                  60

Lys Gly Lys Ala Thr Phe Thr Val Asp Thr Ser Ser Thr Thr Ala Tyr
65                  70                  75                  80

Met Gln Phe Asn Asn Leu Thr Ser Glu Asp Ser Ala Val Tyr Tyr Cys
                85                  90                  95

Ala Arg Gly Gly Tyr Asp Glu Gly Asp Tyr Trp Gly Gln Gly Thr Thr
                100                 105                 110

Leu Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Met Thr Gln Ser Pro Lys Ser Ile Phe Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Met Ile
        35                  40                  45

Tyr Gly Ala Ser Asn Arg Asn Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Thr Tyr Pro Tyr
                85                  90                  95

Thr Phe Gly Gly Gly Thr Lys Leu Glu Ile Lys
                100                 105

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Asn Val Gly Thr Tyr
1               5

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ala Ser
1
```

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gln Ser Tyr Thr Tyr Pro Tyr Thr
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Tyr Ser Phe Thr Gly Tyr Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Ser Cys Tyr Asn Gly Gly Thr
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Arg Gly Gly Tyr Asp Glu Gly Asp Tyr
1               5                   10

<210> SEQ ID NO 11
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggtccagc tgcaacaatc tgggtctgtg ctggtgaggc ctggagcttc agtgaagctg      60
tcctgcaagg cttctggcta caccttcacc aactcctgga tgcactgggc gaagcagagg     120
cctggacaag gccttgtgtg gattggagag attgatccta atactggtaa tactaactac     180
aatgagaact tcaagggcaa ggccacactg actgtagaca catcctccac cacagcctac     240
gtggatctca gcagcctgac atctgaagac tctgcggtct attactgtgc aagaggactc     300
gggctacttg tttactgggg ccaagggact ctggtcactg tctctgca                 348

<210> SEQ ID NO 12
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
caaattgttc tcacccagtc tccagcaatc ctgtctgcat ctccagggga gaaggtcaca     60
atgacttgca gggccagctc aagtgtaagt tacatgcact ggtaccagca gaagccagga    120
tcctccccca aaccctggat ttatgtcaca tccaacctga cttctggagt ccctgttcgc    180
ttcagtggca gtgggtctgg gacctcttac tctctcacaa tcagcagagt ggaggctgaa    240
gatgctgcca cttattactg ccagcagtgg agtaataacc cgtggacgtt cggtggaggc    300
accaagctgg aaatcaaa                                                  318

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Gln Gln Ser Gly Ser Val Leu Val Arg Pro Gly Ala
1               5                   10                  15

Ser Val Lys Leu Ser Cys Lys Ala Ser Gly Tyr Thr Phe Thr Asn Ser
            20                  25                  30

Trp Met His Trp Ala Lys Gln Arg Pro Gly Gln Gly Leu Val Trp Ile
        35                  40                  45

Gly Glu Ile Asp Pro Asn Thr Gly Asn Thr Asn Tyr Asn Glu Asn Phe
    50                  55                  60

Lys Gly Lys Ala Thr Leu Thr Val Asp Thr Ser Ser Thr Thr Ala Tyr
65                  70                  75                  80

Val Asp Leu Ser Ser Leu Thr Ser Glu Asp Ser Ala Val Tyr Tyr Cys
                85                  90                  95

Ala Arg Gly Leu Gly Leu Leu Val Tyr Trp Gly Gln Gly Thr Leu Val
            100                 105                 110

Thr Val Ser Ala
        115

<210> SEQ ID NO 14
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Val Thr Ser Asn Leu Thr Ser Gly Val Pro Val Arg Phe Ser Gly Ser

```
                    50                  55                  60
Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Asn Asn Pro Trp Thr
                 85                  90                  95

Phe Gly Gly Gly Thr Lys Leu Glu Ile Lys
            100                 105
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

```
Ser Ser Val Ser Tyr
1               5
```

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

```
Val Thr Ser
1
```

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

```
Gln Gln Trp Ser Asn Asn Pro Trp Thr
1               5
```

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

```
Gly Tyr Thr Phe Thr Asn Ser Trp
1               5
```

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

```
Ile Asp Pro Asn Thr Gly Asn Thr
```

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Arg Gly Leu Gly Leu Leu Val Tyr
1               5

<210> SEQ ID NO 21
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
caggtgcagc tgaaggagtc aggacctggc ctggtggcgc cctcacagag cctgtccatc        60
acatgcactg tctcagggtt ctcattaagc agatatggtg taagctgggt tcgccagcct       120
ccaggaaagg gtctggagtg gctgggagta atatggggtg acgggagcac aaattatcat       180
tcagctctca tatccagact gagcatcagc aaggataact ccaagagcca gttttctta        240 aaactgaaca gtctgcaaac tgatgacaca gccacgtact actgtgccat gactgggaca       300
gcttactggg gccaagggac tctggtcact gtctctgca                              339

<210> SEQ ID NO 22
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
caaattgttc tcacccagtc tccagcaatc atgtctgcat ctccagggga gaaggtcacc        60
atgacctgca gtgccagctc aagtgtaaat tacatgcact ggtaccagca gaagtcaggc       120
acctccccca aaagatggat ttatgacaca tccaaactgg cttctggagt ccctgctcgc       180
ttcagtggca gtgggtctgg gacctcttac tctctcacaa tcagcggcat ggaggctgaa       240
gatgctgcca cttattactg ccaccagtgg aatagtagcc acacacgtt cggagggggg        300 accaagctgg aaataaaa                                                     318

<210> SEQ ID NO 23
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

-continued

Gly Val Ser Trp Val Arg Gln Pro Pro Gly Lys Gly Leu Glu Trp Leu
                35                  40                  45

Gly Val Ile Trp Gly Asp Gly Ser Thr Asn Tyr His Ser Ala Leu Ile
        50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Met Thr Gly Thr Ala Tyr Trp Gly Gln Gly Thr Leu Val Thr Val Ser
            100                 105                 110

Ala

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys His Gln Trp Asn Ser Ser Pro His Thr
                85                  90                  95

Phe Gly Gly Gly Thr Lys Leu Glu Ile Lys
            100                 105

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Ser Val Asn Tyr
1               5

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Thr Ser
1

<210> SEQ ID NO 27

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Gln Trp Asn Ser Ser Pro His Thr
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Phe Ser Leu Ser Arg Tyr Gly
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Trp Gly Asp Gly Ser Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Met Thr Gly Thr Ala Tyr
1               5

<210> SEQ ID NO 31
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caggtgcagc tgaaggagtc aggacctggc ctggtggcgc cctcacagag cctgtccatc        60
acatgcactg tctcaggatt ctcattaacc agctatggta taagctgggt tcgccagcct       120
ccaggaaagg gtctggagtg gctgggagta atatggggtg acgggagcac aaattatcat       180
tcagctctcg tatccagact gagcatcagc aaggataact ccaagagcca agttttctta       240
aaactgaaca gtctgcaaac tgatgacaca gccacgtact actgtgccaa aactgggaca       300
tcttactggg gccaagggac tctggtcact gtctctgca                              339

<210> SEQ ID NO 32
```

```
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
caaattgttc tcacccagtc tccagcaatc atgtctgcat ctccagggga gaaggtcacc      60
atgacctgca gtgccagctc aagtgtaagt tacatgcact ggtaccagca gaagtcaggc     120
acctccccca aaagatggat ttatgacaca tccaaactgg cttctggagt ccctgctcgc     180
ttcagtggca gtgggtctgg gacctcttac tctctcacaa tcagcagcat ggaggctgaa     240
gatgctgcca cttattactg ccagcagtgg agtagtgccc cacacacgtt cggagggggg     300
accaagctgg aaataaaa                                                  318

<210> SEQ ID NO 33
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Ile Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Val
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Thr Gly Thr Ser Tyr Trp Gly Gln Gly Thr Leu Val Thr Val Ser
            100                 105                 110

Ala

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
```

```
              65                  70                  75                  80
Asp Ala Ala Thr Tyr Tyr Cys Gln Gln Trp Ser Ser Ala Pro His Thr
                  85                  90                  95

Phe Gly Gly Gly Thr Lys Leu Glu Ile Lys
            100                 105
```

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Ser Ser Val Ser Tyr
1               5
```

<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Asp Thr Ser
1
```

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Gln Gln Trp Ser Ser Ala Pro His Thr
1               5
```

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gly Phe Ser Leu Thr Ser Tyr Gly
1               5
```

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Ile Trp Gly Asp Gly Ser Thr
1               5
```

```
<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Lys Thr Gly Thr Ser Tyr
1               5

<210> SEQ ID NO 41
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caggtgcagc tgaaggagtc aggacctggc ctggtggcgc cctcacagag cctgtccatc      60
acatgcactg tctcagggtt ctcattaacc agctatggtg taagctgggt tcgccagcct     120
ccaggaaagg gtctggagtg gctgggagta atatggggtg aggggagcac aaattatcat     180
tcagttctca tatccagact gaccattagt aaggataact ccaagagcca agttttctta     240
aaactgaaca gtctgcaaac tgatgacaca gccacgtact actgtgccat gactgggaca     300
gcttactggg gccaagggac tctggtcact gtctctgca                            339

<210> SEQ ID NO 42
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
caaattgttc tcacccagtc tccagcaatc atgtctgcat ctccagggga gaaggtcacc      60
atgacctgca gtgccagctc aagtgtaagt tacatgcact ggtaccagca gaagtcaggc     120
acctccccca aaagatggat ttatgacaca tccaaactgt cttctggagt ccctggtcgc     180
ttcagtggca gtgggtctgg gacctcttac tctctcacaa tcagcaggtt ggaggctgaa     240
gatgctgcca cttattactg ccatcagtgg agtagtagtc cacacacgtt cggaggggg      300 accaagttgg agataaaa                                                   318

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Leu
        35                  40                  45
```

Gly Val Ile Trp Gly Glu Gly Ser Thr Asn Tyr His Ser Val Leu Ile
        50                  55                  60

Ser Arg Leu Thr Ile Ser Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Met Thr Gly Thr Ala Tyr Trp Gly Gln Gly Thr Leu Val Thr Val Ser
             100                 105                 110

Ala

<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Val Ser Tyr Met
             20                  25                  30

His Trp Tyr Gln Gln Lys Ser Gly Thr Ser Pro Lys Arg Trp Ile Tyr
             35                  40                  45

Asp Thr Ser Lys Leu Ser Ser Gly Val Pro Gly Arg Phe Ser Gly Ser
 50                  55                  60

Gly Ser Gly Thr Ser Tyr Ser Leu Thr Ile Ser Arg Leu Glu Ala Glu
 65                  70                  75                  80

Asp Ala Ala Thr Tyr Tyr Cys His Gln Trp Ser Ser Ser Pro His Thr
                 85                  90                  95

Phe Gly Gly Gly Thr Lys Leu Glu Ile Lys
             100                 105

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Ser Val Ser Tyr
 1               5

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Thr Ser
 1

<210> SEQ ID NO 47
<211> LENGTH: 9
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 47

His Gln Trp Ser Ser Ser Pro His Thr
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Phe Ser Leu Thr Ser Tyr Gly
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Trp Gly Glu Gly Ser Thr
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Met Thr Gly Thr Ala Tyr
1               5

<210> SEQ ID NO 51
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Val Asn Leu Arg Glu Ser Gly Pro Gly Leu Val Lys Pro Ser Gln
1               5                   10                  15

Thr Leu Ser Leu Thr Cys Ala Ile Ser
            20                  25

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

```
Gly Asp Ser Val Ser Ser Ser Ala Ala
1               5                   10
```

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Trp Asn Trp Ile Arg Gln Ser Pro Ser Arg Gly Leu Glu Trp Leu Gly
1               5                   10                  15

Arg
```

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Thr Tyr Tyr Lys Ser Thr Trp His Asn
1               5
```

<210> SEQ ID NO 55
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Gln Val Gln Leu Gln Glu Ser Gly Gly Gly Leu Val Gln Pro Gly Gly
1               5                   10                  15

Ser Leu Arg Leu Ser Cys Gly Ala Ser
            20                  25
```

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Gly Phe Thr Phe Arg Lys Ser Trp
1               5
```

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Met Gly Trp Val Arg Gln Ser Pro Gly Lys Gly Leu Glu Trp Val Ala
1               5                   10                  15

Asn
```

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Asn Asp Asp Ala Lys Glu Lys
1               5

<210> SEQ ID NO 59
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
        35

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Arg Glu Lys Gly Arg Val Arg Ala Phe Asp Ile
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Trp Gly Gln Gly Thr Met Val Thr Val Ser Ser
1               5                   10

<210> SEQ ID NO 62
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Tyr Tyr Gly Asp Ser Val Lys Gly Arg Phe Thr Ile Phe Arg Asp Asn
1               5                   10                  15

Asp Lys Asn Ser Leu Tyr Leu Gln Met Asn Ser Leu Arg Ala Glu Asp
            20                  25                  30

Thr Ala Val Tyr Phe Cys
        35

<210> SEQ ID NO 63
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Ser Leu Ser Ser Val Ser Ala Gly Asp Pro Pro Arg Gly Pro Glu
1               5                   10                  15

Asn Ile Glu Tyr Phe Glu His
            20

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Gly Gln Gly Thr Leu Val Thr Val Ser Ser
1               5                   10

<210> SEQ ID NO 65
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Ile Val Leu Thr Gln Ser Pro Gly Thr Leu Ala Leu Ser Pro Gly
1               5                   10                  15

Glu Arg Ala Thr Leu Ser Cys Arg Ala Ser
            20                  25

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ser Val Gly Asn Lys Tyr
1               5

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Ala Trp Tyr Gln Gln Lys Pro Gly Gln Ala Pro Arg Leu Leu Ile
1               5                   10                  15

Tyr

<210> SEQ ID NO 68
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Ala Ser
1

<210> SEQ ID NO 69
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Ser Ile Ser Asn Tyr
1               5

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Asn Trp Tyr Gln Gln Lys Pro Gly Lys Ala Pro Lys Leu Leu Ile
1               5                   10                  15

Tyr

<210> SEQ ID NO 72
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Ala Ser
1

-continued

```
<210> SEQ ID NO 73
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ser Arg Ala Thr Gly Ile Pro Asp Arg Phe Ser Gly Ser Gly Ser Gly
1               5                  10                  15

Thr Asp Phe Thr Leu Thr Ile Ser Ser Leu Glu Pro Glu Asp Phe Ala
            20                  25                  30

Val Tyr Tyr Cys
        35

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Tyr Gly Arg Ser Arg Arg Leu Thr
1               5                  10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Phe Gly Gly Gly Thr Lys Val Glu Ile Lys Arg
1               5                  10

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ser Leu Gln Ser Gly Val Pro Ser Arg Phe Ser Gly Ser Gly Ser Gly
1               5                  10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Gln Ser Tyr Ser Thr Pro Arg Thr
```

```
<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Phe Gly Gln Gly Thr Lys Val Asp Ile Lys Arg
1               5                   10

<210> SEQ ID NO 79
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Val Gln Leu Lys Glu Ser Gly Pro Gly Leu Val Ala Pro Ser Gln
1               5                   10                  15

Ser Leu Ser Ile Thr Cys Thr Val Ser Gly
            20                  25

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Phe Ser Leu Thr Ser Tyr Gly Val Ser
1               5

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Trp Val Arg Gln Pro Pro Gly Lys Gly Leu Glu Trp Leu
1               5                   10

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Val Ile Trp Gly Glu Gly Ser Thr Asn Tyr His Ser Val Leu Ile
1               5                   10                  15

Ser Arg Leu

<210> SEQ ID NO 83
```

<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Val Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Ile Arg Gln Pro Pro Gly Lys Gly Leu Glu Trp Ile
1               5                   10

<210> SEQ ID NO 85
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Val Gln Leu Lys Gln Ser Gly Pro Gly Leu Val Gln Pro Ser Gln
1               5                   10                  15

Ser Leu Ser Ile Thr Cys Thr Val Ser Gly
            20                  25

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Trp Val Arg Gln Ser Pro Gly Lys Gly Leu Glu Trp Leu
1               5                   10

<210> SEQ ID NO 87
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Val Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 88

<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Trp Ile Arg Gln Pro Pro Gly Lys Gly Leu Glu Trp Ile
1               5                   10

<210> SEQ ID NO 89
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Ile Ser Lys Asp Asn Ser Lys Ser Gln Val Phe Leu Lys Leu Asn
1               5                   10                  15

Ser Leu Gln Thr Asp Asp Thr Ala Thr Tyr Tyr Cys
            20                  25

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Met Thr Gly Thr Ala Tyr
1               5

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Gly Gln Gly Thr Leu Val Thr Val Ser Ala
1               5                   10

<210> SEQ ID NO 92
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Thr Ile Ser Val Asp Thr Ser Lys Asn Gln Phe Ser Leu Lys Leu Ser
1               5                   10                  15

Ser Val Thr Ala Ala Asp Thr Ala Val Tyr Tyr Cys
            20                  25

<210> SEQ ID NO 93
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 93

Trp Gly Gln Gly Thr Leu Val Thr Val Ser Ser
1               5                   10

<210> SEQ ID NO 94
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Ile Asn Lys Asp Asn Ser Lys Ser Gln Val Phe Phe Lys Met Asn
1               5                   10                  15

Ser Leu Gln Ser Asn Asp Thr Ala Ile Tyr Tyr Cys
            20                  25

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Gly Gln Gly Thr Leu Val Thr Val Ser Ala
1               5                   10

<210> SEQ ID NO 96
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Ile Ser Lys Asp Asn Ser Lys Ser Gln Val Phe Leu Lys Leu Asn
1               5                   10                  15

Ser Leu Gln Thr Asp Asp Thr Ala Thr Tyr Tyr Cys
            20                  25

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Trp Gly Gln Gly Thr Leu Val Thr Val Ser Ser
1               5                   10

<210> SEQ ID NO 98
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 98

Gln Ile Val Leu Thr Gln Ser Pro Ala Ile Met Ser Ala Ser Pro Gly
1               5                   10                  15
Glu Lys Val Thr Met Thr Cys
            20

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Ala Ser Ser Ser Val Ser Tyr Met His
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Tyr Gln Gln Lys Ser Gly Thr Ser Pro Lys Arg Trp Ile Tyr
1               5                   10                  15

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asp Thr Ser Lys Leu Ser Ser
1               5

<210> SEQ ID NO 102
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Glu Ile Val Leu Thr Gln Ser Pro Ala Thr Leu Ser Leu Ser Pro Gly
1               5                   10                  15
Glu Arg Ala Thr Leu Ser Cys
            20

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Trp Tyr Gln Gln Lys Pro Gly Leu Ala Pro Arg Leu Leu Ile Tyr
1               5                   10                  15

<210> SEQ ID NO 104
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Trp Tyr Gln Gln Lys Pro Gly Leu Ala Pro Arg Leu Leu Ile Tyr
1               5                   10                  15

<210> SEQ ID NO 106
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Ile Val Leu Thr Gln Ser Pro Ala Ile Met Ser Ala Ser Pro Gly
1               5                   10                  15

Glu Lys Val Thr Met Thr Cys
            20

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Trp Tyr Gln Gln Lys Pro Gly Leu Ala Pro Arg Leu Leu Ile Tyr
1               5                   10                  15

<210> SEQ ID NO 108
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gly Val Pro Gly Arg Phe Ser Gly Ser Gly Ser Gly Thr Ser Tyr Ser
1               5                   10                  15

Leu Thr Ile Ser Arg Leu Glu Ala Glu Asp Ala Ala Thr Tyr Tyr Cys
            20                  25                  30

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

His Gln Trp Ser Ser Ser Pro His Thr
1               5

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Phe Gly Gly Gly Thr Lys Leu Glu Ile Lys Arg
1               5                   10

<210> SEQ ID NO 111
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Phe Gly Gly Gly Thr Lys Val Glu Ile Lys Arg
1               5                   10

<210> SEQ ID NO 113
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gly Val Pro Gly Arg Phe Ser Gly Ser Gly Ser Gly Thr Ser Tyr Ser
1               5                   10                  15

Leu Thr Ile Ser Arg Leu Glu Ala Glu Asp Ala Ala Thr Tyr Tyr Cys
                20                  25                  30

<210> SEQ ID NO 115
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
caggtgcagc tgcaagagtc aggacctggc ctggtgaaac cctcagaaac tctgtccctt      60
acatgcactg tctcagggtt ctcattaacc agctatggtg taagctggat tcgccagcct     120
ccaggaaagg gtctggagtg gattggagta atatggggtg aggggagcac aaattatcat     180
tcagttctca tatccagact gaccattagt gtggatacct ccaagaatca atttagctta     240
aaactgagca gtgttaccgc tgctgacaca gccgtttact actgtgccat gactgggaca     300
gcttactggg gccaagggac tctggtcact gtctctagc                            339

<210> SEQ ID NO 116
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
gagattgtgc tgacccagag ccctgccaca ctgtcactga gcccaggcga gcgagccaca      60
ctgtcctgtt ctgctagctc ctctgtctcc tacatgcatt ggtatcagca gaagccagga     120
ctggcaccac gactgctgat ctatgacact tctaaactga gttcaggcat tcccgccaga     180
ttcagtggct cagggagcgg aaccgacttt actctgacca ttagctccct ggagcctgaa     240
gatttcgccg tgtactattg ccatcagtgg tcatcaagcc ctcataccct cggggggggg     300
actaaggtgg aaatcaaacg c                                               321

<210> SEQ ID NO 117
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
                20                  25                  30

```
Gly Val Ser Trp Ile Arg Gln Pro Pro Gly Lys Gly Leu Glu Trp Ile
            35                  40                  45
Gly Val Ile Trp Gly Glu Gly Ser Thr Asn Tyr His Ser Val Leu Ile
        50                  55                  60
Ser Arg Leu Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Met Thr Gly Thr Ala Tyr Trp Gly Gln Gly Thr Leu Val Thr Val Ser
                100                 105                 110
Ser
```

<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Glu Ile Val Leu Thr Gln Ser Pro Ala Thr Leu Ser Leu Ser Pro Gly
1               5                   10                  15
Glu Arg Ala Thr Leu Ser Cys Ser Ala Ser Ser Val Ser Tyr Met
                20                  25                  30
His Trp Tyr Gln Gln Lys Pro Gly Leu Ala Pro Arg Leu Leu Ile Tyr
            35                  40                  45
Asp Thr Ser Lys Leu Ser Ser Gly Ile Pro Ala Arg Phe Ser Gly Ser
        50                  55                  60
Gly Ser Gly Thr Asp Phe Thr Leu Thr Ile Ser Ser Leu Glu Pro Glu
65                  70                  75                  80
Asp Phe Ala Val Tyr Tyr Cys His Gln Trp Ser Ser Ser Pro His Thr
                85                  90                  95
Phe Gly Gly Gly Thr Lys Val Glu Ile Lys Arg
                100                 105
```

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Ser Ser Val Ser Tyr
1               5
```

<210> SEQ ID NO 120
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Asp Thr Ser
1
```

```
<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

His Gln Trp Ser Ser Ser Pro His Thr
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Phe Ser Leu Thr Ser Tyr Gly
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ile Trp Gly Glu Gly Ser Thr
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Met Thr Gly Thr Ala Tyr
1               5

<210> SEQ ID NO 125
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
caggtgcagc tgaagcagag cggacctggc ctggtgcagc cctcacagag cctgagcatc      60
acttgtaccg tcagtggatt ctccctgaca tcttacggcg tgtcttgggt caggcagagc     120
cctggcaagg ggctggagtg gctgggcgtg atctggggag aaggctcaac taactatcac     180
agcgtcctga tcagtcgcct gtcaattaac aaggacaatt ctaaaagtca ggtgttcttt     240
aaaatgaaca gcctgcagtc caatgatacc gccatctact attgcgctat gaccggcaca     300
gcatactggg ggcagggaac actggtgact gtctccgct                            339
```

<210> SEQ ID NO 126
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126

```
gagattgtgc tgacccagag ccctgccaca ctgtcactga gcccaggcga gcgagccaca      60
ctgtcctgtt ctgctagctc ctctgtctcc tacatgcatt ggtatcagca agaagccagga   120
ctggcaccac gactgctgat ctatgacact tctaaactga gttcaggcat tcccgccaga   180
ttcagtggct cagggagcgg aaccgacttt actctgacca ttagctccct ggagcctgaa   240
gatttcgccg tgtactattg ccatcagtgg tcatcaagcc ctcataccct cgggggggg    300
actaagctgg aaatcaaacg c                                             321
```

<210> SEQ ID NO 127
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

Gln Val Gln Leu Lys Gln Ser Gly Pro Gly Leu Val Gln Pro Ser Gln
1               5                   10                  15
Ser Leu Ser Ile Thr Cys Thr Val Ser Gly Phe Ser Leu Thr Ser Tyr
            20                  25                  30
Gly Val Ser Trp Val Arg Gln Ser Pro Gly Lys Gly Leu Glu Trp Leu
        35                  40                  45
Gly Val Ile Trp Gly Glu Gly Ser Thr Asn Tyr His Ser Val Leu Ile
    50                  55                  60
Ser Arg Leu Ser Ile Asn Lys Asp Asn Ser Lys Ser Gln Val Phe Phe
65                  70                  75                  80
Lys Met Asn Ser Leu Gln Ser Asn Asp Thr Ala Ile Tyr Tyr Cys Ala
                85                  90                  95
Met Thr Gly Thr Ala Tyr Trp Gly Gln Gly Thr Leu Val Thr Val Ser
            100                 105                 110
Ala

<210> SEQ ID NO 128
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

Glu Ile Val Leu Thr Gln Ser Pro Ala Thr Leu Ser Leu Ser Pro Gly
1               5                   10                  15
Glu Arg Ala Thr Leu Ser Cys Ser Ala Ser Ser Ser Val Ser Tyr Met
            20                  25                  30
His Trp Tyr Gln Gln Lys Pro Gly Leu Ala Pro Arg Leu Leu Ile Tyr
        35                  40                  45
Asp Thr Ser Lys Leu Ser Ser Gly Ile Pro Ala Arg Phe Ser Gly Ser
    50                  55                  60

```
Gly Ser Gly Thr Asp Phe Thr Leu Thr Ile Ser Ser Leu Glu Pro Glu
 65                  70                  75                  80

Asp Phe Ala Val Tyr Tyr Cys His Gln Trp Ser Ser Pro His Thr
                 85                  90                  95

Phe Gly Gly Gly Thr Lys Val Leu Glu Ile Lys Arg
            100                 105

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Ser Val Ser Tyr
1               5

<210> SEQ ID NO 130
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Thr Ser
1

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

His Gln Trp Ser Ser Pro His Thr
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Phe Ser Leu Thr Ser Tyr Gly
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ile Trp Gly Glu Gly Ser Thr
1               5
```

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Met Thr Gly Thr Ala Tyr
1               5

<210> SEQ ID NO 135
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
caggtgcagc tgcaggaaag cggacccgga ctggtgaaac ctagcgaaac actgagcctg      60
acttgtaccg tgagcggatt ttccctgacc tcttatggag tgagctggat cagacagccc     120
cctggcaagg gactggagtg gatcggcgtg atttgggag aaggctccac aaactatcac     180
agtgtcctga tctcacgact gactatttct aaggacaact ctaaaagtca ggtcttcctg     240
aaactgaata gtctgcagac tgacgatacc gctacatact attgcgcaat gacagggaca     300
gcatactggg gacagggaac cctggtgaca gtcagctcc                             339

<210> SEQ ID NO 136
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
cagatcgtgc tgacacagtc ccctgcaatt atgtcagcca gcccagggga aaaggtgaca      60
atgacttgta gtgcttctag ttcagtctca tacatgcatt ggtatcagca aagccaggc     120 ctggccccca gactgctgat ctacgacacc tccaaactga gctccggcgt gcccggggaga    180 ttttccggct ctgggagtgg aacttcatat agcctgacca tttctaggct ggaggccgaa    240
gatgccgcta catactattg ccaccagtgg agcagtagcc ccatacatt cggaggcggg     300 accaaagtgg aaatcaaacg c                                                321

<210> SEQ ID NO 137
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val Ser Trp Ile Arg Gln Pro Pro Gly Lys Gly Leu Glu Trp Ile
        35                  40                  45

Gly Val Ile Trp Gly Glu Gly Ser Thr Asn Tyr His Ser Val Leu Ile
            50                  55                  60

Ser Arg Leu Thr Ile Ser Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Met Thr Gly Thr Ala Tyr Trp Gly Gln Gly Thr Leu Val Thr Val Ser
            100                 105                 110

Ser

<210> SEQ ID NO 138
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Ile Val Leu Thr Gln Ser Pro Ala Ile Met Ser Ala Ser Pro Gly
 1               5                   10                  15

Glu Lys Val Thr Met Thr Cys Ser Ala Ser Ser Ser Val Ser Tyr Met
             20                  25                  30

His Trp Tyr Gln Gln Lys Pro Gly Leu Ala Pro Arg Leu Leu Ile Tyr
         35                  40                  45

Asp Thr Ser Lys Leu Ser Ser Gly Val Pro Gly Arg Phe Ser Gly Ser
 50                  55                  60

Gly Ser Gly Thr Ser Tyr Ser Leu Thr Ile Ser Arg Leu Glu Ala Glu
 65                  70                  75                  80

Asp Ala Ala Thr Tyr Tyr Cys His Gln Trp Ser Ser Pro His Thr
                 85                  90                  95

Phe Gly Gly Gly Thr Lys Val Glu Ile Lys Arg
            100                 105

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Ser Val Ser Tyr
 1               5

<210> SEQ ID NO 140
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asp Thr Ser
 1

<210> SEQ ID NO 141
<211> LENGTH: 9
<212> TYPE: PRT

<213> ORGANISM: Artificial Sequence
<220> FEATURE:
<223> OTHER INFORMATION: Description of Artificial Sequence: Synthetic
     peptide

<400> SEQUENCE: 141

His Gln Trp Ser Ser Ser Pro His Thr
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 142

Gly Phe Ser Leu Thr Ser Tyr Gly
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 143

Ile Trp Gly Glu Gly Ser Thr
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 144

Ala Met Thr Gly Thr Ala Tyr
1               5

<210> SEQ ID NO 145
<211> LENGTH: 339
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 145
caggtccagc tgaaagagag cggccccgga ctggtcgccc cttcacagag cctgagcatt      60
acttgcaccg tgagcggatt ttcactgacc agctacggag tgagctggat tagacagcct     120
cctggcaagg gactggagtg gatcggcgtg atttggggag aaggcagcac caactatcac     180
agtgtcctga tctcacgcct gacaatttcc aaggacaaca gcaaatccca ggtcttcctg     240
aaactgaatt ctctgcagac tgacgatacc gctacatact attgcgcaat gacagggaca     300
gcatactggg gacagggaac cctggtgaca gtcagtagt                            339

<210> SEQ ID NO 146
<211> LENGTH: 321
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 146

```
cagatcgtgc tgacacagtc cccagcaatt atgtctgcca gtcccgggga gaaggtgaca      60
atgacttgta gtgccagctc ctctgtctca tacatgcatt ggtatcagca gaagtccggc     120
acatctccta acggtggat ctacgacact tctaaactga gttcaggcgt gcccggaga      180
ttttcaggca gcgggtccgg aacttcttat agtctgacca tttcccgact ggaggccgaa     240
gatgccgcta cctactattg ccatcagtgg tcttcaagcc ctcatacttt tggggggga     300
actaaggtgg aaatcaagcg a                                                321
```

<210> SEQ ID NO 147
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

```
Gln Val Gln Leu Lys Glu Ser Gly Pro Gly Leu Val Ala Pro Ser Gln
1               5                   10                  15
Ser Leu Ser Ile Thr Cys Thr Val Ser Gly Phe Ser Leu Thr Ser Tyr
            20                  25                  30
Gly Val Ser Trp Ile Arg Gln Pro Pro Gly Lys Gly Leu Glu Trp Ile
        35                  40                  45
Gly Val Ile Trp Gly Glu Gly Ser Thr Asn Tyr His Ser Val Leu Ile
    50                  55                  60
Ser Arg Leu Thr Ile Ser Lys Asp Asn Ser Lys Ser Gln Val Phe Leu
65                  70                  75                  80
Lys Leu Asn Ser Leu Gln Thr Asp Asp Thr Ala Thr Tyr Tyr Cys Ala
                85                  90                  95
Met Thr Gly Thr Ala Tyr Trp Gly Gln Gly Thr Leu Val Thr Val Ser
                100                 105                 110
Ser
```

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

```
Gln Ile Val Leu Thr Gln Ser Pro Ala Ile Met Ser Ala Ser Pro Gly
1               5                   10                  15
Glu Lys Val Thr Met Thr Cys Ser Ala Ser Ser Ser Val Ser Tyr Met
            20                  25                  30
His Trp Tyr Gln Gln Lys Ser Gly Thr Ser Pro Lys Arg Trp Ile Tyr
        35                  40                  45
Asp Thr Ser Lys Leu Ser Ser Gly Val Pro Gly Arg Phe Ser Gly Ser
    50                  55                  60
Gly Ser Gly Thr Ser Tyr Ser Leu Thr Ile Ser Arg Leu Glu Ala Glu
65                  70                  75                  80
```

```
Asp Ala Ala Thr Tyr Tyr Cys His Gln Trp Ser Ser Ser Pro His Thr
                85                  90                  95

Phe Gly Gly Gly Thr Lys Val Glu Ile Lys Arg
            100                 105

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Ser Val Ser Tyr
1               5

<210> SEQ ID NO 150
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Thr Ser
1

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

His Gln Trp Ser Ser Ser Pro His Thr
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Phe Ser Leu Thr Ser Tyr Gly
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 153

Ile Trp Gly Glu Gly Ser Thr
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Met Thr Gly Thr Ala Tyr
1               5

<210> SEQ ID NO 155
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gln Ile Val Leu Thr Gln Ser Pro Ala Ile Met Ser Ala Ser Pro Gly
1               5                   10                  15

Glu Lys Val Thr Met Thr Cys Ser Ala Ser
            20                  25

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Met His Trp Tyr Gln Gln Lys Ser Gly Thr Ser Pro Lys Arg Trp Ile
1               5                   10                  15

Tyr

<210> SEQ ID NO 157
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Lys Leu Ser Ser Gly Val Pro Gly Arg Phe Ser Gly Ser Gly Ser Gly
1               5                   10                  15

Thr Ser Tyr Ser Leu Thr Ile Ser Arg Leu Glu Ala Glu Asp Ala Ala
            20                  25                  30

Thr Tyr Tyr Cys
        35

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                         peptide

<400> SEQUENCE: 158

Phe Gly Gly Gly Thr Lys Val Glu Ile Lys Arg
1               5                   10

<210> SEQ ID NO 159
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gln Val Gln Leu Lys Glu Ser Gly Pro Gly Leu Val Ala Pro Ser Gln
1               5                   10                  15

Ser Leu Ser Ile Thr Cys Thr Val Ser
            20                  25

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Val Ser Trp Ile Arg Gln Pro Pro Gly Lys Gly Leu Glu Trp Ile Gly
1               5                   10                  15

Val

<210> SEQ ID NO 161
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asn Tyr His Ser Val Leu Ile Ser Arg Leu Thr Ile Ser Lys Asp Asn
1               5                   10                  15

Ser Lys Ser Gln Val Phe Leu Lys Leu Asn Ser Leu Gln Thr Asp Asp
            20                  25                  30

Thr Ala Thr Tyr Tyr Cys
        35

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Trp Gly Gln Gly Thr Leu Val Thr Val Ser Ser
1               5                   10

<210> SEQ ID NO 163
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 163

Gly Gly Gly Gly Ser Gly Gly Gly Gly Ser Gly Gly Gly Gly Ser
1               5                   10                  15
```